(12) United States Patent
Jowett et al.

(10) Patent No.: US 10,722,590 B2
(45) Date of Patent: Jul. 28, 2020

(54) ELP FUSION PROTEINS FOR CONTROLLED AND SUSTAINED RELEASE

(71) Applicant: PhaseBio Pharmaceuticals, Inc., Malvern, PA (US)

(72) Inventors: James Jowett, Malvern, PA (US); David James Ballance, Malvern, PA (US)

(73) Assignee: PHASEBIO PHARMACEUTICALS, INC., Malvern, PA (US)

( * ) Notice: Subject to any disclaimer, the term of this patent is extended or adjusted under 35 U.S.C. 154(b) by 0 days.

(21) Appl. No.: 15/527,985

(22) PCT Filed: Nov. 20, 2015

(86) PCT No.: PCT/US2015/061955
§ 371 (c)(1),
(2) Date: May 18, 2017

(87) PCT Pub. No.: WO2016/081884
PCT Pub. Date: May 26, 2016

(65) Prior Publication Data
US 2019/0015523 A1 Jan. 17, 2019

Related U.S. Application Data

(60) Provisional application No. 62/082,945, filed on Nov. 21, 2014, provisional application No. 62/098,624, filed on Dec. 31, 2014.

(51) Int. Cl.
*A61K 47/64* (2017.01)
*A61K 38/14* (2006.01)
(Continued)

(52) U.S. Cl.
CPC ........ *A61K 47/6435* (2017.08); *A61K 9/0019* (2013.01); *A61K 9/08* (2013.01);
(Continued)

(58) Field of Classification Search
CPC ........ A61K 38/22; A61K 38/26; A61K 38/28; A61K 47/42; A61K 47/64; A61K 47/6435
See application file for complete search history.

(56) References Cited

U.S. PATENT DOCUMENTS 6,582,926 B1 6/2003 Chilkoti
7,364,859 B2 4/2008 Chilkoti
(Continued)

FOREIGN PATENT DOCUMENTS

WO WO 1996/032406 A1 10/1996
WO WO 2008/155134 A1 12/2008
(Continued)

OTHER PUBLICATIONS

Extended European Search Report, dated Jul. 20, 2018, for European Application No. 15860714.3.
(Continued)

*Primary Examiner* — Jeffrey E. Russel
(74) *Attorney, Agent, or Firm* — Cooley LLP

(57) ABSTRACT

The present disclosure provides pharmaceutical formulations for sustained release, and methods for delivering a treatment regimen with a combination of sustained release and long half-life formulations. The pharmaceutical formulations comprise a therapeutic agent including an active agent and an amino acid sequence capable of forming a reversible matrix at the body temperature of a subject. The disclosure provides improved pharmacokinetics for peptide and small molecule drugs.

28 Claims, 33 Drawing Sheets

Specification includes a Sequence Listing.

A transition temperature near body temperature (37°C) gives the ELP 1 series a slow absorption profile

(51) Int. Cl.

| | | |
|---|---|---|
| *A61K 38/26* | (2006.01) | |
| *A61K 38/27* | (2006.01) | |
| *A61K 38/28* | (2006.01) | |
| *A61K 9/00* | (2006.01) | |
| *A61K 45/06* | (2006.01) | |
| *A61K 47/02* | (2006.01) | |
| *A61K 9/08* | (2006.01) | |
| *A61P 35/00* | (2006.01) | |
| *A61K 31/196* | (2006.01) | |
| *A61K 31/277* | (2006.01) | |
| *A61K 31/337* | (2006.01) | |
| *A61K 31/475* | (2006.01) | |
| *A61K 31/704* | (2006.01) | |
| *C07K 16/26* | (2006.01) | |
| *C07K 16/28* | (2006.01) | |

(52) U.S. Cl.
CPC ............. *A61K 38/14* (2013.01); *A61K 38/26* (2013.01); *A61K 38/27* (2013.01); *A61K 38/28* (2013.01); *A61K 45/06* (2013.01); *A61K 47/02* (2013.01); *A61K 47/64* (2017.08); *A61P 35/00* (2018.01); *A61K 31/196* (2013.01); *A61K 31/277* (2013.01); *A61K 31/337* (2013.01); *A61K 31/475* (2013.01); *A61K 31/704* (2013.01); *A61K 2300/00* (2013.01); *C07K 16/26* (2013.01); *C07K 16/28* (2013.01)

(56) References Cited

U.S. PATENT DOCUMENTS

| | | | |
|---|---|---|---|
| 7,429,458 | B2 | 9/2008 | Chilkoti |
| 7,709,227 | B2 | 5/2010 | Dagher |
| 8,178,495 | B2 | 5/2012 | Chilkoti |
| 8,334,257 | B2 | 12/2012 | Chilkoti |
| 8,729,018 | B2 | 5/2014 | Chilkoti |
| 2001/0034050 | A1 | 10/2001 | Chilkoti |
| 2008/0032400 | A1 | 2/2008 | Dagher |
| 2008/0286808 | A1 | 12/2008 | Schellenberger |
| 2009/0220455 | A1 | 9/2009 | Chilkoti |
| 2010/0189643 | A1 | 7/2010 | Chilkoti et al. |
| 2010/0316623 | A1 | 12/2010 | Turner et al. |
| 2011/0123487 | A1 | 5/2011 | Chilkoti |
| 2011/0178017 | A1 | 7/2011 | Sadeghi et al. |
| 2011/0236384 | A1 | 9/2011 | Setton et al. |
| 2011/0288001 | A1 | 11/2011 | Sadeghi |
| 2013/0079277 | A1 | 3/2013 | Chilkoti |
| 2013/0085099 | A1 | 4/2013 | Chilkoti |
| 2013/0090285 | A1 | 4/2013 | Georgopoulos et al. |
| 2013/0143802 | A1 | 6/2013 | Chilkoti |
| 2013/0150291 | A1 | 6/2013 | Jowett et al. |
| 2013/0172274 | A1 | 7/2013 | Chilkoti |
| 2013/0178416 | A1 | 7/2013 | Chilkoti |
| 2013/0310538 | A1 | 11/2013 | Chilkoti |
| 2014/0024600 | A1 | 1/2014 | Chilkoti et al. |
| 2014/0171370 | A1 | 6/2014 | Arnold et al. |
| 2014/0213516 | A1 | 7/2014 | Chilkoti |
| 2014/0364371 | A1 | 12/2014 | Chilkoti |

FOREIGN PATENT DOCUMENTS

| | | |
|---|---|---|
| WO | WO 2013/003449 A2 | 1/2013 |
| WO | WO 2014/081849 A1 | 5/2014 |
| WO | WO 2014/113434 A1 | 7/2014 |
| WO | WO 2016/081884 A2 | 5/2016 |

OTHER PUBLICATIONS

PCT/US2015/061955, International Search Report and Written Opinion dated Jun. 30, 2016, 11 pages.

PCT/US2015/061955, International Preliminary Report on Patentability dated May 23, 2017, 7 pages.

FIG. 4

| | | |
|---|---|---|
| alpha | 1 VPGVGVPGGGVPGVGVPGVGVPGGVPGVGVPGVG | SEQ ID NO: 63 |
| beta | 1 VPGVGVPGVGVPGAGVPGVGVPGVGVPGAGVPGVG | SEQ ID NO: 64 |
| beta v2 | 1 VPGAGVPGVGVPGAGVPGVGVPGVCVPGAGVPGVG | SEQ ID NO: 65 |
| delta | 1 VPGVGAPGVGVPGAPGVGVPGVGAPGVGVPGVG | SEQ ID NO: 66 |

FIG. 7

```
                 XbaI                                              KpnI
                                                                   Acc65I                                    BglI
ttccctccta gaaataattt tgtttaactt taagaaggag atatacatat ggtaccggc gtggtgtgc cggctgcc gtgataagct    SEQ ID NO: 57
aagggagat ctttattaaa acaaattgaa atcttcctc tatatgtata ccatggcccg caccacacg gccgacgg cactattcga    SEQ ID NO: 67
                                                          >.............................>>
                                                          m  p  g  v  g  v  p  g  w  p  -  -    SEQ ID NO: 58
                                                                  linker
```

FIG. 8

VPGVGVPGVPGGGVPGVGVPGVGVPGVGVPGVGVPGVGVPGVG
VPGVGVPGVGVPGVGVPGVGVPGVGVPGGGVPGVGVPGVGVPGVG
VPGVGVPGVGVPGVGVPGVGVPGVGVPGVGVPGVGVPGVGVPGVG
VPGGGVPGVGVPGVGVPGVGVPGVGVPGVGVPGVGVPGVGVPGGG
VPGVGVPGVGVPGVGVPGVGVPGGGVPGVGVPGVGVPGVGVPGVG
VPGVGVPGVGVPGVGVPGVGVPGVGVPGVGVPGGGVPGVGVPGVG
VPGVGVPGVGVPGVGVPGVGVPGVGVPGVGVPGVGVPGVGVPGVG
VPGVGVPGGGVPGVGVPGVGVPGVGVPGVGVPGVGVPGVGVPGVG
VPGGGVPGVGVPGVGVPGVGVPGVGVPGVGVPGVGVPGVGVPGGG
VPGVGVPGVGVPGVGVPGVGVPGGGVPGVGVPGVGVPGVGVPGVG
VPGVGVPGVGVPGVGVPGVGVPGVGVPGVGVPGGGVPGVGVPGVG
VPGVGVPGVGVPGVGVPGVGVPGVGVPGVGVPGVGVPGVGVPGVG
VPGVGVPGGGVPGVGVPGVGVPGVGVPGVGVPGVGVPGVGVPGVG
VPGGGVPGVGVPGVGVPGVGVPGVGVPGVGVPGVGVPGVGVPGGG
VPGVGVPGVGVPGVGVPGVGVPGGGVPGVGVPGVGVPGVGVPGVG
VPGVGVPGVGVPGVPGGGVPGVGVPGVGVPGWP (SEQ ID NO: 68)

FIG. 10

VPGVGVPGVGVPGVGVPGVGVPGAGVPGVGVPGVGVPGVGVPGVGVPGVGVPGAG
VPGVGVPGVGVPGVGVPGAGVPGVGVPGVGVPGVGVPGVGVPGVGVPGAGVPGVG
VPGVGVPGVGVPGAGVPGVGVPGVGVPGVGVPGVGVPGAGVPGVGVPGVGVPGVG
VPGVGVPGAGVPGVGVPGVGVPGVGVPGVGVPGAGVPGVGVPGVGVPGVGVPGVG
VPGAGVPGVGVPGVGVPGVGVPGVGVPGAGVPGVGVPGVGVPGVGVPGVGVPGAG
VPGVGVPGVGVPGVGVPGVGVPGAGVPGVGVPGVGVPGVGVPGVGVPGAGVPGVG
VPGVGVPGVGVPGVGVPGAGVPGVGVPGVGVPGVGVPGVGVPGAGVPGVGVPGVG
VPGVGVPGVGVPGAGVPGVGVPGVGVPGVGVPGVGVPGAGVPGVGVPGVGVPGVG
VPGAGVPGVGVPGVGVPGVGVPGVGVPGAGVPGVGVPGVGVPGVGVPGVGVPGAG
VPGVGVPGVGVPGVGVPGVGVPGAGVPGVGVPGVGVPGVGVPGVGVPGAGVPGVG
VPGVGVPGVGVPGVGVPGAGVPGVGVPGVGVPGVGVPGVGVPGAGVPGVGVPGVG
VPGVGVPGVGVPGAGVPGVGVPGVGVPGVGVPGVGVPGAGVPGVGVPGVGVPGVG
VPGAGVPGVGVPGVGVPGVGVPGVGVPGAGVPGVGVPGVGVPGVGVPGVGVPGAG
VPGVGVPGVGVPGVGVPGVGVPGAGVPGVGVPGVGVPGVGVPGVGVPGAGVPGVG
VPGAGVPGVGVPGVGVPGVGVPGVGVPGAGVPGVGVPGVGVPGVGVPGVGVPGAG
VPGVGVPGVGVPGVGVPGVGVPGAGWP (SEQ ID NO: 69)

FIG. 12

VPGVGVPGVGVPGAGVPGVGVPGVGVPGAGVPGVGVPGVGVPGAG
VPGVGVPGAGVPGVGVPGVGVPGAGVPGVGVPGVGVPGAGVPGVG
VPGAGVPGVGVPGVGVPGAGVPGVGVPGVGVPGAGVPGVGVPGAG
VPGVGVPGAGVPGVGVPGVGVPGAGVPGVGVPGVGVPGAGVPGVG
VPGAGVPGVGVPGVGVPGAGVPGVGVPGVGVPGAGVPGVGVPGVG
VPGAGVPGVGVPGVGVPGAGVPGVGVPGVGVPGAGVPGVGVPGAG
VPGVGVPGAGVPGVGVPGVGVPGAGVPGVGVPGVGVPGAGVPGVG
VPGAGVPGVGVPGVGVPGAGVPGVGVPGVGVPGAGVPGVGVPGVG
VPGAGVPGVGVPGVGVPGAGVPGVGVPGVGVPGAGVPGVGVPGAG
VPGVGVPGAGVPGVGVPGVGVPGAGVPGVGVPGVGVPGAGVPGVG
VPGAGVPGVGVPGVGVPGAGVPGVGVPGVGVPGAGVPGVGVPGAG
VPGAGVPGVGVPGVGVPGAGVPGVGVPGVGVPGAGVPGVGVPGVG
VPGAGVPGVGVPGVGVPGAGVPGVGVPGVGVPGAGVPGVGVPGAG
VPGVGVPGAGVPGVGVPGVGVPGAGVPGVGVPGVGVPGAGVPGVG
VPGAGVPGVGVPGVGVPGAGVPGVGVPGVGVPGAGVPGVGVPGAG
VPGVGVPGAGVPGVGVPGVGVPGAGVPGVGVPGVGVPGAGVPGVG
VPGVGVPGVGVPGAGVPGVGVPGAGVPGWP (SEQ ID NO: 70)

FIG. 14

VPGVGVPGVPGVGVPGGGVPGVGVPGVGVPGVGVPGGGVPGVG
VPGVGVPGVGVPGVGVPGAGVPGVGVPGVGVPGVGVPGAGVPGVG
VPGVGVPGGGVPGVGVPGVGVPGVGVPGGGVPGAGVPGVGVPGVG
VPGVGVPGAGVPGVGVPGVGVPGVGVPGGGVPGAGVPGVGVPGGG
VPGVGVPGVGVPGVGVPGVGVPGVPGAGVPGVGVPGVGVPGAG
VPGVGVPGVGVPGVGVPGGGVPGAGVPGVGVPGVGVPGVGVPGVG
VPGVGVPGGGVPGVGVPGVGVPGVGVPGAGVPGVGVPGVGVPGVG
VPGVGVPGVGVPGVGVPGAGVPGVGVPGVGVPGVGVPGVGVPGVG
VPGGGVPGVGVPGVGVPGVGVPGGGVPGAGVPGVGVPGVGVPGVG
VPGAGVPGVGVPGVGVPGGGVPGVGVPGVGVPGVGVPGGGVPGVG
VPGVGVPGVGVPGVGVPGAGVPGVGVPGVGVPGVGVPGAGVPGVG
VPGVGVPGGGVPGVGVPGVGVPGVGVPGGGVPGAGVPGVGVPGVG
VPGVGVPGAGVPGVGVPGVGVPGVGVPGVGVPGAGVPGVGVPGVG
VPGVGVPGVGVPGVGVPGVGVPGAGVPGVGVPGVGVPGVGVPGAG
VPGVGVPGVGVPGVGVPGAGVPGWP (SEQ ID NO: 71)

FIG. 16

VPGVGVPGVGVPGVGAPGVGVPGVGAPGVGVPGVGAPGVG
VPGVGVPGVGAPGVGVPGVGAPGVGVPGVGAPGVGVPGVG
VPGVGVPGVGAPGVGVPGVGAPGVGVPGVGAPGVGVPGVG
APGVGVPGVGAPGVGVPGVGAPGVGVPGVGAPGVGVPGVG
VPGVGVPGVGAPGVGVPGVGAPGVGVPGVGAPGVGVPGVG
APGVGVPGVGAPGVGVPGVGAPGVGVPGVGAPGVGVPGVG
VPGVGAPGVGVPGVGAPGVGVPGVGAPGVGVPGVGAPGVG
APGVGVPGVGAPGVGVPGVGAPGVGVPGVGAPGVGVPGVG
VPGVGAPGVGVPGVGAPGVGVPGVGAPGVGVPGVGAPGVG
APGVGVPGVGAPGVGVPGVGAPGVGVPGVGAPGVGVPGVG
APGVGVPGVGAPGVGVPGVGAPGVGVPGVGAPGVGVPGVG
VPGVGVPGVGAPGVGVPGVGAPGVGVPGVGAPGVGVPGVG
VPGVGAPGVGVPGVGAPGVGVPGVGAPGVGVPGVGAPGVG
APGVGVPGVGAPGVGVPGVGAPGVGVPGVGAPGVGVPGVG
VPGVGAPGVGVPGVGAPGVGVPGVGAPGVGVPGVGAPGVG
APGVGVPGVGAPGVGVPGVGAPGVPGVGAPGVGVPGVPGWP (SEQ ID NO: 72)

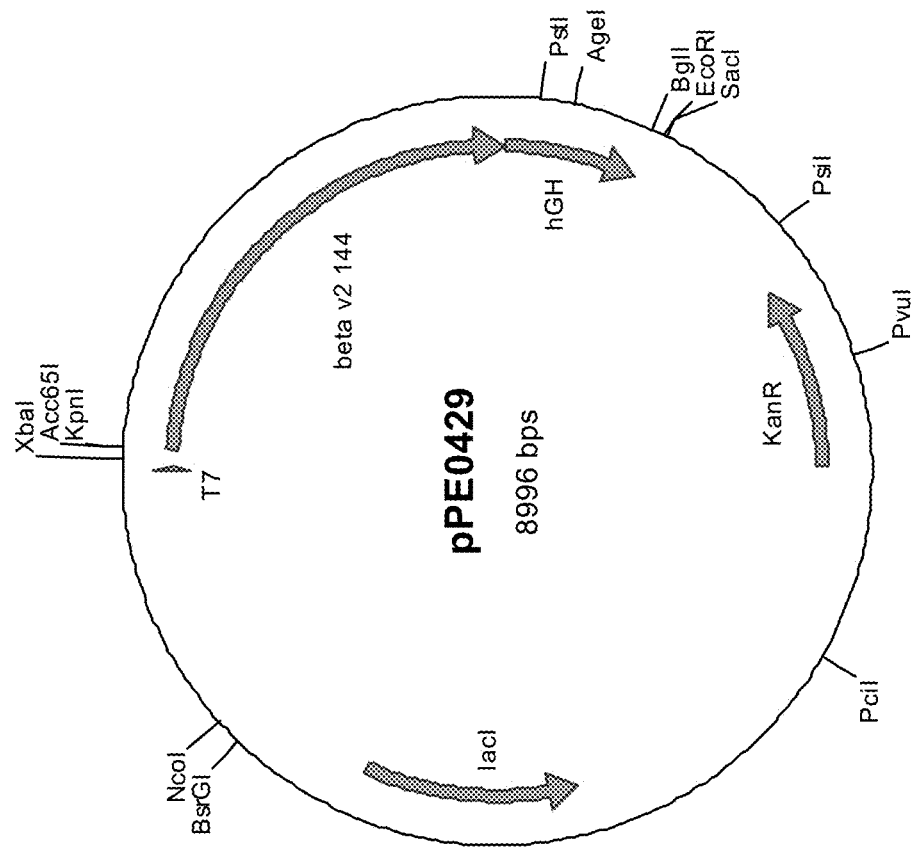
FIG. 23 Plasmid pPE0429

FIG. 24: Amino acid sequence of ELPbetaV2 hGH fusion protein.

hGH (underlined); ELPbetav2-144 sequence (bold); single ELP pentamer (italics)

MVPGVGVPGVGVPGAGVPGVGVPGAGVPGVGVPGAGVPGVGVPGAGVPGVGVPGAGVPG
VGVPGVGVPGAGVPGVGVPGAGVPGVGVPGAGVPGVGVPGAGVPGVGVPGAGVPGVGVP
GAGVPGVGVPGAGVPGVGVPGAGVPGVGVPGAGVPGVGVPGAGVPGVGVPGAGVPGAGV
PGVGVPGAGVPGVGVPGAGVPGVGVPGAGVPGVGVPGAGVPGVGVPGAGVPGVGVPGAG
VPGVGVPGVGVPGAGVPGVGVPGAGVPGVGVPGAGVPGVGVPGAGVPGVGVPGAGVPGV
GVPGAGVPGVGVPGAGVPGVGVPGAGVPGVGVPGAGVPGVGVPGAGVPGVGVPGVGVPG
AGVPGVGVPGAGVPGVGVPGAGVPGVGVPGAGVPGVGVPGAGVPGVGVPGAGVPGVGVP
GAGVPGVGVPGAGVPGVGVPGAGVPGVGVPGAGVPGVGVPGAGVPGVGVPGAGVPGAGV
PGVGVPGAGVPGVGVPGAGVPGVGVPGAGVPGVGVPGAGVPGVGVPGAGVPGVGVPGVG
VPGAGVPGVGVPGAGVPGVGVPGAGVPGVGVPGAGVPGVGVPGAGVPGVGVPGAGVPGVGVPGVGVPGAGVPGVGVPGAGVPGVGVPGAGVPGVGVPGAGVPGVGVPGVGGFTIPLSRLFDN
AMLRAHRLHQLAFDTYQEFEEAYIPKEQKYSFLQNPQTSLCFSESIPTPSNREETQQKSNLELLRISLLLIQSWLEPVQFLRSVF
ANSLVYGASDSNVYDLLKDLEEGIQTLMGRLEDGSPRTGQIFKQTYSKFDTNSHNDDALLKNYGLLYCFRKDMKVETFLR
IVQCRSVEGSCGF*VPGWP* (SEQ ID NO: 73)

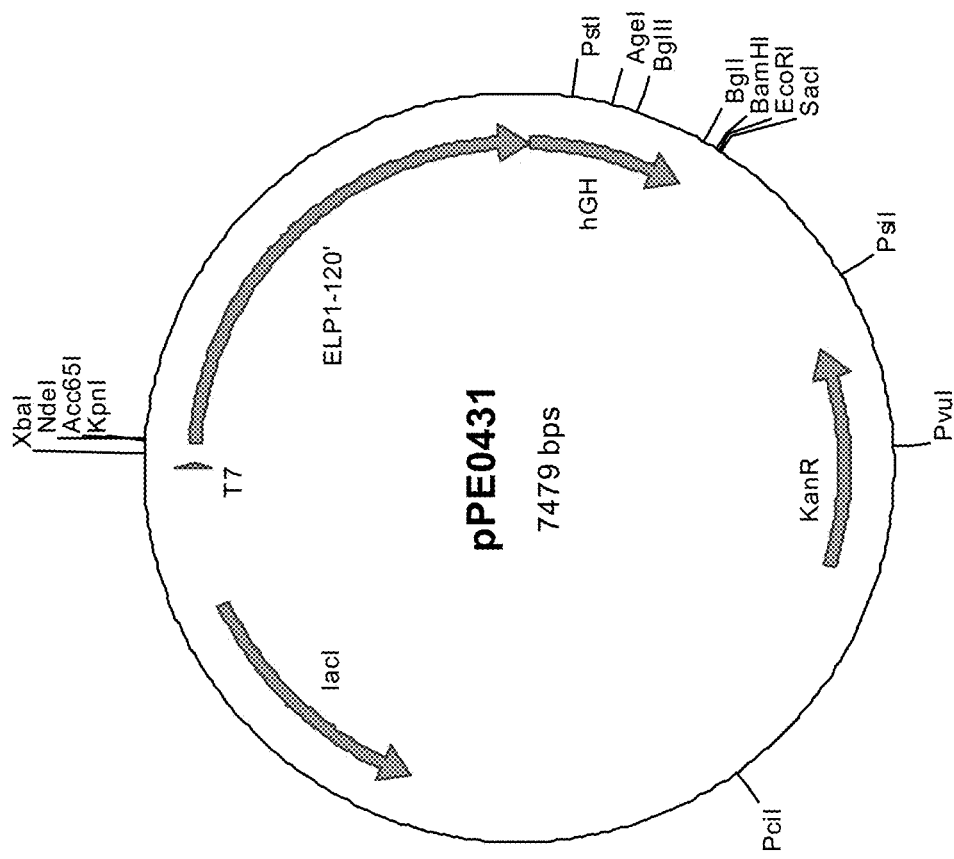
FIG. 25 Plasmid pPE0430 The synthesized hGH sequence was digested with restriction enzymes PflMI25 / Bgl I and sub cloned into the Bgl I site in plasmid pPB1031

FIG. 26 – Amino acid sequence of ELP1-120 hGH fusion protein. The hGH sequence (underlined) is fused to the 1 series 120mer sequence (bold). A single ELP pentamer (italics) remains on the C-terminus of hGH to conserve a Bgl I restriction site for further cloning.

**MVPGVGVPGVGVPGGGVPGAGVPGVGVPGAGVPGGGVPGAGVPGVGVPGAGVPG
VGVPGVGVPGVGVPGGGVPGAGVPGAGVPGVGVPGAGVPGVGVPGGGVPGAGVP
GGGVPGVGVPGVGVPGGGVPGVGVPGAGVPGGGVPGVGVPGVGVPGGGVPGAGV
PGVGVPGVGVPGVGVPGGGVPGAGVPGGGVPGAGVPGAGVPGVGVPGVGVPGAG
VPGGGVPGVGVPGAGVPGAGVPGVGVPGVGVPGGGVPGVGVPGVGVPGGGVPGA
GVPGVGVPGVGVPGVGVPGGGVPGGGVPGAGVPGAGVPGAGVPGVGVPGGGVPG
AGVPGGGVPGVGVPGVGVPGGGVPGGGVPGAGVPGAGVPGGGVPGVGVPGGGVP
GAGVPGVGVPGGGVPGVGVPGVGVPGGGVPGGGVPGVGVPGVGVPGVGVPGGGV
PGAGVPGGGVPGVG**FPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLEDGSPRTGQIFKQTYSKFDTNSHN
DDALLKNYGLLYCFRKDMDKVETFLRIVQCRSVEGSCGF*VPGWP* (SEQ ID NO: 74)

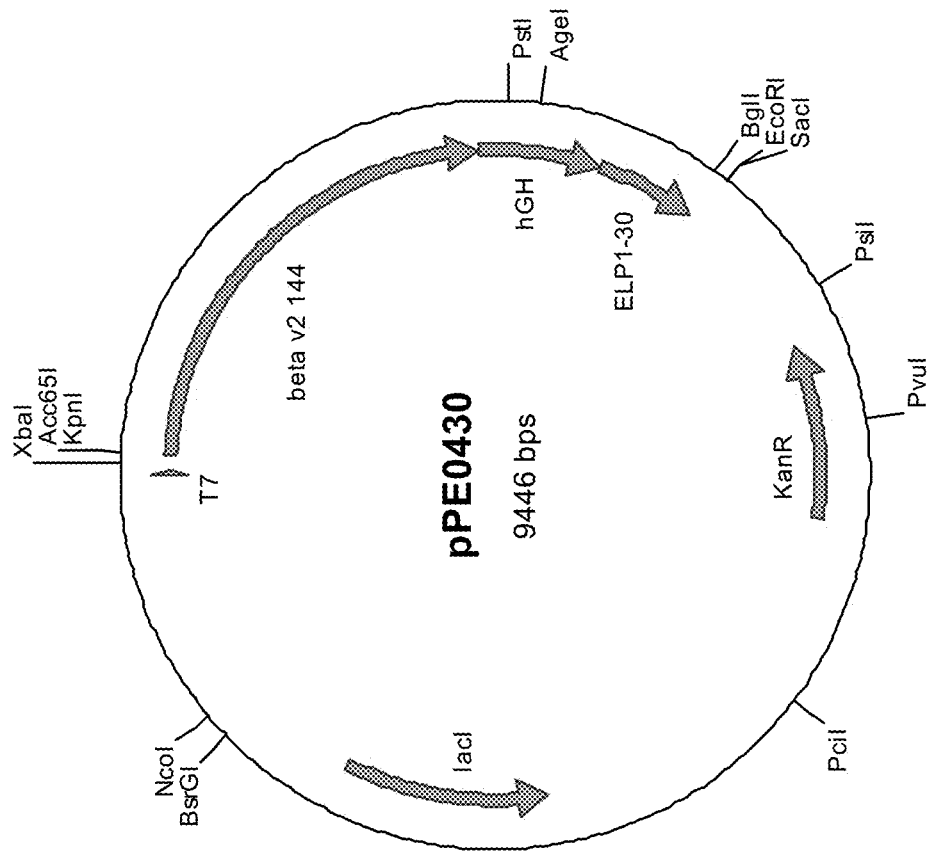
FIG. 27 Plasmid pPE0430

FIG. 28 Amino acid sequence of ELPbetaV2-144—hGH—ELP1-30 fusion protein.

hGH (underlined); ELPbetav2-144 sequence (bold); ELP1 30mer (italics)

MVPGVGVPGVGVPGAGVPGVGVPGAGVPGVGVPGVGVPGAGVPGVGVPGAGVPG
VGVPGVGVPGAGVPGVGVPGAGVPGVGVPGVGVPGAGVPGVGVPGAGVPGVGVP
GAGVPGVGVPGAGVPGVGVPGAGVPGVGVPGVGVPGAGVPGVGVPGAGVPGAGV
PGVPGAGVPGVGVPGAGVPGVGVPGAGVPGVGVPGVGVPGAGVPGVGVPGVPGAG
VPGAGVPGVGVPGAGVPGVGVPGAGVPGVGVPGVGVPGAGVPGVGVPGAGVPGV
GVPGAGVPGVGVPGAGVPGVGVPGAGVPGVGVPGVGVPGAGVPGVGVPGVGVPG
AGVPGVGVPGAGVPGVGVPGAGVPGVGVPGVGVPGAGVPGVGVPGAGVPGVGVP
GAGVPGVGVPGAGVPGVGVPGAGVPGVGVPGVGVPGAGVPGVGVPGAGVPGVGV
PGVGVPGAGVPGVGVPGAGVPGVGVPGAGVPGVGVPGVGVPGAGVPGVGVPGVG
VPGAGVPGVGVPGAGVPGVGVPGAGVPGVGVPGVGVPGAGVPGVGVPGVGVPGVG
VPGAGVPGVGVPGAGVPGVGVPGAGVPGVGVPGAGVPGVGVPGFPTIPLSRLFDN
AMLRAHRLHQLAFDTYQEFEEAYIPKEQKYSFLQNPQTSLCFSESIPTPSNREETQQKSNLELLRISLLLIQSWLEPVQFLRSVF
ANSLVYGASDSNVYDLLKDLEEGIQTLMGRLEDGSPRTGQIFKQTYSKFDTNSHNDDALLKNYGLLYCFRKDMDKVETFLR
IVQCRSVEGSCGF*VPGVGVPGGGVPGAGVPGGGVPGVGVPGGGVPGAGVPGA*
*GVPGVGVPGGGVPGAGVPGGGVPGVGVPGGGVPGAGVPGGGVPGAGVPGGG*
*VPGWP* (SEQ ID NO: 75)

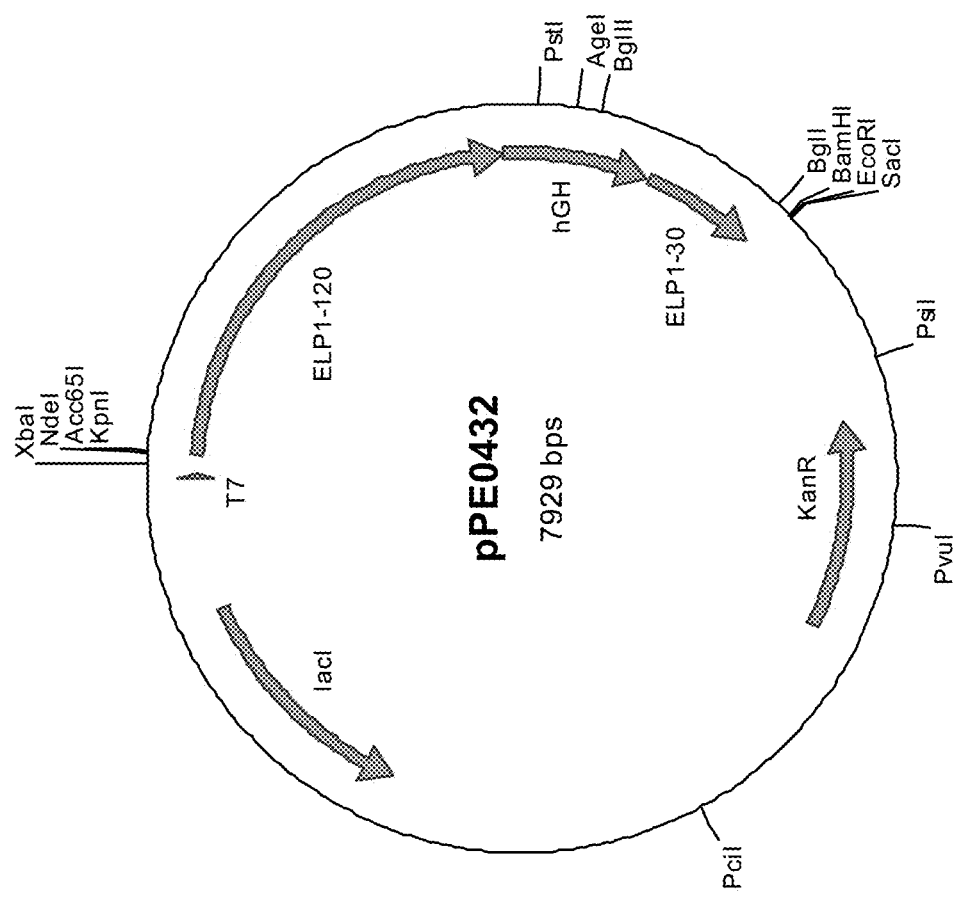
FIG. 29 – Plasmid pPE0432. The ELP 30mer was sub cloned into the Bgl I restriction site of pPE0431 positioning it at the C-terminus of the hGH sequence.

FIG. 30 – Amino acid sequence of an ELP1-120 hGH ELP1-30 fusion protein. The hGH sequence (underlined) is fused to both the ELP1 series 120mer sequence (bold) and the ELP1-30 sequence (italics).

MVPGVGVPGGGVPGAGVPGVGVPGVGVPGGGVPGAGVPG
VGVPGVGVPGVGVPGGGVPGAGVPGVGVPGVGVPGACVP
GGGVPGVGVPGVGVPGAGVPGVGVPGVGVPGGGVPGAGV
PGVGVPGVGVPGVGVPGGGVPGAGVPGVGVPGVGVPGAG
VPGGGVPGVGVPGVGVPGVGVPGAGVPGVGVPGGGVPGA
GVPGGGVPGVGVPGVGVPGAGVPGVGVPGGGVPGGGVPG
AGVPGGGVPGVGVPGVGVPGAGVPGAGVPGGGVPGGGVP
GAGVPGVGVPGVGVPGGGVPGAGVPGAGVPGVGVPGGGV
PGAGVPGGGVPGFPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLEDGSPRTGQIFKQTYSKFDTNSHN
DDALLKNYGLLYCFRKDMDKVETFLRIVQCRSVEGSCGF*VPGVGVPGGGVPGAGVPGVGVPGGGVPGVGVPGGGVP
GAGVPGGGVPGVGVPGVGVPGAGVPGGGVPGVGVPGGGVPGAGVPGVGVPGGGVPGAGVPGGGVPGAGVPG
VGVPGVGVPGGGVPGAGVPGGGVPGGGVPGWP* (SEQ ID NO: 76)

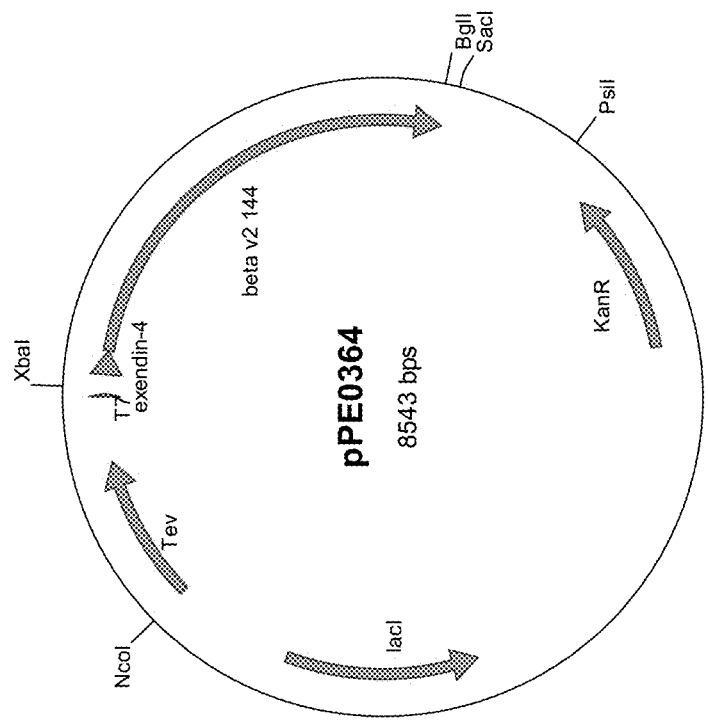
FIG. 31. Plasmid pPE0364 - The synthesized exendin-4 sequence was digested with restriction enzymes *XbaI* / *BsrGI* and subcloned into the plasmid pPE0362 digested *XbaI* / *Acc65i*.

FIG. 32 - Amino acid sequence of exendin-4 ELPbetaV2 fusion protein.

HGEGTFTSDLSKQMEEEAVRLFIEWLKNGGPSSGAPPPSVPGVGVPGAGVPGVGVPGAGVPGVGVPGAGVPGVGVPGAGV
PGVGVPGAGVPGVGVPGAGVPGVGVPGAGVPGVGVPGAGVPGVGVPGAGVPGVGVPGAGVPGVGVPGAGVPGVGVPGAGV
GVGVPGAGVPGVGVPGAGVPGVGVPGAGVPGVGVPGAGVPGVGVPGAGVPGVGVPGAGVPGVGVPGAGVPGVGVPGAGVP
GVGVPGAGVPGVGVPGAGVPGVGVPGAGVPGVGVPGAGVPGVGVPGAGVPGVGVPGAGVPGVGVPGAGVPGVGVPGAG
VPGVGVPGAGVPGVGVPGAGVPGVGVPGAGVPGVGVPGAGVPGVGVPGAGVPGVGVPGAGVPGVGVPGAGVPGVGVPG
AGVPGVGVPGAGVPGVGVPGAGVPGVGVPGAGVPGVGVPGAGVPGVGVPGAGVPGVGVPGAGVPGVGVPGAGVPGVGVPGAGV
PGVGVPGAGVPGVGVPGAGVPGVGVPGAGVPGVGVPGAGVPGVGVPGAGVPGVGVPGAGVPGVGVPGAGVPGVGVPGA
GVPGVGVPGAGVPGVGVPGAGVPGVGVPGAGVPGVGVPGAGVPGVGVPGAGVPGVGVPGAGVPGVGVPGAGVPGVGVP
GAGVPGVGVPGAGVPGVGVPGAGVPGVGVPGAGVPGVGVPGAGVPGVGVPGAGVPGVGVPGAGVPGVGVPGAGVPGVG
VPGAGVPGVGVPGAGVPGVGVPGAGVPGVGVPGAGVPGVGVPGAGVPGVGVPGAGVPGVGVPGAGVPGWP (SEQ ID NO: 77)

SEQUENCE LISTING

<160> NUMBER OF SEQ ID NOS: 77

<210> SEQ ID NO 1
<211> LENGTH: 4
<212> TYPE: PRT
<213> ORGANISM: Artificial Sequence
<220> FEATURE:
<223> OTHER INFORMATION: ELP component sequence

<400> SEQUENCE: 1

Val Pro Gly Gly
1

<210> SEQ ID NO 2
<211> LENGTH: 4
<212> TYPE: PRT
<213> ORGANISM: Artificial Sequence
<220> FEATURE:
<223> OTHER INFORMATION: ELP component sequence

<400> SEQUENCE: 2

Ile Pro Gly Gly
1

<210> SEQ ID NO 3
<211> LENGTH: 1000
<212> TYPE: PRT
<213> ORGANISM: Artificial Sequence
<220> FEATURE:
<223> OTHER INFORMATION: ELP component sequence
<220> FEATURE:
<221> NAME/KEY: misc_feature
<222> LOCATION: (4)..(4)
<223> OTHER INFORMATION: Xaa can be any naturally occurring or non-
      natural amino acid
<220> FEATURE:
<221> NAME/KEY: misc_feature
<222> LOCATION: (6)..(1000)
<223> OTHER INFORMATION: May be present or absent in groups of 5
      residues of the distinct repeat unit Val Pro Gly Xaa Gly
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature

```
<222> LOCATION: (49)..(49)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (99)..(99)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (109)..(109)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (119)..(119)
<223> OTHER INFORMATION: Xaa can be any naturally occurring amino acid
<220> FEATURE:
<221> NAME/KEY: misc_feature
<222> LOCATION: (124)..(124)
<223> OTHER INFORMATION: Xaa can be any naturally occurring amino acid
<220> FEATURE:
<221> NAME/KEY: misc_feature
<222> LOCATION: (129)..(129)
<223> OTHER INFORMATION: Xaa can be any naturally occurring amino acid
<220> FEATURE:
<221> NAME/KEY: misc_feature
<222> LOCATION: (134)..(134)
<223> OTHER INFORMATION: Xaa can be any naturally occurring amino acid
<220> FEATURE:
<221> NAME/KEY: misc_feature
<222> LOCATION: (139)..(139)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
```

```
<221> NAME/KEY: misc_feature
<222> LOCATION: (149)..(149)
<223> OTHER INFORMATION: Xaa can be any naturally occurring amino acid
<220> FEATURE:
<221> NAME/KEY: misc_feature
<222> LOCATION: (154)..(154)
<223> OTHER INFORMATION: Xaa can be any naturally occurring amino acid
<220> FEATURE:
<221> NAME/KEY: misc_feature
<222> LOCATION: (159)..(159)
<223> OTHER INFORMATION: Xaa can be any naturally occurring amino acid
<220> FEATURE:
<221> NAME/KEY: misc_feature
<222> LOCATION: (164)..(164)
<223> OTHER INFORMATION: Xaa can be any naturally occurring amino acid
<220> FEATURE:
<221> NAME/KEY: misc_feature
<222> LOCATION: (169)..(169)
<223> OTHER INFORMATION: Xaa can be any naturally occurring amino acid
<220> FEATURE:
<221> NAME/KEY: misc_feature
<222> LOCATION: (174)..(174)
<223> OTHER INFORMATION: Xaa can be any naturally occurring amino acid
<220> FEATURE:
<221> NAME/KEY: misc_feature
<222> LOCATION: (179)..(179)
<223> OTHER INFORMATION: Xaa can be any naturally occurring amino acid
<220> FEATURE:
<221> NAME/KEY: misc_feature
<222> LOCATION: (184)..(184)
<223> OTHER INFORMATION: Xaa can be any naturally occurring amino acid
<220> FEATURE:
<221> NAME/KEY: misc_feature
<222> LOCATION: (189)..(189)
<223> OTHER INFORMATION: Xaa can be any naturally occurring amino acid
<220> FEATURE:
<221> NAME/KEY: misc_feature
<222> LOCATION: (194)..(194)
<223> OTHER INFORMATION: Xaa can be any naturally occurring amino acid
<220> FEATURE:
<221> NAME/KEY: misc_feature
<222> LOCATION: (199)..(199)
<223> OTHER INFORMATION: Xaa can be any naturally occurring amino acid
<220> FEATURE:
<221> NAME/KEY: misc_feature
<222> LOCATION: (204)..(204)
<223> OTHER INFORMATION: Xaa can be any naturally occurring amino acid
<220> FEATURE:
<221> NAME/KEY: misc_feature
<222> LOCATION: (209)..(209)
<223> OTHER INFORMATION: Xaa can be any naturally occurring amino acid
<220> FEATURE:
<221> NAME/KEY: misc_feature
<222> LOCATION: (214)..(214)
<223> OTHER INFORMATION: Xaa can be any naturally occurring amino acid
<220> FEATURE:
<221> NAME/KEY: misc_feature
<222> LOCATION: (219)..(219)
<223> OTHER INFORMATION: Xaa can be any naturally occurring amino acid
<220> FEATURE:
<221> NAME/KEY: misc_feature
<222> LOCATION: (224)..(224)
<223> OTHER INFORMATION: Xaa can be any naturally occurring amino acid
<220> FEATURE:
<221> NAME/KEY: misc_feature
<222> LOCATION: (229)..(229)
<223> OTHER INFORMATION: Xaa can be any naturally occurring amino acid
<220> FEATURE:
<221> NAME/KEY: misc_feature
<222> LOCATION: (234)..(234)
<223> OTHER INFORMATION: Xaa can be any naturally occurring amino acid
<220> FEATURE:
<221> NAME/KEY: misc_feature
<222> LOCATION: (239)..(239)
<223> OTHER INFORMATION: Xaa can be any naturally occurring amino acid
<220> FEATURE:
<221> NAME/KEY: misc_feature
<222> LOCATION: (244)..(244)
<223> OTHER INFORMATION: Xaa can be any naturally occurring amino acid
```

```
<220> FEATURE:
<221> NAME/KEY: misc_feature
<222> LOCATION: (249)..(249)
<223> OTHER INFORMATION: Xaa can be any naturally occurring amino acid
<220> FEATURE:
<221> NAME/KEY: misc_feature
<222> LOCATION: (254)..(254)
<223> OTHER INFORMATION: Xaa can be any naturally occurring amino acid
<220> FEATURE:
<221> NAME/KEY: misc_feature
<222> LOCATION: (259)..(259)
<223> OTHER INFORMATION: Xaa can be any naturally occurring amino acid
<220> FEATURE:
<221> NAME/KEY: misc_feature
<222> LOCATION: (264)..(264)
<223> OTHER INFORMATION: Xaa can be any naturally occurring amino acid
<220> FEATURE:
<221> NAME/KEY: misc_feature
<222> LOCATION: (269)..(269)
<223> OTHER INFORMATION: Xaa can be any naturally occurring amino acid
<220> FEATURE:
<221> NAME/KEY: misc_feature
<222> LOCATION: (274)..(274)
<223> OTHER INFORMATION: Xaa can be any naturally occurring amino acid
<220> FEATURE:
<221> NAME/KEY: misc_feature
<222> LOCATION: (279)..(279)
<223> OTHER INFORMATION: Xaa can be any naturally occurring amino acid
<220> FEATURE:
<221> NAME/KEY: misc_feature
<222> LOCATION: (284)..(284)
<223> OTHER INFORMATION: Xaa can be any naturally occurring amino acid
<220> FEATURE:
<221> NAME/KEY: misc_feature
<222> LOCATION: (289)..(289)
<223> OTHER INFORMATION: Xaa can be any naturally occurring amino acid
<220> FEATURE:
<221> NAME/KEY: misc_feature
<222> LOCATION: (294)..(294)
<223> OTHER INFORMATION: Xaa can be any naturally occurring amino acid
<220> FEATURE:
<221> NAME/KEY: misc_feature
<222> LOCATION: (299)..(299)
<223> OTHER INFORMATION: Xaa can be any naturally occurring amino acid
<220> FEATURE:
<221> NAME/KEY: misc_feature
<222> LOCATION: (304)..(304)
<223> OTHER INFORMATION: Xaa can be any naturally occurring amino acid
<220> FEATURE:
<221> NAME/KEY: misc_feature
<222> LOCATION: (309)..(309)
<223> OTHER INFORMATION: Xaa can be any naturally occurring amino acid
<220> FEATURE:
<221> NAME/KEY: misc_feature
<222> LOCATION: (314)..(314)
<223> OTHER INFORMATION: Xaa can be any naturally occurring amino acid
<220> FEATURE:
<221> NAME/KEY: misc_feature
<222> LOCATION: (319)..(319)
<223> OTHER INFORMATION: Xaa can be any naturally occurring amino acid
<220> FEATURE:
<221> NAME/KEY: misc_feature
<222> LOCATION: (324)..(324)
<223> OTHER INFORMATION: Xaa can be any naturally occurring amino acid
<220> FEATURE:
<221> NAME/KEY: misc_feature
<222> LOCATION: (329)..(329)
<223> OTHER INFORMATION: Xaa can be any naturally occurring amino acid
<220> FEATURE:
<221> NAME/KEY: misc_feature
<222> LOCATION: (334)..(334)
<223> OTHER INFORMATION: Xaa can be any naturally occurring amino acid
<220> FEATURE:
<221> NAME/KEY: misc_feature
<222> LOCATION: (339)..(339)
<223> OTHER INFORMATION: Xaa can be any naturally occurring amino acid
<220> FEATURE:
<221> NAME/KEY: misc_feature
<222> LOCATION: (344)..(344)
```

-continued

```
<223> OTHER INFORMATION: Xaa can be any naturally occurring amino acid
<220> FEATURE:
<221> NAME/KEY: misc_feature
<222> LOCATION: (349)..(349)
<223> OTHER INFORMATION: Xaa can be any naturally occurring amino acid
<220> FEATURE:
<221> NAME/KEY: misc_feature
<222> LOCATION: (354)..(354)
<223> OTHER INFORMATION: Xaa can be any naturally occurring amino acid
<220> FEATURE:
<221> NAME/KEY: misc_feature
<222> LOCATION: (359)..(359)
<223> OTHER INFORMATION: Xaa can be any naturally occurring amino acid
<220> FEATURE:
<221> NAME/KEY: misc_feature
<222> LOCATION: (364)..(364)
<223> OTHER INFORMATION: Xaa can be any naturally occurring amino acid
<220> FEATURE:
<221> NAME/KEY: misc_feature
<222> LOCATION: (369)..(369)
<223> OTHER INFORMATION: Xaa can be any naturally occurring amino acid
<220> FEATURE:
<221> NAME/KEY: misc_feature
<222> LOCATION: (374)..(374)
<223> OTHER INFORMATION: Xaa can be any naturally occurring amino acid
<220> FEATURE:
<221> NAME/KEY: misc_feature
<222> LOCATION: (379)..(379)
<223> OTHER INFORMATION: Xaa can be any naturally occurring amino acid
<220> FEATURE:
<221> NAME/KEY: misc_feature
<222> LOCATION: (384)..(384)
<223> OTHER INFORMATION: Xaa can be any naturally occurring amino acid
<220> FEATURE:
<221> NAME/KEY: misc_feature
<222> LOCATION: (389)..(389)
<223> OTHER INFORMATION: Xaa can be any naturally occurring amino acid
<220> FEATURE:
<221> NAME/KEY: misc_feature
<222> LOCATION: (394)..(394)
<223> OTHER INFORMATION: Xaa can be any naturally occurring amino acid
<220> FEATURE:
<221> NAME/KEY: misc_feature
<222> LOCATION: (399)..(399)
<223> OTHER INFORMATION: Xaa can be any naturally occurring amino acid
<220> FEATURE:
<221> NAME/KEY: misc_feature
<222> LOCATION: (404)..(404)
<223> OTHER INFORMATION: Xaa can be any naturally occurring amino acid
<220> FEATURE:
<221> NAME/KEY: misc_feature
<222> LOCATION: (409)..(409)
<223> OTHER INFORMATION: Xaa can be any naturally occurring amino acid
<220> FEATURE:
<221> NAME/KEY: misc_feature
<222> LOCATION: (414)..(414)
<223> OTHER INFORMATION: Xaa can be any naturally occurring amino acid
<220> FEATURE:
<221> NAME/KEY: misc_feature
<222> LOCATION: (419)..(419)
<223> OTHER INFORMATION: Xaa can be any naturally occurring amino acid
<220> FEATURE:
<221> NAME/KEY: misc_feature
<222> LOCATION: (424)..(424)
<223> OTHER INFORMATION: Xaa can be any naturally occurring amino acid
<220> FEATURE:
<221> NAME/KEY: misc_feature
<222> LOCATION: (429)..(429)
<223> OTHER INFORMATION: Xaa can be any naturally occurring amino acid
<220> FEATURE:
<221> NAME/KEY: misc_feature
<222> LOCATION: (434)..(434)
<223> OTHER INFORMATION: Xaa can be any naturally occurring amino acid
<220> FEATURE:
<221> NAME/KEY: misc_feature
<222> LOCATION: (439)..(439)
<223> OTHER INFORMATION: Xaa can be any naturally occurring amino acid
<220> FEATURE:
<221> NAME/KEY: misc_feature
```

```
<222> LOCATION: (444)..(444)
<223> OTHER INFORMATION: Xaa can be any naturally occurring amino acid
<220> FEATURE:
<221> NAME/KEY: misc_feature
<222> LOCATION: (449)..(449)
<223> OTHER INFORMATION: Xaa can be any naturally occurring amino acid
<220> FEATURE:
<221> NAME/KEY: misc_feature
<222> LOCATION: (454)..(454)
<223> OTHER INFORMATION: Xaa can be any naturally occurring amino acid
<220> FEATURE:
<221> NAME/KEY: misc_feature
<222> LOCATION: (459)..(459)
<223> OTHER INFORMATION: Xaa can be any naturally occurring amino acid
<220> FEATURE:
<221> NAME/KEY: misc_feature
<222> LOCATION: (464)..(464)
<223> OTHER INFORMATION: Xaa can be any naturally occurring amino acid
<220> FEATURE:
<221> NAME/KEY: misc_feature
<222> LOCATION: (469)..(469)
<223> OTHER INFORMATION: Xaa can be any naturally occurring amino acid
<220> FEATURE:
<221> NAME/KEY: misc_feature
<222> LOCATION: (474)..(474)
<223> OTHER INFORMATION: Xaa can be any naturally occurring amino acid
<220> FEATURE:
<221> NAME/KEY: misc_feature
<222> LOCATION: (479)..(479)
<223> OTHER INFORMATION: Xaa can be any naturally occurring amino acid
<220> FEATURE:
<221> NAME/KEY: misc_feature
<222> LOCATION: (484)..(484)
<223> OTHER INFORMATION: Xaa can be any naturally occurring amino acid
<220> FEATURE:
<221> NAME/KEY: misc_feature
<222> LOCATION: (489)..(489)
<223> OTHER INFORMATION: Xaa can be any naturally occurring amino acid
<220> FEATURE:
<221> NAME/KEY: misc_feature
<222> LOCATION: (494)..(494)
<223> OTHER INFORMATION: Xaa can be any naturally occurring amino acid
<220> FEATURE:
<221> NAME/KEY: misc_feature
<222> LOCATION: (499)..(499)
<223> OTHER INFORMATION: Xaa can be any naturally occurring amino acid
<220> FEATURE:
<221> NAME/KEY: misc_feature
<222> LOCATION: (504)..(504)
<223> OTHER INFORMATION: Xaa can be any naturally occurring amino acid
<220> FEATURE:
<221> NAME/KEY: misc_feature
<222> LOCATION: (509)..(509)
<223> OTHER INFORMATION: Xaa can be any naturally occurring amino acid
<220> FEATURE:
<221> NAME/KEY: misc_feature
<222> LOCATION: (514)..(514)
<223> OTHER INFORMATION: Xaa can be any naturally occurring amino acid
<220> FEATURE:
<221> NAME/KEY: misc_feature
<222> LOCATION: (519)..(519)
<223> OTHER INFORMATION: Xaa can be any naturally occurring amino acid
<220> FEATURE:
<221> NAME/KEY: misc_feature
<222> LOCATION: (524)..(524)
<223> OTHER INFORMATION: Xaa can be any naturally occurring amino acid
<220> FEATURE:
<221> NAME/KEY: misc_feature
<222> LOCATION: (529)..(529)
<223> OTHER INFORMATION: Xaa can be any naturally occurring amino acid
<220> FEATURE:
<221> NAME/KEY: misc_feature
<222> LOCATION: (534)..(534)
<223> OTHER INFORMATION: Xaa can be any naturally occurring amino acid
<220> FEATURE:
<221> NAME/KEY: misc_feature
<222> LOCATION: (539)..(539)
<223> OTHER INFORMATION: Xaa can be any naturally occurring amino acid
<220> FEATURE:
```

```
<221> NAME/KEY: misc_feature
<222> LOCATION: (544)..(544)
<223> OTHER INFORMATION: Xaa can be any naturally occurring amino acid
<220> FEATURE:
<221> NAME/KEY: misc_feature
<222> LOCATION: (549)..(549)
<223> OTHER INFORMATION: Xaa can be any naturally occurring amino acid
<220> FEATURE:
<221> NAME/KEY: misc_feature
<222> LOCATION: (554)..(554)
<223> OTHER INFORMATION: Xaa can be any naturally occurring amino acid
<220> FEATURE:
<221> NAME/KEY: misc_feature
<222> LOCATION: (559)..(559)
<223> OTHER INFORMATION: Xaa can be any naturally occurring amino acid
<220> FEATURE:
<221> NAME/KEY: misc_feature
<222> LOCATION: (564)..(564)
<223> OTHER INFORMATION: Xaa can be any naturally occurring amino acid
<220> FEATURE:
<221> NAME/KEY: misc_feature
<222> LOCATION: (569)..(569)
<223> OTHER INFORMATION: Xaa can be any naturally occurring amino acid
<220> FEATURE:
<221> NAME/KEY: misc_feature
<222> LOCATION: (574)..(574)
<223> OTHER INFORMATION: Xaa can be any naturally occurring amino acid
<220> FEATURE:
<221> NAME/KEY: misc_feature
<222> LOCATION: (579)..(579)
<223> OTHER INFORMATION: Xaa can be any naturally occurring amino acid
<220> FEATURE:
<221> NAME/KEY: misc_feature
<222> LOCATION: (584)..(584)
<223> OTHER INFORMATION: Xaa can be any naturally occurring amino acid
<220> FEATURE:
<221> NAME/KEY: misc_feature
<222> LOCATION: (589)..(589)
<223> OTHER INFORMATION: Xaa can be any naturally occurring amino acid
<220> FEATURE:
<221> NAME/KEY: misc_feature
<222> LOCATION: (594)..(594)
<223> OTHER INFORMATION: Xaa can be any naturally occurring amino acid
<220> FEATURE:
<221> NAME/KEY: misc_feature
<222> LOCATION: (599)..(599)
<223> OTHER INFORMATION: Xaa can be any naturally occurring amino acid
<220> FEATURE:
<221> NAME/KEY: misc_feature
<222> LOCATION: (604)..(604)
<223> OTHER INFORMATION: Xaa can be any naturally occurring amino acid
<220> FEATURE:
<221> NAME/KEY: misc_feature
<222> LOCATION: (609)..(609)
<223> OTHER INFORMATION: Xaa can be any naturally occurring amino acid
<220> FEATURE:
<221> NAME/KEY: misc_feature
<222> LOCATION: (614)..(614)
<223> OTHER INFORMATION: Xaa can be any naturally occurring amino acid
<220> FEATURE:
<221> NAME/KEY: misc_feature
<222> LOCATION: (619)..(619)
<223> OTHER INFORMATION: Xaa can be any naturally occurring amino acid
<220> FEATURE:
<221> NAME/KEY: misc_feature
<222> LOCATION: (624)..(624)
<223> OTHER INFORMATION: Xaa can be any naturally occurring amino acid
<220> FEATURE:
<221> NAME/KEY: misc_feature
<222> LOCATION: (629)..(629)
<223> OTHER INFORMATION: Xaa can be any naturally occurring amino acid
<220> FEATURE:
<221> NAME/KEY: misc_feature
<222> LOCATION: (634)..(634)
<223> OTHER INFORMATION: Xaa can be any naturally occurring amino acid
<220> FEATURE:
<221> NAME/KEY: misc_feature
<222> LOCATION: (639)..(639)
<223> OTHER INFORMATION: Xaa can be any naturally occurring amino acid
```

```
<220> FEATURE:
<221> NAME/KEY: misc_feature
<222> LOCATION: (644)..(644)
<223> OTHER INFORMATION: Xaa can be any naturally occurring amino acid
<220> FEATURE:
<221> NAME/KEY: misc_feature
<222> LOCATION: (649)..(649)
<223> OTHER INFORMATION: Xaa can be any naturally occurring amino acid
<220> FEATURE:
<221> NAME/KEY: misc_feature
<222> LOCATION: (654)..(654)
<223> OTHER INFORMATION: Xaa can be any naturally occurring amino acid
<220> FEATURE:
<221> NAME/KEY: misc_feature
<222> LOCATION: (659)..(659)
<223> OTHER INFORMATION: Xaa can be any naturally occurring amino acid
<220> FEATURE:
<221> NAME/KEY: misc_feature
<222> LOCATION: (664)..(664)
<223> OTHER INFORMATION: Xaa can be any naturally occurring amino acid
<220> FEATURE:
<221> NAME/KEY: misc_feature
<222> LOCATION: (669)..(669)
<223> OTHER INFORMATION: Xaa can be any naturally occurring amino acid
<220> FEATURE:
<221> NAME/KEY: misc_feature
<222> LOCATION: (674)..(674)
<223> OTHER INFORMATION: Xaa can be any naturally occurring amino acid
<220> FEATURE:
<221> NAME/KEY: misc_feature
<222> LOCATION: (679)..(679)
<223> OTHER INFORMATION: Xaa can be any naturally occurring amino acid
<220> FEATURE:
<221> NAME/KEY: misc_feature
<222> LOCATION: (684)..(684)
<223> OTHER INFORMATION: Xaa can be any naturally occurring amino acid
<220> FEATURE:
<221> NAME/KEY: misc_feature
<222> LOCATION: (689)..(689)
<223> OTHER INFORMATION: Xaa can be any naturally occurring amino acid
<220> FEATURE:
<221> NAME/KEY: misc_feature
<222> LOCATION: (694)..(694)
<223> OTHER INFORMATION: Xaa can be any naturally occurring amino acid
<220> FEATURE:
<221> NAME/KEY: misc_feature
<222> LOCATION: (699)..(699)
<223> OTHER INFORMATION: Xaa can be any naturally occurring amino acid
<220> FEATURE:
<221> NAME/KEY: misc_feature
<222> LOCATION: (704)..(704)
<223> OTHER INFORMATION: Xaa can be any naturally occurring amino acid
<220> FEATURE:
<221> NAME/KEY: misc_feature
<222> LOCATION: (709)..(709)
<223> OTHER INFORMATION: Xaa can be any naturally occurring amino acid
<220> FEATURE:
<221> NAME/KEY: misc_feature
<222> LOCATION: (714)..(714)
<223> OTHER INFORMATION: Xaa can be any naturally occurring amino acid
<220> FEATURE:
<221> NAME/KEY: misc_feature
<222> LOCATION: (719)..(719)
<223> OTHER INFORMATION: Xaa can be any naturally occurring amino acid
<220> FEATURE:
<221> NAME/KEY: misc_feature
<222> LOCATION: (724)..(724)
<223> OTHER INFORMATION: Xaa can be any naturally occurring amino acid
<220> FEATURE:
<221> NAME/KEY: misc_feature
<222> LOCATION: (729)..(729)
<223> OTHER INFORMATION: Xaa can be any naturally occurring amino acid
<220> FEATURE:
<221> NAME/KEY: misc_feature
<222> LOCATION: (734)..(734)
<223> OTHER INFORMATION: Xaa can be any naturally occurring amino acid
<220> FEATURE:
<221> NAME/KEY: misc_feature
<222> LOCATION: (739)..(739)
```

```
<223> OTHER INFORMATION: Xaa can be any naturally occurring amino acid
<220> FEATURE:
<221> NAME/KEY: misc_feature
<222> LOCATION: (744)..(744)
<223> OTHER INFORMATION: Xaa can be any naturally occurring amino acid
<220> FEATURE:
<221> NAME/KEY: misc_feature
<222> LOCATION: (749)..(749)
<223> OTHER INFORMATION: Xaa can be any naturally occurring amino acid
<220> FEATURE:
<221> NAME/KEY: misc_feature
<222> LOCATION: (754)..(754)
<223> OTHER INFORMATION: Xaa can be any naturally occurring amino acid
<220> FEATURE:
<221> NAME/KEY: misc_feature
<222> LOCATION: (759)..(759)
<223> OTHER INFORMATION: Xaa can be any naturally occurring amino acid
<220> FEATURE:
<221> NAME/KEY: misc_feature
<222> LOCATION: (764)..(764)
<223> OTHER INFORMATION: Xaa can be any naturally occurring amino acid
<220> FEATURE:
<221> NAME/KEY: misc_feature
<222> LOCATION: (769)..(769)
<223> OTHER INFORMATION: Xaa can be any naturally occurring amino acid
<220> FEATURE:
<221> NAME/KEY: misc_feature
<222> LOCATION: (774)..(774)
<223> OTHER INFORMATION: Xaa can be any naturally occurring amino acid
<220> FEATURE:
<221> NAME/KEY: misc_feature
<222> LOCATION: (779)..(779)
<223> OTHER INFORMATION: Xaa can be any naturally occurring amino acid
<220> FEATURE:
<221> NAME/KEY: misc_feature
<222> LOCATION: (784)..(784)
<223> OTHER INFORMATION: Xaa can be any naturally occurring amino acid
<220> FEATURE:
<221> NAME/KEY: misc_feature
<222> LOCATION: (789)..(789)
<223> OTHER INFORMATION: Xaa can be any naturally occurring amino acid
<220> FEATURE:
<221> NAME/KEY: misc_feature
<222> LOCATION: (794)..(794)
<223> OTHER INFORMATION: Xaa can be any naturally occurring amino acid
<220> FEATURE:
<221> NAME/KEY: misc_feature
<222> LOCATION: (799)..(799)
<223> OTHER INFORMATION: Xaa can be any naturally occurring amino acid
<220> FEATURE:
<221> NAME/KEY: misc_feature
<222> LOCATION: (804)..(804)
<223> OTHER INFORMATION: Xaa can be any naturally occurring amino acid
<220> FEATURE:
<221> NAME/KEY: misc_feature
<222> LOCATION: (809)..(809)
<223> OTHER INFORMATION: Xaa can be any naturally occurring amino acid
<220> FEATURE:
<221> NAME/KEY: misc_feature
<222> LOCATION: (814)..(814)
<223> OTHER INFORMATION: Xaa can be any naturally occurring amino acid
<220> FEATURE:
<221> NAME/KEY: misc_feature
<222> LOCATION: (819)..(819)
<223> OTHER INFORMATION: Xaa can be any naturally occurring amino acid
<220> FEATURE:
<221> NAME/KEY: misc_feature
<222> LOCATION: (824)..(824)
<223> OTHER INFORMATION: Xaa can be any naturally occurring amino acid
<220> FEATURE:
<221> NAME/KEY: misc_feature
<222> LOCATION: (829)..(829)
<223> OTHER INFORMATION: Xaa can be any naturally occurring amino acid
<220> FEATURE:
<221> NAME/KEY: misc_feature
<222> LOCATION: (834)..(834)
<223> OTHER INFORMATION: Xaa can be any naturally occurring amino acid
<220> FEATURE:
<221> NAME/KEY: misc_feature
```

```
<222> LOCATION: (839)..(839)
<223> OTHER INFORMATION: Xaa can be any naturally occurring amino acid
<220> FEATURE:
<221> NAME/KEY: misc_feature
<222> LOCATION: (844)..(844)
<223> OTHER INFORMATION: Xaa can be any naturally occurring amino acid
<220> FEATURE:
<221> NAME/KEY: misc_feature
<222> LOCATION: (849)..(849)
<223> OTHER INFORMATION: Xaa can be any naturally occurring amino acid
<220> FEATURE:
<221> NAME/KEY: misc_feature
<222> LOCATION: (854)..(854)
<223> OTHER INFORMATION: Xaa can be any naturally occurring amino acid
<220> FEATURE:
<221> NAME/KEY: misc_feature
<222> LOCATION: (859)..(859)
<223> OTHER INFORMATION: Xaa can be any naturally occurring amino acid
<220> FEATURE:
<221> NAME/KEY: misc_feature
<222> LOCATION: (864)..(864)
<223> OTHER INFORMATION: Xaa can be any naturally occurring amino acid
<220> FEATURE:
<221> NAME/KEY: misc_feature
<222> LOCATION: (869)..(869)
<223> OTHER INFORMATION: Xaa can be any naturally occurring amino acid
<220> FEATURE:
<221> NAME/KEY: misc_feature
<222> LOCATION: (874)..(874)
<223> OTHER INFORMATION: Xaa can be any naturally occurring amino acid
<220> FEATURE:
<221> NAME/KEY: misc_feature
<222> LOCATION: (879)..(879)
<223> OTHER INFORMATION: Xaa can be any naturally occurring amino acid
<220> FEATURE:
<221> NAME/KEY: misc_feature
<222> LOCATION: (884)..(884)
<223> OTHER INFORMATION: Xaa can be any naturally occurring amino acid
<220> FEATURE:
<221> NAME/KEY: misc_feature
<222> LOCATION: (889)..(889)
<223> OTHER INFORMATION: Xaa can be any naturally occurring amino acid
<220> FEATURE:
<221> NAME/KEY: misc_feature
<222> LOCATION: (894)..(894)
<223> OTHER INFORMATION: Xaa can be any naturally occurring amino acid
<220> FEATURE:
<221> NAME/KEY: misc_feature
<222> LOCATION: (899)..(899)
<223> OTHER INFORMATION: Xaa can be any naturally occurring amino acid
<220> FEATURE:
<221> NAME/KEY: misc_feature
<222> LOCATION: (904)..(904)
<223> OTHER INFORMATION: Xaa can be any naturally occurring amino acid
<220> FEATURE:
<221> NAME/KEY: misc_feature
<222> LOCATION: (909)..(909)
<223> OTHER INFORMATION: Xaa can be any naturally occurring amino acid
<220> FEATURE:
<221> NAME/KEY: misc_feature
<222> LOCATION: (914)..(914)
<223> OTHER INFORMATION: Xaa can be any naturally occurring amino acid
<220> FEATURE:
<221> NAME/KEY: misc_feature
<222> LOCATION: (919)..(919)
<223> OTHER INFORMATION: Xaa can be any naturally occurring amino acid
<220> FEATURE:
<221> NAME/KEY: misc_feature
<222> LOCATION: (924)..(924)
<223> OTHER INFORMATION: Xaa can be any naturally occurring amino acid
<220> FEATURE:
<221> NAME/KEY: misc_feature
<222> LOCATION: (929)..(929)
<223> OTHER INFORMATION: Xaa can be any naturally occurring amino acid
<220> FEATURE:
<221> NAME/KEY: misc_feature
<222> LOCATION: (934)..(934)
<223> OTHER INFORMATION: Xaa can be any naturally occurring amino acid
<220> FEATURE:
```

```
<221> NAME/KEY: misc_feature
<222> LOCATION: (939)..(939)
<223> OTHER INFORMATION: Xaa can be any naturally occurring amino acid
<220> FEATURE:
<221> NAME/KEY: misc_feature
<222> LOCATION: (944)..(944)
<223> OTHER INFORMATION: Xaa can be any naturally occurring amino acid
<220> FEATURE:
<221> NAME/KEY: misc_feature
<222> LOCATION: (949)..(949)
<223> OTHER INFORMATION: Xaa can be any naturally occurring amino acid
<220> FEATURE:
<221> NAME/KEY: misc_feature
<222> LOCATION: (954)..(954)
<223> OTHER INFORMATION: Xaa can be any naturally occurring amino acid
<220> FEATURE:
<221> NAME/KEY: misc_feature
<222> LOCATION: (959)..(959)
<223> OTHER INFORMATION: Xaa can be any naturally occurring amino acid
<220> FEATURE:
<221> NAME/KEY: misc_feature
<222> LOCATION: (964)..(964)
<223> OTHER INFORMATION: Xaa can be any naturally occurring amino acid
<220> FEATURE:
<221> NAME/KEY: misc_feature
<222> LOCATION: (969)..(969)
<223> OTHER INFORMATION: Xaa can be any naturally occurring amino acid
<220> FEATURE:
<221> NAME/KEY: misc_feature
<222> LOCATION: (974)..(974)
<223> OTHER INFORMATION: Xaa can be any naturally occurring amino acid
<220> FEATURE:
<221> NAME/KEY: misc_feature
<222> LOCATION: (979)..(979)
<223> OTHER INFORMATION: Xaa can be any naturally occurring amino acid
<220> FEATURE:
<221> NAME/KEY: misc_feature
<222> LOCATION: (984)..(984)
<223> OTHER INFORMATION: Xaa can be any naturally occurring amino acid
<220> FEATURE:
<221> NAME/KEY: misc_feature
<222> LOCATION: (989)..(989)
<223> OTHER INFORMATION: Xaa can be any naturally occurring amino acid
<220> FEATURE:
<221> NAME/KEY: misc_feature
<222> LOCATION: (994)..(994)
<223> OTHER INFORMATION: Xaa can be any naturally occurring amino acid
<220> FEATURE:
<221> NAME/KEY: misc_feature
<222> LOCATION: (999)..(999)
<223> OTHER INFORMATION: Xaa can be any naturally occurring amino acid

<400> SEQUENCE: 3

Val Pro Gly Xaa Gly Val Pro Gly Xaa Gly Val Pro Gly Xaa Gly Val
1               5                   10                  15

Pro Gly Xaa Gly Val Pro Gly Xaa Gly Val Pro Gly Xaa Gly Val Pro
            20                  25                  30

Gly Xaa Gly Val Pro Gly Xaa Gly Val Pro Gly Xaa Gly Val Pro Gly
        35                  40                  45

Xaa Gly Val Pro Gly Xaa Gly Val Pro Gly Xaa Gly Val Pro Gly Xaa
    50                  55                  60

Gly Val Pro Gly Xaa Gly Val Pro Gly Xaa Gly Val Pro Gly Xaa Gly
65                  70                  75                  80

Val Pro Gly Xaa Gly Val Pro Gly Xaa Gly Val Pro Gly Xaa Gly Val
                85                  90                  95

Pro Gly Xaa Gly Val Pro Gly Xaa Gly Val Pro Gly Xaa Gly Val Pro
            100                 105                 110

Gly Xaa Gly Val Pro Gly Xaa Gly Val Pro Gly Xaa Gly Val Pro Gly
        115                 120                 125

Xaa Gly Val Pro Gly Xaa Gly Val Pro Gly Xaa Gly Val Pro Gly Xaa
```

```
            130                 135                 140
Gly Val Pro Gly Xaa Gly Val Pro Gly Xaa Gly Val Pro Gly Xaa Gly
145                 150                 155                 160

Val Pro Gly Xaa Gly Val Pro Gly Xaa Gly Val Pro Gly Xaa Gly Val
            165                 170                 175

Pro Gly Xaa Gly Val Pro Gly Xaa Gly Val Pro Gly Xaa Gly Val Pro
        180                 185                 190

Gly Xaa Gly Val Pro Gly Xaa Gly Val Pro Gly Xaa Gly Val Pro Gly
    195                 200                 205

Xaa Gly Val Pro Gly Xaa Gly Val Pro Gly Xaa Gly Val Pro Gly Xaa
210                 215                 220

Gly Val Pro Gly Xaa Gly Val Pro Gly Xaa Gly Val Pro Gly Xaa Gly
225                 230                 235                 240

Val Pro Gly Xaa Gly Val Pro Gly Xaa Gly Val Pro Gly Xaa Gly Val
            245                 250                 255

Pro Gly Xaa Gly Val Pro Gly Xaa Gly Val Pro Gly Xaa Gly Val Pro
        260                 265                 270

Gly Xaa Gly Val Pro Gly Xaa Gly Val Pro Gly Xaa Gly Val Pro Gly
    275                 280                 285

Xaa Gly Val Pro Gly Xaa Gly Val Pro Gly Xaa Gly Val Pro Gly Xaa
290                 295                 300

Gly Val Pro Gly Xaa Gly Val Pro Gly Xaa Gly Val Pro Gly Xaa Gly
305                 310                 315                 320

Val Pro Gly Xaa Gly Val Pro Gly Xaa Gly Val Pro Gly Xaa Gly Val
            325                 330                 335

Pro Gly Xaa Gly Val Pro Gly Xaa Gly Val Pro Gly Xaa Gly Val Pro
        340                 345                 350

Gly Xaa Gly Val Pro Gly Xaa Gly Val Pro Gly Xaa Gly Val Pro Gly
    355                 360                 365

Xaa Gly Val Pro Gly Xaa Gly Val Pro Gly Xaa Gly Val Pro Gly Xaa
370                 375                 380

Gly Val Pro Gly Xaa Gly Val Pro Gly Xaa Gly Val Pro Gly Xaa Gly
385                 390                 395                 400

Val Pro Gly Xaa Gly Val Pro Gly Xaa Gly Val Pro Gly Xaa Gly Val
            405                 410                 415

Pro Gly Xaa Gly Val Pro Gly Xaa Gly Val Pro Gly Xaa Gly Val Pro
        420                 425                 430

Gly Xaa Gly Val Pro Gly Xaa Gly Val Pro Gly Xaa Gly Val Pro Gly
    435                 440                 445

Xaa Gly Val Pro Gly Xaa Gly Val Pro Gly Xaa Gly Val Pro Gly Xaa
450                 455                 460

Gly Val Pro Gly Xaa Gly Val Pro Gly Xaa Gly Val Pro Gly Xaa Gly
465                 470                 475                 480

Val Pro Gly Xaa Gly Val Pro Gly Xaa Gly Val Pro Gly Xaa Gly Val
            485                 490                 495

Pro Gly Xaa Gly Val Pro Gly Xaa Gly Val Pro Gly Xaa Gly Val Pro
        500                 505                 510

Gly Xaa Gly Val Pro Gly Xaa Gly Val Pro Gly Xaa Gly Val Pro Gly
    515                 520                 525

Xaa Gly Val Pro Gly Xaa Gly Val Pro Gly Xaa Gly Val Pro Gly Xaa
530                 535                 540

Gly Val Pro Gly Xaa Gly Val Pro Gly Xaa Gly Val Pro Gly Xaa Gly
545                 550                 555                 560
```

```
Val Pro Gly Xaa Gly Val Pro Gly Xaa Gly Val Pro Gly Xaa Gly Val
            565                 570                 575

Pro Gly Xaa Gly Val Pro Gly Xaa Gly Val Pro Gly Xaa Gly Val Pro
            580                 585                 590

Gly Xaa Gly Val Pro Gly Xaa Gly Val Pro Gly Xaa Gly Val Pro Gly
            595                 600                 605

Xaa Gly Val Pro Gly Xaa Gly Val Pro Gly Xaa Gly Val Pro Gly Xaa
            610                 615                 620

Gly Val Pro Gly Xaa Gly Val Pro Gly Xaa Gly Val Pro Gly Xaa Gly
625                 630                 635                 640

Val Pro Gly Xaa Gly Val Pro Gly Xaa Gly Val Pro Gly Xaa Gly Val
            645                 650                 655

Pro Gly Xaa Gly Val Pro Gly Xaa Gly Val Pro Gly Xaa Gly Val Pro
            660                 665                 670

Gly Xaa Gly Val Pro Gly Xaa Gly Val Pro Gly Xaa Gly Val Pro Gly
            675                 680                 685

Xaa Gly Val Pro Gly Xaa Gly Val Pro Gly Xaa Gly Val Pro Gly Xaa
            690                 695                 700

Gly Val Pro Gly Xaa Gly Val Pro Gly Xaa Gly Val Pro Gly Xaa Gly
705                 710                 715                 720

Val Pro Gly Xaa Gly Val Pro Gly Xaa Gly Val Pro Gly Xaa Gly Val
            725                 730                 735

Pro Gly Xaa Gly Val Pro Gly Xaa Gly Val Pro Gly Xaa Gly Val Pro
            740                 745                 750

Gly Xaa Gly Val Pro Gly Xaa Gly Val Pro Gly Xaa Gly Val Pro Gly
            755                 760                 765

Xaa Gly Val Pro Gly Xaa Gly Val Pro Gly Xaa Gly Val Pro Gly Xaa
            770                 775                 780

Gly Val Pro Gly Xaa Gly Val Pro Gly Xaa Gly Val Pro Gly Xaa Gly
785                 790                 795                 800

Val Pro Gly Xaa Gly Val Pro Gly Xaa Gly Val Pro Gly Xaa Gly Val
            805                 810                 815

Pro Gly Xaa Gly Val Pro Gly Xaa Gly Val Pro Gly Xaa Gly Val Pro
            820                 825                 830

Gly Xaa Gly Val Pro Gly Xaa Gly Val Pro Gly Xaa Gly Val Pro Gly
            835                 840                 845

Xaa Gly Val Pro Gly Xaa Gly Val Pro Gly Xaa Gly Val Pro Gly Xaa
            850                 855                 860

Gly Val Pro Gly Xaa Gly Val Pro Gly Xaa Gly Val Pro Gly Xaa Gly
865                 870                 875                 880

Val Pro Gly Xaa Gly Val Pro Gly Xaa Gly Val Pro Gly Xaa Gly Val
            885                 890                 895

Pro Gly Xaa Gly Val Pro Gly Xaa Gly Val Pro Gly Xaa Gly Val Pro
            900                 905                 910

Gly Xaa Gly Val Pro Gly Xaa Gly Val Pro Gly Xaa Gly Val Pro Gly
            915                 920                 925

Xaa Gly Val Pro Gly Xaa Gly Val Pro Gly Xaa Gly Val Pro Gly Xaa
            930                 935                 940

Gly Val Pro Gly Xaa Gly Val Pro Gly Xaa Gly Val Pro Gly Xaa Gly
945                 950                 955                 960

Val Pro Gly Xaa Gly Val Pro Gly Xaa Gly Val Pro Gly Xaa Gly Val
            965                 970                 975
```

```
Pro Gly Xaa Gly Val Pro Gly Xaa Gly Val Pro Gly Xaa Gly Val Pro
            980                 985                 990
Gly Xaa Gly Val Pro Gly Xaa Gly
        995                 1000

<210> SEQ ID NO 4
<211> LENGTH: 5
<212> TYPE: PRT
<213> ORGANISM: Artificial Sequence
<220> FEATURE:
<223> OTHER INFORMATION: ELP component sequence

<400> SEQUENCE: 4

Ala Val Gly Val Pro
1               5

<210> SEQ ID NO 5
<211> LENGTH: 5
<212> TYPE: PRT
<213> ORGANISM: Artificial Sequence
<220> FEATURE:
<223> OTHER INFORMATION: ELP component sequence
<220> FEATURE:
<221> NAME/KEY: misc_feature
<222> LOCATION: (4)..(4)
<223> OTHER INFORMATION: Xaa can be any naturally occurring or non-
      natural amino acid

<400> SEQUENCE: 5

Ile Pro Gly Xaa Gly
1               5

<210> SEQ ID NO 6
<211> LENGTH: 5
<212> TYPE: PRT
<213> ORGANISM: Artificial Sequence
<220> FEATURE:
<223> OTHER INFORMATION: ELP component sequence

<400> SEQUENCE: 6

Ile Pro Gly Val Gly
1               5

<210> SEQ ID NO 7
<211> LENGTH: 5
<212> TYPE: PRT
<213> ORGANISM: Artificial Sequence
<220> FEATURE:
<223> OTHER INFORMATION: ELP component sequence
<220> FEATURE:
<221> NAME/KEY: misc_feature
<222> LOCATION: (4)..(4)
<223> OTHER INFORMATION: Xaa can be any naturally occurring or non-
      natural amino acid

<400> SEQUENCE: 7

Leu Pro Gly Xaa Gly
1               5

<210> SEQ ID NO 8
<211> LENGTH: 5
<212> TYPE: PRT
<213> ORGANISM: Artificial Sequence
<220> FEATURE:
<223> OTHER INFORMATION: ELP component sequence

<400> SEQUENCE: 8

Leu Pro Gly Val Gly
```

```
<210> SEQ ID NO 9
<211> LENGTH: 6
<212> TYPE: PRT
<213> ORGANISM: Artificial Sequence
<220> FEATURE:
<223> OTHER INFORMATION: ELP component sequence

<400> SEQUENCE: 9

Val Ala Pro Gly Val Gly
1               5

<210> SEQ ID NO 10
<211> LENGTH: 8
<212> TYPE: PRT
<213> ORGANISM: Artificial Sequence
<220> FEATURE:
<223> OTHER INFORMATION: ELP component sequence

<400> SEQUENCE: 10

Gly Val Gly Val Pro Gly Val Gly
1               5

<210> SEQ ID NO 11
<211> LENGTH: 9
<212> TYPE: PRT
<213> ORGANISM: Artificial Sequence
<220> FEATURE:
<223> OTHER INFORMATION: ELP component sequence

<400> SEQUENCE: 11

Val Pro Gly Phe Gly Val Gly Ala Gly
1               5

<210> SEQ ID NO 12
<211> LENGTH: 9
<212> TYPE: PRT
<213> ORGANISM: Artificial Sequence
<220> FEATURE:
<223> OTHER INFORMATION: ELP component sequence

<400> SEQUENCE: 12

Val Pro Gly Val Gly Val Pro Gly Gly
1               5

<210> SEQ ID NO 13
<211> LENGTH: 5
<212> TYPE: PRT
<213> ORGANISM: Artificial Sequence
<220> FEATURE:
<223> OTHER INFORMATION: ELP component sequence
<220> FEATURE:
<221> NAME/KEY: misc_feature
<222> LOCATION: (1)..(1)
<223> OTHER INFORMATION: Xaa can be any naturally occurring or non-
      natural amino acid

<400> SEQUENCE: 13

Xaa Pro Gly Val Gly
1               5

<210> SEQ ID NO 14
<211> LENGTH: 927
<212> TYPE: PRT
<213> ORGANISM: Artificial Sequence
<220> FEATURE:
<223> OTHER INFORMATION: ELPbetaV2 hGH fusion protein
```

<400> SEQUENCE: 14

```
Met Val Pro Gly Val Gly Val Pro Gly Val Gly Val Pro Gly Ala Gly
1               5                   10                  15

Val Pro Gly Val Gly Val Pro Gly Ala Gly Val Pro Gly Val Gly Val
                20                  25                  30

Pro Gly Val Gly Val Pro Gly Ala Gly Val Pro Gly Val Gly Val Pro
                35                  40                  45

Gly Ala Gly Val Pro Gly Val Gly Val Pro Gly Ala Gly Val Pro Gly
        50                  55                  60

Val Gly Val Pro Gly Ala Gly Val Pro Gly Val Gly Val Pro Gly Val
65                  70                  75                  80

Gly Val Pro Gly Ala Gly Val Pro Gly Val Gly Val Pro Gly Ala Gly
                85                  90                  95

Val Pro Gly Val Gly Val Pro Gly Ala Gly Val Pro Gly Val Gly Val
                100                 105                 110

Pro Gly Ala Gly Val Pro Gly Val Gly Val Pro Gly Val Gly Val Pro
                115                 120                 125

Gly Ala Gly Val Pro Gly Val Gly Val Pro Gly Ala Gly Val Pro Gly
        130                 135                 140

Val Gly Val Pro Gly Ala Gly Val Pro Gly Val Gly Val Pro Gly Ala
145                 150                 155                 160

Gly Val Pro Gly Val Gly Val Pro Gly Val Gly Val Pro Gly Ala Gly
                165                 170                 175

Val Pro Gly Val Gly Val Pro Gly Ala Gly Val Pro Gly Val Gly Val
                180                 185                 190

Pro Gly Ala Gly Val Pro Gly Val Gly Val Pro Gly Ala Gly Val Pro
                195                 200                 205

Gly Val Gly Val Pro Gly Val Gly Val Pro Gly Ala Gly Val Pro Gly
        210                 215                 220

Val Gly Val Pro Gly Ala Gly Val Pro Gly Val Gly Val Pro Gly Ala
225                 230                 235                 240

Gly Val Pro Gly Val Gly Val Pro Gly Ala Gly Val Pro Gly Val Gly
                245                 250                 255

Val Pro Gly Val Gly Val Pro Gly Ala Gly Val Pro Gly Val Gly Val
                260                 265                 270

Pro Gly Ala Gly Val Pro Gly Val Gly Val Pro Gly Ala Gly Val Pro
                275                 280                 285

Gly Val Gly Val Pro Gly Ala Gly Val Pro Gly Val Gly Val Pro Gly
        290                 295                 300

Val Gly Val Pro Gly Ala Gly Val Pro Gly Val Gly Val Pro Gly Ala
305                 310                 315                 320

Gly Val Pro Gly Val Gly Val Pro Gly Ala Gly Val Pro Gly Val Gly
                325                 330                 335

Val Pro Gly Ala Gly Val Pro Gly Val Gly Val Pro Gly Val Gly Val
                340                 345                 350

Pro Gly Ala Gly Val Pro Gly Val Gly Val Pro Gly Ala Gly Val Pro
                355                 360                 365

Gly Val Gly Val Pro Gly Ala Gly Val Pro Gly Val Gly Val Pro Gly
        370                 375                 380

Ala Gly Val Pro Gly Val Gly Val Pro Gly Val Gly Val Pro Gly Ala
385                 390                 395                 400

Gly Val Pro Gly Val Gly Val Pro Gly Ala Gly Val Pro Gly Val Gly
```

```
                405                 410                 415
Val Pro Gly Ala Gly Val Pro Gly Val Gly Val Pro Gly Ala Gly Val
            420                 425                 430

Pro Gly Val Gly Val Pro Gly Val Gly Val Pro Gly Ala Gly Val Pro
            435                 440                 445

Gly Val Gly Val Pro Gly Ala Gly Val Pro Gly Val Gly Val Pro Gly
            450                 455                 460

Ala Gly Val Pro Gly Val Gly Val Pro Gly Ala Gly Val Pro Gly Val
465                 470                 475                 480

Gly Val Pro Gly Val Gly Val Pro Gly Ala Gly Val Pro Gly Val Gly
            485                 490                 495

Val Pro Gly Ala Gly Val Pro Gly Val Gly Val Pro Gly Ala Gly Val
            500                 505                 510

Pro Gly Val Gly Val Pro Gly Ala Gly Val Pro Gly Val Gly Val Pro
            515                 520                 525

Gly Val Gly Val Pro Gly Ala Gly Val Pro Gly Val Gly Val Pro Gly
            530                 535                 540

Ala Gly Val Pro Gly Val Gly Val Pro Gly Ala Gly Val Pro Gly Val
545                 550                 555                 560

Gly Val Pro Gly Ala Gly Val Pro Gly Val Gly Val Pro Gly Val Gly
            565                 570                 575

Val Pro Gly Ala Gly Val Pro Gly Val Gly Val Pro Gly Ala Gly Val
            580                 585                 590

Pro Gly Val Gly Val Pro Gly Ala Gly Val Pro Gly Val Gly Val Pro
            595                 600                 605

Gly Ala Gly Val Pro Gly Val Gly Val Pro Gly Val Gly Val Pro Gly
610                 615                 620

Ala Gly Val Pro Gly Val Gly Val Pro Gly Ala Gly Val Pro Gly Val
625                 630                 635                 640

Gly Val Pro Gly Ala Gly Val Pro Gly Val Gly Val Pro Gly Ala Gly
            645                 650                 655

Val Pro Gly Val Gly Val Pro Gly Val Gly Val Pro Gly Ala Gly Val
            660                 665                 670

Pro Gly Val Gly Val Pro Gly Ala Gly Val Pro Gly Val Gly Val Pro
            675                 680                 685

Gly Ala Gly Val Pro Gly Val Gly Val Pro Gly Ala Gly Val Pro Gly
            690                 695                 700

Val Gly Val Pro Gly Val Gly Val Pro Gly Ala Gly Val Pro Gly Val
705                 710                 715                 720

Gly Val Pro Gly Ala Gly Val Pro Gly Val Gly Phe Pro Thr Ile Pro
            725                 730                 735

Leu Ser Arg Leu Phe Asp Asn Ala Met Leu Arg Ala His Arg Leu His
            740                 745                 750

Gln Leu Ala Phe Asp Thr Tyr Gln Glu Phe Glu Glu Ala Tyr Ile Pro
            755                 760                 765

Lys Glu Gln Lys Tyr Ser Phe Leu Gln Asn Pro Gln Thr Ser Leu Cys
            770                 775                 780

Phe Ser Glu Ser Ile Pro Thr Pro Ser Asn Arg Glu Glu Thr Gln Gln
785                 790                 795                 800

Lys Ser Asn Leu Glu Leu Leu Arg Ile Ser Leu Leu Leu Ile Gln Ser
            805                 810                 815

Trp Leu Glu Pro Val Gln Phe Leu Arg Ser Val Phe Ala Asn Ser Leu
            820                 825                 830
```

```
Val Tyr Gly Ala Ser Asp Ser Asn Val Tyr Asp Leu Leu Lys Asp Leu
        835                 840                 845

Glu Glu Gly Ile Gln Thr Leu Met Gly Arg Leu Glu Asp Gly Ser Pro
850                 855                 860

Arg Thr Gly Gln Ile Phe Lys Gln Thr Tyr Ser Lys Phe Asp Thr Asn
865                 870                 875                 880

Ser His Asn Asp Asp Ala Leu Leu Lys Asn Tyr Gly Leu Leu Tyr Cys
                885                 890                 895

Phe Arg Lys Asp Met Asp Lys Val Glu Thr Phe Leu Arg Ile Val Gln
                900                 905                 910

Cys Arg Ser Val Glu Gly Ser Cys Gly Phe Val Pro Gly Trp Pro
                915                 920                 925

<210> SEQ ID NO 15
<211> LENGTH: 802
<212> TYPE: PRT
<213> ORGANISM: Artificial Sequence
<220> FEATURE:
<223> OTHER INFORMATION: ELP1-120 hGH fusion protein

<400> SEQUENCE: 15

Met Val Pro Gly Val Gly Val Pro Gly Val Gly Val Pro Gly Gly Gly
1               5                   10                  15

Val Pro Gly Ala Gly Val Pro Gly Val Gly Val Pro Gly Val Gly Val
                20                  25                  30

Pro Gly Val Gly Val Pro Gly Gly Gly Val Pro Gly Ala Gly Val Pro
            35                  40                  45

Gly Gly Gly Val Pro Gly Val Gly Val Pro Gly Val Gly Val Pro Gly
50                  55                  60

Gly Gly Val Pro Gly Ala Gly Val Pro Gly Gly Gly Val Pro Gly Val
65                  70                  75                  80

Gly Val Pro Gly Val Gly Val Pro Gly Gly Gly Val Pro Gly Ala Gly
                85                  90                  95

Val Pro Gly Gly Gly Val Pro Gly Val Gly Val Pro Gly Val Gly Val
                100                 105                 110

Pro Gly Gly Gly Val Pro Gly Ala Gly Val Pro Gly Val Gly Val Pro
            115                 120                 125

Gly Val Gly Val Pro Gly Val Gly Val Pro Gly Gly Gly Val Pro Gly
            130                 135                 140

Ala Gly Val Pro Gly Gly Val Pro Gly Val Gly Val Pro Gly Val
145                 150                 155                 160

Gly Val Pro Gly Gly Gly Val Pro Gly Ala Gly Val Pro Gly Val Gly
                165                 170                 175

Val Pro Gly Val Gly Val Pro Gly Val Gly Val Pro Gly Gly Gly Val
                180                 185                 190

Pro Gly Ala Gly Val Pro Gly Gly Gly Val Pro Gly Val Gly Val Pro
            195                 200                 205

Gly Val Gly Val Pro Gly Gly Gly Val Pro Gly Ala Gly Val Pro Gly
            210                 215                 220

Val Gly Val Pro Gly Val Gly Val Pro Gly Val Gly Val Pro Gly Gly
225                 230                 235                 240

Gly Val Pro Gly Ala Gly Val Pro Gly Gly Gly Val Pro Gly Val Gly
                245                 250                 255

Val Pro Gly Val Gly Val Pro Gly Gly Gly Val Pro Gly Ala Gly Val
                260                 265                 270
```

-continued

```
Pro Gly Val Gly Val Pro Gly Val Gly Val Pro Gly Val Gly Val Pro
            275                 280                 285
Gly Gly Gly Val Pro Gly Ala Gly Val Pro Gly Gly Gly Val Pro Gly
        290                 295                 300
Val Gly Val Pro Gly Val Gly Val Pro Gly Gly Gly Val Pro Gly Ala
305                 310                 315                 320
Gly Val Pro Gly Val Gly Val Pro Gly Val Gly Val Pro Gly Val Gly
                325                 330                 335
Val Pro Gly Gly Gly Val Pro Gly Ala Gly Val Pro Gly Gly Gly Val
            340                 345                 350
Pro Gly Val Gly Val Pro Gly Val Gly Val Pro Gly Gly Gly Val Pro
            355                 360                 365
Gly Ala Gly Val Pro Gly Val Gly Val Pro Gly Val Gly Val Pro Gly
        370                 375                 380
Val Gly Val Pro Gly Gly Gly Val Pro Gly Ala Gly Val Pro Gly Gly
385                 390                 395                 400
Gly Val Pro Gly Val Gly Val Pro Gly Val Gly Val Pro Gly Gly Gly
                405                 410                 415
Val Pro Gly Ala Gly Val Pro Gly Val Gly Val Pro Gly Val Gly Val
            420                 425                 430
Pro Gly Val Gly Val Pro Gly Gly Gly Val Pro Gly Ala Gly Val Pro
            435                 440                 445
Gly Gly Gly Val Pro Gly Val Gly Val Pro Gly Val Gly Val Pro Gly
        450                 455                 460
Gly Gly Val Pro Gly Ala Gly Val Pro Gly Val Gly Val Pro Gly Val
465                 470                 475                 480
Gly Val Pro Gly Val Gly Val Pro Gly Gly Gly Val Pro Gly Ala Gly
                485                 490                 495
Val Pro Gly Gly Gly Val Pro Gly Val Gly Val Pro Gly Val Gly Val
            500                 505                 510
Pro Gly Gly Gly Val Pro Gly Ala Gly Val Pro Gly Val Gly Val Pro
            515                 520                 525
Gly Val Gly Val Pro Gly Val Gly Val Pro Gly Gly Gly Val Pro Gly
        530                 535                 540
Ala Gly Val Pro Gly Gly Val Pro Gly Val Gly Val Pro Gly Val
545                 550                 555                 560
Gly Val Pro Gly Gly Gly Val Pro Gly Ala Gly Val Pro Gly Val Gly
                565                 570                 575
Val Pro Gly Val Gly Val Pro Gly Val Gly Val Pro Gly Gly Gly Val
            580                 585                 590
Pro Gly Ala Gly Val Pro Gly Gly Gly Val Pro Gly Val Gly Phe Pro
            595                 600                 605
Thr Ile Pro Leu Ser Arg Leu Phe Asp Asn Ala Met Leu Arg Ala His
        610                 615                 620
Arg Leu His Gln Leu Ala Phe Asp Thr Tyr Gln Glu Phe Glu Glu Ala
625                 630                 635                 640
Tyr Ile Pro Lys Glu Gln Lys Tyr Ser Phe Leu Gln Asn Pro Gln Thr
                645                 650                 655
Ser Leu Cys Phe Ser Glu Ser Ile Pro Thr Pro Ser Asn Arg Glu Glu
            660                 665                 670
Thr Gln Gln Lys Ser Asn Leu Glu Leu Leu Arg Ile Ser Leu Leu Leu
            675                 680                 685
```

```
Ile Gln Ser Trp Leu Glu Pro Val Gln Phe Leu Arg Ser Val Phe Ala
    690             695                 700

Asn Ser Leu Val Tyr Gly Ala Ser Asp Ser Asn Val Tyr Asp Leu Leu
705                 710                 715                 720

Lys Asp Leu Glu Glu Gly Ile Gln Thr Leu Met Gly Arg Leu Glu Asp
                725                 730                 735

Gly Ser Pro Arg Thr Gly Gln Ile Phe Lys Gln Thr Tyr Ser Lys Phe
            740                 745                 750

Asp Thr Asn Ser His Asn Asp Asp Ala Leu Leu Lys Asn Tyr Gly Leu
        755                 760                 765

Leu Tyr Cys Phe Arg Lys Asp Met Asp Lys Val Glu Thr Phe Leu Arg
770                 775                 780

Ile Val Gln Cys Arg Ser Val Glu Gly Ser Cys Gly Phe Val Pro Gly
785                 790                 795                 800

Trp Pro

<210> SEQ ID NO 16
<211> LENGTH: 1077
<212> TYPE: PRT
<213> ORGANISM: Artificial Sequence
<220> FEATURE:
<223> OTHER INFORMATION: ELPbetaV2-144-hGH-ELP1-30

<400> SEQUENCE: 16

Met Val Pro Gly Val Gly Val Pro Gly Val Gly Val Pro Gly Ala Gly
1               5                   10                  15

Val Pro Gly Val Gly Val Pro Gly Ala Gly Val Pro Gly Val Gly Val
                20                  25                  30

Pro Gly Val Gly Val Pro Gly Ala Gly Val Pro Gly Val Gly Val Pro
            35                  40                  45

Gly Ala Gly Val Pro Gly Val Gly Val Pro Gly Ala Gly Val Pro Gly
        50                  55                  60

Val Gly Val Pro Gly Ala Gly Val Pro Gly Val Gly Val Pro Gly Val
65                  70                  75                  80

Gly Val Pro Gly Ala Gly Val Pro Gly Val Gly Val Pro Gly Ala Gly
                85                  90                  95

Val Pro Gly Val Gly Val Pro Gly Ala Gly Val Pro Gly Val Gly Val
            100                 105                 110

Pro Gly Ala Gly Val Pro Gly Val Gly Val Pro Gly Val Gly Val Pro
        115                 120                 125

Gly Ala Gly Val Pro Gly Val Gly Val Pro Gly Ala Gly Val Pro Gly
    130                 135                 140

Val Gly Val Pro Gly Ala Gly Val Pro Gly Val Gly Val Pro Gly Ala
145                 150                 155                 160

Gly Val Pro Gly Val Gly Val Pro Gly Val Gly Val Pro Gly Ala Gly
                165                 170                 175

Val Pro Gly Val Gly Val Pro Gly Ala Gly Val Pro Gly Val Gly Val
            180                 185                 190

Pro Gly Ala Gly Val Pro Gly Val Gly Val Pro Gly Ala Gly Val Pro
        195                 200                 205

Gly Val Gly Val Pro Gly Val Gly Val Pro Gly Ala Gly Val Pro Gly
    210                 215                 220

Val Gly Val Pro Gly Ala Gly Val Pro Gly Val Gly Val Pro Gly Ala
225                 230                 235                 240

Gly Val Pro Gly Val Gly Val Pro Gly Ala Gly Val Pro Gly Val Gly
```

-continued

```
                    245                 250                 255
Val Pro Gly Val Gly Val Pro Gly Ala Gly Val Pro Gly Val Gly Val
                260                 265                 270

Pro Gly Ala Gly Val Pro Gly Val Gly Val Pro Gly Ala Gly Val Pro
                275                 280                 285

Gly Val Gly Val Pro Gly Ala Gly Val Pro Gly Val Gly Val Pro Gly
                290                 295                 300

Val Gly Val Pro Gly Ala Gly Val Pro Gly Val Gly Val Pro Gly Ala
305                 310                 315                 320

Gly Val Pro Gly Val Gly Val Pro Gly Ala Gly Val Pro Gly Val Gly
                325                 330                 335

Val Pro Gly Ala Gly Val Pro Gly Val Gly Val Pro Gly Val Gly Val
                340                 345                 350

Pro Gly Ala Gly Val Pro Gly Val Gly Val Pro Gly Ala Gly Val Pro
                355                 360                 365

Gly Val Gly Val Pro Gly Ala Gly Val Pro Gly Val Gly Val Pro Gly
                370                 375                 380

Ala Gly Val Pro Gly Val Gly Val Pro Gly Val Gly Val Pro Gly Ala
385                 390                 395                 400

Gly Val Pro Gly Val Gly Val Pro Gly Ala Gly Val Pro Gly Val Gly
                405                 410                 415

Val Pro Gly Ala Gly Val Pro Gly Val Gly Val Pro Gly Ala Gly Val
                420                 425                 430

Pro Gly Val Gly Val Pro Gly Val Gly Val Pro Gly Ala Gly Val Pro
                435                 440                 445

Gly Val Gly Val Pro Gly Ala Gly Val Pro Gly Val Gly Val Pro Gly
                450                 455                 460

Ala Gly Val Pro Gly Val Gly Val Pro Gly Ala Gly Val Pro Gly Val
465                 470                 475                 480

Gly Val Pro Gly Val Gly Val Pro Gly Ala Gly Val Pro Gly Val Gly
                485                 490                 495

Val Pro Gly Ala Gly Val Pro Gly Val Gly Val Pro Gly Ala Gly Val
                500                 505                 510

Pro Gly Val Gly Val Pro Gly Ala Gly Val Pro Gly Val Gly Val Pro
                515                 520                 525

Gly Val Gly Val Pro Gly Ala Gly Val Pro Gly Val Gly Val Pro Gly
                530                 535                 540

Ala Gly Val Pro Gly Val Gly Val Pro Gly Ala Gly Val Pro Gly Val
545                 550                 555                 560

Gly Val Pro Gly Ala Gly Val Pro Gly Val Gly Val Pro Gly Val Gly
                565                 570                 575

Val Pro Gly Ala Gly Val Pro Gly Val Gly Val Pro Gly Ala Gly Val
                580                 585                 590

Pro Gly Val Gly Val Pro Gly Ala Gly Val Pro Gly Val Gly Val Pro
                595                 600                 605

Gly Ala Gly Val Pro Gly Val Gly Val Pro Gly Val Gly Val Pro Gly
                610                 615                 620

Ala Gly Val Pro Gly Val Gly Val Pro Gly Ala Gly Val Pro Gly Val
625                 630                 635                 640

Gly Val Pro Gly Ala Gly Val Pro Gly Val Gly Val Pro Gly Ala Gly
                645                 650                 655

Val Pro Gly Val Gly Val Pro Gly Val Gly Val Pro Gly Ala Gly Val
                660                 665                 670
```

```
Pro Gly Val Gly Val Pro Gly Ala Gly Val Pro Gly Val Gly Val Pro
        675                 680                 685
Gly Ala Gly Val Pro Gly Val Gly Val Pro Gly Ala Gly Val Pro Gly
    690                 695                 700
Val Gly Val Pro Gly Val Gly Val Pro Gly Ala Gly Val Pro Gly Val
705                 710                 715                 720
Gly Val Pro Gly Ala Gly Val Pro Gly Val Gly Phe Pro Thr Ile Pro
            725                 730                 735
Leu Ser Arg Leu Phe Asp Asn Ala Met Leu Arg Ala His Arg Leu His
            740                 745                 750
Gln Leu Ala Phe Asp Thr Tyr Gln Glu Phe Glu Glu Ala Tyr Ile Pro
            755                 760                 765
Lys Glu Gln Lys Tyr Ser Phe Leu Gln Asn Pro Gln Thr Ser Leu Cys
        770                 775                 780
Phe Ser Glu Ser Ile Pro Thr Pro Ser Asn Arg Glu Glu Thr Gln Gln
785                 790                 795                 800
Lys Ser Asn Leu Glu Leu Leu Arg Ile Ser Leu Leu Leu Ile Gln Ser
            805                 810                 815
Trp Leu Glu Pro Val Gln Phe Leu Arg Ser Val Phe Ala Asn Ser Leu
            820                 825                 830
Val Tyr Gly Ala Ser Asp Ser Asn Val Tyr Asp Leu Leu Lys Asp Leu
            835                 840                 845
Glu Glu Gly Ile Gln Thr Leu Met Gly Arg Leu Glu Asp Gly Ser Pro
        850                 855                 860
Arg Thr Gly Gln Ile Phe Lys Gln Thr Tyr Ser Lys Phe Asp Thr Asn
865                 870                 875                 880
Ser His Asn Asp Asp Ala Leu Leu Lys Asn Tyr Gly Leu Leu Tyr Cys
            885                 890                 895
Phe Arg Lys Asp Met Asp Lys Val Glu Thr Phe Leu Arg Ile Val Gln
            900                 905                 910
Cys Arg Ser Val Glu Gly Ser Cys Gly Phe Val Pro Gly Val Gly Val
        915                 920                 925
Pro Gly Val Gly Val Pro Gly Gly Val Pro Gly Ala Gly Val Pro
    930                 935                 940
Gly Val Gly Val Pro Gly Val Gly Val Pro Gly Val Gly Val Pro Gly
945                 950                 955                 960
Gly Gly Val Pro Gly Ala Gly Val Pro Gly Gly Val Pro Gly Val
            965                 970                 975
Gly Val Pro Gly Val Gly Val Pro Gly Gly Val Pro Gly Ala Gly
        980                 985                 990
Val Pro Gly Val Gly Val Pro Gly  Val Gly Val Pro Gly  Val Gly Val
        995                 1000                1005
Pro Gly  Gly Gly Val Pro Gly  Ala Gly Val Pro Gly  Gly Gly Val
    1010                1015                1020
Pro Gly  Val Gly Val Pro Gly  Val Gly Val Pro Gly  Gly Gly Val
    1025                1030                1035
Pro Gly  Ala Gly Val Pro Gly  Val Gly Val Pro Gly  Val Gly Val
    1040                1045                1050
Pro Gly  Val Gly Val Pro Gly  Gly Gly Val Pro Gly  Ala Gly Val
    1055                1060                1065
Pro Gly  Gly Gly Val Pro Gly  Trp Pro
    1070                1075
```

<210> SEQ ID NO 17
<211> LENGTH: 952
<212> TYPE: PRT
<213> ORGANISM: Artificial Sequence
<220> FEATURE:
<223> OTHER INFORMATION: ELP1-120 hGH ELP1-30

<400> SEQUENCE: 17

```
Met Val Pro Gly Val Gly Val Pro Gly Val Gly Val Pro Gly Gly
1               5                   10                  15

Val Pro Gly Ala Gly Val Pro Gly Val Gly Val Pro Gly Val Gly Val
                20                  25                  30

Pro Gly Val Gly Val Pro Gly Gly Val Pro Gly Ala Gly Val Pro
                35                  40                  45

Gly Gly Gly Val Pro Gly Val Gly Val Pro Gly Val Gly Val Pro Gly
    50                  55                  60

Gly Gly Val Pro Gly Ala Gly Val Pro Gly Val Gly Val Pro Gly Val
65                  70                  75                  80

Gly Val Pro Gly Val Gly Val Pro Gly Gly Gly Val Pro Gly Ala Gly
                85                  90                  95

Val Pro Gly Gly Gly Val Pro Gly Val Gly Val Pro Gly Val Gly Val
                100                 105                 110

Pro Gly Gly Gly Val Pro Gly Ala Gly Val Pro Gly Val Gly Val Pro
                115                 120                 125

Gly Val Gly Val Pro Gly Val Gly Val Pro Gly Gly Gly Val Pro Gly
    130                 135                 140

Ala Gly Val Pro Gly Gly Gly Val Pro Gly Val Gly Val Pro Gly Val
145                 150                 155                 160

Gly Val Pro Gly Gly Gly Val Pro Gly Ala Gly Val Pro Gly Val Gly
                165                 170                 175

Val Pro Gly Val Gly Val Pro Gly Val Gly Val Pro Gly Gly Gly Val
                180                 185                 190

Pro Gly Ala Gly Val Pro Gly Gly Gly Val Pro Gly Val Gly Val Pro
                195                 200                 205

Gly Val Gly Val Pro Gly Gly Val Pro Gly Ala Gly Val Pro Gly
    210                 215                 220

Val Gly Val Pro Gly Val Gly Val Pro Gly Val Gly Val Pro Gly Gly
225                 230                 235                 240

Gly Val Pro Gly Ala Gly Val Pro Gly Gly Gly Val Pro Gly Val Gly
                245                 250                 255

Val Pro Gly Val Gly Val Pro Gly Gly Gly Val Pro Gly Ala Gly Val
                260                 265                 270

Pro Gly Val Gly Val Pro Gly Val Gly Val Pro Gly Val Gly Val Pro
                275                 280                 285

Gly Gly Gly Val Pro Gly Ala Gly Val Pro Gly Gly Gly Val Pro Gly
    290                 295                 300

Val Gly Val Pro Gly Val Gly Val Pro Gly Gly Gly Val Pro Gly Ala
305                 310                 315                 320

Gly Val Pro Gly Val Gly Val Pro Gly Val Gly Val Pro Gly Val Gly
                325                 330                 335

Val Pro Gly Gly Gly Val Pro Gly Ala Gly Val Pro Gly Gly Gly Val
                340                 345                 350

Pro Gly Val Gly Val Pro Gly Val Gly Val Pro Gly Gly Gly Val Pro
                355                 360                 365
```

```
Gly Ala Gly Val Pro Gly Val Gly Val Pro Gly Val Gly Val Pro Gly
        370                 375                 380
Val Gly Val Pro Gly Gly Val Pro Gly Ala Gly Val Pro Gly Gly
385                 390                 395                 400
Gly Val Pro Gly Val Gly Val Pro Gly Val Gly Val Pro Gly Gly
                405                 410                 415
Val Pro Gly Ala Gly Val Pro Gly Val Gly Val Pro Gly Val Gly Val
            420                 425                 430
Pro Gly Gly Val Pro Gly Gly Val Pro Gly Ala Gly Val Pro
        435                 440                 445
Gly Gly Gly Val Pro Gly Val Gly Val Pro Gly Val Gly Val Pro Gly
    450                 455                 460
Gly Gly Val Pro Gly Ala Gly Val Pro Gly Val Gly Val Pro Gly Val
465                 470                 475                 480
Gly Val Pro Gly Val Gly Val Pro Gly Gly Val Pro Gly Ala Gly
                485                 490                 495
Val Pro Gly Gly Gly Val Pro Gly Val Gly Val Pro Gly Val Gly Val
            500                 505                 510
Pro Gly Gly Gly Val Pro Gly Ala Gly Val Pro Gly Val Gly Val Pro
        515                 520                 525
Gly Val Gly Val Pro Gly Val Gly Val Pro Gly Gly Gly Val Pro Gly
    530                 535                 540
Ala Gly Val Pro Gly Gly Gly Val Pro Gly Gly Gly Val Pro Gly Val
545                 550                 555                 560
Gly Val Pro Gly Gly Val Pro Gly Ala Gly Val Pro Gly Val Gly
                565                 570                 575
Val Pro Gly Val Gly Val Pro Gly Val Gly Val Pro Gly Gly Gly Val
            580                 585                 590
Pro Gly Ala Gly Val Pro Gly Gly Val Pro Gly Val Gly Phe Pro
        595                 600                 605
Thr Ile Pro Leu Ser Arg Leu Phe Asp Asn Ala Met Leu Arg Ala His
    610                 615                 620
Arg Leu His Gln Leu Ala Phe Asp Thr Tyr Gln Glu Phe Glu Glu Ala
625                 630                 635                 640
Tyr Ile Pro Lys Glu Gln Lys Tyr Ser Phe Leu Gln Asn Pro Gln Thr
                645                 650                 655
Ser Leu Cys Phe Ser Glu Ser Ile Pro Thr Pro Ser Asn Arg Glu Glu
            660                 665                 670
Thr Gln Gln Lys Ser Asn Leu Glu Leu Leu Arg Ile Ser Leu Leu Leu
        675                 680                 685
Ile Gln Ser Trp Leu Glu Pro Val Gln Phe Leu Arg Ser Val Phe Ala
    690                 695                 700
Asn Ser Leu Val Tyr Gly Ala Ser Asp Ser Asn Val Tyr Asp Leu Leu
705                 710                 715                 720
Lys Asp Leu Glu Glu Gly Ile Gln Thr Leu Met Gly Arg Leu Glu Asp
                725                 730                 735
Gly Ser Pro Arg Thr Gly Gln Ile Phe Lys Gln Thr Tyr Ser Lys Phe
            740                 745                 750
Asp Thr Asn Ser His Asn Asp Asp Ala Leu Leu Lys Asn Tyr Gly Leu
        755                 760                 765
Leu Tyr Cys Phe Arg Lys Asp Met Asp Lys Val Glu Thr Phe Leu Arg
    770                 775                 780
Ile Val Gln Cys Arg Ser Val Glu Gly Ser Cys Gly Phe Val Pro Gly
```

```
                785                 790                 795                 800
Val Gly Val Pro Gly Val Gly Val Pro Gly Gly Val Pro Gly Ala
                    805                 810                 815

Gly Val Pro Gly Val Gly Val Pro Gly Val Gly Val Pro Gly Val Gly
                820                 825                 830

Val Pro Gly Val Gly Val Pro Gly Ala Gly Val Pro Gly Gly Val
                835                 840                 845

Pro Gly Val Gly Val Pro Gly Val Gly Val Pro Gly Gly Val Pro
    850                 855                 860

Gly Ala Gly Val Pro Gly Val Gly Val Pro Gly Val Gly Val Pro Gly
865                 870                 875                 880

Val Gly Val Pro Gly Gly Val Pro Gly Ala Gly Val Pro Gly Gly
                885                 890                 895

Gly Val Pro Gly Val Gly Val Pro Gly Val Gly Val Pro Gly Gly
                900                 905                 910

Val Pro Gly Ala Gly Val Pro Gly Val Gly Val Pro Gly Val Gly Val
                915                 920                 925

Pro Gly Val Gly Val Pro Gly Gly Val Pro Gly Ala Gly Val Pro
    930                 935                 940

Gly Gly Gly Val Pro Gly Trp Pro
945                 950

<210> SEQ ID NO 18
<211> LENGTH: 769
<212> TYPE: PRT
<213> ORGANISM: Artificial Sequence
<220> FEATURE:
<223> OTHER INFORMATION: exendin-4 ELPbetaV2

<400> SEQUENCE: 18

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Val Pro Gly Val Gly Val Pro Gly Val
        35                  40                  45

Gly Val Pro Gly Ala Gly Val Pro Gly Val Gly Val Pro Gly Ala Gly
    50                  55                  60

Val Pro Gly Val Gly Val Pro Gly Val Gly Val Pro Gly Ala Gly Val
65                  70                  75                  80

Pro Gly Val Gly Val Pro Gly Ala Gly Val Pro Gly Val Gly Val Pro
                85                  90                  95

Gly Ala Gly Val Pro Gly Val Gly Val Pro Gly Ala Gly Val Pro Gly
            100                 105                 110

Val Gly Val Pro Gly Val Gly Val Pro Gly Ala Gly Val Pro Gly Val
        115                 120                 125

Gly Val Pro Gly Ala Gly Val Pro Gly Val Gly Val Pro Gly Ala Gly
    130                 135                 140

Val Pro Gly Val Gly Val Pro Gly Ala Gly Val Pro Gly Val Gly Val
145                 150                 155                 160

Pro Gly Val Gly Val Pro Gly Ala Gly Val Pro Gly Val Gly Val Pro
                165                 170                 175

Gly Ala Gly Val Pro Gly Val Gly Val Pro Gly Ala Gly Val Pro Gly
            180                 185                 190

Val Gly Val Pro Gly Ala Gly Val Pro Gly Val Gly Val Pro Gly Val
```

-continued

```
                195                 200                 205
Gly Val Pro Gly Ala Gly Val Pro Gly Val Gly Val Pro Gly Ala Gly
            210                 215                 220

Val Pro Gly Val Gly Val Pro Gly Ala Gly Val Pro Gly Val Gly Val
225                 230                 235                 240

Pro Gly Ala Gly Val Pro Gly Val Gly Val Pro Gly Ala Gly Val Pro
            245                 250                 255

Gly Ala Gly Val Pro Gly Val Gly Val Pro Gly Ala Gly Val Pro Gly
            260                 265                 270

Val Gly Val Pro Gly Ala Gly Val Pro Gly Val Gly Val Pro Gly Ala
            275                 280                 285

Gly Val Pro Gly Val Gly Val Pro Gly Val Gly Val Pro Gly Ala Gly
            290                 295                 300

Val Pro Gly Val Gly Val Pro Gly Ala Gly Val Pro Gly Val Gly Val
305                 310                 315                 320

Pro Gly Ala Gly Val Pro Gly Val Gly Val Pro Gly Ala Gly Val Pro
            325                 330                 335

Gly Val Gly Val Pro Gly Val Gly Val Pro Gly Ala Gly Val Pro Gly
            340                 345                 350

Val Gly Val Pro Gly Ala Gly Val Pro Gly Val Gly Val Pro Gly Ala
            355                 360                 365

Gly Val Pro Gly Val Gly Val Pro Gly Ala Gly Val Pro Gly Val Gly
            370                 375                 380

Val Pro Gly Val Gly Val Pro Gly Ala Gly Val Pro Gly Val Gly Val
385                 390                 395                 400

Pro Gly Ala Gly Val Pro Gly Val Gly Val Pro Gly Ala Gly Val Pro
            405                 410                 415

Gly Val Gly Val Pro Gly Ala Gly Val Pro Gly Val Gly Val Pro Gly
            420                 425                 430

Val Gly Val Pro Gly Ala Gly Val Pro Gly Val Gly Val Pro Gly Ala
            435                 440                 445

Gly Val Pro Gly Val Gly Val Pro Gly Ala Gly Val Pro Gly Val Gly
            450                 455                 460

Val Pro Gly Ala Gly Val Pro Gly Val Gly Val Pro Gly Val Gly Val
465                 470                 475                 480

Pro Gly Ala Gly Val Pro Gly Val Gly Val Pro Gly Ala Gly Val Pro
            485                 490                 495

Gly Val Gly Val Pro Gly Ala Gly Val Pro Gly Val Gly Val Pro Gly
            500                 505                 510

Ala Gly Val Pro Gly Val Gly Val Pro Gly Val Gly Val Pro Gly Ala
            515                 520                 525

Gly Val Pro Gly Val Gly Val Pro Gly Ala Gly Val Pro Gly Val Gly
            530                 535                 540

Val Pro Gly Ala Gly Val Pro Gly Val Gly Val Pro Gly Ala Gly Val
545                 550                 555                 560

Pro Gly Val Gly Val Pro Gly Val Gly Val Pro Gly Ala Gly Val Pro
            565                 570                 575

Gly Val Gly Val Pro Gly Ala Gly Val Pro Gly Val Gly Val Pro Gly
            580                 585                 590

Ala Gly Val Pro Gly Val Gly Val Pro Gly Ala Gly Val Pro Gly Val
            595                 600                 605

Gly Val Pro Gly Val Gly Val Pro Gly Ala Gly Val Pro Gly Val Gly
            610                 615                 620
```

Val Pro Gly Ala Gly Val Pro Gly Val Gly Val Pro Gly Ala Gly Val
625                 630                 635                 640

Pro Gly Val Gly Val Pro Gly Ala Gly Val Pro Gly Val Gly Val Pro
                645                 650                 655

Gly Val Gly Val Pro Gly Ala Gly Val Pro Gly Val Gly Val Pro Gly
            660                 665                 670

Ala Gly Val Pro Gly Val Gly Val Pro Gly Ala Gly Val Pro Gly Val
        675                 680                 685

Gly Val Pro Gly Ala Gly Val Pro Gly Val Gly Val Pro Gly Val Gly
    690                 695                 700

Val Pro Gly Ala Gly Val Pro Gly Val Gly Val Pro Gly Ala Gly Val
705                 710                 715                 720

Pro Gly Val Gly Val Pro Gly Ala Gly Val Pro Gly Val Gly Val Pro
                725                 730                 735

Gly Ala Gly Val Pro Gly Val Gly Val Pro Gly Val Gly Val Pro Gly
            740                 745                 750

Ala Gly Val Pro Gly Val Gly Val Pro Gly Ala Gly Val Pro Gly Trp
        755                 760                 765

Pro

<210> SEQ ID NO 19
<211> LENGTH: 606
<212> TYPE: PRT
<213> ORGANISM: Artificial Sequence
<220> FEATURE:
<223> OTHER INFORMATION: ELP1-120

<400> SEQUENCE: 19

Met Val Pro Gly Val Gly Val Pro Gly Val Gly Val Pro Gly Gly Gly
1               5                   10                  15

Val Pro Gly Ala Gly Val Pro Gly Val Gly Val Pro Gly Val Gly Val
                20                  25                  30

Pro Gly Val Gly Val Pro Gly Gly Gly Val Pro Gly Ala Gly Val Pro
            35                  40                  45

Gly Gly Gly Val Pro Gly Val Gly Val Pro Gly Val Gly Val Pro Gly
        50                  55                  60

Gly Gly Val Pro Gly Ala Gly Val Pro Gly Val Gly Val Pro Gly Val
65                  70                  75                  80

Gly Val Pro Gly Val Gly Val Pro Gly Gly Gly Val Pro Gly Ala Gly
                85                  90                  95

Val Pro Gly Gly Gly Val Pro Gly Val Gly Val Pro Gly Val Gly Val
            100                 105                 110

Pro Gly Gly Gly Val Pro Gly Ala Gly Val Pro Gly Val Gly Val Pro
        115                 120                 125

Gly Val Gly Val Pro Gly Val Gly Val Pro Gly Gly Gly Val Pro Gly
    130                 135                 140

Ala Gly Val Pro Gly Gly Gly Val Pro Gly Val Gly Val Pro Gly Val
145                 150                 155                 160

Gly Val Pro Gly Gly Gly Val Pro Gly Ala Gly Val Pro Gly Val Gly
                165                 170                 175

Val Pro Gly Val Gly Val Pro Gly Val Gly Val Pro Gly Gly Gly Val
            180                 185                 190

Pro Gly Ala Gly Val Pro Gly Gly Gly Val Pro Gly Val Gly Val Pro
        195                 200                 205

Gly Val Gly Val Pro Gly Gly Val Pro Gly Ala Gly Val Pro Gly
210                 215                 220

Val Gly Val Pro Gly Val Gly Val Pro Gly Val Gly Val Pro Gly Gly
225                 230                 235                 240

Gly Val Pro Gly Ala Gly Val Pro Gly Gly Val Pro Gly Val Gly
            245                 250                 255

Val Pro Gly Val Gly Val Pro Gly Gly Val Pro Gly Ala Gly Val
        260                 265                 270

Pro Gly Val Gly Val Pro Gly Val Gly Val Pro Gly Gly Val Pro
    275                 280                 285

Gly Gly Gly Val Pro Gly Ala Gly Val Pro Gly Gly Gly Val Pro Gly
290                 295                 300

Val Gly Val Pro Gly Val Gly Val Pro Gly Gly Gly Val Pro Gly Ala
305                 310                 315                 320

Gly Val Pro Gly Val Gly Val Pro Gly Val Gly Val Pro Gly Val Gly
            325                 330                 335

Val Pro Gly Gly Gly Val Pro Gly Ala Gly Val Pro Gly Gly Gly Val
        340                 345                 350

Pro Gly Val Gly Val Pro Gly Val Gly Val Pro Gly Gly Gly Val Pro
    355                 360                 365

Gly Ala Gly Val Pro Gly Val Gly Val Pro Gly Val Gly Val Pro Gly
370                 375                 380

Val Gly Val Pro Gly Gly Gly Val Pro Gly Ala Gly Val Pro Gly Gly
385                 390                 395                 400

Gly Val Pro Gly Val Gly Val Pro Gly Val Gly Val Pro Gly Gly Gly
            405                 410                 415

Val Pro Gly Ala Gly Val Pro Gly Val Gly Val Pro Gly Val Gly Val
        420                 425                 430

Pro Gly Val Gly Val Pro Gly Gly Gly Val Pro Gly Ala Gly Val Pro
    435                 440                 445

Gly Gly Gly Val Pro Gly Val Gly Val Pro Gly Val Gly Val Pro Gly
450                 455                 460

Gly Gly Val Pro Gly Ala Gly Val Pro Gly Val Gly Val Pro Gly Val
465                 470                 475                 480

Gly Val Pro Gly Val Gly Val Pro Gly Gly Gly Val Pro Gly Ala Gly
            485                 490                 495

Val Pro Gly Gly Gly Val Pro Gly Val Gly Val Pro Gly Val Gly Val
        500                 505                 510

Pro Gly Gly Gly Val Pro Gly Ala Gly Val Pro Gly Val Gly Val Pro
    515                 520                 525

Gly Val Gly Val Pro Gly Val Gly Val Pro Gly Gly Gly Val Pro Gly
530                 535                 540

Ala Gly Val Pro Gly Gly Gly Val Pro Gly Val Gly Val Pro Gly Val
545                 550                 555                 560

Gly Val Pro Gly Gly Gly Val Pro Gly Ala Gly Val Pro Gly Val Gly
            565                 570                 575

Val Pro Gly Val Gly Val Pro Gly Val Gly Val Pro Gly Gly Gly Val
        580                 585                 590

Pro Gly Ala Gly Val Pro Gly Gly Gly Val Pro Gly Val Gly
    595                 600                 605

<210> SEQ ID NO 20
<211> LENGTH: 155
<212> TYPE: PRT

<213> ORGANISM: Artificial Sequence
<220> FEATURE:
<223> OTHER INFORMATION: ELP1-30

<400> SEQUENCE: 20

```
Val Pro Gly Val Gly Val Pro Gly Val Gly Val Pro Gly Gly Val
1               5                   10                  15

Pro Gly Ala Gly Val Pro Gly Val Gly Val Pro Gly Val Gly Val Pro
            20                  25                  30

Gly Val Gly Val Pro Gly Gly Val Pro Gly Ala Gly Val Pro Gly
        35                  40                  45

Gly Gly Val Pro Gly Val Gly Val Pro Gly Val Gly Val Pro Gly Gly
50                  55                  60

Gly Val Pro Gly Ala Gly Val Pro Gly Val Gly Val Pro Gly Val Gly
65                  70                  75                  80

Val Pro Gly Val Gly Val Pro Gly Gly Val Pro Gly Ala Gly Val
            85                  90                  95

Pro Gly Gly Gly Val Pro Gly Val Gly Val Pro Gly Val Gly Val Pro
            100                 105                 110

Gly Gly Gly Val Pro Gly Ala Gly Val Pro Gly Val Gly Val Pro Gly
        115                 120                 125

Val Gly Val Pro Gly Val Gly Val Pro Gly Gly Gly Val Pro Gly Ala
        130                 135                 140

Gly Val Pro Gly Gly Gly Val Pro Gly Trp Pro
145                 150                 155
```

<210> SEQ ID NO 21
<211> LENGTH: 730
<212> TYPE: PRT
<213> ORGANISM: Artificial Sequence
<220> FEATURE:
<223> OTHER INFORMATION: ELPbetaV2-144

<400> SEQUENCE: 21

```
Val Pro Gly Val Gly Val Pro Gly Val Gly Val Pro Gly Ala Gly Val
1               5                   10                  15

Pro Gly Val Gly Val Pro Gly Ala Gly Val Pro Gly Val Gly Val Pro
            20                  25                  30

Gly Val Gly Val Pro Gly Ala Gly Val Pro Gly Val Gly Val Pro Gly
        35                  40                  45

Ala Gly Val Pro Gly Val Gly Val Pro Gly Ala Gly Val Pro Gly Val
        50                  55                  60

Gly Val Pro Gly Ala Gly Val Pro Gly Val Gly Val Pro Gly Val Gly
65                  70                  75                  80

Val Pro Gly Ala Gly Val Pro Gly Val Gly Val Pro Gly Ala Gly Val
            85                  90                  95

Pro Gly Val Gly Val Pro Gly Ala Gly Val Pro Gly Val Gly Val Pro
            100                 105                 110

Gly Ala Gly Val Pro Gly Val Gly Val Pro Gly Val Gly Val Pro Gly
        115                 120                 125

Ala Gly Val Pro Gly Val Gly Val Pro Gly Ala Gly Val Pro Gly Val
        130                 135                 140

Gly Val Pro Gly Ala Gly Val Pro Gly Val Gly Val Pro Gly Ala Gly
145                 150                 155                 160

Val Pro Gly Val Gly Val Pro Gly Val Gly Val Pro Gly Ala Gly Val
                165                 170                 175
```

Pro Gly Val Gly Val Pro Gly Ala Gly Val Pro Gly Val Pro
                180                 185                 190

Gly Ala Gly Val Pro Gly Val Gly Val Pro Gly Ala Gly Val Pro Gly
            195                 200                 205

Val Gly Val Pro Gly Val Gly Val Pro Gly Ala Gly Val Pro Gly Val
        210                 215                 220

Gly Val Pro Gly Ala Gly Val Pro Gly Val Gly Val Pro Gly Ala Gly
225                 230                 235                 240

Val Pro Gly Val Gly Val Pro Gly Ala Gly Val Pro Gly Val Gly Val
                245                 250                 255

Pro Gly Val Gly Val Pro Gly Ala Gly Val Pro Gly Val Gly Val Pro
            260                 265                 270

Gly Ala Gly Val Pro Gly Val Gly Val Pro Gly Ala Gly Val Pro Gly
        275                 280                 285

Val Gly Val Pro Gly Ala Gly Val Pro Gly Val Gly Val Pro Gly Val
        290                 295                 300

Gly Val Pro Gly Ala Gly Val Pro Gly Val Gly Val Pro Gly Ala Gly
305                 310                 315                 320

Val Pro Gly Val Gly Val Pro Gly Ala Gly Val Pro Gly Val Gly Val
                325                 330                 335

Pro Gly Ala Gly Val Pro Gly Val Gly Val Pro Gly Ala Gly Val Pro
            340                 345                 350

Gly Ala Gly Val Pro Gly Val Gly Val Pro Gly Ala Gly Val Pro Gly
        355                 360                 365

Val Gly Val Pro Gly Ala Gly Val Pro Gly Val Gly Val Pro Gly Ala
        370                 375                 380

Gly Val Pro Gly Val Gly Val Pro Gly Val Gly Val Pro Gly Ala Gly
385                 390                 395                 400

Val Pro Gly Val Gly Val Pro Gly Ala Gly Val Pro Gly Val Gly Val
                405                 410                 415

Pro Gly Ala Gly Val Pro Gly Val Gly Val Pro Gly Ala Gly Val Pro
            420                 425                 430

Gly Val Gly Val Pro Gly Val Gly Val Pro Gly Ala Gly Val Pro Gly
        435                 440                 445

Val Gly Val Pro Gly Ala Gly Val Pro Gly Val Gly Val Pro Gly Ala
        450                 455                 460

Gly Val Pro Gly Val Gly Val Pro Gly Ala Gly Val Pro Gly Val Gly
465                 470                 475                 480

Val Pro Gly Val Gly Val Pro Gly Ala Gly Val Pro Gly Val Gly Val
                485                 490                 495

Pro Gly Ala Gly Val Pro Gly Val Gly Val Pro Gly Ala Gly Val Pro
            500                 505                 510

Gly Val Gly Val Pro Gly Ala Gly Val Pro Gly Val Gly Val Pro Gly
        515                 520                 525

Val Gly Val Pro Gly Ala Gly Val Pro Gly Val Gly Val Pro Gly Ala
        530                 535                 540

Gly Val Pro Gly Val Gly Val Pro Gly Ala Gly Val Pro Gly Val Gly
545                 550                 555                 560

Val Pro Gly Ala Gly Val Pro Gly Val Gly Val Pro Gly Val Gly Val
                565                 570                 575

Pro Gly Ala Gly Val Pro Gly Val Gly Val Pro Gly Ala Gly Val Pro
            580                 585                 590

Gly Val Gly Val Pro Gly Ala Gly Val Pro Gly Val Gly Val Pro Gly

```
                595                 600                 605
Ala Gly Val Pro Gly Val Gly Val Pro Gly Val Gly Val Pro Gly Ala
    610                 615                 620

Gly Val Pro Gly Val Gly Val Pro Gly Ala Gly Val Pro Gly Val Gly
625                 630                 635                 640

Val Pro Gly Ala Gly Val Pro Gly Val Gly Val Pro Gly Ala Gly Val
                645                 650                 655

Pro Gly Val Gly Val Pro Gly Val Gly Val Pro Gly Ala Gly Val Pro
                    660                 665                 670

Gly Val Gly Val Pro Gly Ala Gly Val Pro Gly Val Gly Val Pro Gly
                675                 680                 685

Ala Gly Val Pro Gly Val Gly Val Pro Gly Ala Gly Val Pro Gly Val
    690                 695                 700

Gly Val Pro Gly Val Gly Val Pro Gly Ala Gly Val Pro Gly Val Gly
705                 710                 715                 720

Val Pro Gly Ala Gly Val Pro Gly Val Gly
                725                 730

<210> SEQ ID NO 22
<211> LENGTH: 191
<212> TYPE: PRT
<213> ORGANISM: Unknown
<220> FEATURE:
<223> OTHER INFORMATION: hGH

<400> SEQUENCE: 22

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190

<210> SEQ ID NO 23
<211> LENGTH: 39
<212> TYPE: PRT
<213> ORGANISM: Unknown
<220> FEATURE:
<223> OTHER INFORMATION: Exendin-4
```

```
<400> SEQUENCE: 23

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 24
<211> LENGTH: 31
<212> TYPE: PRT
<213> ORGANISM: Unknown
<220> FEATURE:
<223> OTHER INFORMATION: Exendin-4 (1-31)

<400> SEQUENCE: 24

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro
            20                  25                  30

<210> SEQ ID NO 25
<211> LENGTH: 30
<212> TYPE: PRT
<213> ORGANISM: Unknown
<220> FEATURE:
<223> OTHER INFORMATION: Exendin-4 (1-30)

<400> SEQUENCE: 25

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 26
<211> LENGTH: 32
<212> TYPE: PRT
<213> ORGANISM: Unknown
<220> FEATURE:
<223> OTHER INFORMATION: Exendin-4 (1-32)

<400> SEQUENCE: 26

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

<210> SEQ ID NO 27
<211> LENGTH: 33
<212> TYPE: PRT
<213> ORGANISM: Unknown
<220> FEATURE:
<223> OTHER INFORMATION: Exendin-4 (1-33)

<400> SEQUENCE: 27

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser
```

```
<210> SEQ ID NO 28
<211> LENGTH: 34
<212> TYPE: PRT
<213> ORGANISM: Unknown
<220> FEATURE:
<223> OTHER INFORMATION: Exendin-4 (1-34)

<400> SEQUENCE: 28

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly

<210> SEQ ID NO 29
<211> LENGTH: 35
<212> TYPE: PRT
<213> ORGANISM: Unknown
<220> FEATURE:
<223> OTHER INFORMATION: Exendin-4 (1-35)

<400> SEQUENCE: 29

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala
        35

<210> SEQ ID NO 30
<211> LENGTH: 36
<212> TYPE: PRT
<213> ORGANISM: Unknown
<220> FEATURE:
<223> OTHER INFORMATION: Exendin-4 (1-36)

<400> SEQUENCE: 30

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro
        35

<210> SEQ ID NO 31
<211> LENGTH: 37
<212> TYPE: PRT
<213> ORGANISM: Unknown
<220> FEATURE:
<223> OTHER INFORMATION: Exendin-4 (1-37)

<400> SEQUENCE: 31

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro
        35

<210> SEQ ID NO 32
<211> LENGTH: 38
<212> TYPE: PRT
<213> ORGANISM: Unknown
```

```
<220> FEATURE:
<223> OTHER INFORMATION: Exendin-4 (1-38)

<400> SEQUENCE: 32

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro
        35

<210> SEQ ID NO 33
<211> LENGTH: 31
<212> TYPE: PRT
<213> ORGANISM: Unknown
<220> FEATURE:
<223> OTHER INFORMATION: Exendin-4 (9-39)

<400> SEQUENCE: 33

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 34
<211> LENGTH: 23
<212> TYPE: PRT
<213> ORGANISM: Unknown
<220> FEATURE:
<223> OTHER INFORMATION: Exendin-4 (9-31)

<400> SEQUENCE: 34

Asp Leu Ser Lys Gln Met Glu Glu Glu Ala Val Arg Leu Phe Ile Glu
1               5                   10                  15

Trp Leu Lys Asn Gly Gly Pro
            20

<210> SEQ ID NO 35
<211> LENGTH: 46
<212> TYPE: PRT
<213> ORGANISM: Unknown
<220> FEATURE:
<223> OTHER INFORMATION: Exendin-4/ELP sequence with N-terminal Tev
      cleavage site

<400> SEQUENCE: 35

Met Glu Asn Leu Tyr Phe Gln His Gly Glu Gly Thr Phe Thr Ser Asp
1               5                   10                  15

Leu Ser Lys Gln Met Glu Glu Glu Ala Val Arg Leu Phe Ile Glu Trp
            20                  25                  30

Leu Lys Asn Gly Gly Pro Ser Ser Gly Ala Pro Pro Pro Ser
        35                  40                  45

<210> SEQ ID NO 36
<211> LENGTH: 58
<212> TYPE: PRT
<213> ORGANISM: Unknown
<220> FEATURE:
<223> OTHER INFORMATION: Exendin-4/ELP sequence with DsbA leader
      sequence

<400> SEQUENCE: 36

Met Lys Lys Ile Trp Leu Ala Leu Ala Gly Leu Val Leu Ala Phe Ser
1               5                   10                  15
```

Ala Ser Ala His Gly Glu Gly Thr Phe Thr Ser Asp Leu Ser Lys Gln
           20                  25                  30

Met Glu Glu Glu Ala Val Arg Leu Phe Ile Glu Trp Leu Lys Asn Gly
         35                  40                  45

Gly Pro Ser Ser Gly Ala Pro Pro Ser
         50                  55

<210> SEQ ID NO 37
<211> LENGTH: 31
<212> TYPE: PRT
<213> ORGANISM: Unknown
<220> FEATURE:
<223> OTHER INFORMATION: GLP-1 (A8G, 7-37).

<400> SEQUENCE: 37

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 38
<211> LENGTH: 30
<212> TYPE: PRT
<213> ORGANISM: Unknown
<220> FEATURE:
<223> OTHER INFORMATION: GLP-1[7-36]

<400> SEQUENCE: 38

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 39
<211> LENGTH: 30
<212> TYPE: PRT
<213> ORGANISM: Unknown
<220> FEATURE:
<223> OTHER INFORMATION: GLP-1[7-36] with G at position 2

<400> SEQUENCE: 39

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 40
<211> LENGTH: 38
<212> TYPE: PRT
<213> ORGANISM: Unknown
<220> FEATURE:
<223> OTHER INFORMATION: GLP-1(A8G,1-37)

<400> SEQUENCE: 40

Met Glu Asn Leu Tyr Phe Gln His Gly Glu Gly Thr Phe Thr Ser Asp
1               5                   10                  15

Val Ser Ser Tyr Leu Glu Gly Gln Ala Ala Lys Glu Phe Ile Ala Trp
            20                  25                  30

Leu Val Lys Gly Arg Gly
        35

<210> SEQ ID NO 41

```
<211> LENGTH: 44
<212> TYPE: PRT
<213> ORGANISM: Unknown
<220> FEATURE:
<223> OTHER INFORMATION: GLP-1 receptor agonist

<400> SEQUENCE: 41

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 42
<211> LENGTH: 31
<212> TYPE: PRT
<213> ORGANISM: Unknown
<220> FEATURE:
<223> OTHER INFORMATION: GLP-1 receptor agonist

<400> SEQUENCE: 42

His Val Glu Gly Thr Phe Thr Ser Asp Val Ser Ser Tyr Leu Glu Glu
1               5                   10                  15

Gln Ala Ala Lys Glu Phe Ile Ala Trp Leu Ile Lys Gly Arg Gly
            20                  25                  30

<210> SEQ ID NO 43
<211> LENGTH: 48
<212> TYPE: PRT
<213> ORGANISM: Unknown
<220> FEATURE:
<223> OTHER INFORMATION: GLP-1 A8G

<400> SEQUENCE: 43

Met Glu Asn Leu Tyr Phe Gln His Gly Glu Gly Thr Phe Thr Ser Asp
1               5                   10                  15

Val Ser Ser Tyr Leu Glu Gly Gln Ala Ala Lys Glu Phe Ile Ala Trp
            20                  25                  30

Leu Val Lys Gly Arg Gly Leu Glu Gly Met Gly Gly Pro Gly Val Gly
        35                  40                  45

<210> SEQ ID NO 44
<211> LENGTH: 86
<212> TYPE: PRT
<213> ORGANISM: Homo sapiens

<400> SEQUENCE: 44

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85
```

<210> SEQ ID NO 45
<211> LENGTH: 261
<212> TYPE: DNA
<213> ORGANISM: Homo sapiens

<400> SEQUENCE: 45

```
atgtttgtga accaacacct gtgcggctca cacctggtgg aagctctcta cctagtgtgc      60
ggggaacgag gcttcttcta cacacccaag acccgccggg aggcagagga cctgcaggtg     120
gggcaggtgg agctgggcgg gggccctggt gcaggcagcc tgcagccctt ggccctggag     180
gggtccctgc agaagcgtgg cattgtggaa caatgctgta ccagcatctg ctccctctac     240
cagctggaga actactgcaa c                                               261
```

<210> SEQ ID NO 46
<211> LENGTH: 87
<212> TYPE: PRT
<213> ORGANISM: Homo sapiens

<400> SEQUENCE: 46

```
Met Phe Val Asn Gln His Leu Cys Gly Ser His Leu Val Glu Ala Leu
1               5                   10                  15

Tyr Leu Val Cys Gly Glu Arg Gly Phe Phe Tyr Thr Pro Lys Thr Arg
            20                  25                  30

Arg Glu Ala Glu Asp Leu Gln Val Gly Gln Val Glu Leu Gly Gly Gly
        35                  40                  45

Pro Gly Ala Gly Ser Leu Gln Pro Leu Ala Leu Glu Gly Ser Leu Gln
    50                  55                  60

Lys Arg Gly Ile Val Glu Gln Cys Cys Thr Ser Ile Cys Ser Leu Tyr
65                  70                  75                  80

Gln Leu Glu Asn Tyr Cys Asn
                85
```

<210> SEQ ID NO 47
<211> LENGTH: 21
<212> TYPE: PRT
<213> ORGANISM: Homo sapiens

<400> SEQUENCE: 47

```
Gly Ile Val Glu Gln Cys Cys Thr Ser Ile Cys Ser Leu Tyr Gln Leu
1               5                   10                  15

Glu Asn Tyr Cys Asn
            20
```

<210> SEQ ID NO 48
<211> LENGTH: 30
<212> TYPE: PRT
<213> ORGANISM: Homo sapiens

<400> SEQUENCE: 48

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

<210> SEQ ID NO 49
<211> LENGTH: 21
<212> TYPE: PRT
<213> ORGANISM: Bos taurus

<400> SEQUENCE: 49

```
Gly Ile Val Glu Gln Cys Cys Ala Ser Val Cys Ser Leu Tyr Gln Leu
1               5                   10                  15

Glu Asn Tyr Cys Asn
            20
```

<210> SEQ ID NO 50
<211> LENGTH: 30
<212> TYPE: PRT
<213> ORGANISM: Bos taurus

<400> SEQUENCE: 50

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala
            20                  25                  30
```

<210> SEQ ID NO 51
<211> LENGTH: 12
<212> TYPE: PRT
<213> ORGANISM: Artificial Sequence
<220> FEATURE:
<223> OTHER INFORMATION: Linker peptide

<400> SEQUENCE: 51

```
Lys Asp Asp Asn Pro Asn Leu Pro Arg Leu Val Arg
1               5                   10
```

<210> SEQ ID NO 52
<211> LENGTH: 12
<212> TYPE: PRT
<213> ORGANISM: Artificial Sequence
<220> FEATURE:
<223> OTHER INFORMATION: Linker peptide

<400> SEQUENCE: 52

```
Gly Ala Gly Ser Ser Ser Arg Arg Ala Pro Gln Thr
1               5                   10
```

<210> SEQ ID NO 53
<211> LENGTH: 29
<212> TYPE: PRT
<213> ORGANISM: Unknown
<220> FEATURE:
<223> OTHER INFORMATION: M-VIP

<400> SEQUENCE: 53

```
Met His Ser Asp Ala Val Phe Thr Asp Asn Tyr Thr Arg Leu Arg Lys
1               5                   10                  15

Gln Met Ala Val Lys Lys Tyr Leu Asn Ser Ile Leu Asn
            20                  25
```

<210> SEQ ID NO 54
<211> LENGTH: 50
<212> TYPE: PRT
<213> ORGANISM: Unknown
<220> FEATURE:
<223> OTHER INFORMATION: MAA-VIP

<400> SEQUENCE: 54

```
Met Ala Ala His Ser Asp Ala Val Phe Thr Asp Asn Tyr Thr Arg Leu
1               5                   10                  15

Arg Lys Gln Met Ala Val Lys Lys Tyr Leu Asn Ser Ile Leu Asn Val
            20                  25                  30

Pro Gly Val Gly Val Pro Gly Val Gly Val Pro Gly Gly Gly Val Pro
```

```
                35                  40                  45

Gly Ala
    50

<210> SEQ ID NO 55
<211> LENGTH: 28
<212> TYPE: PRT
<213> ORGANISM: Unknown
<220> FEATURE:
<223> OTHER INFORMATION: VIP

<400> SEQUENCE: 55

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 56
<211> LENGTH: 22
<212> TYPE: PRT
<213> ORGANISM: Unknown
<220> FEATURE:
<223> OTHER INFORMATION: Exendin-4 (9-30)

<400> SEQUENCE: 56

Asp Leu Ser Lys Gln Met Glu Glu Glu Ala Val Arg Leu Phe Ile Glu
1               5                   10                  15

Trp Leu Lys Asn Gly Gly
            20

<210> SEQ ID NO 57
<211> LENGTH: 180
<212> TYPE: DNA
<213> ORGANISM: Artificial Sequence
<220> FEATURE:
<223> OTHER INFORMATION: pPE0248 linker nucleotide

<400> SEQUENCE: 57
ttcccctcta gaaataattt tgtttaactt taagaaggag atatacatat ggtaccgggc    60
gtgggtgtgc cgggctggcc gtgataagct aagggagat ctttattaaa acaaattgaa   120
attcttcctc tatatgtata ccatggcccg cacccacacg gcccgaccgg cactattcga   180

<210> SEQ ID NO 58
<211> LENGTH: 11
<212> TYPE: PRT
<213> ORGANISM: Artificial Sequence
<220> FEATURE:
<223> OTHER INFORMATION: pPE0248 linker peptide

<400> SEQUENCE: 58

Met Val Pro Gly Val Gly Val Pro Gly Trp Pro
1               5                   10

<210> SEQ ID NO 59
<211> LENGTH: 730
<212> TYPE: PRT
<213> ORGANISM: Artificial Sequence
<220> FEATURE:
<223> OTHER INFORMATION: ELP-alpha 144-mer

<400> SEQUENCE: 59

Val Pro Gly Val Gly Val Pro Gly Val Gly Val Pro Gly Val Gly Val
1               5                   10                  15
```

-continued

```
Pro Gly Gly Gly Val Pro Gly Val Gly Val Pro Gly Val Pro
             20                  25                  30
Gly Val Gly Val Pro Gly Val Gly Val Pro Gly Gly Gly Val Pro Gly
             35                  40                  45
Val Gly Val Pro Gly Val Gly Val Pro Gly Val Gly Val Pro Gly Gly
         50                  55                  60
Gly Val Pro Gly Val Gly Val Pro Gly Val Gly Val Pro Gly Val Gly
65                  70                  75                  80
Val Pro Gly Val Gly Val Pro Gly Gly Gly Val Pro Gly Val Gly Val
             85                  90                  95
Pro Gly Val Gly Val Pro Gly Val Gly Val Pro Gly Gly Gly Val Pro
             100                 105                 110
Gly Val Gly Val Pro Gly Val Gly Val Pro Gly Val Gly Val Pro Gly
             115                 120                 125
Val Gly Val Pro Gly Gly Gly Val Pro Gly Val Gly Val Pro Gly Val
         130                 135                 140
Gly Val Pro Gly Val Gly Val Pro Gly Gly Gly Val Pro Gly Val Gly
145                 150                 155                 160
Val Pro Gly Val Gly Val Pro Gly Val Gly Val Pro Gly Val Gly Val
             165                 170                 175
Pro Gly Gly Gly Val Pro Gly Val Gly Val Pro Gly Val Gly Val Pro
             180                 185                 190
Gly Val Gly Val Pro Gly Gly Gly Val Pro Gly Val Gly Val Pro Gly
             195                 200                 205
Val Gly Val Pro Gly Val Gly Val Pro Gly Val Gly Val Pro Gly Gly
         210                 215                 220
Gly Val Pro Gly Val Gly Val Pro Gly Val Gly Val Pro Gly Val Gly
225                 230                 235                 240
Val Pro Gly Gly Gly Val Pro Gly Val Gly Val Pro Gly Val Gly Val
             245                 250                 255
Pro Gly Val Gly Val Pro Gly Val Gly Val Pro Gly Gly Gly Val Pro
             260                 265                 270
Gly Val Gly Val Pro Gly Val Gly Val Pro Gly Val Gly Val Pro Gly
             275                 280                 285
Gly Gly Val Pro Gly Val Gly Val Pro Gly Val Gly Val Pro Gly Val
         290                 295                 300
Gly Val Pro Gly Val Gly Val Pro Gly Gly Gly Val Pro Gly Val Gly
305                 310                 315                 320
Val Pro Gly Val Gly Val Pro Gly Val Gly Val Pro Gly Gly Gly Val
             325                 330                 335
Pro Gly Val Gly Val Pro Gly Val Gly Val Pro Gly Val Gly Val Pro
             340                 345                 350
Gly Val Gly Val Pro Gly Gly Gly Val Pro Gly Val Gly Val Pro Gly
             355                 360                 365
Val Gly Val Pro Gly Val Gly Val Pro Gly Gly Gly Val Pro Gly Val
         370                 375                 380
Gly Val Pro Gly Val Gly Val Pro Gly Val Gly Val Pro Gly Val Gly
385                 390                 395                 400
Val Pro Gly Gly Gly Val Pro Gly Val Gly Val Pro Gly Val Gly Val
             405                 410                 415
Pro Gly Val Gly Val Pro Gly Gly Gly Val Pro Gly Val Gly Val Pro
             420                 425                 430
Gly Val Gly Val Pro Gly Val Gly Val Pro Gly Val Gly Val Pro Gly
```

```
                435                 440                 445
Gly Gly Val Pro Gly Val Gly Val Pro Gly Val Gly Val Pro Gly Val
            450                 455                 460
Gly Val Pro Gly Gly Val Pro Gly Val Gly Val Pro Gly Val Gly
465                 470                 475                 480
Val Pro Gly Val Gly Val Pro Gly Val Gly Val Pro Gly Gly Val
                485                 490                 495
Pro Gly Val Gly Val Pro Gly Gly Val Pro Gly Val Gly Val Pro
            500                 505                 510
Gly Gly Val Pro Gly Val Gly Val Pro Gly Val Gly Val Pro Gly
            515                 520                 525
Val Gly Val Pro Gly Val Gly Val Pro Gly Gly Val Pro Gly Val
            530                 535                 540
Gly Val Pro Gly Val Gly Val Pro Gly Val Gly Val Pro Gly Gly
545                 550                 555                 560
Val Pro Gly Val Gly Val Pro Gly Val Gly Val Pro Gly Val Gly
                565                 570                 575
Pro Gly Val Gly Val Pro Gly Gly Val Pro Gly Val Gly Val Pro
            580                 585                 590
Gly Val Gly Val Pro Gly Val Gly Val Pro Gly Val Gly Val Pro Gly
            595                 600                 605
Val Gly Val Pro Gly Val Gly Val Pro Gly Val Gly Val Pro Gly Val
            610                 615                 620
Gly Val Pro Gly Gly Val Pro Gly Val Gly Val Pro Gly Val Gly
625                 630                 635                 640
Val Pro Gly Val Gly Val Pro Gly Gly Val Pro Gly Val Gly Val
                645                 650                 655
Pro Gly Val Gly Val Pro Gly Val Gly Val Pro Gly Val Gly Val Pro
            660                 665                 670
Gly Gly Gly Val Pro Gly Val Gly Val Pro Gly Val Gly Val Pro Gly
            675                 680                 685
Val Gly Val Pro Gly Gly Gly Val Pro Gly Val Gly Val Pro Gly Val
            690                 695                 700
Gly Val Pro Gly Val Gly Val Pro Gly Val Gly Val Pro Gly Gly Gly
705                 710                 715                 720
Val Pro Gly Val Gly Val Pro Gly Trp Pro
                725                 730

<210> SEQ ID NO 60
<211> LENGTH: 730
<212> TYPE: PRT
<213> ORGANISM: Artificial Sequence
<220> FEATURE:
<223> OTHER INFORMATION: ELPbetaV1 144-mer

<400> SEQUENCE: 60

Val Pro Gly Val Gly Val Pro Gly Val Gly Val Pro Gly Val Gly Val
1               5                   10                  15
Pro Gly Val Gly Val Pro Gly Ala Gly Val Pro Gly Val Gly Val Pro
            20                  25                  30
Gly Val Gly Val Pro Gly Val Gly Val Pro Gly Val Gly Val Pro Gly
            35                  40                  45
Ala Gly Val Pro Gly Val Gly Val Pro Gly Val Gly Val Pro Gly Val
            50                  55                  60
Gly Val Pro Gly Ala Gly Val Pro Gly Val Gly Val Pro Gly Val Gly
```

-continued

```
            65                  70                  75                  80
Val Pro Gly Val Gly Val Pro Gly Val Gly Val Pro Gly Ala Gly Val
                    85                  90                  95
Pro Gly Val Gly Val Pro Gly Val Gly Val Pro Gly Val Gly Val Pro
                   100                 105                 110
Gly Ala Gly Val Pro Gly Val Gly Val Pro Gly Val Gly Val Pro Gly
                   115                 120                 125
Val Gly Val Pro Gly Val Gly Val Pro Gly Ala Gly Val Pro Gly Val
                   130                 135                 140
Gly Val Pro Gly Val Gly Val Pro Gly Val Gly Val Pro Gly Ala Gly
145                 150                 155                 160
Val Pro Gly Val Gly Val Pro Gly Val Gly Val Pro Gly Val Gly Val
                   165                 170                 175
Pro Gly Val Gly Val Pro Gly Ala Gly Val Pro Gly Val Gly Val Pro
                   180                 185                 190
Gly Val Gly Val Pro Gly Val Gly Val Pro Gly Ala Gly Val Pro Gly
                   195                 200                 205
Val Gly Val Pro Gly Val Gly Val Pro Gly Val Gly Val Pro Gly Val
                   210                 215                 220
Gly Val Pro Gly Ala Gly Val Pro Gly Val Gly Val Pro Gly Val Gly
225                 230                 235                 240
Val Pro Gly Val Gly Val Pro Gly Ala Gly Val Pro Gly Val Gly Val
                   245                 250                 255
Pro Gly Val Gly Val Pro Gly Val Gly Val Pro Gly Val Gly Val Pro
                   260                 265                 270
Gly Ala Gly Val Pro Gly Val Gly Val Pro Gly Val Gly Val Pro Gly
                   275                 280                 285
Val Gly Val Pro Gly Ala Gly Val Pro Gly Val Gly Val Pro Gly Val
                   290                 295                 300
Gly Val Pro Gly Val Gly Val Pro Gly Val Gly Val Pro Gly Ala Gly
305                 310                 315                 320
Val Pro Gly Val Gly Val Pro Gly Val Gly Val Pro Gly Val Gly Val
                   325                 330                 335
Pro Gly Ala Gly Val Pro Gly Val Gly Val Pro Gly Val Gly Val Pro
                   340                 345                 350
Gly Val Gly Val Pro Gly Val Gly Val Pro Gly Ala Gly Val Pro Gly
                   355                 360                 365
Val Gly Val Pro Gly Val Gly Val Pro Gly Val Gly Val Pro Gly Ala
                   370                 375                 380
Gly Val Pro Gly Val Gly Val Pro Gly Val Gly Val Pro Gly Val Gly
385                 390                 395                 400
Val Pro Gly Val Gly Val Pro Gly Ala Gly Val Pro Gly Val Gly Val
                   405                 410                 415
Pro Gly Val Gly Val Pro Gly Val Gly Val Pro Gly Ala Gly Val Pro
                   420                 425                 430
Gly Val Gly Val Pro Gly Val Gly Val Pro Gly Val Gly Val Pro Gly
                   435                 440                 445
Val Gly Val Pro Gly Ala Gly Val Pro Gly Val Gly Val Pro Gly Val
                   450                 455                 460
Gly Val Pro Gly Val Gly Val Pro Gly Ala Gly Val Pro Gly Val Gly
465                 470                 475                 480
Val Pro Gly Val Gly Val Pro Gly Val Gly Val Pro Gly Val Gly Val
                   485                 490                 495
```

```
Pro Gly Ala Gly Val Pro Val Gly Val Pro Val Gly Val Pro
            500                 505                 510
Gly Val Gly Val Pro Gly Ala Gly Val Pro Gly Val Gly Val Pro Gly
        515                 520                 525
Val Gly Val Pro Gly Val Gly Val Pro Gly Val Gly Val Pro Gly Ala
    530                 535                 540
Gly Val Pro Gly Val Gly Val Pro Gly Val Gly Val Pro Gly Val Gly
545                 550                 555                 560
Val Pro Gly Ala Gly Val Pro Gly Val Gly Val Pro Gly Val Gly Val
                565                 570                 575
Pro Gly Val Gly Val Pro Gly Val Gly Val Pro Gly Ala Gly Val Pro
            580                 585                 590
Gly Val Gly Val Pro Gly Val Gly Val Pro Gly Val Gly Val Pro Gly
        595                 600                 605
Ala Gly Val Pro Gly Val Gly Val Pro Gly Val Gly Val Pro Gly Val
    610                 615                 620
Gly Val Pro Gly Val Gly Val Pro Gly Ala Gly Val Pro Gly Val Gly
625                 630                 635                 640
Val Pro Gly Val Gly Val Pro Gly Val Gly Val Pro Gly Ala Gly Val
                645                 650                 655
Pro Gly Val Gly Val Pro Gly Val Gly Val Pro Gly Val Gly Val Pro
            660                 665                 670
Gly Val Gly Val Pro Gly Ala Gly Val Pro Gly Val Gly Val Pro Gly
        675                 680                 685
Val Gly Val Pro Gly Val Gly Val Pro Gly Ala Gly Val Pro Gly Val
    690                 695                 700
Gly Val Pro Gly Val Gly Val Pro Gly Val Gly Val Pro Gly Val Gly
705                 710                 715                 720
Val Pro Gly Ala Gly Val Pro Gly Trp Pro
                725                 730

<210> SEQ ID NO 61
<211> LENGTH: 730
<212> TYPE: PRT
<213> ORGANISM: artificial sequence
<220> FEATURE:
<223> OTHER INFORMATION: ELP gamma 144-mer

<400> SEQUENCE: 61

Val Pro Gly Val Gly Val Pro Gly Val Gly Val Pro Gly Val Gly Val
1               5                   10                  15
Pro Gly Gly Gly Val Pro Gly Val Gly Val Pro Gly Val Gly Val Pro
            20                  25                  30
Gly Val Gly Val Pro Gly Val Gly Val Pro Gly Gly Val Pro Gly
        35                  40                  45
Val Gly Val Pro Gly Val Gly Val Pro Gly Val Gly Val Pro Gly Val
    50                  55                  60
Gly Val Pro Gly Ala Gly Val Pro Gly Val Gly Val Pro Gly Val Gly
65                  70                  75                  80
Val Pro Gly Val Gly Val Pro Gly Val Gly Val Pro Gly Ala Gly Val
                85                  90                  95
Pro Gly Val Gly Val Pro Gly Val Gly Val Pro Gly Gly Gly Val Pro
            100                 105                 110
Gly Val Gly Val Pro Gly Val Gly Val Pro Gly Val Gly Val Pro Gly
        115                 120                 125
```

```
Val Gly Val Pro Gly Gly Val Pro Gly Val Pro Gly Val
    130                 135                 140
Gly Val Pro Gly Val Gly Val Pro Gly Val Pro Gly Ala Gly
145                 150                 155                 160
Val Pro Gly Val Gly Val Pro Gly Val Gly Val Pro Gly Val Gly Val
                    165                 170                 175
Pro Gly Val Gly Val Pro Gly Ala Gly Val Pro Gly Val Gly Val Pro
                180                 185                 190
Gly Val Gly Val Pro Gly Gly Val Pro Gly Val Gly Val Pro Gly
            195                 200                 205
Val Gly Val Pro Gly Val Gly Val Pro Gly Val Gly Val Pro Gly Gly
    210                 215                 220
Gly Val Pro Gly Val Gly Val Pro Gly Val Gly Val Pro Gly Val Gly
225                 230                 235                 240
Val Pro Gly Val Gly Val Pro Gly Ala Gly Val Pro Gly Val Gly Val
                    245                 250                 255
Pro Gly Val Gly Val Pro Gly Val Gly Val Pro Gly Val Gly Val Pro
                260                 265                 270
Gly Ala Gly Val Pro Gly Val Gly Val Pro Gly Val Gly Val Pro Gly
            275                 280                 285
Gly Gly Val Pro Gly Val Gly Val Pro Gly Val Gly Val Pro Gly Val
290                 295                 300
Gly Val Pro Gly Val Gly Val Pro Gly Gly Val Pro Gly Val Gly
305                 310                 315                 320
Val Pro Gly Val Gly Val Pro Gly Val Gly Val Pro Gly Val Gly Val
                    325                 330                 335
Pro Gly Ala Gly Val Pro Gly Val Gly Val Pro Gly Val Gly Val Pro
                340                 345                 350
Gly Val Gly Val Pro Gly Val Gly Val Pro Gly Ala Gly Val Pro Gly
            355                 360                 365
Val Gly Val Pro Gly Val Gly Val Pro Gly Gly Gly Val Pro Gly Val
    370                 375                 380
Gly Val Pro Gly Val Gly Val Pro Gly Val Gly Val Pro Gly Val Gly
385                 390                 395                 400
Val Pro Gly Gly Gly Val Pro Gly Val Gly Val Pro Gly Val Gly Val
                    405                 410                 415
Pro Gly Val Gly Val Pro Gly Val Gly Val Pro Gly Ala Gly Val Pro
                420                 425                 430
Gly Val Gly Val Pro Gly Val Gly Val Pro Gly Val Gly Val Pro Gly
            435                 440                 445
Val Gly Val Pro Gly Ala Gly Val Pro Gly Val Gly Val Pro Gly Val
    450                 455                 460
Gly Val Pro Gly Gly Gly Val Pro Gly Val Gly Val Pro Gly Val Gly
465                 470                 475                 480
Val Pro Gly Val Gly Val Pro Gly Val Gly Val Pro Gly Gly Gly Val
                    485                 490                 495
Pro Gly Val Gly Val Pro Gly Val Gly Val Pro Gly Val Gly Val Pro
                500                 505                 510
Gly Val Gly Val Pro Gly Ala Gly Val Pro Gly Val Gly Val Pro Gly
            515                 520                 525
Val Gly Val Pro Gly Val Gly Val Pro Gly Val Gly Val Pro Gly Ala
    530                 535                 540
```

Gly Val Pro Gly Val Gly Val Pro Gly Val Pro Gly Gly Gly
545                 550                 555                 560

Val Pro Gly Val Gly Val Pro Gly Val Gly Val Pro Gly Val Gly Val
                565                 570                 575

Pro Gly Val Gly Val Pro Gly Gly Val Pro Gly Val Gly Val Pro
            580                 585                 590

Gly Val Gly Val Pro Gly Val Gly Val Pro Gly Val Gly Val Pro Gly
        595                 600                 605

Ala Gly Val Pro Gly Val Gly Val Pro Gly Val Gly Val Pro Gly Val
    610                 615                 620

Gly Val Pro Gly Val Gly Val Pro Gly Ala Gly Val Pro Gly Val Gly
625                 630                 635                 640

Val Pro Gly Val Gly Val Pro Gly Gly Val Pro Gly Val Gly Val
            645                 650                 655

Pro Gly Val Gly Val Pro Gly Val Gly Val Pro Gly Val Gly Val Pro
            660                 665                 670

Gly Gly Gly Val Pro Gly Val Gly Val Pro Gly Val Gly Val Pro Gly
        675                 680                 685

Val Gly Val Pro Gly Val Gly Val Pro Gly Ala Gly Val Pro Gly Val
    690                 695                 700

Gly Val Pro Gly Val Gly Val Pro Gly Val Gly Val Pro Gly Val Gly
705                 710                 715                 720

Val Pro Gly Ala Gly Val Pro Gly Trp Pro
            725                 730

<210> SEQ ID NO 62
<211> LENGTH: 730
<212> TYPE: PRT
<213> ORGANISM: artificial sequence
<220> FEATURE:
<223> OTHER INFORMATION: ELP delta 144-mer

<400> SEQUENCE: 62

Val Pro Gly Val Gly Val Pro Gly Val Gly Val Pro Gly Val Gly Ala
1               5                   10                  15

Pro Gly Val Gly Val Pro Gly Val Gly Ala Pro Gly Val Gly Val Pro
            20                  25                  30

Gly Val Gly Ala Pro Gly Val Gly Val Pro Gly Val Gly Ala Pro Gly
        35                  40                  45

Val Gly Val Pro Gly Val Gly Val Pro Gly Val Gly Ala Pro Gly Val
    50                  55                  60

Gly Val Pro Gly Val Gly Ala Pro Gly Val Gly Val Pro Gly Val Gly
65                  70                  75                  80

Ala Pro Gly Val Gly Val Pro Gly Val Gly Ala Pro Gly Val Gly Val
                85                  90                  95

Pro Gly Val Gly Val Pro Gly Val Gly Ala Pro Gly Val Gly Val Pro
            100                 105                 110

Gly Val Gly Ala Pro Gly Val Gly Val Pro Gly Val Gly Ala Pro Gly
        115                 120                 125

Val Gly Val Pro Gly Val Gly Ala Pro Gly Val Gly Val Pro Gly Val
    130                 135                 140

Gly Val Pro Gly Val Gly Ala Pro Gly Val Gly Val Pro Gly Val Gly
145                 150                 155                 160

Ala Pro Gly Val Gly Val Pro Gly Val Gly Ala Pro Gly Val Gly Val
                165                 170                 175

Pro Gly Val Gly Ala Pro Gly Val Gly Val Pro Gly Val Pro
                180                 185                 190

Gly Val Gly Ala Pro Gly Val Gly Val Pro Gly Val Gly Ala Pro Gly
            195                 200                 205

Val Gly Val Pro Gly Val Gly Ala Pro Gly Val Gly Val Pro Gly Val
        210                 215                 220

Gly Ala Pro Gly Val Gly Val Pro Gly Val Gly Val Pro Gly Val Gly
225                 230                 235                 240

Ala Pro Gly Val Gly Val Pro Gly Val Gly Ala Pro Gly Val Gly Val
                245                 250                 255

Pro Gly Val Gly Ala Pro Gly Val Gly Val Pro Gly Val Gly Ala Pro
            260                 265                 270

Gly Val Gly Val Pro Gly Val Gly Val Pro Gly Val Gly Ala Pro Gly
        275                 280                 285

Val Gly Val Pro Gly Val Gly Ala Pro Gly Val Gly Val Pro Gly Val
        290                 295                 300

Gly Ala Pro Gly Val Gly Val Pro Gly Val Gly Ala Pro Gly Val Gly
305                 310                 315                 320

Val Pro Gly Val Gly Val Pro Gly Val Gly Ala Pro Gly Val Gly Val
                325                 330                 335

Pro Gly Val Gly Ala Pro Gly Val Gly Val Pro Gly Val Gly Ala Pro
            340                 345                 350

Gly Val Gly Val Pro Gly Val Gly Ala Pro Gly Val Gly Val Pro Gly
        355                 360                 365

Val Gly Val Pro Gly Val Gly Ala Pro Gly Val Gly Val Pro Gly Val
        370                 375                 380

Gly Ala Pro Gly Val Gly Val Pro Gly Val Gly Ala Pro Gly Val Gly
385                 390                 395                 400

Val Pro Gly Val Gly Ala Pro Gly Val Gly Val Pro Gly Val Gly Val
                405                 410                 415

Pro Gly Val Gly Ala Pro Gly Val Gly Val Pro Gly Val Gly Ala Pro
            420                 425                 430

Gly Val Gly Val Pro Gly Val Gly Ala Pro Gly Val Gly Val Pro Gly
        435                 440                 445

Val Gly Ala Pro Gly Val Gly Val Pro Gly Val Gly Val Pro Gly Val
        450                 455                 460

Gly Ala Pro Gly Val Gly Val Pro Gly Val Gly Ala Pro Gly Val Gly
465                 470                 475                 480

Val Pro Gly Val Gly Ala Pro Gly Val Gly Val Pro Gly Val Gly Ala
                485                 490                 495

Pro Gly Val Gly Val Pro Gly Val Gly Val Pro Gly Val Gly Ala Pro
            500                 505                 510

Gly Val Gly Val Pro Gly Val Gly Ala Pro Gly Val Gly Val Pro Gly
        515                 520                 525

Val Gly Ala Pro Gly Val Gly Val Pro Gly Val Gly Ala Pro Gly Val
        530                 535                 540

Gly Val Pro Gly Val Gly Val Pro Gly Val Gly Ala Pro Gly Val Gly
545                 550                 555                 560

Val Pro Gly Val Gly Ala Pro Gly Val Gly Val Pro Gly Val Gly Ala
                565                 570                 575

Pro Gly Val Gly Val Pro Gly Val Gly Ala Pro Gly Val Gly Val Pro
            580                 585                 590

Gly Val Gly Val Pro Gly Val Gly Ala Pro Gly Val Gly Val Pro Gly

```
                 595                 600                 605

Val Gly Ala Pro Gly Val Gly Val Pro Gly Val Gly Ala Pro Gly Val
            610                 615                 620

Gly Val Pro Gly Val Gly Ala Pro Gly Val Gly Val Pro Gly Val Gly
625                 630                 635                 640

Val Pro Gly Val Gly Ala Pro Gly Val Gly Val Pro Gly Val Gly Ala
                645                 650                 655

Pro Gly Val Gly Val Pro Gly Val Gly Ala Pro Gly Val Gly Val Pro
            660                 665                 670

Gly Val Gly Ala Pro Gly Val Gly Val Pro Gly Val Gly Val Pro Gly
                675                 680                 685

Val Gly Ala Pro Gly Val Gly Val Pro Gly Val Gly Ala Pro Gly Val
            690                 695                 700

Gly Val Pro Gly Val Gly Ala Pro Gly Val Gly Val Pro Gly Val Gly
705                 710                 715                 720

Ala Pro Gly Val Gly Val Pro Gly Trp Pro
                725                 730

<210> SEQ ID NO 63
<211> LENGTH: 45
<212> TYPE: PRT
<213> ORGANISM: Artificial sequence
<220> FEATURE:
<223> OTHER INFORMATION: alpha ELP component sequence

<400> SEQUENCE: 63

Val Pro Gly Val Gly Val Pro Gly Gly Gly Val Pro Gly Val Gly Val
1               5                   10                  15

Pro Gly Val Gly Val Pro Gly Val Gly Val Pro Gly Val Gly Val Pro
            20                  25                  30

Gly Gly Gly Val Pro Gly Val Gly Val Pro Gly Val Gly
        35                  40                  45

<210> SEQ ID NO 64
<211> LENGTH: 45
<212> TYPE: PRT
<213> ORGANISM: Artificial Sequence
<220> FEATURE:
<223> OTHER INFORMATION: BetaV1 ELP component

<400> SEQUENCE: 64

Val Pro Gly Val Gly Val Pro Gly Val Gly Val Pro Gly Ala Gly Val
1               5                   10                  15

Pro Gly Val Gly Val Pro Gly Val Gly Val Pro Gly Val Gly Val Pro
            20                  25                  30

Gly Val Gly Val Pro Gly Ala Gly Val Pro Gly Val Gly
        35                  40                  45

<210> SEQ ID NO 65
<211> LENGTH: 45
<212> TYPE: PRT
<213> ORGANISM: Artificial Sequence
<220> FEATURE:
<223> OTHER INFORMATION: BetaV2 ELP component

<400> SEQUENCE: 65

Val Pro Gly Ala Gly Val Pro Gly Val Gly Pro Gly Ala Gly Val
1               5                   10                  15

Pro Gly Val Gly Val Pro Gly Val Gly Val Pro Gly Ala Gly Val Pro
            20                  25                  30
```

```
Gly Val Gly Val Pro Gly Ala Gly Val Pro Gly Val Gly
        35                  40                  45

<210> SEQ ID NO 66
<211> LENGTH: 45
<212> TYPE: PRT
<213> ORGANISM: Artificial Sequence
<220> FEATURE:
<223> OTHER INFORMATION: Delta ELP component

<400> SEQUENCE: 66

Val Pro Gly Val Gly Ala Pro Gly Val Gly Val Pro Gly Val Gly Ala
1               5                   10                  15

Pro Gly Val Gly Val Pro Gly Val Gly Ala Pro Gly Val Gly Val Pro
            20                  25                  30

Gly Val Gly Ala Pro Gly Val Gly Val Pro Gly Val Gly
        35                  40                  45

<210> SEQ ID NO 67
<211> LENGTH: 180
<212> TYPE: DNA
<213> ORGANISM: Artificial Sequence
<220> FEATURE:
<223> OTHER INFORMATION: pPE0248 linker complement

<400> SEQUENCE: 67 aagggagat ctttattaaa acaaattgaa attcttcctc tatatgtata ccatggcccg    60
cacccacacg gcccgaccgg cactattcga ttcccctcta gaaataattt tgtttaactt   120
taagaaggag atatacatat ggtaccgggc gtgggtgtgc cgggctggcc gtgataagct   180

<210> SEQ ID NO 68
<211> LENGTH: 730
<212> TYPE: PRT
<213> ORGANISM: Artificial Sequence
<220> FEATURE:
<223> OTHER INFORMATION: alpha ELP 144-mer

<400> SEQUENCE: 68

Val Pro Gly Val Gly Val Pro Gly Val Gly Val Pro Gly Val Gly Val
1               5                   10                  15

Pro Gly Gly Gly Val Pro Gly Val Gly Val Pro Gly Val Gly Val Pro
            20                  25                  30

Gly Val Gly Val Pro Gly Val Gly Val Pro Gly Gly Gly Val Pro Gly
        35                  40                  45

Val Gly Val Pro Gly Val Gly Val Pro Gly Val Gly Val Pro Gly Gly
    50                  55                  60

Gly Val Pro Gly Val Gly Val Pro Gly Val Gly Val Pro Gly Val Gly
65                  70                  75                  80

Val Pro Gly Val Gly Val Pro Gly Gly Gly Val Pro Gly Val Gly Val
                85                  90                  95

Pro Gly Val Gly Val Pro Gly Val Gly Val Pro Gly Gly Gly Val Pro
            100                 105                 110

Gly Val Gly Val Pro Gly Val Gly Val Pro Gly Val Gly Val Pro Gly
        115                 120                 125

Val Gly Val Pro Gly Gly Gly Val Pro Gly Val Gly Val Pro Gly Val
    130                 135                 140

Gly Val Pro Gly Val Gly Val Pro Gly Gly Gly Val Pro Gly Val Gly
145                 150                 155                 160
```

```
Val Pro Gly Val Gly Val Pro Gly Val Gly Val Pro Gly Val
                165                 170                 175

Pro Gly Gly Gly Val Pro Gly Val Gly Val Pro Gly Val Gly Val Pro
            180                 185                 190

Gly Val Gly Val Pro Gly Gly Val Pro Gly Val Gly Val Pro Gly
        195                 200                 205

Val Gly Val Pro Gly Val Gly Val Pro Gly Val Gly Val Pro Gly Gly
        210                 215                 220

Gly Val Pro Gly Val Gly Val Pro Gly Val Gly Val Pro Gly Val Gly
225                 230                 235                 240

Val Pro Gly Gly Gly Val Pro Gly Val Gly Val Pro Gly Val Gly Val
                245                 250                 255

Pro Gly Val Gly Val Pro Gly Gly Val Pro Gly Val Gly Gly Val Pro
            260                 265                 270

Gly Val Gly Val Pro Gly Val Gly Val Pro Gly Val Gly Val Pro Gly
        275                 280                 285

Gly Gly Val Pro Gly Val Gly Val Pro Gly Val Gly Val Pro Gly Val
    290                 295                 300

Gly Val Pro Gly Val Gly Val Pro Gly Gly Val Pro Gly Val Gly Val
305                 310                 315                 320

Val Pro Gly Val Gly Val Pro Gly Val Gly Val Pro Gly Gly Gly Val
                325                 330                 335

Pro Gly Val Gly Val Pro Gly Val Gly Val Pro Gly Val Gly Val Pro
            340                 345                 350

Gly Val Gly Val Pro Gly Gly Val Pro Gly Val Gly Val Pro Gly
        355                 360                 365

Val Gly Val Pro Gly Val Gly Val Pro Gly Gly Gly Val Pro Gly Val
        370                 375                 380

Gly Val Pro Gly Val Gly Val Pro Gly Val Gly Val Pro Gly Val Gly
385                 390                 395                 400

Val Pro Gly Gly Gly Val Pro Gly Val Gly Val Pro Gly Val Gly Val
                405                 410                 415

Pro Gly Val Gly Val Pro Gly Gly Gly Val Pro Gly Val Gly Val Pro
            420                 425                 430

Gly Val Gly Val Pro Gly Val Gly Val Pro Gly Val Gly Val Pro Gly
        435                 440                 445

Gly Gly Val Pro Gly Val Gly Val Pro Gly Val Gly Val Pro Gly Val
    450                 455                 460

Gly Val Pro Gly Gly Gly Val Pro Gly Val Gly Val Pro Gly Val Gly
465                 470                 475                 480

Val Pro Gly Val Gly Val Pro Gly Val Gly Val Pro Gly Gly Gly Val
                485                 490                 495

Pro Gly Val Gly Val Pro Gly Val Gly Val Pro Gly Val Gly Val Pro
            500                 505                 510

Gly Gly Gly Val Pro Gly Val Gly Val Pro Gly Val Gly Val Pro Gly
        515                 520                 525

Val Gly Val Pro Gly Val Gly Val Pro Gly Gly Gly Val Pro Gly Val
        530                 535                 540

Gly Val Pro Gly Val Gly Val Pro Gly Val Gly Val Pro Gly Gly Gly
545                 550                 555                 560

Val Pro Gly Val Gly Val Pro Gly Val Gly Val Pro Gly Val Gly Val
                565                 570                 575

Pro Gly Val Gly Val Pro Gly Gly Gly Val Pro Gly Val Gly Val Pro
```

```
                     580                 585                 590
Gly Val Gly Val Pro Gly Val Gly Val Pro Gly Gly Val Pro Gly
                595                 600                 605

Val Gly Val Pro Gly Val Gly Val Pro Gly Val Gly Val Pro Gly Val
                610                 615                 620

Gly Val Pro Gly Gly Val Pro Gly Val Gly Val Pro Gly Val Gly
625                 630                 635                 640

Val Pro Gly Val Gly Val Pro Gly Gly Val Pro Gly Val Gly Val
                645                 650                 655

Pro Gly Val Gly Val Pro Gly Val Gly Val Pro Gly Val Gly Val Pro
                660                 665                 670

Gly Gly Val Pro Gly Val Gly Val Pro Gly Val Gly Val Pro Gly
                675                 680                 685

Val Gly Val Pro Gly Gly Val Pro Gly Val Gly Val Pro Gly Val
                690                 695                 700

Gly Val Pro Gly Val Gly Val Pro Gly Val Gly Val Pro Gly Gly
705                 710                 715                 720

Val Pro Gly Val Gly Val Pro Gly Trp Pro
                725                 730

<210> SEQ ID NO 69
<211> LENGTH: 730
<212> TYPE: PRT
<213> ORGANISM: Artificial Sequence
<220> FEATURE:
<223> OTHER INFORMATION: betaV1 ELP 144-mer

<400> SEQUENCE: 69

Val Pro Gly Val Gly Val Pro Gly Val Gly Val Pro Gly Val Gly Val
1               5                   10                  15

Pro Gly Val Gly Val Pro Gly Ala Gly Val Pro Gly Val Gly Val Pro
                20                  25                  30

Gly Val Gly Val Pro Gly Val Gly Val Pro Gly Val Gly Val Pro Gly
                35                  40                  45

Ala Gly Val Pro Gly Val Gly Val Pro Gly Val Gly Val Pro Gly Val
                50                  55                  60

Gly Val Pro Gly Ala Gly Val Pro Gly Val Gly Val Pro Gly Val Gly
65                  70                  75                  80

Val Pro Gly Val Gly Val Pro Gly Val Gly Val Pro Gly Ala Gly Val
                85                  90                  95

Pro Gly Val Gly Val Pro Gly Val Gly Val Pro Gly Val Gly Val Pro
                100                 105                 110

Gly Ala Gly Val Pro Gly Val Gly Val Pro Gly Val Gly Val Pro Gly
                115                 120                 125

Val Gly Val Pro Gly Val Gly Val Pro Gly Ala Gly Val Pro Gly Val
                130                 135                 140

Gly Val Pro Gly Val Gly Val Pro Gly Val Gly Val Pro Gly Ala Gly
145                 150                 155                 160

Val Pro Gly Val Gly Val Pro Gly Val Gly Val Pro Gly Val Gly Val
                165                 170                 175

Pro Gly Val Gly Val Pro Gly Ala Gly Val Pro Gly Val Gly Val Pro
                180                 185                 190

Gly Val Gly Val Pro Gly Val Gly Val Pro Gly Ala Gly Val Pro Gly
                195                 200                 205

Val Gly Val Pro Gly Val Gly Val Pro Gly Val Gly Val Pro Gly Val
```

-continued

```
            210                 215                 220
Gly Val Pro Gly Ala Gly Val Pro Gly Val Pro Gly Val Gly
225                 230                 235                 240

Val Pro Gly Val Gly Val Pro Gly Ala Gly Val Pro Gly Val
                245                 250                 255

Pro Gly Val Gly Val Pro Gly Val Gly Val Pro Gly Val Pro
                260                 265                 270

Gly Ala Gly Val Pro Gly Val Gly Val Pro Gly Val Gly Val
            275                 280                 285

Pro Gly Val Gly Val Pro Gly Ala Gly Val Pro Gly Val Gly
                290                 295                 300

Val Pro Gly Val Gly Val Pro Gly Val Gly Val Pro Gly Ala
305                 310                 315                 320

Gly Val Pro Gly Val Gly Val Pro Gly Val Gly Val Pro Gly
                325                 330                 335

Val Gly Val Pro Gly Ala Gly Val Pro Gly Val Gly Val Pro
            340                 345                 350

Gly Val Gly Val Pro Gly Val Gly Val Pro Gly Ala Gly Val
                355                 360                 365

Pro Gly Val Gly Val Pro Gly Val Gly Val Pro Gly Val Gly
            370                 375                 380

Val Pro Gly Ala Gly Val Pro Gly Val Gly Val Pro Gly Val
385                 390                 395                 400

Gly Val Pro Gly Val Gly Val Pro Gly Ala Gly Val Pro Gly
                405                 410                 415

Val Gly Val Pro Gly Val Gly Val Pro Gly Val Gly Val Pro
                420                 425                 430

Gly Ala Gly Val Pro Gly Val Gly Val Pro Gly Val Gly Val
            435                 440                 445

Pro Gly Val Gly Val Pro Gly Ala Gly Val Pro Gly Val Gly
                450                 455                 460

Val Pro Gly Val Gly Val Pro Gly Val Gly Val Pro Gly Ala
465                 470                 475                 480

Gly Val Pro Gly Val Gly Val Pro Gly Val Gly Val Pro Gly
                485                 490                 495

Val Gly Val Pro Gly Ala Gly Val Pro Gly Val Gly Val Pro
            500                 505                 510

Gly Val Gly Val Pro Gly Val Gly Val Pro Gly Ala Gly Val
            515                 520                 525

Pro Gly Val Gly Val Pro Gly Val Gly Val Pro Gly Val Gly
            530                 535                 540

Val Pro Gly Ala Gly Val Pro Gly Val Gly Val Pro Gly Val
545                 550                 555                 560

Gly Val Pro Gly Val Gly Val Pro Gly Ala Gly Val Pro Gly
                565                 570                 575

Val Gly Val Pro Gly Val Gly Val Pro Gly Val Gly Val Pro
            580                 585                 590

Gly Ala Gly Val Pro Gly Val Gly Val Pro Gly Val Gly Val
                595                 600                 605

Pro Gly Val Gly Val Pro Gly Ala Gly Val Pro Gly Val Gly
            610                 615                 620

Val Pro Gly Val Gly Val Pro Gly Val Gly Val Pro Gly Ala
625                 630                 635                 640
```

```
Val Pro Gly Val Gly Val Pro Gly Val Gly Val Pro Gly Ala Gly Val
                645                 650                 655

Pro Gly Val Gly Val Pro Gly Val Gly Val Pro Gly Val Gly Val Pro
            660                 665                 670

Gly Val Gly Val Pro Gly Ala Gly Val Pro Gly Val Gly Val Pro Gly
        675                 680                 685

Val Gly Val Pro Gly Val Gly Val Pro Gly Ala Gly Val Pro Gly Val
    690                 695                 700

Gly Val Pro Gly Val Gly Val Pro Gly Val Gly Val Pro Gly Val Gly
705                 710                 715                 720

Val Pro Gly Ala Gly Val Pro Gly Trp Pro
                725                 730

<210> SEQ ID NO 70
<211> LENGTH: 730
<212> TYPE: PRT
<213> ORGANISM: Artificial Sequence
<220> FEATURE:
<223> OTHER INFORMATION: betaV2 ELP 144-mer

<400> SEQUENCE: 70

Val Pro Gly Val Gly Val Pro Gly Val Gly Val Pro Gly Ala Gly Val
1               5                   10                  15

Pro Gly Val Gly Val Pro Gly Ala Gly Val Pro Gly Val Gly Val Pro
            20                  25                  30

Gly Val Gly Val Pro Gly Ala Gly Val Pro Gly Val Gly Val Pro Gly
        35                  40                  45

Ala Gly Val Pro Gly Val Gly Val Pro Gly Ala Gly Val Pro Gly Val
    50                  55                  60

Gly Val Pro Gly Ala Gly Val Pro Gly Val Gly Val Pro Gly Val Gly
65                  70                  75                  80

Val Pro Gly Ala Gly Val Pro Gly Val Gly Val Pro Gly Ala Gly Val
                85                  90                  95

Pro Gly Val Gly Val Pro Gly Ala Gly Val Pro Gly Val Gly Val Pro
            100                 105                 110

Gly Ala Gly Val Pro Gly Val Gly Val Pro Gly Val Gly Val Pro Gly
        115                 120                 125

Ala Gly Val Pro Gly Val Gly Val Pro Gly Ala Gly Val Pro Gly Val
    130                 135                 140

Gly Val Pro Gly Ala Gly Val Pro Gly Val Gly Val Pro Gly Ala Gly
145                 150                 155                 160

Val Pro Gly Val Gly Val Pro Gly Val Gly Val Pro Gly Ala Gly Val
                165                 170                 175

Pro Gly Val Gly Val Pro Gly Ala Gly Val Pro Gly Val Gly Val Pro
            180                 185                 190

Gly Ala Gly Val Pro Gly Val Gly Val Pro Gly Ala Gly Val Pro Gly
        195                 200                 205

Val Gly Val Pro Gly Val Gly Val Pro Gly Ala Gly Val Pro Gly Val
    210                 215                 220

Gly Val Pro Gly Ala Gly Val Pro Gly Val Gly Val Pro Gly Ala Gly
225                 230                 235                 240

Val Pro Gly Val Gly Val Pro Gly Ala Gly Val Pro Gly Val Gly Val
                245                 250                 255

Pro Gly Val Gly Val Pro Gly Ala Gly Val Pro Gly Val Gly Val Pro
            260                 265                 270
```

```
Gly Ala Gly Val Pro Gly Val Gly Val Pro Gly Ala Gly Val Pro Gly
            275                 280                 285
Val Gly Val Pro Gly Ala Gly Val Pro Gly Val Gly Val Pro Gly Val
            290                 295                 300
Gly Val Pro Gly Ala Gly Val Pro Gly Val Gly Val Pro Gly Ala Gly
305                 310                 315                 320
Val Pro Gly Val Gly Val Pro Gly Ala Gly Val Pro Gly Val Gly Val
            325                 330                 335
Pro Gly Ala Gly Val Pro Gly Val Gly Val Pro Gly Val Gly Val Pro
            340                 345                 350
Gly Ala Gly Val Pro Gly Val Gly Val Pro Gly Ala Gly Val Pro Gly
            355                 360                 365
Val Gly Val Pro Gly Ala Gly Val Pro Gly Val Gly Val Pro Gly Ala
            370                 375                 380
Gly Val Pro Gly Val Gly Val Pro Gly Val Gly Val Pro Gly Ala Gly
385                 390                 395                 400
Val Pro Gly Val Gly Val Pro Gly Ala Gly Val Pro Gly Val Gly Val
            405                 410                 415
Pro Gly Ala Gly Val Pro Gly Val Gly Val Pro Gly Ala Gly Val Pro
            420                 425                 430
Gly Val Gly Val Pro Gly Val Gly Val Pro Gly Ala Gly Val Pro Gly
            435                 440                 445
Val Gly Val Pro Gly Ala Gly Val Pro Gly Val Gly Val Pro Gly Ala
            450                 455                 460
Gly Val Pro Gly Val Gly Val Pro Gly Ala Gly Val Pro Gly Val Gly
465                 470                 475                 480
Val Pro Gly Val Gly Val Pro Gly Ala Gly Val Pro Gly Val Gly Val
            485                 490                 495
Pro Gly Ala Gly Val Pro Gly Val Gly Val Pro Gly Ala Gly Val Pro
            500                 505                 510
Gly Val Gly Val Pro Gly Ala Gly Val Pro Gly Val Gly Val Pro Gly
            515                 520                 525
Val Gly Val Pro Gly Ala Gly Val Pro Gly Val Gly Val Pro Gly Ala
            530                 535                 540
Gly Val Pro Gly Val Gly Val Pro Gly Ala Gly Val Pro Gly Val Gly
545                 550                 555                 560
Val Pro Gly Ala Gly Val Pro Gly Val Gly Val Pro Gly Val Gly Val
            565                 570                 575
Pro Gly Ala Gly Val Pro Gly Val Gly Val Pro Gly Ala Gly Val Pro
            580                 585                 590
Gly Val Gly Val Pro Gly Ala Gly Val Pro Gly Val Gly Val Pro Gly
            595                 600                 605
Ala Gly Val Pro Gly Val Gly Val Pro Gly Val Gly Val Pro Gly Ala
            610                 615                 620
Gly Val Pro Gly Val Gly Val Pro Gly Ala Gly Val Pro Gly Val Gly
625                 630                 635                 640
Val Pro Gly Ala Gly Val Pro Gly Val Gly Val Pro Gly Ala Gly Val
            645                 650                 655
Pro Gly Val Gly Val Pro Gly Val Gly Val Pro Gly Ala Gly Val Pro
            660                 665                 670
Gly Val Gly Val Pro Gly Ala Gly Val Pro Gly Val Gly Val Pro Gly
            675                 680                 685
```

```
Ala Gly Val Pro Gly Val Gly Val Pro Gly Ala Gly Val Pro Gly Val
        690                 695                 700
Gly Val Pro Gly Val Gly Val Pro Gly Ala Gly Val Pro Gly Val Gly
    705                 710                 715                 720
Val Pro Gly Ala Gly Val Pro Gly Trp Pro
                725                 730

<210> SEQ ID NO 71
<211> LENGTH: 730
<212> TYPE: PRT
<213> ORGANISM: Artificial Sequence
<220> FEATURE:
<223> OTHER INFORMATION: gamma ELP 144-mer

<400> SEQUENCE: 71

Val Pro Gly Val Gly Val Pro Gly Val Gly Val Pro Gly Val Gly Val
  1               5                  10                  15
Pro Gly Gly Gly Val Pro Gly Val Gly Val Pro Gly Val Gly Val Pro
                20                  25                  30
Gly Val Gly Val Pro Gly Val Gly Val Pro Gly Val Gly Val Pro Gly
            35                  40                  45
Val Gly Val Pro Gly Val Gly Val Pro Gly Val Gly Val Pro Gly Val
         50                  55                  60
Gly Val Pro Gly Ala Gly Val Pro Gly Val Gly Val Pro Gly Val Gly
 65                  70                  75                  80
Val Pro Gly Val Gly Val Pro Gly Val Gly Val Pro Gly Ala Gly Val
                85                  90                  95
Pro Gly Val Gly Val Pro Gly Val Gly Val Pro Gly Val Gly Val Pro
                100                 105                 110
Gly Val Gly Val Pro Gly Val Gly Val Pro Gly Val Gly Val Pro Gly
            115                 120                 125
Val Gly Val Pro Gly Gly Val Pro Gly Val Gly Val Pro Gly Val
            130                 135                 140
Gly Val Pro Gly Val Gly Val Pro Gly Val Gly Val Pro Gly Ala Gly
145                 150                 155                 160
Val Pro Gly Val Gly Val Pro Gly Val Gly Val Pro Gly Val Gly Val
                165                 170                 175
Pro Gly Val Gly Val Pro Gly Ala Gly Val Pro Gly Val Gly Val Pro
            180                 185                 190
Gly Val Gly Val Pro Gly Gly Val Pro Gly Val Gly Val Pro Gly
            195                 200                 205
Val Gly Val Pro Gly Val Gly Val Pro Gly Val Gly Val Pro Gly Gly
            210                 215                 220
Gly Val Pro Gly Val Gly Val Pro Gly Val Gly Val Pro Gly Val Gly
225                 230                 235                 240
Val Pro Gly Val Gly Val Pro Gly Ala Gly Val Pro Gly Val Gly Val
                245                 250                 255
Pro Gly Val Gly Val Pro Gly Val Gly Val Pro Gly Val Gly Val Pro
                260                 265                 270
Gly Ala Gly Val Pro Gly Val Gly Val Pro Gly Val Gly Val Pro Gly
            275                 280                 285
Gly Gly Val Pro Gly Val Gly Val Pro Gly Val Gly Val Pro Gly Val
            290                 295                 300
Gly Val Pro Gly Val Gly Val Pro Gly Gly Val Pro Gly Val Gly
305                 310                 315                 320
```

```
Val Pro Gly Val Gly Val Pro Gly Val Gly Val Pro Gly Val Gly Val
                325                 330                 335
Pro Gly Ala Gly Val Pro Gly Val Gly Val Pro Gly Val Gly Val Pro
            340                 345                 350
Gly Val Gly Val Pro Gly Val Gly Val Pro Gly Ala Gly Val Pro Gly
                355                 360                 365
Val Gly Val Pro Gly Val Gly Val Pro Gly Gly Gly Val Pro Gly Val
            370                 375                 380
Gly Val Pro Gly Val Gly Val Pro Gly Val Gly Val Pro Gly Val Gly
385                 390                 395                 400
Val Pro Gly Gly Val Pro Gly Val Gly Val Pro Gly Val Gly Val
                405                 410                 415
Pro Gly Val Gly Val Pro Gly Val Gly Val Pro Gly Ala Gly Val Pro
            420                 425                 430
Gly Val Gly Val Pro Gly Val Gly Val Pro Gly Val Gly Val Pro Gly
                435                 440                 445
Val Gly Val Pro Gly Ala Gly Val Pro Gly Val Gly Val Pro Gly Val
            450                 455                 460
Gly Val Pro Gly Gly Val Pro Gly Val Gly Val Pro Gly Val Gly
465                 470                 475                 480
Val Pro Gly Val Gly Val Pro Gly Val Gly Val Pro Gly Gly Gly Val
                485                 490                 495
Pro Gly Val Gly Val Pro Gly Val Gly Val Pro Gly Val Gly Val Pro
            500                 505                 510
Gly Val Gly Val Pro Gly Ala Gly Val Pro Gly Val Gly Val Pro Gly
                515                 520                 525
Val Gly Val Pro Gly Val Gly Val Pro Gly Val Gly Val Pro Gly Ala
            530                 535                 540
Gly Val Pro Gly Val Gly Val Pro Gly Val Gly Val Pro Gly Gly Gly
545                 550                 555                 560
Val Pro Gly Val Gly Val Pro Gly Val Gly Val Pro Gly Val Gly Val
                565                 570                 575
Pro Gly Val Gly Val Pro Gly Gly Gly Val Pro Gly Val Gly Val Pro
            580                 585                 590
Gly Val Gly Val Pro Gly Val Gly Val Pro Gly Val Gly Val Pro Gly
                595                 600                 605
Ala Gly Val Pro Gly Val Gly Val Pro Gly Val Gly Val Pro Gly Val
            610                 615                 620
Gly Val Pro Gly Val Gly Val Pro Gly Ala Gly Val Pro Gly Val Gly
625                 630                 635                 640
Val Pro Gly Val Gly Val Pro Gly Gly Gly Val Pro Gly Val Gly Val
                645                 650                 655
Pro Gly Val Gly Val Pro Gly Val Gly Val Pro Gly Val Gly Val Pro
            660                 665                 670
Gly Gly Gly Val Pro Gly Val Gly Val Pro Gly Val Gly Val Pro Gly
                675                 680                 685
Val Gly Val Pro Gly Val Gly Val Pro Gly Ala Gly Val Pro Gly Val
            690                 695                 700
Gly Val Pro Gly Val Gly Val Pro Gly Val Gly Val Pro Gly Val Gly
705                 710                 715                 720
Val Pro Gly Ala Gly Val Pro Gly Trp Pro
                725                 730
```

```
<210> SEQ ID NO 72
<211> LENGTH: 730
<212> TYPE: PRT
<213> ORGANISM: Artificial Sequence
<220> FEATURE:
<223> OTHER INFORMATION: delta ELP 144-mer

<400> SEQUENCE: 72

Val Pro Gly Val Gly Val Pro Gly Val Gly Val Pro Gly Val Gly Ala
1               5                   10                  15

Pro Gly Val Gly Val Pro Gly Val Gly Ala Pro Gly Val Gly Val Pro
            20                  25                  30

Gly Val Gly Ala Pro Gly Val Gly Val Pro Gly Val Gly Ala Pro Gly
        35                  40                  45

Val Gly Val Pro Gly Val Gly Val Pro Gly Val Gly Ala Pro Gly Val
    50                  55                  60

Gly Val Pro Gly Val Gly Ala Pro Gly Val Gly Pro Gly Val Gly
65                  70                  75                  80

Ala Pro Gly Val Gly Val Pro Gly Val Gly Ala Pro Gly Val Gly Val
                85                  90                  95

Pro Gly Val Gly Val Pro Gly Val Gly Ala Pro Gly Val Gly Val Pro
            100                 105                 110

Gly Val Gly Ala Pro Gly Val Gly Val Pro Gly Val Gly Ala Pro Gly
        115                 120                 125

Val Gly Val Pro Gly Val Gly Ala Pro Gly Val Gly Val Pro Gly Val
    130                 135                 140

Gly Val Pro Gly Val Gly Ala Pro Gly Val Gly Val Pro Gly Val Gly
145                 150                 155                 160

Ala Pro Gly Val Gly Val Pro Gly Val Gly Ala Pro Gly Val Gly Val
                165                 170                 175

Pro Gly Val Gly Ala Pro Gly Val Gly Val Pro Gly Val Gly Val Pro
            180                 185                 190

Gly Val Gly Ala Pro Gly Val Gly Val Pro Gly Val Gly Ala Pro Gly
        195                 200                 205

Val Gly Val Pro Gly Val Gly Ala Pro Gly Val Gly Val Pro Gly Val
    210                 215                 220

Gly Ala Pro Gly Val Gly Val Pro Gly Val Gly Val Pro Gly Val Gly
225                 230                 235                 240

Ala Pro Gly Val Gly Val Pro Gly Val Gly Ala Pro Gly Val Gly Val
                245                 250                 255

Pro Gly Val Gly Ala Pro Gly Val Gly Val Pro Gly Val Gly Ala Pro
            260                 265                 270

Gly Val Gly Val Pro Gly Val Gly Val Pro Gly Val Gly Ala Pro Gly
        275                 280                 285

Val Gly Val Pro Gly Val Gly Ala Pro Gly Val Gly Val Pro Gly Val
    290                 295                 300

Gly Ala Pro Gly Val Gly Val Pro Gly Val Gly Ala Pro Gly Val Gly
305                 310                 315                 320

Val Pro Gly Val Gly Val Pro Gly Val Gly Ala Pro Gly Val Gly Val
                325                 330                 335

Pro Gly Val Gly Ala Pro Gly Val Gly Val Pro Gly Val Gly Ala Pro
            340                 345                 350

Gly Val Gly Val Pro Gly Val Gly Ala Pro Gly Val Gly Val Pro Gly
        355                 360                 365

Val Gly Val Pro Gly Val Gly Ala Pro Gly Val Gly Val Pro Gly Val
```

```
                    370                 375                 380
Gly Ala Pro Gly Val Gly Val Pro Gly Val Gly Ala Pro Gly Val Gly
385                 390                 395                 400

Val Pro Gly Val Gly Ala Pro Gly Val Gly Val Pro Gly Val Gly Val
                405                 410                 415

Pro Gly Val Gly Ala Pro Gly Val Gly Val Pro Gly Val Gly Ala Pro
            420                 425                 430

Gly Val Gly Val Pro Gly Val Gly Ala Pro Gly Val Gly Val Pro Gly
        435                 440                 445

Val Gly Ala Pro Gly Val Gly Val Pro Gly Val Gly Val Pro Gly Val
    450                 455                 460

Gly Ala Pro Gly Val Gly Val Pro Gly Val Gly Ala Pro Gly Val Gly
465                 470                 475                 480

Val Pro Gly Val Gly Ala Pro Gly Val Gly Val Pro Gly Val Gly Ala
                485                 490                 495

Pro Gly Val Gly Val Pro Gly Val Gly Val Pro Gly Val Gly Ala Pro
            500                 505                 510

Gly Val Gly Val Pro Gly Val Gly Ala Pro Gly Val Gly Val Pro Gly
        515                 520                 525

Val Gly Ala Pro Gly Val Gly Val Pro Gly Val Gly Ala Pro Gly Val
    530                 535                 540

Gly Val Pro Gly Val Gly Val Pro Gly Val Gly Ala Pro Gly Val Gly
545                 550                 555                 560

Val Pro Gly Val Gly Ala Pro Gly Val Gly Val Pro Gly Val Gly Ala
                565                 570                 575

Pro Gly Val Gly Val Pro Gly Val Gly Ala Pro Gly Val Gly Val Pro
            580                 585                 590

Gly Val Gly Val Pro Gly Val Gly Ala Pro Gly Val Gly Val Pro Gly
        595                 600                 605

Val Gly Ala Pro Gly Val Gly Val Pro Gly Val Gly Ala Pro Gly Val
    610                 615                 620

Gly Val Pro Gly Val Gly Ala Pro Gly Val Gly Val Pro Gly Val Gly
625                 630                 635                 640

Val Pro Gly Val Gly Ala Pro Gly Val Gly Val Pro Gly Val Gly Ala
                645                 650                 655

Pro Gly Val Gly Val Pro Gly Val Gly Ala Pro Gly Val Gly Val Pro
            660                 665                 670

Gly Val Gly Ala Pro Gly Val Gly Val Pro Gly Val Gly Val Pro Gly
        675                 680                 685

Val Gly Ala Pro Gly Val Gly Val Pro Gly Val Gly Ala Pro Gly Val
    690                 695                 700

Gly Val Pro Gly Val Gly Ala Pro Gly Val Gly Val Pro Gly Val Gly
705                 710                 715                 720

Ala Pro Gly Val Gly Val Pro Gly Trp Pro
                725                 730

<210> SEQ ID NO 73
<211> LENGTH: 853
<212> TYPE: PRT
<213> ORGANISM: Artificial Sequence
<220> FEATURE:
<223> OTHER INFORMATION: hGH betaV2 144-mer

<400> SEQUENCE: 73

Val Gly Val Pro Gly Val Gly Val Pro Gly Ala Gly Val Pro Gly Val
```

```
1               5                   10                  15
Gly Val Pro Gly Ala Gly Val Pro Gly Val Gly Val Pro Gly Ala Gly
                20                  25                  30

Val Pro Gly Val Gly Val Pro Gly Ala Gly Val Pro Gly Val Gly Val
                35                  40                  45

Pro Gly Val Gly Val Pro Gly Ala Gly Val Pro Gly Val Gly Val Pro
            50                  55                  60

Gly Ala Gly Val Pro Gly Val Gly Val Pro Gly Ala Gly Val Pro Gly
 65                 70                  75                  80

Val Gly Val Pro Gly Ala Gly Val Pro Gly Val Gly Val Pro Gly Val
                85                  90                  95

Gly Val Pro Gly Ala Gly Val Pro Gly Val Gly Val Pro Gly Ala Gly
            100                 105                 110

Val Pro Gly Val Gly Val Pro Gly Ala Gly Val Pro Gly Val Gly Val
                115                 120                 125

Pro Gly Ala Gly Val Pro Gly Val Gly Val Pro Gly Val Gly Val Pro
130                 135                 140

Gly Ala Gly Val Pro Gly Val Gly Val Pro Gly Ala Gly Val Pro Gly
145                 150                 155                 160

Val Gly Val Pro Gly Ala Gly Val Pro Gly Val Gly Val Pro Gly Ala
                165                 170                 175

Gly Val Pro Gly Val Gly Val Pro Gly Val Gly Val Pro Gly Ala Gly
            180                 185                 190

Val Pro Gly Val Gly Val Pro Gly Ala Gly Val Pro Gly Val Gly Val
                195                 200                 205

Pro Gly Ala Gly Val Pro Gly Val Gly Val Pro Gly Ala Gly Val Pro
210                 215                 220

Gly Val Gly Val Pro Gly Val Gly Val Pro Gly Ala Gly Val Pro Gly
225                 230                 235                 240

Val Gly Val Pro Gly Ala Gly Val Pro Gly Val Gly Val Pro Gly Ala
                245                 250                 255

Gly Val Pro Gly Val Gly Val Pro Gly Ala Gly Val Pro Gly Val Gly
            260                 265                 270

Val Pro Gly Val Gly Val Pro Gly Ala Gly Val Pro Gly Val Gly Val
            275                 280                 285

Pro Gly Ala Gly Val Pro Gly Val Gly Val Pro Gly Ala Gly Val Pro
        290                 295                 300

Gly Val Gly Val Pro Gly Ala Gly Val Pro Gly Val Gly Val Pro Gly
305                 310                 315                 320

Val Gly Val Pro Gly Ala Gly Val Pro Gly Val Gly Val Pro Gly Ala
                325                 330                 335

Gly Val Pro Gly Val Gly Val Pro Gly Ala Gly Val Pro Gly Val Gly
            340                 345                 350

Val Pro Gly Ala Gly Val Pro Gly Val Gly Val Pro Gly Val Gly Val
            355                 360                 365

Pro Gly Ala Gly Val Pro Gly Val Gly Val Pro Gly Ala Gly Val Pro
        370                 375                 380

Gly Val Gly Val Pro Gly Ala Gly Val Pro Gly Val Gly Val Pro Gly
385                 390                 395                 400

Ala Gly Val Pro Gly Val Gly Val Pro Gly Val Gly Val Pro Gly Ala
            405                 410                 415

Gly Val Pro Gly Val Gly Val Pro Gly Ala Gly Val Pro Gly Val Gly
            420                 425                 430
```

```
Val Pro Gly Ala Gly Val Pro Gly Val Gly Val Pro Gly Ala Gly Val
            435                 440                 445

Pro Gly Val Gly Val Pro Gly Val Gly Val Pro Gly Ala Gly Val Pro
    450                 455                 460

Gly Val Gly Val Pro Gly Ala Gly Val Pro Gly Val Gly Val Pro Gly
465                 470                 475                 480

Ala Gly Val Pro Gly Val Gly Val Pro Gly Ala Gly Val Pro Gly Val
                485                 490                 495

Gly Val Pro Gly Val Gly Val Pro Gly Ala Gly Val Pro Gly Val Gly
            500                 505                 510

Val Pro Gly Ala Gly Val Pro Gly Val Gly Val Pro Gly Ala Gly Val
        515                 520                 525

Pro Gly Val Gly Val Pro Gly Ala Gly Val Pro Gly Val Gly Val Pro
    530                 535                 540

Gly Val Gly Val Pro Gly Ala Gly Val Pro Gly Val Gly Val Pro Gly
545                 550                 555                 560

Ala Gly Val Pro Gly Val Gly Val Pro Gly Ala Gly Val Pro Gly Val
                565                 570                 575

Gly Val Pro Gly Ala Gly Val Pro Gly Val Gly Val Pro Gly Val Gly
            580                 585                 590

Val Pro Gly Ala Gly Val Pro Gly Val Gly Val Pro Gly Ala Gly Val
        595                 600                 605

Pro Gly Val Gly Val Pro Gly Ala Gly Val Pro Gly Val Gly Val Pro
    610                 615                 620

Gly Ala Gly Val Pro Gly Val Gly Val Pro Gly Val Gly Val Pro Gly
625                 630                 635                 640

Ala Gly Val Pro Gly Val Gly Val Pro Gly Ala Gly Val Pro Gly Val
                645                 650                 655

Gly Phe Pro Thr Ile Pro Leu Ser Arg Leu Phe Asp Asn Ala Met Leu
            660                 665                 670

Arg Ala His Arg Leu His Gln Leu Ala Phe Asp Thr Tyr Gln Glu Phe
        675                 680                 685

Glu Glu Ala Tyr Ile Pro Lys Glu Gln Lys Tyr Ser Phe Leu Gln Asn
    690                 695                 700

Pro Gln Thr Ser Leu Cys Phe Ser Glu Ser Ile Pro Thr Pro Ser Asn
705                 710                 715                 720

Arg Glu Glu Thr Gln Gln Lys Ser Asn Leu Glu Leu Leu Arg Ile Ser
                725                 730                 735

Leu Leu Leu Ile Gln Ser Trp Leu Glu Pro Val Gln Phe Leu Arg Ser
            740                 745                 750

Val Phe Ala Asn Ser Leu Val Tyr Gly Ala Ser Asp Ser Asn Val Tyr
        755                 760                 765

Asp Leu Leu Lys Asp Leu Glu Glu Gly Ile Gln Thr Leu Met Gly Arg
    770                 775                 780

Leu Glu Asp Gly Ser Pro Arg Thr Gly Gln Ile Phe Lys Gln Thr Tyr
785                 790                 795                 800

Ser Lys Phe Asp Thr Asn Ser His Asn Asp Asp Ala Leu Leu Lys Asn
                805                 810                 815

Tyr Gly Leu Leu Tyr Cys Phe Arg Lys Asp Met Asp Lys Val Glu Thr
            820                 825                 830

Phe Leu Arg Ile Val Gln Cys Arg Ser Val Glu Gly Ser Cys Gly Phe
        835                 840                 845
```

-continued

```
Val Pro Gly Trp Pro
        850

<210> SEQ ID NO 74
<211> LENGTH: 802
<212> TYPE: PRT
<213> ORGANISM: Artificial Sequence
<220> FEATURE:
<223> OTHER INFORMATION: hGH ELP1-120

<400> SEQUENCE: 74

Met Val Pro Gly Val Gly Val Pro Gly Val Gly Val Pro Gly Gly Gly
1               5                   10                  15

Val Pro Gly Ala Gly Val Pro Gly Val Gly Val Pro Gly Val Gly Val
                20                  25                  30

Pro Gly Val Gly Val Pro Gly Gly Gly Val Pro Gly Ala Gly Val Pro
            35                  40                  45

Gly Gly Gly Val Pro Gly Val Gly Val Pro Gly Val Gly Val Pro Gly
        50                  55                  60

Gly Gly Val Pro Gly Ala Gly Val Pro Gly Val Gly Val Pro Gly Val
65                  70                  75                  80

Gly Val Pro Gly Val Gly Val Pro Gly Gly Gly Val Pro Gly Ala Gly
                85                  90                  95

Val Pro Gly Gly Gly Val Pro Gly Val Gly Val Pro Gly Val Gly Val
            100                 105                 110

Pro Gly Gly Gly Val Pro Gly Ala Gly Val Pro Gly Val Gly Val Pro
        115                 120                 125

Gly Val Gly Val Pro Gly Val Gly Val Pro Gly Gly Gly Val Pro Gly
        130                 135                 140

Ala Gly Val Pro Gly Gly Gly Val Pro Gly Val Gly Val Pro Gly Val
145                 150                 155                 160

Gly Val Pro Gly Gly Gly Val Pro Gly Ala Gly Val Pro Gly Val Gly
                165                 170                 175

Val Pro Gly Val Gly Val Pro Gly Val Gly Val Pro Gly Gly Gly Val
            180                 185                 190

Pro Gly Ala Gly Val Pro Gly Gly Gly Val Pro Gly Val Gly Val Pro
        195                 200                 205

Gly Val Gly Val Pro Gly Gly Gly Val Pro Gly Ala Gly Val Pro Gly
    210                 215                 220

Val Gly Val Pro Gly Val Gly Val Pro Gly Val Gly Val Pro Gly Gly
225                 230                 235                 240

Gly Val Pro Gly Ala Gly Val Pro Gly Gly Gly Val Pro Gly Val Gly
                245                 250                 255

Val Pro Gly Val Gly Val Pro Gly Gly Gly Val Pro Gly Ala Gly Val
            260                 265                 270

Pro Gly Val Gly Val Pro Gly Val Gly Val Pro Gly Val Gly Val Pro
        275                 280                 285

Gly Gly Gly Val Pro Gly Ala Gly Val Pro Gly Gly Gly Val Pro Gly
    290                 295                 300

Val Gly Val Pro Gly Val Gly Val Pro Gly Gly Gly Val Pro Gly Ala
305                 310                 315                 320

Gly Val Pro Gly Val Gly Val Pro Gly Val Gly Val Pro Gly Val Gly
                325                 330                 335

Val Pro Gly Gly Gly Val Pro Gly Ala Gly Val Pro Gly Gly Gly Val
            340                 345                 350
```

-continued

```
Pro Gly Val Gly Val Pro Gly Val Pro Gly Gly Val Pro
        355                 360                 365
Gly Ala Gly Val Pro Gly Val Gly Val Pro Gly Val Pro Gly
    370                 375                 380
Val Gly Val Pro Gly Gly Val Pro Gly Ala Gly Val Pro Gly Gly
385                 390                 395                 400
Gly Val Pro Gly Val Gly Val Pro Gly Val Gly Val Pro Gly Gly Gly
                405                 410                 415
Val Pro Gly Ala Gly Val Pro Gly Val Gly Val Pro Gly Val Gly Val
            420                 425                 430
Pro Gly Val Gly Val Pro Gly Gly Val Pro Gly Ala Gly Val Pro
        435                 440                 445
Gly Gly Gly Val Pro Gly Val Gly Val Pro Gly Val Gly Val Pro Gly
    450                 455                 460
Gly Gly Val Pro Gly Ala Gly Val Pro Gly Val Gly Val Pro Gly Val
465                 470                 475                 480
Gly Val Pro Gly Val Gly Val Pro Gly Gly Val Pro Gly Ala Gly
                485                 490                 495
Val Pro Gly Gly Gly Val Pro Gly Val Gly Val Pro Gly Val Gly Val
            500                 505                 510
Pro Gly Gly Gly Val Pro Gly Ala Gly Val Pro Gly Val Gly Val Pro
        515                 520                 525
Gly Val Gly Val Pro Gly Val Gly Val Pro Gly Gly Gly Val Pro Gly
    530                 535                 540
Ala Gly Val Pro Gly Gly Val Pro Gly Val Gly Val Pro Gly Val
545                 550                 555                 560
Gly Val Pro Gly Gly Gly Val Pro Gly Ala Gly Val Pro Gly Val Gly
                565                 570                 575
Val Pro Gly Val Gly Val Pro Gly Val Gly Val Pro Gly Gly Gly Val
            580                 585                 590
Pro Gly Ala Gly Val Pro Gly Gly Val Pro Gly Val Gly Phe Pro
        595                 600                 605
Thr Ile Pro Leu Ser Arg Leu Phe Asp Asn Ala Met Leu Arg Ala His
    610                 615                 620
Arg Leu His Gln Leu Ala Phe Asp Thr Tyr Gln Glu Phe Glu Glu Ala
625                 630                 635                 640
Tyr Ile Pro Lys Glu Gln Lys Tyr Ser Phe Leu Gln Asn Pro Gln Thr
                645                 650                 655
Ser Leu Cys Phe Ser Glu Ser Ile Pro Thr Pro Ser Asn Arg Glu Glu
            660                 665                 670
Thr Gln Gln Lys Ser Asn Leu Glu Leu Leu Arg Ile Ser Leu Leu Leu
        675                 680                 685
Ile Gln Ser Trp Leu Glu Pro Val Gln Phe Leu Arg Ser Val Phe Ala
    690                 695                 700
Asn Ser Leu Val Tyr Gly Ala Ser Asp Ser Asn Val Tyr Asp Leu Leu
705                 710                 715                 720
Lys Asp Leu Glu Glu Gly Ile Gln Thr Leu Met Gly Arg Leu Glu Asp
                725                 730                 735
Gly Ser Pro Arg Thr Gly Gln Ile Phe Lys Gln Thr Tyr Ser Lys Phe
            740                 745                 750
Asp Thr Asn Ser His Asn Asp Asp Ala Leu Leu Lys Asn Tyr Gly Leu
        755                 760                 765
Leu Tyr Cys Phe Arg Lys Asp Met Asp Lys Val Glu Thr Phe Leu Arg
```

```
                    770              775              780
Ile Val Gln Cys Arg Ser Val Glu Gly Ser Cys Gly Phe Val Pro Gly
785                 790              795              800

Trp Pro

<210> SEQ ID NO 75
<211> LENGTH: 1077
<212> TYPE: PRT
<213> ORGANISM: Artificial Sequence
<220> FEATURE:
<223> OTHER INFORMATION: betaV2-144mer -hGH-ELP1-30

<400> SEQUENCE: 75

Met Val Pro Gly Val Gly Val Pro Gly Val Gly Val Pro Gly Ala Gly
1               5                   10                  15

Val Pro Gly Val Gly Val Pro Gly Ala Gly Val Pro Gly Val Gly Val
                20                  25                  30

Pro Gly Val Gly Val Pro Gly Ala Gly Val Pro Gly Val Gly Val Pro
            35                  40                  45

Gly Ala Gly Val Pro Gly Val Gly Val Pro Gly Ala Gly Val Pro Gly
        50                  55                  60

Val Gly Val Pro Gly Ala Gly Val Pro Gly Val Gly Val Pro Gly Val
65                  70                  75                  80

Gly Val Pro Gly Ala Gly Val Pro Gly Val Gly Val Pro Gly Ala Gly
                85                  90                  95

Val Pro Gly Val Gly Val Pro Gly Ala Gly Val Pro Gly Val Gly Val
                100                 105                 110

Pro Gly Ala Gly Val Pro Gly Val Gly Val Pro Gly Val Gly Val Pro
            115                 120                 125

Gly Ala Gly Val Pro Gly Val Gly Val Pro Gly Ala Gly Val Pro Gly
        130                 135                 140

Val Gly Val Pro Gly Ala Gly Val Pro Gly Val Gly Val Pro Gly Ala
145                 150                 155                 160

Gly Val Pro Gly Val Gly Val Pro Gly Val Gly Val Pro Gly Ala Gly
                165                 170                 175

Val Pro Gly Val Gly Val Pro Gly Ala Gly Val Pro Gly Val Gly Val
                180                 185                 190

Pro Gly Ala Gly Val Pro Gly Val Gly Val Pro Gly Ala Gly Val Pro
            195                 200                 205

Gly Val Gly Val Pro Gly Val Gly Val Pro Gly Ala Gly Val Pro Gly
        210                 215                 220

Val Gly Val Pro Gly Ala Gly Val Pro Gly Val Gly Val Pro Gly Ala
225                 230                 235                 240

Gly Val Pro Gly Val Gly Val Pro Gly Ala Gly Val Pro Gly Val Gly
                245                 250                 255

Val Pro Gly Val Gly Val Pro Gly Ala Gly Val Pro Gly Val Gly Val
                260                 265                 270

Pro Gly Ala Gly Val Pro Gly Val Gly Val Pro Gly Ala Gly Val Pro
            275                 280                 285

Gly Val Gly Val Pro Gly Ala Gly Val Pro Gly Val Gly Val Pro Gly
        290                 295                 300

Val Gly Val Pro Gly Ala Gly Val Pro Gly Val Gly Val Pro Gly Ala
305                 310                 315                 320

Gly Val Pro Gly Val Gly Val Pro Gly Ala Gly Val Pro Gly Val Gly
                325                 330                 335
```

```
Val Pro Gly Ala Gly Val Pro Gly Val Gly Val Pro Gly Val Gly Val
                340                 345                 350

Pro Gly Ala Gly Val Pro Gly Val Gly Val Pro Gly Ala Gly Val Pro
                355                 360                 365

Gly Val Gly Val Pro Gly Ala Gly Val Pro Gly Val Gly Val Pro Gly
                370                 375                 380

Ala Gly Val Pro Gly Val Gly Val Pro Gly Val Gly Val Pro Gly Ala
385                 390                 395                 400

Gly Val Pro Gly Val Gly Val Pro Gly Ala Gly Val Pro Gly Val Gly
                405                 410                 415

Val Pro Gly Ala Gly Val Pro Gly Val Gly Val Pro Gly Ala Gly Val
                420                 425                 430

Pro Gly Val Gly Val Pro Gly Val Gly Val Pro Gly Ala Gly Val Pro
                435                 440                 445

Gly Val Gly Val Pro Gly Ala Gly Val Pro Gly Val Gly Val Pro Gly
                450                 455                 460

Ala Gly Val Pro Gly Val Gly Val Pro Gly Ala Gly Val Pro Gly Val
465                 470                 475                 480

Gly Val Pro Gly Val Gly Val Pro Gly Ala Gly Val Pro Gly Val Gly
                485                 490                 495

Val Pro Gly Ala Gly Val Pro Gly Val Gly Val Pro Gly Ala Gly Val
                500                 505                 510

Pro Gly Val Gly Val Pro Gly Ala Gly Val Pro Gly Val Gly Val Pro
                515                 520                 525

Gly Val Gly Val Pro Gly Ala Gly Val Pro Gly Val Gly Val Pro Gly
                530                 535                 540

Ala Gly Val Pro Gly Val Gly Val Pro Gly Ala Gly Val Pro Gly Val
545                 550                 555                 560

Gly Val Pro Gly Ala Gly Val Pro Gly Val Gly Val Pro Gly Val Gly
                565                 570                 575

Val Pro Gly Ala Gly Val Pro Gly Val Gly Val Pro Gly Ala Gly Val
                580                 585                 590

Pro Gly Val Gly Val Pro Gly Ala Gly Val Pro Gly Val Gly Val Pro
                595                 600                 605

Gly Ala Gly Val Pro Gly Val Gly Val Pro Gly Val Gly Val Pro Gly
                610                 615                 620

Ala Gly Val Pro Gly Val Gly Val Pro Gly Ala Gly Val Pro Gly Val
625                 630                 635                 640

Gly Val Pro Gly Ala Gly Val Pro Gly Val Gly Val Pro Gly Ala Gly
                645                 650                 655

Val Pro Gly Val Gly Val Pro Gly Val Gly Val Pro Gly Ala Gly Val
                660                 665                 670

Pro Gly Val Gly Val Pro Gly Ala Gly Val Pro Gly Val Gly Val Pro
                675                 680                 685

Gly Ala Gly Val Pro Gly Val Gly Val Pro Gly Ala Gly Val Pro Gly
                690                 695                 700

Val Gly Val Pro Gly Val Gly Val Pro Gly Ala Gly Val Pro Gly Val
705                 710                 715                 720

Gly Val Pro Gly Ala Gly Val Pro Gly Val Gly Phe Pro Thr Ile Pro
                725                 730                 735

Leu Ser Arg Leu Phe Asp Asn Ala Met Leu Arg Ala His Arg Leu His
                740                 745                 750
```

-continued

```
Gln Leu Ala Phe Asp Thr Tyr Gln Glu Phe Glu Ala Tyr Ile Pro
            755                 760                 765
Lys Glu Gln Lys Tyr Ser Phe Leu Gln Asn Pro Gln Thr Ser Leu Cys
770                 775                 780
Phe Ser Glu Ser Ile Pro Thr Pro Ser Asn Arg Glu Glu Thr Gln Gln
785                 790                 795                 800
Lys Ser Asn Leu Glu Leu Leu Arg Ile Ser Leu Leu Leu Ile Gln Ser
            805                 810                 815
Trp Leu Glu Pro Val Gln Phe Leu Arg Ser Val Phe Ala Asn Ser Leu
            820                 825                 830
Val Tyr Gly Ala Ser Asp Ser Asn Val Tyr Asp Leu Leu Lys Asp Leu
            835                 840                 845
Glu Glu Gly Ile Gln Thr Leu Met Gly Arg Leu Glu Asp Gly Ser Pro
850                 855                 860
Arg Thr Gly Gln Ile Phe Lys Gln Thr Tyr Ser Lys Phe Asp Thr Asn
865                 870                 875                 880
Ser His Asn Asp Asp Ala Leu Leu Lys Asn Tyr Gly Leu Leu Tyr Cys
            885                 890                 895
Phe Arg Lys Asp Met Asp Lys Val Glu Thr Phe Leu Arg Ile Val Gln
            900                 905                 910
Cys Arg Ser Val Glu Gly Ser Cys Gly Phe Val Pro Gly Val Gly Val
            915                 920                 925
Pro Gly Val Gly Val Pro Gly Gly Val Pro Gly Ala Gly Val Pro
            930                 935                 940
Gly Val Gly Val Pro Gly Val Gly Val Pro Gly Val Gly Val Pro Gly
945                 950                 955                 960
Gly Gly Val Pro Gly Ala Gly Val Pro Gly Gly Val Pro Gly Val
            965                 970                 975
Gly Val Pro Gly Val Gly Val Pro Gly Gly Val Pro Gly Ala Gly
            980                 985                 990
Val Pro Gly Val Gly Val Pro Gly  Val Gly Val Pro Gly  Val Gly Val
            995                 1000                1005
Pro Gly  Gly Gly Val Pro Gly  Ala Gly Val Pro Gly  Gly Gly Val
    1010                1015                1020
Pro Gly  Val Gly Val Pro Gly  Val Gly Val Pro Gly  Gly Gly Val
    1025                1030                1035
Pro Gly  Ala Gly Val Pro Gly  Val Gly Val Pro Gly  Val Gly Val
    1040                1045                1050
Pro Gly  Val Gly Val Pro Gly  Gly Gly Val Pro Gly  Ala Gly Val
    1055                1060                1065
Pro Gly  Gly Gly Val Pro Gly  Trp Pro
    1070                1075
```

<210> SEQ ID NO 76
<211> LENGTH: 952
<212> TYPE: PRT
<213> ORGANISM: Artificial Sequence
<220> FEATURE:
<223> OTHER INFORMATION: ELP1-120 hGH ELP1-30

<400> SEQUENCE: 76

```
Met Val Pro Gly Val Gly Val Pro Gly Val Gly Val Pro Gly Gly
1               5                   10                  15
Val Pro Gly Ala Gly Val Pro Gly Val Gly Val Pro Gly Val Gly Val
            20                  25                  30
```

-continued

Pro Gly Val Gly Val Pro Gly Gly Val Pro Ala Gly Val Pro
         35                  40                  45
Gly Gly Gly Val Pro Gly Val Gly Val Pro Gly Val Gly Val Pro Gly
50                  55                  60
Gly Gly Val Pro Gly Ala Gly Val Pro Gly Val Gly Val Pro Gly Val
65                  70                  75                  80
Gly Val Pro Gly Val Gly Val Pro Gly Gly Val Pro Gly Ala Gly
                85                  90                  95
Val Pro Gly Gly Gly Val Pro Gly Val Gly Val Pro Gly Val Gly Val
                100                 105                 110
Pro Gly Gly Gly Val Pro Gly Ala Gly Val Pro Gly Val Gly Val Pro
            115                 120                 125
Gly Val Gly Val Pro Gly Val Gly Val Pro Gly Gly Gly Val Pro Gly
130                 135                 140
Ala Gly Val Pro Gly Gly Val Pro Gly Val Gly Val Pro Gly Val
145                 150                 155                 160
Gly Val Pro Gly Gly Val Pro Gly Ala Gly Val Pro Gly Val Gly
                165                 170                 175
Val Pro Gly Val Gly Val Pro Gly Val Gly Val Pro Gly Gly Gly Val
            180                 185                 190
Pro Gly Ala Gly Val Pro Gly Gly Val Pro Gly Val Gly Val Pro
            195                 200                 205
Gly Val Gly Val Pro Gly Val Gly Val Pro Gly Ala Gly Val Pro Gly
            210                 215                 220
Val Gly Val Pro Gly Val Gly Val Pro Gly Val Gly Val Pro Gly Gly
225                 230                 235                 240
Gly Val Pro Gly Ala Gly Val Pro Gly Gly Val Pro Gly Val Gly
            245                 250                 255
Val Pro Gly Val Gly Val Pro Gly Gly Val Pro Gly Ala Gly Val
            260                 265                 270
Pro Gly Val Gly Val Pro Gly Val Gly Val Pro Gly Val Gly Val Pro
            275                 280                 285
Gly Gly Gly Val Pro Gly Ala Gly Val Pro Gly Gly Gly Val Pro Gly
290                 295                 300
Val Gly Val Pro Gly Val Gly Val Pro Gly Gly Gly Val Pro Gly Ala
305                 310                 315                 320
Gly Val Pro Gly Val Gly Val Pro Gly Val Gly Val Pro Gly Val Gly
                325                 330                 335
Val Pro Gly Gly Gly Val Pro Gly Ala Gly Val Pro Gly Gly Gly Val
            340                 345                 350
Pro Gly Val Gly Val Pro Gly Val Gly Val Pro Gly Gly Gly Val Pro
            355                 360                 365
Gly Ala Gly Val Pro Gly Val Gly Val Pro Gly Val Gly Val Pro Gly
370                 375                 380
Val Gly Val Pro Gly Gly Gly Val Pro Gly Ala Gly Val Pro Gly Gly
385                 390                 395                 400
Gly Val Pro Gly Val Gly Val Pro Gly Val Gly Val Pro Gly Gly Gly
                405                 410                 415
Val Pro Gly Ala Gly Val Pro Gly Val Gly Val Pro Gly Val Gly Val
            420                 425                 430
Pro Gly Val Gly Val Pro Gly Gly Val Pro Gly Ala Gly Val Pro
            435                 440                 445
Gly Gly Gly Val Pro Gly Val Gly Val Pro Gly Val Gly Val Pro Gly

```
              450                 455                 460
Gly Gly Val Pro Gly Ala Gly Val Pro Gly Val Gly Val Pro Gly Val
465                 470                 475                 480

Gly Val Pro Gly Val Gly Val Pro Gly Gly Val Pro Gly Ala Gly
                485                 490                 495

Val Pro Gly Val Gly Val Pro Gly Val Gly Val Pro Gly Val Gly Val
                500                 505                 510

Pro Gly Gly Gly Val Pro Gly Ala Gly Val Pro Gly Val Gly Val Pro
            515                 520                 525

Gly Val Gly Val Pro Gly Val Gly Val Pro Gly Gly Gly Val Pro Gly
            530                 535                 540

Ala Gly Val Pro Gly Gly Val Pro Gly Val Gly Val Pro Gly Val
545                 550                 555                 560

Gly Val Pro Gly Gly Gly Val Pro Gly Ala Gly Val Pro Gly Val Gly
                565                 570                 575

Val Pro Gly Val Gly Val Pro Gly Val Gly Val Pro Gly Gly Gly Val
                580                 585                 590

Pro Gly Ala Gly Val Pro Gly Gly Val Pro Gly Val Gly Phe Pro
            595                 600                 605

Thr Ile Pro Leu Ser Arg Leu Phe Asp Asn Ala Met Leu Arg Ala His
610                 615                 620

Arg Leu His Gln Leu Ala Phe Asp Thr Tyr Gln Glu Phe Glu Glu Ala
625                 630                 635                 640

Tyr Ile Pro Lys Glu Gln Lys Tyr Ser Phe Leu Gln Asn Pro Gln Thr
                645                 650                 655

Ser Leu Cys Phe Ser Glu Ser Ile Pro Thr Pro Ser Asn Arg Glu Glu
                660                 665                 670

Thr Gln Gln Lys Ser Asn Leu Glu Leu Leu Arg Ile Ser Leu Leu Leu
            675                 680                 685

Ile Gln Ser Trp Leu Glu Pro Val Gln Phe Leu Arg Ser Val Phe Ala
690                 695                 700

Asn Ser Leu Val Tyr Gly Ala Ser Asp Ser Asn Val Tyr Asp Leu Leu
705                 710                 715                 720

Lys Asp Leu Glu Glu Gly Ile Gln Thr Leu Met Gly Arg Leu Glu Asp
                725                 730                 735

Gly Ser Pro Arg Thr Gly Gln Ile Phe Lys Gln Thr Tyr Ser Lys Phe
            740                 745                 750

Asp Thr Asn Ser His Asn Asp Asp Ala Leu Leu Lys Asn Tyr Gly Leu
            755                 760                 765

Leu Tyr Cys Phe Arg Lys Asp Met Asp Lys Val Glu Thr Phe Leu Arg
770                 775                 780

Ile Val Gln Cys Arg Ser Val Glu Gly Ser Cys Gly Phe Val Pro Gly
785                 790                 795                 800

Val Gly Val Pro Gly Val Gly Val Pro Gly Gly Val Pro Gly Ala
                805                 810                 815

Gly Val Pro Gly Val Gly Val Pro Gly Val Gly Val Pro Gly Val Gly
                820                 825                 830

Val Pro Gly Gly Val Pro Gly Ala Gly Val Pro Gly Gly Val
            835                 840                 845

Pro Gly Val Gly Val Pro Gly Val Gly Val Pro Gly Gly Gly Val Pro
            850                 855                 860

Gly Ala Gly Val Pro Gly Val Gly Val Pro Gly Val Gly Val Pro Gly
865                 870                 875                 880
```

```
Val Gly Val Pro Gly Gly Val Pro Gly Ala Val Pro Gly Gly
                885                 890                 895

Gly Val Pro Gly Val Gly Val Pro Gly Val Gly Val Pro Gly Gly
            900                 905                 910

Val Pro Gly Ala Gly Val Pro Gly Val Gly Val Pro Gly Val Gly Val
            915                 920                 925

Pro Gly Val Gly Val Pro Gly Gly Val Pro Gly Ala Gly Val Pro
            930                 935                 940

Gly Gly Gly Val Pro Gly Trp Pro
945                 950

<210> SEQ ID NO 77
<211> LENGTH: 769
<212> TYPE: PRT
<213> ORGANISM: Artificial Sequence
<220> FEATURE:
<223> OTHER INFORMATION: exendin-4 ELPbetaV2

<400> SEQUENCE: 77

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Val Pro Gly Val Gly Val Pro Gly Val
        35                  40                  45

Gly Val Pro Gly Ala Gly Val Pro Gly Val Gly Val Pro Gly Ala Gly
    50                  55                  60

Val Pro Gly Val Gly Val Pro Gly Val Gly Val Pro Gly Ala Gly Val
65                  70                  75                  80

Pro Gly Val Gly Val Pro Gly Ala Gly Val Pro Gly Val Gly Val Pro
                85                  90                  95

Gly Ala Gly Val Pro Gly Val Gly Val Pro Gly Ala Gly Val Pro Gly
            100                 105                 110

Val Gly Val Pro Gly Val Gly Val Pro Gly Ala Gly Val Pro Gly Val
        115                 120                 125

Gly Val Pro Gly Ala Gly Val Pro Gly Val Gly Val Pro Gly Ala Gly
    130                 135                 140

Val Pro Gly Val Gly Val Pro Gly Ala Gly Val Pro Gly Val Gly Val
145                 150                 155                 160

Pro Gly Val Gly Val Pro Gly Ala Gly Val Pro Gly Val Gly Val Pro
                165                 170                 175

Gly Ala Gly Val Pro Gly Val Gly Val Pro Gly Ala Gly Val Pro Gly
            180                 185                 190

Val Gly Val Pro Gly Ala Gly Val Pro Gly Val Gly Val Pro Gly Val
        195                 200                 205

Gly Val Pro Gly Ala Gly Val Pro Gly Val Gly Val Pro Gly Ala Gly
    210                 215                 220

Val Pro Gly Val Gly Val Pro Gly Ala Gly Val Pro Gly Val Gly Val
225                 230                 235                 240

Pro Gly Ala Gly Val Pro Gly Val Gly Val Pro Gly Gly Val Pro
                245                 250                 255

Gly Ala Gly Val Pro Gly Val Gly Val Pro Gly Ala Gly Val Pro Gly
            260                 265                 270

Val Gly Val Pro Gly Ala Gly Val Pro Gly Val Gly Val Pro Gly Ala
        275                 280                 285
```

```
Gly Val Pro Gly Val Gly Val Pro Gly Val Gly Val Pro Gly Ala Gly
            290                 295                 300

Val Pro Gly Val Gly Val Pro Gly Ala Gly Val Pro Gly Val Gly Val
305                 310                 315                 320

Pro Gly Ala Gly Val Pro Gly Val Gly Val Pro Gly Ala Gly Val Pro
                325                 330                 335

Gly Val Gly Val Pro Gly Val Gly Val Pro Gly Ala Gly Val Pro Gly
            340                 345                 350

Val Gly Val Pro Gly Ala Gly Val Pro Gly Val Gly Val Pro Gly Ala
            355                 360                 365

Gly Val Pro Gly Val Gly Val Pro Gly Ala Gly Val Pro Gly Val Gly
            370                 375                 380

Val Pro Gly Val Gly Val Pro Gly Ala Gly Val Pro Gly Val Gly Val
385                 390                 395                 400

Pro Gly Ala Gly Val Pro Gly Val Gly Val Pro Gly Ala Gly Val Pro
                405                 410                 415

Gly Val Gly Val Pro Gly Ala Gly Val Pro Gly Val Gly Val Pro Gly
            420                 425                 430

Val Gly Val Pro Gly Ala Gly Val Pro Gly Val Gly Val Pro Gly Ala
            435                 440                 445

Gly Val Pro Gly Val Gly Val Pro Gly Ala Gly Val Pro Gly Val Gly
            450                 455                 460

Val Pro Gly Ala Gly Val Pro Gly Val Gly Val Pro Gly Val Gly Val
465                 470                 475                 480

Pro Gly Ala Gly Val Pro Gly Val Gly Val Pro Gly Ala Gly Val Pro
                485                 490                 495

Gly Val Gly Val Pro Gly Ala Gly Val Pro Gly Val Gly Val Pro Gly
            500                 505                 510

Ala Gly Val Pro Gly Val Gly Val Pro Gly Val Gly Val Pro Gly Ala
            515                 520                 525

Gly Val Pro Gly Val Gly Val Pro Gly Ala Gly Val Pro Gly Val Gly
            530                 535                 540

Val Pro Gly Ala Gly Val Pro Gly Val Gly Val Pro Gly Ala Gly Val
545                 550                 555                 560

Pro Gly Val Gly Val Pro Gly Val Gly Val Pro Gly Ala Gly Val Pro
                565                 570                 575

Gly Val Gly Val Pro Gly Ala Gly Val Pro Gly Val Gly Val Pro Gly
            580                 585                 590

Ala Gly Val Pro Gly Val Gly Val Pro Gly Ala Gly Val Pro Gly Val
            595                 600                 605

Gly Val Pro Gly Val Gly Val Pro Gly Ala Gly Val Pro Gly Val Gly
            610                 615                 620

Val Pro Gly Ala Gly Val Pro Gly Val Gly Val Pro Gly Ala Gly Val
625                 630                 635                 640

Pro Gly Val Gly Val Pro Gly Ala Gly Val Pro Gly Val Gly Val Pro
                645                 650                 655

Gly Val Gly Val Pro Gly Ala Gly Val Pro Gly Val Gly Val Pro Gly
            660                 665                 670

Ala Gly Val Pro Gly Val Gly Val Pro Gly Ala Gly Val Pro Gly Val
            675                 680                 685

Gly Val Pro Gly Ala Gly Val Pro Gly Val Gly Val Pro Gly Val Gly
            690                 695                 700
```

```
Val Pro Gly Ala Gly Val Pro Gly Val Gly Val Pro Gly Ala Gly Val
705                 710                 715                 720

Pro Gly Val Gly Val Pro Gly Ala Gly Val Pro Gly Val Gly Val Pro
            725                 730                 735

Gly Ala Gly Val Pro Gly Val Gly Val Pro Gly Val Gly Val Pro Gly
                740                 745                 750

Ala Gly Val Pro Gly Val Gly Val Pro Gly Ala Gly Val Pro Gly Trp
            755                 760                 765

Pro
```

ELP FUSION PROTEINS FOR CONTROLLED AND SUSTAINED RELEASE

CROSS REFERENCE TO RELATED APPLICATIONS

This application is a U.S. National Phase of PCT/US2015/061955, filed Nov. 20, 2015, which claims benefit of Provisional U.S. Application No. 62/082,945, filed Nov. 21, 2014 and Provisional U.S. Application No. 62/098,624 filed Dec. 31, 2014, the contents of each of which are incorporated by reference in their entireties for all purposes.

DESCRIPTION OF THE TEXT FILE SUBMITTED ELECTRONICALLY

The contents of the text file submitted electronically herewith are incorporated herein by reference in their entirety: a computer readable format copy of the sequence listing (filename: PHAS_031_02US_SUB_SEQLIST_02_20_2020.TXT, date recorded: Feb. 20, 2020, file size 193 kilobytes).

FIELD OF INVENTION

The present disclosure relates to pharmaceutical formulations for sustained release, and methods for delivering a treatment regimen with the sustained release formulations.

BACKGROUND

The effectiveness of peptide and small molecule drugs is often limited by the half-life of such drugs in the circulation, as well as difficulties in obtaining substantially constant plasma levels. For example, the incretin GLP-1 must be administered at relatively high doses to counter its short half-life in the circulation, and these high doses are associated with nausea, among other things. Murphy and Bloom, *Nonpeptidic glucagon-like peptide 1 receptor agonists: A magic bullet for diabetes? PNAS* 104 (3):689-690 (2007). Further, the peptide agent vasoactive intestinal peptide (VIP) exhibits a half-life, in some estimates, of less than one minute, making this agent impractical for pharmaceutical use. Domschke et al., *Vasoactive intestinal peptide in man: pharmacokinetics, metabolic and circulatory effects, Gut* 19:1049-1053 (1978); Henning and Sawmiller, *Vasoactive intestinal peptide: cardiovascular effects, Cardiovascular Research* 49:27-37 (2001). A short plasma half life for peptide drugs is often due to fast renal clearance as well as to enzymatic degradation during systemic circulation.

Strategies for improving the pharmacokinetics of peptide and small molecule drugs are in great demand.

SUMMARY OF THE INVENTION

The present disclosure provides pharmaceutical formulations for sustained release, and methods for delivering a treatment regimen with the sustained release formulations. The disclosure thereby provides improved pharmacokinetics for peptide and small molecule drugs.

In some aspects, the disclosure provides a sustained release pharmaceutical formulation. The formulation includes a therapeutic agent for systemic administration, where the therapeutic agent includes an active agent and an amino acid sequence capable of forming a reversible matrix at the body temperature of a subject. The reversible matrix is formed from hydrogen bonds (e.g., intra- and/or intermolecular hydrogen bonds) as well as from hydrophobic contributions. The formulation further includes one or more pharmaceutically acceptable excipients and/or diluents. The matrix provides for a slow absorption to the circulation from an injection site. The sustained release, or slow absorption from the injection site, is due to a slow reversal of the matrix as the concentration dissipates at the injection site. Once product moves into the circulation, the formulation confers long half-life and improved stability. Thus, a unique combination of slow absorption and long half-life is achieved leading to a desirable PK profile with a shallow peak to trough ratio and/or long Tmax.

In certain embodiments, the amino acid sequence capable of forming a reversible matrix at the body temperature of a subject is an Elastin-Like-Protein (ELP) sequence. The ELP sequence includes or consists of structural peptide units or sequences that are related to, or mimics of, the elastin protein. The ELP amino acid sequence may exhibit a visible and reversible inverse phase transition with the selected formulation. That is, the amino acid sequence may be structurally disordered and highly soluble in the formulation below a transition temperature (Tt), but exhibit a sharp (2-3° C. range) disorder-to-order phase transition when the temperature of the formulation is raised above the Tt. In some embodiments, the present disclosure provides therapeutic agents having transition temperatures between about 26° C. and about 37° C. In addition to temperature, length of the ELP polymer, amino acid composition of the ELP, ionic strength, pH, pressure, selected solvents, presence of organic solutes, and protein concentration may also affect the transition properties, and these may be tailored for the desired absorption profile. In some embodiments the protein concentration and salt concentration affect the transition properties (e.g. transition temperature). Exemplary sequences or structures for the ELP amino acid sequence forming the matrix are disclosed herein.

In certain embodiments, the active agent for systemic administration is a protein or peptide, which may have a short circulatory half-life, such as from about 30 seconds to about 1 hour, to about 2 hours, or to about 5 hours. In some embodiments, the protein or peptide has a circulatory half-life of from 30 seconds to about 10 hours. The therapeutic agent may be a recombinant fusion protein between the protein active agent and the amino acid sequence capable of forming the matrix. Exemplary peptide active agents include GLP-1 receptor agonists (e.g., GLP-1 or derivative thereof), exendin-4 or derivatives thereof, glucagon receptor agonists (e.g. glucagon, oxyntomodulin or derivatives thereof), VPAC2 selective agonists (e.g. vasoactive intestinal peptide (VIP) or derivatives thereof), GIP receptor agonists (e.g. glucose-dependent insulinotropic peptide (GIP) or derivatives thereof), insulin or derivatives thereof, a clotting factor, such as Factor VII, Factor VIII, or Factor IX, or a growth hormone receptor agonist (e.g., human growth hormone (hGH), or functional derivatives thereof). Peptide active agents include sequences that activate more than one receptor, for instance dual agonists of GLP-1 and glucagon receptors, dual agonists of GLP-1 and GIP receptors, or triple agonists able to activate GLP-1, GIP and glucagon receptors. Other protein and small molecule drugs for delivery in accordance with the disclosure are disclosed herein. By providing a slow absorption from the injection site, renal clearance and degradation can be controlled, thereby achieving the desired PK profile.

In other aspects, the disclosure provides methods for delivering a sustained release regimen of an active agent. The methods include administering the formulation described herein to a subject in need, wherein the formulation is administered from about 1 to about 8 times per month. In some embodiments, the formulation is administered about weekly, and may be administered subcutaneously or intramuscularly (for example). In some embodiments, the site of administration is not a pathological site, that is, the therapeutic agent is not administered directly to the intended site of action.

DESCRIPTION OF THE DRAWINGS

FIG. 4 shows the amino acid alignment of ELP 9mers (alpha (SEQ ID NO: 63), beta V (SEQ ID NO: 64), betaV2 (SEQ ID NO: 65), and delta (SEQ ID NO: 66)). In this example, each ELP unit consists of nine copies of the VPGXG SEQ ID NO: 3) ELP pentamer motif, or the XPGVG (SEQ ID NO: 13) ELP pentamer motif with three guest residue amino acids in different ratios.

FIG. 7 shows the pPE0248 linker. This linker allows the insertion of a VPGXG (SEQ ID NO:3) repeat polymer in frame of an initiator methionine and two stop codons for expression and termination using the unique Bgl I restriction enzyme site. N-terminal fusions can be subsequently added using the unique Xba I and Acc65i sites.

FIG. 8 shows the amino acid sequence of the ELP alpha 144mer biopolymer.

FIG. 10 shows the amino acid sequence of the ELP beta v1 144mer biopolymer.

FIG. 12 shows the amino acid sequence of the ELP beta v2 144mer biopolymer.

FIG. 14 shows the amino acid sequence of the ELP gamma 144mer biopolymer.

FIG. 16 shows the amino acid sequence of the ELP delta 144mer biopolymer.

FIG. 23 shows a plasmid map of the vector pPE0429, which contains an hGH sequence inserted into plasmid pPE0362. The synthesized hGH sequence was digested with restriction enzymes PflMI/Bgl I and sub cloned into the Bgl I site in plasmid pPE0362.

FIG. 24 shows an amino acid sequence for an ELP-betaV2-144-hGH fusion protein (SEQ ID NO: 73). The hGH (underlined) is fused to the ELP beta v2-144 sequence (bold). A single ELP pentamer (italics) remains on the C-terminus and conserves a Bgl I restriction site. The site may be used for further cloning steps.

FIG. 25 shows a plasmid map of the vector pPE0431, which contains an ELP1 series 30mer sequence inserted into plasmid pPE0429, which places the ELP1 series 120mer at the N-terminus of the hGH sequence.

FIG. 26 shows the amino acid sequence of the ELP1-120mer hGH fusion protein (SEQ ID NO: 74). The hGH sequence (underlined) is fused to the ELP 1 series 120mer sequence (bold).

FIG. 27 shows a plasmid map of the vector pPE0430, which contains an ELP1 series 30mer sequence inserted into plasmid pPE0429, which places the ELP1 series 30mer at the C-terminus of the ELPbetaV2-144-hGH sequence. Adding the ELP1 series 30mer disrupts receptor mediated clearance and thus further increases circulatory half-life of the ELPbetaV2-144 hGH fusion protein.

FIG. 28 shows an amino acid sequence for an ELP-betaV2-144-hGH fusion protein with an ELP1 series 30mer (SEQ ID NO: 75). The hGH (underlined) is fused to the ELP beta v2-144 sequence (bold). The ELP1 series 30mer (italics) is at the C-terminus of the ELPbetaV2-144-hGH sequence.

FIG. 29 shows a plasmid map of the vector pPE0432, which contains an ELP1 series 30mer sequence inserted into plasmid pPE0431, which places the ELP1 series 30mer at the C-terminus of the ELP1-120-hGH sequence. Adding the ELP1 series 30mer disrupts receptor mediated clearance and thus further increases circulatory half-life of the ELP1 series hGH fusion protein.

FIG. 30 shows the amino acid sequence of the ELP1-120 hGH fusion protein with an ELP1-30mer on the C-terminus (SEQ ID NO: 76). The hGH sequence (underlined) is fused to the ELP 1 series 120mer sequence (bold) and the ELP1-30 sequence (italics).

FIG. 31 shows a plasmid map of the vector pPE0364, which contains a beta v2 series 144mer sequence. The synthesized exendin-4 sequence was digested with restriction enzymes XbaI/BsrGI and sub cloned into the plasmid pPE0362 digested XbaI/Acc65i.

FIG. 32 shows the amino acid sequence of the exendin-4 ELPbeta V2 fusion protein with an ELPbeta V2-144mer on the C-terminus (SEQ ID NO: 77). The exendin-4 sequence (underlined) is fused to the ELPbeta V2-144mer sequence.

DETAILED DESCRIPTION

Figure 1:
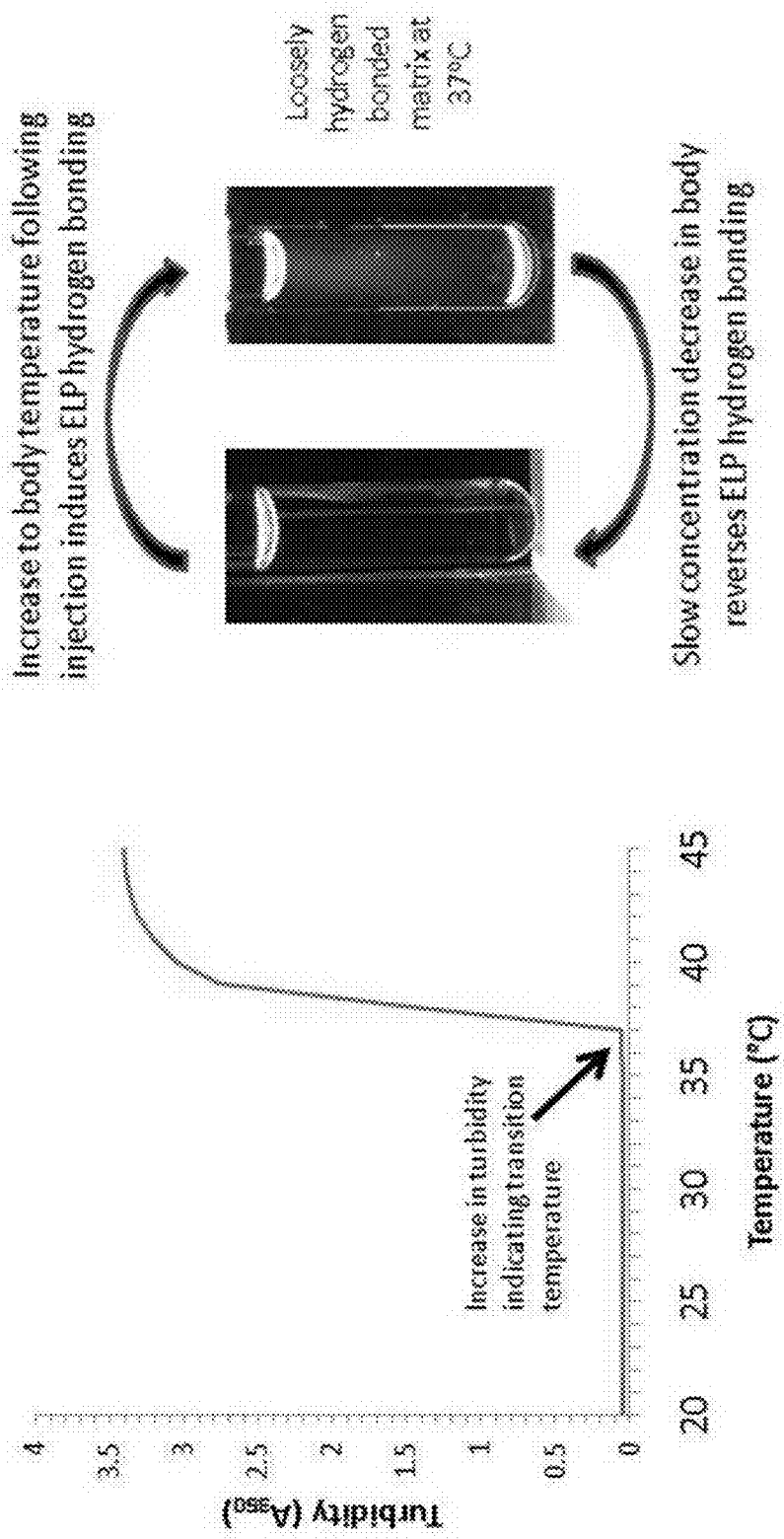
FIG. 1 shows the phase transition (as shown by an increase in turbidity) of an ELP1 protein, induced by a change in temperature to 37° C. or above. This property provides for a slow absorption from an injection site.

The present disclosure provides pharmaceutical formulations for sustained release, and methods for delivering a treatment regimen with the sustained release formulations. In certain embodiments, the pharmaceutical compositions disclosed herein have enhanced efficacy, bioavailability, therapeutic half-life, persistence, degradation assistance, etc. The disclosure thereby provides improved pharmacokinetics for active agents, such as peptides and small molecule drugs, including a relatively flat PK profile with a low ratio of peak to trough, and/or a long Tmax. The PK profile can be maintained with a relatively infrequent administration schedule, such as from one to eight injections per month in some embodiments.

In some aspects, the disclosure provides sustained release pharmaceutical formulations. The formulation includes therapeutic agents for systemic administration, where the therapeutic agent includes an active agent and an amino acid sequence capable of forming a matrix at the body temperature of a subject. The reversible matrix is formed from hydrogen bonds (e.g., intra- and/or intermolecular hydrogen bonds) as well as from hydrophobic contributions. The formulation further includes one or more pharmaceutically acceptable excipients and/or diluents. The matrix provides for a slow absorption to the circulation from an injection site. Without being bound by theory, this slow absorption is due to the slow reversal of the matrix as protein concentration decreases at the injection site. The slow absorption profile provides for a flat PK profile, as well as convenient and comfortable administration regimen. For example, in various embodiments, the plasma concentration of the active agent over the course of days (e.g., from 2 to about 60 days, or from about 4 to about 30 days) does not change by more than a factor of 10, or by more than a factor of about 5, or by more than a factor of about 3. Generally, this flat PK profile is seen over a plurality of (substantially evenly spaced) administrations, such as at least about 2, at least about 5, or at least about 10 administrations of the formulation. In some embodiments, the slow absorption is exhibited by a Tmax (time to maximum plasma concentration) of greater than about 5 hours, greater than about 10 hours, greater than about 20 hours, greater than about 30 hours, or greater than about 50 hours.

Amino Acid Sequences Forming a Reversible Matrix

The sustained release, or slow absorption from the injection site, is controlled by the amino acid sequence capable of forming a hydrogen-bonded matrix at the body temperature of the subject, as well as the components of the formulation.

In some embodiments, the amino acid sequence contains structural units that form hydrogen-bonds through protein backbone groups and/or side chain groups, and which may contribute hydrophobic interactions to matrix formation. In some embodiments, the amino acid side chains do not contain hydrogen bond donor groups, with hydrogen bonds being formed substantially through the protein backbone. Exemplary amino acids include proline, alanine, valine, glycine, and isoleucine, and similar amino acids. In some embodiments, the structural units are substantially repeating structural units, so as to create a substantially repeating structural motif, and substantially repeating hydrogen-bonding capability. In these and other embodiments, the amino acid sequence contains at least about 10%, at least about 20%, at least about 40%, or at least about 50% proline, which may be positioned in a substantially repeating pattern. In this context, a substantially repeating pattern means that at least about 50% or at least about 75% of the proline residues of the amino acid sequence are part of a definable structural unit. In still other embodiments, the amino acid sequence contains amino acids with hydrogen-bond donor side chains, such as serine, threonine, and/or tyrosine. In some embodiments, the repeating sequence may contain from one to about four proline residues, with remaining residues independently selected from non-polar residues, such as glycine, alanine, leucine, isoleucine, and valine. Non-polar or hydrophobic residues may contribute hydrophobic interactions to the formation of the matrix.

In other embodiments, the amino acid sequence capable of forming the matrix at body temperature may include a random coil or non-globular extended structure. For example, the amino acid sequence capable of forming the matrix at body temperature may comprise an amino acid sequence disclosed in U.S. Patent Publication No. 2008/0286808, WIPO Patent Publication No. 2008/155134, and U.S. Patent Publication No. 2011/0123487, each of which is hereby incorporated by reference. In some embodiments the amino acid sequence includes an unstructured recombinant polymer of at least 40 amino acids. The unstructured polymer may include more than about 100, about 150, about 200 or more contiguous amino acids. In some embodiments, the amino acid sequence forms a random coil domain. In particular, a polypeptide or amino acid polymer having or forming "random coil conformation" substantially lacks a defined secondary and tertiary structure. In some embodiments, the unstructured polymer is defined as a polymer having at least 40 amino acids where the total number of glycine (G), aspartate (D), alanine (A), serine (S), threonine (T), glutamate (E) and proline (P) residues constitutes more than about 80% of the total amino acids in the polymer. In some embodiments, at least 50% of the amino acids are devoid of secondary structure as determined by the Chou-Fasman algorithm.

The amino acid sequences may form a "gel-like" state upon injection at a temperature higher than the storage temperature. Exemplary sequences have repeating peptide units, and/or may be relatively unstructured at the lower temperature, and achieve a hydrogen-bonded, structured, state at the higher temperature.

Elastin-Like Peptides (ELPs)

In some embodiments, the amino acid sequence capable of forming a matrix at body temperature is a peptide having repeating units of from four to ten amino acids. The repeating unit may form one, two, or three hydrogen bonds in the formation of the matrix. In certain embodiments, the amino acid sequence capable of forming a matrix at body temperature is an amino acid sequence of silk, elastin, collagen, keratin, or mimic thereof, or an amino acid sequence disclosed in U.S. Pat. No. 6,355,776, which is hereby incorporated by reference.

In certain embodiments, the amino acid sequence is an Elastin-Like-Protein (ELP) sequence. The ELP sequence includes or consists of structural peptide units or sequences that are related to, or mimics of, the elastin protein. The ELP sequence is constructed from structural units of from three to about twenty amino acids, or in some embodiments, from about four to about ten amino acids, such as about four, about five or about six amino acids. The length of the individual structural units may vary or may be uniform. Exemplary structural units are defined by SEQ ID NOS: 1-13 (below), which may be employed as repeating structural units, including tandem-repeating units, or may be employed in some combination. Thus, the ELP may comprise or consist essentially of structural unit(s) selected from SEQ ID NOS: 1-13, as defined below.

In some embodiments, including embodiments in which the structural units are ELP units, the amino acid sequence includes or consists essentially of from about 1 to about 500 structural units, or in certain embodiments about 9 to about 200 structural units, or in certain embodiments about 10 to 200 structural units, or in certain embodiments about 50 to about 200 structural units, or in certain embodiments from about 80 to about 200 structural units, or from about 80 to about 150 structural units. In some embodiments, the structural units are ELP units defined by one or more of SEQ ID NOs: 1-13. In some embodiments, the ELP includes a combination of units defined by SEQ ID NOS: 1-13. Thus, the structural units collectively may have a length of from about 50 to about 2000 amino acid residues, or from about 100 to about 800 amino acid residues, or from about 200 to about 700 amino acid residues, or from about 400 to about 600 amino acid residues. In exemplary embodiments, the amino acid sequence of the ELP structural unit includes or consists essentially of about 3 structural units, of about 7 structural units, of about 9 structural units, of about 10 structural units, of about 15 structural units, of about 20 structural units, of about 40 structural units, of about 80 structural units, of about 90 structural units, of about 100 structural units, of about 120 structural units, of about 140 structural units, about 144 structural units, of about 160 structural units, of about 180 structural units, of about 200 structural units, or of about 500 structural units. In exemplary embodiments, the structural units collectively have a length of about 45 amino acid residues, of about 90 amino acid residues, of about 100 amino acid residues, of about 200 amino acid residues, of about 300 amino acid residues, of about 400 amino acid residues, of about 500 amino acid residues, of about 600 amino acid residues, of about 700 amino acid residues, of about 800 amino acid residues, or of about 1000 amino acid residues.

The amino acid sequence may exhibit a visible and reversible inverse phase transition with the selected formulation. That is, the amino acid sequence may be structurally disordered and highly soluble in the formulation below a transition temperature (Tt), but exhibit a sharp (2-3° C. range) disorder-to-order phase transition, or coacervation, when the temperature of the formulation is raised above the Tt. In addition to temperature, length of the amino acid polymer, amino acid composition, ionic strength, pH, pressure, selected solvents, presence of organic solutes, and protein concentration may also affect the transition properties, and these may be tailored in the formulation for the desired absorption profile. Absorption profile can be easily tested by determining plasma concentration or activity of the active agent over time.

In certain embodiments, the ELP component(s) may be formed of structural units, including but not limited to:

(SEQ ID NO: 1)
(a) the tetrapeptide Val-Pro-Gly-Gly, or VPGG;

(SEQ ID NO: 2)
(b) the tetrapeptide Ile-Pro-Gly-Gly, or IPGG;

(SEQ ID NO: 3)
(c) the pentapeptide Val-Pro-Gly-X-Gly or VPGXG, where X is any natural or non-natural amino acid residue, and where X optionally varies among polymeric or oligomeric repeats;

(SEQ ID NO: 4)
(d) the pentapeptide Ala-Val-Gly-Val-Pro, or AVGVP;

(SEQ ID NO: 5)
(e) the pentapeptide Ile-Pro-Gly-X-Gly, or IPGXG, where X is any natural or non-natural amino acid residue, and where X optionally varies among polymeric or oligomeric repeats;

(SEQ ID NO: 6)
(e) the pentapeptide Ile-Pro-Gly-Val-Gly, or IPGVG;

(SEQ ID NO: 7)
(f) the pentapeptide Leu-Pro-Gly-X-Gly, or LPGXG, where X is any natural or non-natural amino acid residue, and where X optionally varies among polymeric or oligomeric repeats;

(SEQ ID NO: 8)
(g) the pentapeptide Leu-Pro-Gly-Val-Gly, or LPGVG;

(SEQ ID NO: 9)
(h) the pentapeptide Val-Ala-Pro-Gly-Val-Gly, or VAPGVG;

(SEQ ID NO: 10)
(i) the octapeptide Gly-Val-Gly-Val-Pro-Gly-Val-Gly, or GVGVPGVG;

(SEQ ID NO: 11)
(j) the nonapeptide Val-Pro-Gly-Phe-Gly-Val-Gly-Ala-Gly or VPGFGVGAG;

(SEQ ID NO: 12)
(k) the nonapeptides Val-Pro-Gly-Val-Gly-Val-Pro-Gly-Gly, or VPGVGVPGG;
and (SEQ ID NO: 13)
(l) the pentapeptide Xaa-Pro-Gly-Val-Gly, or XPGVG where X is any natural or non-natural amino acid residue, and where X optionally varies among polymeric or oligomeric repeats.

Such structural units defined by SEQ ID NOS: 1-13 may form structural repeating units, or may be used in combination to form an ELP. In some embodiments, the ELP component is formed entirely (or almost entirely) of one or a combination of (e.g., 2, 3, 4, 5, 6, 7, 8, 9, or 10) structural units selected from SEQ ID NOS: 1-13. In other embodiments, at least about 75%, or at least about 80%, or at least about 90% of the ELP component is formed from one or a combination of structural units selected from SEQ ID NOS: 1-13, and which may be present as repeating units.

In certain embodiments, the ELP contains repeat units, including tandem repeating units, of Val-Pro-Gly-X-Gly (SEQ ID NO: 3), where X is as defined above, and where the percentage of Val-Pro-Gly-X-Gly (SEQ ID NO: 3) units taken with respect to the entire ELP component (which may comprise structural units other than VPGXG (SEQ ID NO:

3)) is greater than about 50%, or greater than about 75%, or greater than about 85%, or greater than about 95% of the ELP. The ELP may contain motifs of 5 to 15 structural units (e.g. about 9 or about 10 structural units) of SEQ ID NO: 3, with the guest residue X varying among at least 2 or at least 3 of the units in the motif. The guest residues may be independently selected, such as from non-polar or hydrophobic residues, such as the amino acids V, I, L, A, G, and W (and may be selected so as to retain a desired inverse phase transition property). In certain embodiments, the guest residues are selected from V, G, and A.

In certain embodiments, the ELP contains repeat units, including tandem repeating units, of Xaa-Pro-Gly-Val-Gly (SEQ ID NO: 13), where X is as defined above, and where the percentage of Xaa-Pro-Gly-Val-Gly (SEQ ID NO: 13) units taken with respect to the entire ELP component (which may comprise structural units other than XPGVG (SEQ ID NO: 13)) is greater than about 50%, or greater than about 75%, or greater than about 85%, or greater than about 95% of the ELP. The ELP may contain motifs of 5 to 15 structural units (e.g. about 9 or about 10 structural units) of SEQ ID NO: 13, with the guest residue X varying among at least 2 or at least 3 of the units in the motif. The guest residues may be independently selected, such as from non-polar or hydrophobic residues, such as the amino acids V, I, L, A, G, and W (and may be selected so as to retain a desired inverse phase transition property). In certain embodiments, the guest residues are selected from V and A.

In certain embodiments, the ELP contains repeating units, including tandem repeating units of any of SEQ ID NOs: 1-13 either alone or in combination. In some embodiments, the ELP contains repeats of two or more of any of SEQ ID NOs: 1-13 in combination. In certain embodiments, the ELP contains repeats of SEQ ID NO: 3 and SEQ ID NO: 13. In some embodiments, the ELP contains repeats of SEQ ID NO: 3 and SEQ ID NO: 13, wherein the guest residues are independently selected, such as from non-polar or hydrophobic residues, such as the amino acids V, I, L, A, G, and W (and may be selected so as to retain a desired inverse phase transition property). In certain embodiments, the guest residues are selected from V, G, and A.

In some embodiments, the ELP includes 9mers including nine copies of one or more ELP structural units disclosed herein. In some embodiments, the ELP includes 9mers including nine copies of a pentapeptide disclosed herein. In some embodiments, the ELP includes 9mers including SEQ ID NOs: 3 and 13 in any combination. In some embodiments, the ELP includes a sequence alternating between SEQ ID NOs: 3 and 13. ELPs of varying numbers of 9mers can be combined to produce ELPs with, for instance, 18, 27, 36, 45, 54, 63, 72, 81, 90, 99, 108, 117, 126, 135, 144, 153, 162, 171, or 180 copies of the 9mer.

In certain embodiments, the ELP includes 9mers including SEQ ID NO: 3, wherein the guest residue is selected from V, G, and A. In certain embodiments, the ELP includes 9 mers including SEQ ID NO: 3, wherein V, G, and A are in the ratio of 7:2:0 (alpha). In certain embodiments, the ELP includes 9mers including SEQ ID NO:3, wherein V, G, and A are in the ratio of 7:0:2 (beta v1). In certain embodiments, the ELP includes 9mers including SEQ ID NO:3, wherein V, G, and A are in the ratio of 6:0:3 (beta v2). In certain embodiments, the ELP includes 9mers including SEQ ID NO:3, wherein V, G, and A are in the ratio of 5:2:2 (gamma). In certain embodiments, the ELP includes 9mers including SEQ ID NO: 13, wherein the guest residue is selected from V, G, and A. In certain embodiments, the ELP includes 9mers including SEQ ID NO:13, wherein V, G, and A are in the ratio of 5:0:4 (delta). Exemplary 9mers are disclosed in Table 1. Table 2 demonstrates the transition temperatures of several exemplary 9mers.

TABLE 1

Guest residue ratios in exemplary 9mers. The ELP polymers have hydrophobicities between the ELP 1 series (least hydrophobic) and the ELP 4 series (most hydrophobic).

| ELP series | Pentamer motif | Guest residue ratio |
| --- | --- | --- |
| 1 series | VPG*X*G (SEQ ID NO: 3) | 5 Val:3 Gly:2 Ala |
| alpha | VPG*X*G (SEQ ID NO: 3) | 7 Val:2 Gly:0 Ala |
| beta v1 | VPG*X*G (SEQ ID NO: 3) | 7 Val:0 Gly:2 Ala |
| beta v2 | VPG*X*G (SEQ ID NO: 3) | 6 Val:0 Gly:3 Ala |
| gamma | VPG*X*G (SEQ ID NO: 3) | 5 Val:2 Gly:2 Ala |
| delta | *X*PGVG (SEQ ID NO: 3) | 5 Val:0 Gly:4 Ala |
|  | VPG*X*G (SEQ ID NO: 13) | 6 Val:3 Gly:0 Ala |
|  | VPG*X*G (SEQ ID NO: 3) | 6 Val:2 Gly:1 Ala |
|  | VPG*X*G (SEQ ID NO: 3) | 6 Val:1 Gly:2 Ala |
|  | VPG*X*G (SEQ ID NO: 3) | 6 Val:0 Gly:3 Ala |
|  | VPG*X*G (SEQ ID NO: 3) | 7 Val:1 Gly:1 Ala |
|  | VPG*X*G (SEQ ID NO: 3) | 8 Val:0 Gly:1 Ala |
|  | VPG*X*G (SEQ ID NO: 3) | 8 Val:1 Gly:0 Ala |
| 4 series | VPG*X*G (SEQ ID NO: 3) | 10 Val:0 Gly:0 Ala |

TABLE 2

Comparison of measured transition temperatures of exemplary 9mers. The inflection of turbidity measured using a Cary spectrophotometer is the result of the ELP biopolymer phase transitioning.

| ELP series (10 mg/ml) | Transition temp |
| --- | --- |
| 1 series (pPB1023) | 37° C. |
| alpha (pPE0253) | 29° C. |
| beta v1 (pPE0254) | 28° C. |
| beta v2 (pPE0311) | 31° C. |
| gamma (pPE0255) | 29° C. |
| delta (pPE0256) | 35° C. |
| 4 series (pPE0002) | 26° C. |

In some embodiments, the ELP includes combinations of the 9mers listed in Table 1. In some embodiments, the ELP includes combinations of the alpha, beta v1, beta v2, and/or delta 9mers. For example, the gamma ELP is constructed by alternating between an alpha 9mer and a beta v1 9mer for 16 copies until a 144mer is constructed. In certain embodiments, the ELP includes combinations of alpha and beta v1 9mers. In certain embodiments, the ELP includes combinations of alpha and beta v2 9mers. In certain embodiments, the ELP includes combinations of alpha and delta 9mers. In certain embodiments, the ELP includes combinations of beta v1 and beta v2 9mers. In certain embodiments, the ELP includes combinations of beta v1 and delta 9mers. In certain embodiments, the ELP includes combinations of beta v2 and delta 9mers. In certain embodiments, the ELP includes combinations of alpha, beta v1, and beta v2 9mers. In certain embodiments, the ELP includes combinations of alpha, beta v1, and delta 9mers. In certain embodiments, the ELP includes combinations of alpha, beta v2, and delta 9mers. For example, in particular arrangements, the ELPbeta v2 may include the following guest residues in structural units iterated in the following sequence: A-V-A-V-V-A-V-A-V (e.g. amino acid residues 2-10 of SEQ ID NO: 14). The iterated sequence may be repeated sequentially in the ELP about 10 times, about 15 times, about 16 times, about 20 times, about 25 times, about 30 times, about 35 times or more. In some aspects, the ELP contains about 10 to about 20 iterated sequences. In other aspects, the ELP contains about 15 to 20 iterated sequences. In some aspects, the ELP contains about 16 iterated sequences.

In some embodiments, the ELP includes 10mers including ten copies of one or more ELP structural units disclosed herein. In some embodiments, the ELP includes 10mers including ten copies of a pentapeptide disclosed herein. In some embodiments, the ELP includes 10mers including SEQ ID NOs: 3 and 13 in any combination, In some embodiments, the ELP includes a sequence alternating between SEQ ID NOs: 3 and 13. ELPs of varying numbers of 10mers can be combined to produce ELPs with, for instance, 20, 30, 40, 60, 90, 100, 120, 150, 160, or 200 copies of the 10mer. Exemplary 10mers are disclosed in Table 3.

TABLE 3

Guest residue ratios in exemplary 10mers. The ELP polymers have hydrophobicities between the ELP 1 series (least hydrophobic) and the ELP 4 series (most hydrophobic).

| ELP series | Pentamer motif | Guest residue ratio |
| --- | --- | --- |
| 1 series | VPGXG (SEQ ID NO: 3) | 5 Val:3 Gly:2 Ala |
| | VPGXG (SEQ ID NO: 3) | 5 Val:4 Gly:1 Ala |
| | VPGXG (SEQ ID NO: 3) | 5 Val:5 Gly:0 Ala |
| | VPGXG (SEQ ID NO: 3) | 5 Val:2 Gly:3 Ala |
| | VPGXG (SEQ ID NO: 3) | 5 Val:1 Gly:4 Ala |
| | VPGXG (SEQ ID NO: 3) | 5 Val:0 Gly:5 Ala |
| | VPGXG (SEQ ID NO: 3) | 6 Val:4 Gly:0 Ala |
| | VPGXG (SEQ ID NO: 3) | 6 Val:3 Gly:1 Ala |
| | VPGXG (SEQ ID NO: 3) | 6 Val:2 Gly:2 Ala |
| | VPGXG (SEQ ID NO: 3) | 6 Val:1 Gly:3 Ala |
| | VPGXG (SEQ ID NO: 3) | 6 Val:0 Gly:4 Ala |
| | VPGXG (SEQ ID NO: 3) | 7 Val:3 Gly:0 Ala |
| | VPGXG (SEQ ID NO: 3) | 7 Val:2 Gly:1 Ala |
| | VPGXG (SEQ ID NO: 3) | 7 Val:1 Gly:2 Ala |
| | VPGXG (SEQ ID NO: 3) | 7 Val:0 Gly:3 Ala |
| | VPGXG (SEQ ID NO: 3) | 8 Val:2 Gly:0 Ala |
| | VPGXG (SEQ ID NO: 3) | 8 Val:0 Gly:2 Ala |
| | VPGXG (SEQ ID NO: 3) | 8 Val:1 Gly:1 Ala |
| | VPGXG (SEQ ID NO: 3) | 9 Val:1 Gly:1 Ala |
| | VPGXG (SEQ ID NO: 3) | 9 Val:0 Gly:1 Ala |
| 4 series | VPGXG (SEQ ID NO: 3) | 10 Val:0 Gly:0 Ala |

In some embodiments, the ELP may form a β-turn structure. Exemplary peptide sequences suitable for creating a β-turn structure are described in International Patent Application PCT/US96/05186, which is hereby incorporated by reference in its entirety. For example, the fourth residue (X) in the sequence VPGXG (SEQ ID NO: 3), can be varied without eliminating the formation of a β-turn.

The structure of exemplary ELPs may be described using the notation $ELP_k$ [$X_iY_j$-n], where k designates a particular ELP repeat unit, the bracketed capital letters are single letter amino acid codes, and their corresponding subscripts designate the relative ratio of each guest residue X in the structural units (where applicable), and n describes the total length of the ELP in number of the structural repeats. For example, ELP1 [$V_5A_2G_3$-10] designates an ELP component containing 10 repeating units of the pentapeptide VPGXG (SEQ ID NO: 3), where X is valine, alanine, and glycine at a relative ratio of about 5:2:3; ELP1 [$K_1V_2F_1$-4] designates an ELP component containing 4 repeating units of the pentapeptide VPGXG (SEQ ID NO: 3), where X is lysine, valine, and phenylalanine at a relative ratio of about 1:2:1; ELP1 [$K_1V_7F_1$-9] designates a polypeptide containing 9 repeating units of the pentapeptide VPGXG (SEQ ID NO: 3), where X is lysine, valine, and phenylalanine at a relative ratio of about 1:7:1; ELP1 [V-5] designates a polypeptide containing 5 repeating units of the pentapeptide VPGXG (SEQ ID NO:3), where X is valine; ELP1 [V-20] designates a polypeptide containing 20 repeating units of the pentapeptide VPGXG (SEQ ID NO: 3), where X is valine; ELP2 [5] designates a polypeptide containing 5 repeating units of the pentapeptide AVGVP (SEQ ID NO: 4); ELP3 [V-5] designates a polypeptide containing 5 repeating units of the pentapeptide IPGXG (SEQ ID NO: 5), where X is valine; ELP4 [V-5] designates a polypeptide containing 5 repeating units of the pentapeptide LPGXG (SEQ ID NO: 7), where X is valine.

With respect to ELP, the Tt is a function of the hydrophobicity of the guest residue. Thus, by varying the identity of the guest residue(s) and their mole fraction(s), ELPs can be synthesized that exhibit an inverse transition over a broad range. Thus, the Tt at a given ELP length may be decreased by incorporating a larger fraction of hydrophobic guest residues in the ELP sequence. Examples of suitable hydrophobic guest residues include valine, leucine, isoleucine, phenylalanine, tryptophan and methionine. Tyrosine, which is moderately hydrophobic, may also be used. Conversely, the Tt may be increased by incorporating residues, such as those selected from: glutamic acid, cysteine, lysine, aspartate, alanine, asparagine, serine, threonine, glycine, arginine, and glutamine.

For polypeptides having a molecular weight >100,000, the hydrophobicity scale disclosed in PCT/US96/05186 (which is hereby incorporated by reference in its entirety) provides one means for predicting the approximate Tt of a specific ELP sequence. For polypeptides having a molecular weight <100,000, the Tt may be predicted or determined by the following quadratic function: $Tt = M0 + M1X + M2X^2$ where X is the MW of the fusion protein, and M0=116.21; M1=−1.7499; M2=0.010349.

The ELP in some embodiments is selected or designed to provide a Tt ranging from about 10 to about 37° C. at formulation conditions, such as from about 20 to about 37° C., or from about 25° C. to about 37° C. In some embodiments, the transition temperature at physiological conditions (e.g., 0.9% saline) is from about 34° C. to 36° C., to take into account a slightly lower peripheral body temperature.

In certain embodiments, the ELP includes [VPGXG]m, (SEQ ID NO:3) where m is any number from 1 to 200. In certain embodiments, the ELP includes $[VPGXG]_m$ (SEQ ID NO:3), where m is any number from 1 to 200, and each X is selected from V, G, and A. In certain embodiments, the ELP includes $[VPGXG]_m$ (SEQ ID NO:3), where m is any number from 1 to 200, each X is selected from V, G, and A, and wherein the ratio of V:G:A may be about 5:3:2. In certain embodiments, the ELP includes [VPGXG]90 (SEQ ID NO:3), where each X is selected from V, G, and A, and wherein the ratio of V:G:A may be about 5:3:2. For example, the amino acid sequence capable of forming the hydrogen-bonded matrix at body temperature includes [VPGXG]120 (SEQ ID NO: 19), where each X is selected from V, G, and A, and wherein the ratio of V:G:A may be about 5:3:2. As shown herein, 120 structural units of this ELP can provide a transition temperature at about 37° C. with about 5 to 15 mg/ml (e.g., about 10 mg/ml) of protein. At concentrations of about 50 to about 100 mg/mL the phase transition temperature is about 35.5 degrees centigrade (just below body temperature), which allows for peripheral body temperature to be just less than 37° C. In some embodiments, the ELP may include [VPGXG]144 (SEQ ID NO:3), where each X is selected from V, G, and A, and wherein the ratio of V:G:A may be about 5:3:2. In some embodiments, the ELP includes $[VPGXG]_{180}$ (SEQ ID NO:3), where each X is selected from V, G, and A, and wherein the ratio of V:G:A may be about 5:3:2.

In certain embodiments, the ELP includes [VPGXG]$_m$ (SEQ ID NO:3), where m is any number from 1 to 200, where each X is selected from V, G, and A, and wherein the ratio of V:G:A is about 7:2:0. In certain embodiments, the ELP includes [VPGXG]$_{90}$ (SEQ ID NO:3), where each X is selected from V, G, and A, and wherein the ratio of V:G:A is about 7:2:0. In certain embodiments, the ELP includes [VPGXG]120 (SEQ ID NO:3), where each X is selected from V, G, and A, and wherein the ratio of V:G:A is about 7:2:0. In certain embodiments, the ELP includes [VPGXG] 144 (SEQ ID NO:3), where each X is selected from V, G, and A, and wherein the ratio of V:G:A is about 7:2:0. In certain embodiments, the ELP includes [VPGXG]$_{180}$ (SEQ ID NO:3), where each X is selected from V, G, and A, and wherein the ratio of V:G:A is about 7:2:0.

In certain embodiments, the ELP includes [VPGXG]$_m$ (SEQ ID NO:3), where m is any number from 1 to 200, where each X is selected from V, G, and A, and wherein the ratio of V:G:A is about 7:0:2. In certain embodiments, the ELP includes [VPGXG]$_{90}$ (SEQ ID NO:3), where each X is selected from V, G, and A, and wherein the ratio of V:G:A is about 7:0:2. In certain embodiments, the ELP includes [VPGXG]$_{120}$ (SEQ ID NO:3), where each X is selected from V, G, and A, and wherein the ratio of V:G:A is about 7:0:2. In certain embodiments, the ELP includes [VPGXG]$_{144}$ (SEQ ID NO:3), where each X is selected from V, G, and A, and wherein the ratio of V:G:A is about 7:0:2. In certain embodiments, the ELP includes [VPGXG]$_{180}$ (SEQ ID NO:3), where each X is selected from V, G, and A, and wherein the ratio of V:G:A is about 7:0:2.

In certain embodiments, the ELP includes [VPGXG]$_m$ (SEQ ID NO:3), where m is any number from 1 to 200, where each X is selected from V, G, and A, and wherein the ratio of V:G:A is about 6:0:3. In certain embodiments, the ELP includes [VPGXG]$_{90}$ (SEQ ID NO:3), where each X is selected from V, G, and A, and wherein the ratio of V:G:A is about 6:0:3. In certain embodiments, the ELP includes [VPGXG]$_{120}$ (SEQ ID NO:3), where each X is selected from V, G, and A, and wherein the ratio of V:G:A is about 6:0:3. In certain embodiments, the ELP includes [VPGXG]$_{144}$ (SEQ ID NO:3), where each X is selected from V, G, and A, and wherein the ratio of V:G:A is about 6:0:3. In certain embodiments, the ELP includes [VPGXG]$_{180}$ (SEQ ID NO:3), where each X is selected from V, G, and A, and wherein the ratio of V:G:A is about 6:0:3.

In certain embodiments, the ELP includes [VPGXG]$_m$ (SEQ ID NO:3), where m is any number from 1 to 200, where each X is selected from V, G, and A, and wherein the ratio of V:G:A is about 5:2:2. In certain embodiments, the ELP includes [VPGXG]$_{90}$(SEQ ID NO:3), where each X is selected from V, G, and A, and wherein the ratio of V:G:A is about 5:2:2. In certain embodiments, the ELP includes [VPGXG]$_{120}$ (SEQ ID NO:3), where each X is selected from V, G, and A, and wherein the ratio of V:G:A is about 5:2:2. In certain embodiments, the ELP includes [VPGXG]$_{144}$ (SEQ ID NO:3), where each X is selected from V, G, and A, and wherein the ratio of V:G:A is about 5:2:2. In certain embodiments, the ELP includes [VPGXG]$_{180}$ (SEQ ID NO:3), where each X is selected from V, G, and A, and wherein the ratio of V:G:A is about 5:2:2.

In certain embodiments, the ELP includes [XPGVG]$_m$ (SEQ ID NO:3), where m is any number from 1 to 200. In certain embodiments, the ELP includes [XPGVG]$_m$ (SEQ ID NO:3), where m is any number from 1 to 200, and each X is selected from V, G, and A. In certain embodiments, the ELP includes [XPGVG]$_m$ (SEQ ID NO:3), where m is any number from 1 to 200, each X is selected from V, G, and A and wherein the ratio of V:G:A is about 5:0:4. In certain embodiments, the ELP includes [XPGVG]$_{90}$ (SEQ ID NO:3), where each X is selected from V, G, and A, and wherein the ratio of V:G:A is about 5:0:4. In certain embodiments, the ELP includes [XPGVG]$_{120}$ (SEQ ID NO:3), where each X is selected from V, G, and A, and wherein the ratio of V:G:A is about 5:0:4. In certain embodiments, the ELP includes [XPGVG]$_{144}$ (SEQ ID NO:3), where each X is selected from V, G, and A, and wherein the ratio of V:G:A is about 5:0:4. In certain embodiments, the ELP includes [XPGVG]$_{180}$ (SEQ ID NO:3), where each X is selected from V, G, and A, and wherein the ratio of V:G:A is about 5:0:4.

In certain embodiments, the ELP includes [VPGVG]$_m$ (SEQ ID NO:3) where m is any number from 1 to 200. In some embodiments, the ELP includes [VPGVG]$_{90}$ (SEQ ID NO:3), or [VPGVG]$_{120}$ (SEQ ID NO:3). As shown herein, 120 structural units of this ELP can provide a transition temperature at about 37° C. with about 0.005 to about 0.05 mg/ml (e.g., about 0.01 mg/ml) of protein. Alternatively, the ELP includes [VPGXG]$_{144}$ (SEQ ID NO:3) or [XPGVG]$_{144}$ (SEQ ID NO:3). As shown herein (Table 2), 144 structural units of either of these ELPs can provide a transition temperature at 28° C. to 35° C. inclusive.

In various embodiments, the intended subject is human, and the body temperature is about 37° C., and thus the therapeutic agent is designed to provide a sustained release at or near this temperature (e.g. between about 28° C. to about 37° C.). A slow release into the circulation with reversal of hydrogen bonding and/or hydrophobic interactions is driven by a drop in concentration as the product diffuses at the injection site, even though body temperature remains constant. In other embodiments, the subject is a non-human mammal, and the therapeutic agent is designed to exhibit a sustained release at the body temperature of the mammal, which may be from about 30 to about 40° C. in some embodiments, such as for certain domesticated pets (e.g., dog or cat) or livestock (e.g., cow, horse, sheep, or pig). Generally, the Tt is higher than the storage conditions of the formulation (which may be from 10 to about 25° C., or from 15 to 22° C.), such that the therapeutic agent remains in solution for injection.

In some embodiments, the ELP can provide a transition temperature at a range of 27° C. to 36° C. inclusive. In some embodiments, the ELP can provide a transition temperature at a range of 28° C. to 35° C. inclusive. In some embodiments, the ELP can provide a transition temperature at a range of 29° C. to 34° C. inclusive. In some embodiments, the ELP can provide a transition temperature at a range of 27° C. to 33° C. inclusive. In some embodiments, the ELP can provide a transition temperature at a range of 30° C. to 33° C. inclusive. In some embodiments, the ELP can provide a transition temperature at a range of 31° C. to 31° C. inclusive. In some embodiments, the ELP can provide a transition temperature of 27° C., 28° C., 29° C., 30° C., 31° C., 32° C., 33° C., 34° C., 35° C., or 36° C. In some embodiments, the ELP can provide a transition temperature at a range of 28° C. to 35° C. inclusive at a protein concentration of 10 mg/mL in 110 mM NaCl.

Elastin-like-peptide (ELP) protein polymers and recombinant fusion proteins can be prepared as described in U.S. Patent Publication No. 2010/0022455, which is hereby incorporated by reference. In some embodiments, the ELP protein polymers are constructed through recursive ligation to rapidly clone DNA encoding highly repetitive polypeptides of any sequence and specified length over a large range of molecular weights. In a single cycle, two halves of a parent plasmid, each containing a copy of an oligomer, are ligated together, thereby dimerizing the oligomer and reconstituting a functional plasmid. This process is carried out recursively to assemble an oligomeric gene with the desired number of repeats. For example, one ELP structural subunit (e.g. a pentapeptide or a 9mer of pentapeptides) is inserted into a vector. The vector is digested, and another ELP structural unit (e.g. a pentapeptide or a 9mer of pentapeptides) is inserted. Each subsequent round of digestion and ligation doubles the number of ELP structural units contained in the resulting vector until the ELP polymer is the desired length. By varying the number of pentapeptides in the initial structural unit, ELPs of varying length can easily be constructed. Alternative means of construction (i.e. other than recursive ligation) can be used to produce alternative lengths of ELP.

Figure 6:
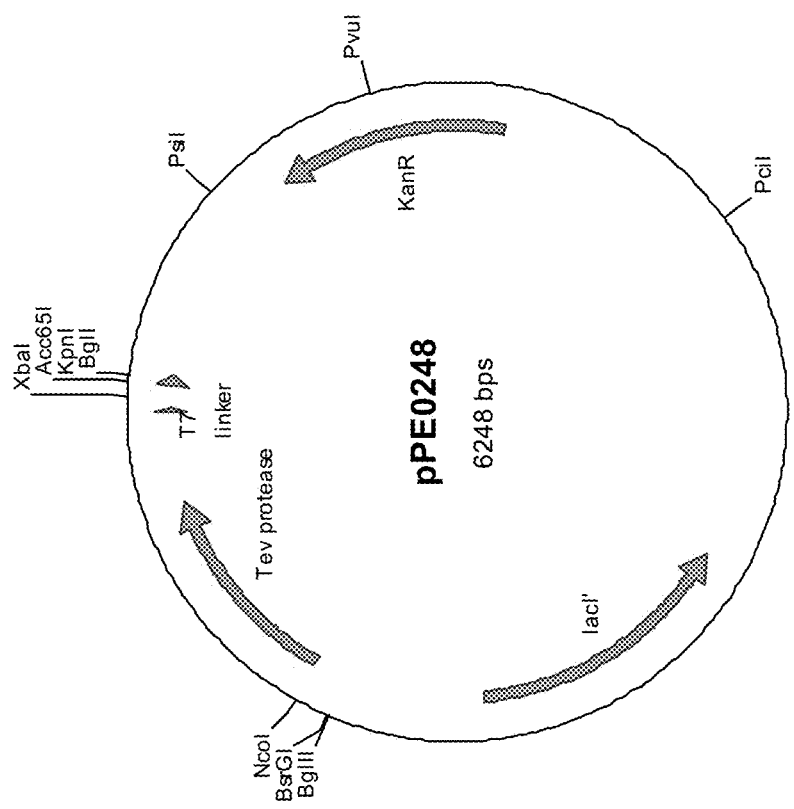
FIG. 6 shows the pPE0248 plasmid map.
Figure 9:
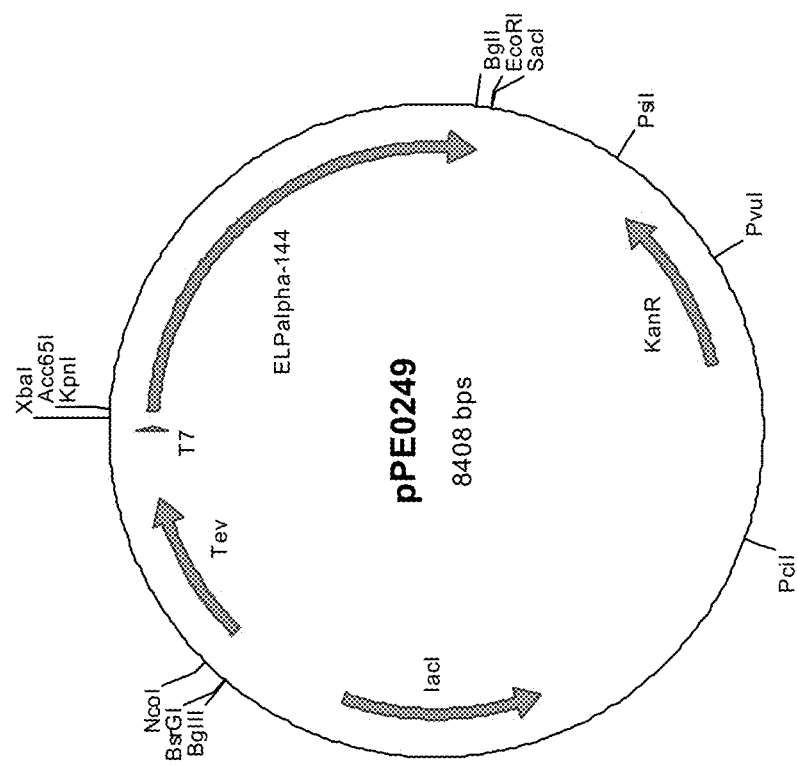
FIG. 9 shows the pPE0249 plasmid map.
Figure 11:
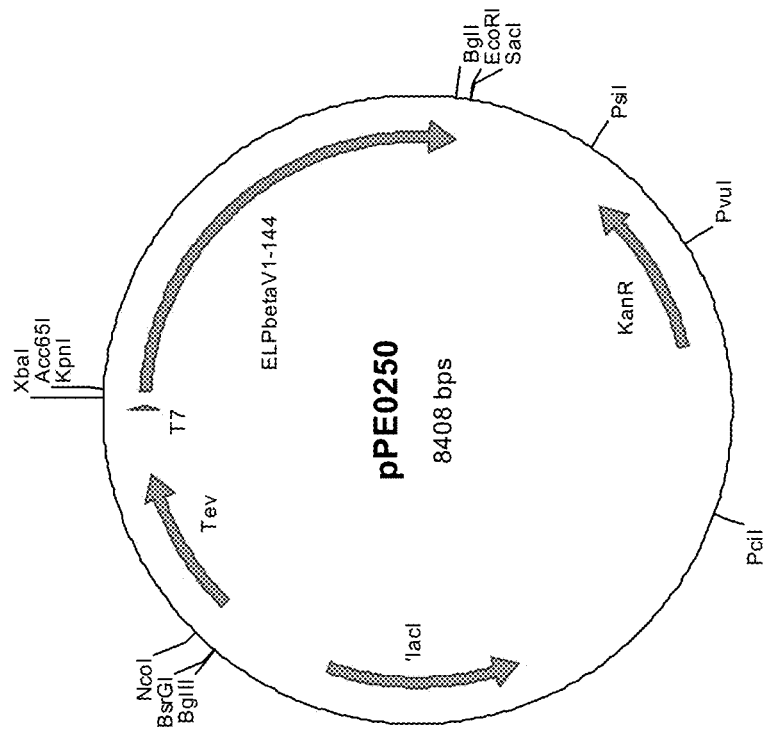
FIG. 11 shows the pPE0250 plasmid map.
Figure 13:
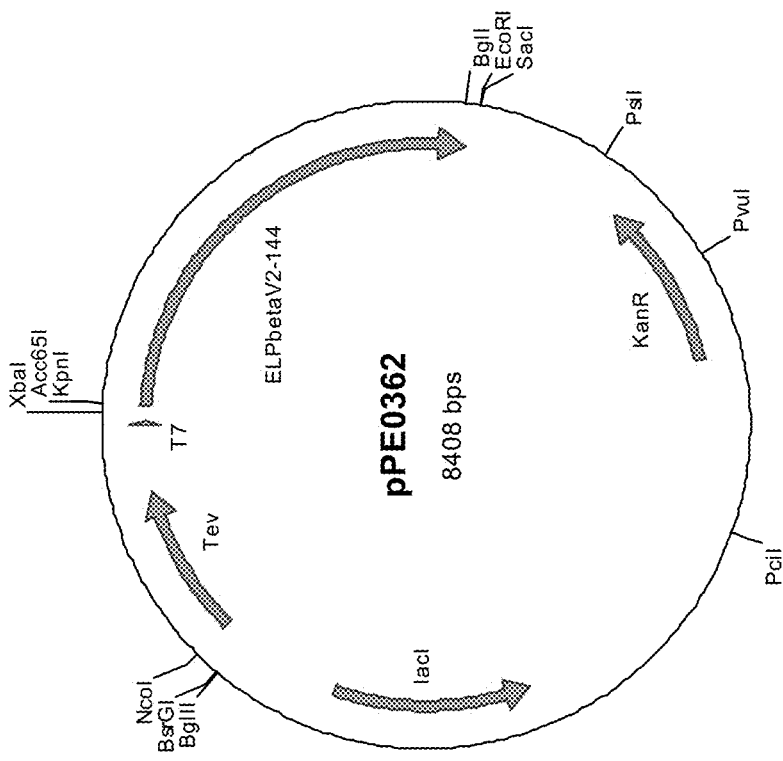
FIG. 13 shows the pPE0362 plasmid map.
Figure 15:
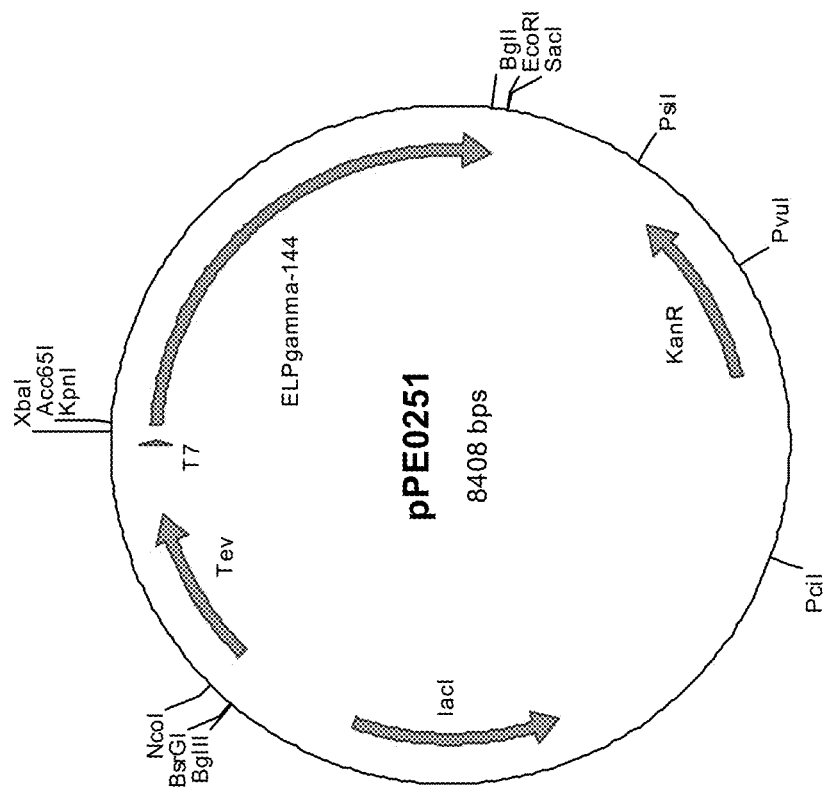
FIG. 15 shows the pPE0251 plasmid map.
Figure 17:
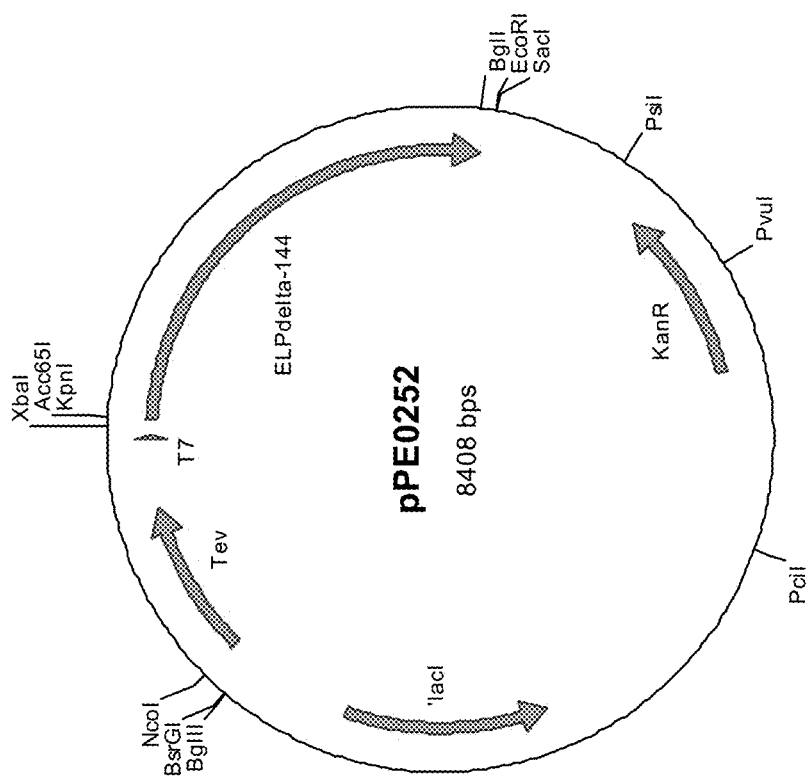
FIG. 17 shows the pPE0252 plasmid map.

In some embodiments, the vector contains one or more additional amino acids or ELP structural unit repeats. For example, pPE0248 (FIG. 6) adds an additional pentamer repeat to the N terminus of the 144mer with valine in the guest position and an additional pentamer to the C terminus with a tryptophan in the guest residue. The tryptophan may be used as a means to increase the extinction coefficient of the molecule, allowing for better measurement of absorbance, for instance at 280 nm, which can be useful for determination of protein concentration, or for monitoring protein content during purification. The pentamers added to either end can also be designed so as the encoding DNA contains restriction enzyme recognition sites for cloning of fusion partners on to either end of the ELP coding sequence.

In some embodiments, the therapeutic agent includes an active agent and one or more ELPs. In some embodiments, the therapeutic agent includes an active agent with one or more ELPs at either the N- or C-terminus. In some embodiments, the therapeutic agent includes an active agent with one or more ELPs at both the N- or C-termini. In some embodiments, the ELPs are approximately the same size. In some embodiments, the ELPs differ in size. In some embodiments, an ELP at one terminus is larger than an ELP at the other terminus. In some embodiments, an ELP at the N-terminus is larger than an ELP at the C-terminus. In some embodiments, an ELP at the C-terminus is larger than an ELP at the N-terminus.

Active Agents

Peptide Active Agents

In various embodiments, the active agent is a protein or peptide, which by itself may have a short circulatory half-life, such as from about 30 seconds to about 1 hour. The therapeutic agent may be a recombinant fusion protein between the protein active agent and the amino acid sequence capable of forming the hydrogen-bonded matrix at the body temperature of the subject (e.g. an ELP). Any appropriate peptide active agent may be used in the therapeutic agents of the present disclosure. Exemplary peptide active agents include GIP receptor agonists such as glucose-dependent insulinotropic peptide (GIP) or a derivative thereof. Further exemplary peptide active agents include GLP1 receptor agonists such as GLP-1 or derivatives thereof (including GLP1 7-36 or GLP1 7-37), or exendin-4 or derivatives thereof. In other embodiments, the protein or peptide agent is, a glucagon receptor agonist (including glucagon, oxyntomodulin or derivatives thereof). In other embodiments, the disclosure provides for a co-formulation of any two of a GLP1 receptor agonist, a glucagon receptor agonist, a GIP receptor agonist, a VPAC2 selective agonist, such as vasoactive intestinal peptide (VIP) or a derivative thereof, a clotting factor, such as Factor VII, Factor VIII, or Factor IX, insulin (e.g., single chain insulin or an A chain or a B chain fusion protein, as described in U.S. Patent Publication No. 2013/0150291, which is hereby incorporated by reference), or a monoclonal antibody or single chain antibody. Alternatively, the active agent is as described in U.S. Patent Publication No. 2011/0123487, which is hereby incorporated by reference.

The half-life of protein therapeutics can be extended by a variety of means, including increasing the size and thus the hydrodynamic volume of the protein therapeutic, adding modified or unnatural amino acids, conjugation of moieties (e.g. pegylation), the addition of synthetic sequences (e.g. XTEN® sequences, PASylation®), carboxy-terminal extension from hCG (CTP), addition of albumin-binding sequences (e.g. AlbudAb®), conjugation of albumin-binding fatty acids, post-translational modifications such as N-glycosylation and fusion to other peptides, or fusion with a mammalian heterologous protein, such as albumin, transferrin, or antibody Fc sequences. Such sequences are described in See U.S. Pat. No. 7,238,667 (particularly with respect to albumin conjugates), U.S. Pat. No. 7,176,278 (particularly with respect to transferrin conjugates), and U.S. Pat. No. 5,766,883.

In some embodiments, the disclosure provides derivatives, variants, or mutants of one or more active peptide agents disclosed herein. In some embodiments, the derivative, variant, or mutant contains one or more amino acid substitutions compared to the amino acid sequence of the native therapeutic peptide agent. In some embodiments, one to 20 amino acids are substituted. In some embodiments, the derivative, variant, or mutant contains about 1, about 2, about 3, about 4, about 5, about 6, about 7, about 8, about 9, or about 10 amino acid substitutions compared to the amino acid sequence of the native therapeutic peptide agent. In some embodiments, the derivative, variant, or mutant contains one or more amino acid deletions compared to the amino acid sequence of the native therapeutic peptide agent. In some embodiments, one to 20 amino acids are deleted compared to the amino acid sequence of the native therapeutic peptide agent. In some embodiments, the derivative, variant, or mutant has about 1, about 2, about 3, about 4, about 5, about 6, about 7, about 8, about 9, or about 10 amino acid deletions compared to the amino acid sequence of the native therapeutic peptide agent. In some embodiments, one to ten amino acids are deleted at either terminus compared to the amino acid sequence of the native therapeutic peptide agent. In some embodiments, one to ten amino acids are deleted from both termini compared to the amino acid sequence of the native therapeutic peptide agent. In some embodiments, the amino acid sequence of the derivative, variant, or mutant is at least about 70% identical to the amino acid sequence of the native peptide therapeutic agent. In some embodiments, the amino acid sequence of the derivative, variant, or mutant is about 70%, about 80%, about 85%, about 90%, about 95%, about 96%, about 97%, about 98%, or about 99% identical to the amino acid sequence of the native therapeutic peptide agent.

Methods to determine identity are well-known in the art. Preferred methods to determine identity are designed to give the best match between the sequences tested. Methods to determine identity and similarity are codified in publicly available computer programs. Sequence alignments and percent identity calculations may be performed using the "Clustal W method of alignment" (described by Higgins and Sharp, CABIOS. 5:151-153 (1989); Higgins, D. G. et al., Comput. Appl. Biosci. 8:189-191 (1992)) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

In some embodiments, the disclosure provides for co-formulation of any two or more active agents disclosed herein. In some embodiments, the co-formulation includes two or more peptide active agents and small molecule active agents. In some embodiments, the co-formulation includes two or more small molecule active agents. In some embodiments, the co-formulation includes two or more peptide active agents. In some embodiments, the peptide active agents are insulin or derivatives thereof and a GLP-1 receptor agonist or derivatives thereof. In some embodiments, the peptide active agents are insulin or derivatives thereof and exendin-4 or derivatives thereof. In some embodiments, one or more of the active agents in the co-formulation is not conjugated to an ELP. In some embodiments, all of the active agents in the co-formulation are conjugated to an ELP.

Glucagon-Like Peptide (GLP)-1 Receptor Agonists

In certain embodiments of the disclosure, the therapeutic agent includes an ELP component fused or conjugated to a GLP-1 receptor agonist, such as GLP-1, exendin-4, or functional analogs thereof.

Human GLP-1 is a 37 amino acid residue peptide originating from preproglucagon which is synthesized in the L-cells in the distal ileum, in the pancreas, and in the brain.

Processing of preproglucagon to give GLP-1 (7-36) amide, GLP-1 (7-37) and GLP-2 occurs mainly in the L-cells. A simple system is used to describe fragments and analogs of this peptide. For example, Gly$^8$-GLP-1 (7-37) designates a fragment of GLP-1 formally derived from GLP-1 by deleting the amino acid residues Nos. 1 to 6 and substituting the naturally occurring amino acid residue in position 8 (Ala) by Gly. Similarly, Lys$^{34}$ (N$^\varepsilon$-tetradecanoyl)-GLP-1(7-37) designates GLP-1 (7-37) wherein the $\varepsilon$-amino group of the Lys residue in position 34 has been tetradecanoylated. Where reference in this text is made to C-terminally extended GLP-1 analogues, the amino acid residue in position 38 is Arg unless otherwise indicated, the optional amino acid residue in position 39 is also Arg unless otherwise indicated and the optional amino acid residue in position 40 is Asp unless otherwise indicated. Also, if a C-terminally extended analogue extends to position 41, 42, 43, 44 or 45, the amino acid sequence of this extension is as in the corresponding sequence in human preproglucagon unless otherwise indicated.

The parent peptide of GLP-1, proglucagon (PG), has several cleavage sites that produce various peptide products dependent on the tissue of origin including glucagon (PG [32-62]) and GLP-1[7-36]NH$_2$ (PG[72-107]) in the pancreas, and GLP-1[7-37] (PG[78-108]) and GLP-1[7-36]NH$_2$ (PG [78-107]) in the L cells of the intestine where GLP-1 [7-36]NH$_2$ (78-107 PG) is the major product. The GLP-1 component in accordance with the disclosure may be any biologically active product or derivative of proglocagon, or functional analog thereof, including: GLP-1 (1-35), GLP-1 (1-36), GLP-1 (1-36)amide, GLP-1 (1-37), GLP-1 (1-38), GLP-1 (1-39), GLP-1 (1-40), GLP-1 (1-41), GLP-1 (7-35), GLP-1 (7-36), GLP-1 (7-36)amide, GLP-1 (7-37), GLP-1 (7-38), GLP-1 (7-39), GLP-1 (7-40) and GLP-1 (7-41), or a analog of the foregoing. Generally, the GLP-1 component in some embodiments may be expressed as GLP-1 (A-B), where A is an integer from 1 to 7 and B is an integer from 38 to 45, optionally with one or more amino acid substitutions as defined below.

After processing in the intestinal L-cells, GLP-1 is released into the circulation, most notably in response to a meal. The plasma concentration of GLP-1 rises from a fasting level of approximately 15 pmol/L to a peak postprandial level of 40 pmol/L. For a given rise in plasma glucose concentration, the increase in plasma insulin is approximately threefold greater when glucose is administered orally compared with intravenously (Kreymann et al., 1987, *Lancet* 2(8571): 1300-4). This alimentary enhancement of insulin release, known as the incretin effect, is primarily humoral and GLP-1 is now thought to be the most potent physiological incretin in humans. GLP-1 mediates insulin production via binding to the GLP-1 receptor, known to be expressed in pancreatic β cells. In addition to the insulinotropic effect, GLP-1 suppresses glucagon secretion, delays gastric emptying (Wettergen et al., 1993, *Dig Dis Sci* 38: 665-73) and may enhance peripheral glucose disposal (D'Alessio et al., 1994, *J Clin Invest* 93: 2293-6).

A combination of actions gives GLP-1 unique therapeutic advantages over other agents currently used to treat non-insulin-dependent diabetes mellitus (NIDDM). First, a single subcutaneous dose of GLP-1 can completely normalize post prandial glucose levels in patients with NIDDM (Gutniak et al., 1994, *Diabetes Care* 17: 1039-44). This effect may be mediated both by increased insulin release and by a reduction in glucagon secretion. Second, intravenous infusion of GLP-1 can delay postprandial gastric emptying in patients with NIDDM (Williams et al., 1996, *J. Clin Endo Metab* 81: 327-32). Third, unlike sulphonylureas, the insulinotropic action of GLP-1 is dependent on plasma glucose concentration (Holz et al., 1993, *Nature* 361:362-5). Thus, the loss of GLP-1-mediated insulin release at low plasma glucose concentration protects against severe hypoglycemia.

When given to healthy subjects, GLP-1 potently influences glycemic levels as well as insulin and glucagon concentrations (Orskov, 1992, *Diabetologia* 35:701-11), effects which are glucose dependent (Weir et al., 1989, *Diabetes* 38: 338-342). Moreover, it is also effective in patients with diabetes (Gutniak, M., 1992, *N. Engl J Med* 226: 1316-22), normalizing blood glucose levels in type 2 diabetic subjects and improving glycemic control in type 1 patients (Nauck et al., 1993, *Diabetologia* 36: 741-4, Creutzfeldt et al., 1996, *Diabetes Care* 19:580-6).

GLP-1 is, however, metabolically unstable, having a plasma half-life ($t_{1/2}$) of only 1-2 minutes in vivo. Moreover, exogenously administered GLP-1 is also rapidly degraded (Deacon et al., 1995, *Diabetes* 44: 1126-31). This metabolic instability has limited the therapeutic potential of native GLP-1.

GLP-1[7-36]NH$_2$ has the following amino acid sequence: HAEGTFTSDVSSYLEGQAAKEFIAWLVKGR (SEQ ID NO: 38), which may be employed as the GLP-1 component in accordance with the disclosure. Alternatively, the GLP-1 component may contain glycine (G) at the second position, giving, for example, the sequence HGEGTFTSDVS-SYLEGQAAKEFIAWLVKGR (SEQ ID NO: 39). The GLP-1 component may be a biologically active fragment of GLP-1, for example, as disclosed in US 2007/0041951, which is hereby incorporated by reference in its entirety. Other fragments and modified sequences of GLP-1 are known in the art (U.S. Pat. Nos. 5,614,492; 5,545,618; European Patent Application, Publication No. EP 0658568 A1; WO 93/25579, which are hereby incorporated by reference in their entireties). Such fragments and modified sequences may be used in connection with the present disclosure, as well as those described below.

Certain structural and functional analogs of GLP-1 have been isolated from the venom of the Gila monster lizards (*Heloderma suspectum* and *Heloderma horridum*) and have shown clinical utility. Such molecules find use in accordance with the present disclosure. In particular, exendin-4 is a 39 amino acid residue peptide isolated from the venom of *Heloderma suspectum* and shares approximately 52% homology with human GLP-1. Exendin-4 is a potent GLP-1 receptor agonist that stimulates insulin release, thereby lowering blood glucose levels. Exendin-4 has the following amino acid sequence: HGEGTFTSDLSKQMEEEAVR-LFIEWLKNGGPSSGAPPPS (SEQ ID NO: 23). A synthetic version of exendin-4 known as exenatide (marketed as Byetta®) has been approved for the treatment of Type-2 Diabetes. Although exenatide is structurally analogous to native GLP-1, it has a longer half-life after injection.

While exenatide has the ability to lower blood glucose levels on its own, it can also be combined with other medications such as metformin, a thiozolidinedione, a sulfonylureas, and/or insulin to improve glucose control. Exenatide is administered by injection subcutaneously twice per day using a pre-filled pen device. Typical human responses to exenatide include improvements in the initial rapid release of endogenous insulin, an increase in β-cell growth and replication, suppression of pancreatic glucagon release, delayed gastric emptying, and reduced appetite—all of which function to lower blood glucose. Unlike sulfonylureas and meglitinides, exenatide increases insulin synthesis and secretion in the presence of glucose only, thus lessening the risk of hypoglycemia. Despite the therapeutic utility of exenatide, it has certain undesirable traits, including the requirement of twice daily injections, gastrointestinal side effects, and similar to native GLP-1, a relatively short half-life (i.e. approximately 2 hr).

Various functional analogs of GLP-1 and exendin-4 are known, and which find use in accordance with the disclosure. These include liraglutide (Novo Nordisk, WO98/008871), R1583/taspoglutide (Roche, WO00/034331), CJC-1131 (ConjuChem, WO00/069911), ZP-10/AVE0010 (Zealand Pharma, Sanofi-Aventis, WO01/004156), and LY548806 (Eli Lilly, WO03/018516).

Liraglutide, also known as NN2211, is a GLP-1 receptor agonist analog that has been designed for once-daily injection (Harder et al., 2004, *Diabetes Care* 27: 1915-21). Liraglutide has been tested in patients with type-2 diabetes in a number of studies and has been shown to be effective over a variety of durations. In one study, treatment with liraglutide improved glycemic control, improved β-cell function, and reduced endogenous glucose release in patients with type-2 diabetes after one week of treatment (Degn et al., 2004, *Diabetes* 53: 1187-94). In a similar study, eight weeks of 0.6-mg liraglutide therapy significantly improved glycemic control without increasing weight in subjects with type 2 diabetes compared with those on placebo (Harder et al., 2004, *Diabetes Care* 27: 1915-21).

Thus, in certain embodiments, the GLP-1 receptor agonist in accordance with the disclosure is as described in WO98/008871, which is hereby incorporated by reference in its entirety. The GLP-1 receptor agonist may have at least one lipophilic substituent, in addition to one, two, or more amino acid substitutions with respect to native GLP-1. For example, the lipophilic substituent may be an acyl group selected from $CH_3(CH_2)_nCO-$, wherein n is an integer from 4 to 38, such as an integer from 4 to 24. The lipophilic substituent may be an acyl group of a straight-chain or branched alkyl or fatty acid (for example, as described in WO98/008871, which description is hereby incorporated by reference).

In certain embodiments, the GLP-1 component is $Arg^{26}$-GLP-1 (7-37), $Arg^{34}$-GLP-1(7-37), $Lys^{36}$-GLP-1 (7-37), $Arg^{26,34}Lys^{36}$-GLP-I (7-37), $Arg^{26,34}Lys^{38}$-GLP-1 (7-38), $Arg^{28,34}Lys^{39}$-GLP-1 (7-39), $Arg^{26,34}Lys^{40}$-GLP-1(7-40), $Arg^{26}Lys^{36}$-GLP-1(7-37), $Arg^{34}Lys^{36}$-GLP-1(7-37), $Arg^{26}Lys^{39}$-GLP-1(7-39), $Arg^{34}Lys^{40}$-GLP-1(7-40), $Arg^{26,34}Lys^{36,39}$-GLP-I (7-39), $Arg^{26,34}Lys^{36,40}$-GLP-1(7-40), $Gly^8Arg^{26}$-GLP-1(7-37); $Gly^8Arg^{34}$-GLP-1 (7-37); $Gly^8Lys^{38}$-GLP-1(7-37); $Gly^8Arg^{26,34}Lys^{36}$-GLP-1(7-37), $Gly^8Arg^{26,34}Lys^{39}$-GLP-1(7-39), $Gly^8Arg^{26,34}Lys^{40}$-GLP-1 (7-40), $Gly^8Arg^{26}Lys^{36}$-GLP-1(7-37), $Gly^8Arg^{34}Lys^{36}$-GLP-1(7-37), $Gly^8Arg^{26}Lys^{39}$-GLP-1(7-39); $Gly^8Arg^{34}Lys^{40}$-GLP-1(7-40), $Gly^8Arg^{28,34}Lys^{36,39}$-GLP-1 (7-39) and $Gly^8Arg^{26,34}Lys^{35,40}$-GLP-1(7-40), each optionally having a lipophilic substituent. For example, the GLP-1 receptor agonist may have the sequence/structure $Arg^{34}Lys^{26}$-(N-6-(γ-Glu(N-α-hexadecanoyl)))-GLP-1(7-37).

Taspoglutide, also known as R1583 or BIM 51077, is a GLP-1 receptor agonist that has been shown to improve glycemic control and lower body weight in subjects with type 2 diabetes mellitus treated with metformin (Abstract No. A-1604, Jun. 7, 2008, 68th American Diabetes Association Meeting, San Francisco, Calif.).

Thus, in certain embodiments, the GLP-1 receptor agonist is as described in WO00/034331, which is hereby incorporated by reference in its entirety. In certain exemplary embodiments, the GLP-1 receptor agonist has the sequence $[Aib^{8,35}]hGLP-1(7-36)NH_2$ (e.g. taspoglutide), wherein Aib is alpha-aminoisobutyric acid.

CJC-1131 is a GLP-1 analog that consists of a DPP-IV-resistant form of GLP-1 joined to a reactive chemical linker group that allows GLP-1 to form a covalent and irreversible bond with serum albumin following subcutaneous injection (Kim et al., 2003, *Diabetes* 52: 751-9). In a 12-week, randomized, double-blind, placebo-controlled multicenter study, CJC-1131 and metformin treatment was effective in reducing fasting blood glucose levels in type 2 diabetes patients (Ratner et al., Abstract No. 10-OR, June 10-14th, 2005, 65th American Diabetes Association Meeting, San Francisco, Calif.).

Thus, in certain embodiments, the GLP-1 receptor agonist is as described in WO00/069911, which is hereby incorporated by reference in its entirety. In some embodiments, the GLP-1 receptor agonist is modified with a reactive group which reacts with amino groups, hydroxyl groups or thiol groups on blood components to form a stable covalent bond. In certain embodiments, the GLP-1 receptor agonist is modified with a reactive group selected from the group consisting of succinimidyl and maleimido groups. In certain exemplary embodiments, the GLP-1 receptor agonist has the sequence/structure: $D-Ala^8Lys^{37}$-(2-(2-(2-maleimidopropionamido(ethoxy)ethoxy)acetamide))-GLP-1(7-37) (e.g. CJC-1131).

AVE0010, also known as ZP-10, is a GLP-1 receptor agonist that may be employed in connection with the disclosure. In a recent double-blind study, patients treated with once daily dosing of AVE0010 demonstrated significant reductions in HbA1c levels (Ratner et al., Abstract No. 433-P, 68th American Diabetes Association Meeting, San Francisco, Calif.). At the conclusion of the study, the percentages of patients with HbA1c<7% ranged from 47-69% for once daily dosing compared to 32% for placebo. In addition, AVE0010 treated patients showed dose-dependent reductions in weight and post-prandial plasma glucose.

Thus, in certain embodiments, the GLP-1 receptor agonist is as described in WO01/004156, which is hereby incorporated by reference in its entirety. For example, the GLP-1 receptor agonist may have the sequence:

(SEQ ID NO: 41)
HGEGTFTSDLSKQMEEEAVRLFIEWLKNGGPSSGAPPSKKKKKK-NH2

(e.g. AVE0010).

LY548806 is a GLP-1 derivative designed to be resistant to proteolysis by dipeptidase-peptidyl IV (DPP-IV) (Jackson et al., Abstract No. 562, Jun. 10-14th, 2005, 65th American Diabetes Association Meeting, San Francisco, Calif.). In an animal model of hyperglycemia, LY548806 has been shown to produce a significant lowering of blood glucose levels during the hyperglycemic phase (Saha et al., 2006, J. Pharm. Exp. Ther. 316: 1159-64). Moreover, LY548806 was shown to produce a significant increase in insulin levels consistent with its known mechanism of action, namely stimulation of insulin release in the presence of hyperglycemia.

Thus, in certain embodiments, the GLP-1 receptor agonist is as described in WO03/018516, which is hereby incorporated by reference in its entirety. In some embodiments, the therapeutic agents of the present disclosure comprise GLP-1 analogs wherein the backbone for such analogs or fragments contains an amino acid other than alanine at position 8 (position 8 analogs). The backbone may also include L-histidine, D-histidine, or modified forms of histidine such as desamino-histidine, 2-amino-histidine, β-hydroxy-histidine, homohistidine, α-fluoromethyl-histidine, or α-methyl-histidine at position 7. In some embodiments, these position 8 analogs may contain one or more additional changes at positions 12, 16, 18, 19, 20, 22, 25, 27, 30, 33, and 37 compared to the corresponding amino acid of native GLP-1. In other embodiments, these position 8 analogs may contain one or more additional changes at positions 16, 18, 22, 25 and 33 compared to the corresponding amino acid of native GLP-1. In certain exemplary embodiments, the GLP-1 receptor agonist has the sequence:

(SEQ ID NO: 42)
HVEGTFTSDVSSYLEEQAAKEFIAWLIKGRG-OH (e.g. LY548806).

In some embodiments, when processed, the mature form of such fusion protein will begin with the His$^7$ of GLP.

Thus, the present disclosure provides therapeutic agents including an elastin-like peptide (ELP) and a GLP-1 receptor agonist. For example, in certain embodiments, the GLP-1 receptor agonist is GLP-1 (SEQ ID NOs: 37, 38, or 39) or a functional analog thereof. In other embodiments, the GLP-1 receptor agonist is exendin-4 (SEQ ID NO: 23) or a functional analog thereof. Such functional analogs of GLP-1 or exendin-4 include functional fragments truncated at the C-terminus by from 1 to 10 amino acids, including by 1, 2, 3, or up to about 5 amino acids (with respect to SEQ ID NOs: 23, 37, 38, or 39). Such functional analogs may contain from 1 to 10 amino acid insertions, deletions, and/or substitutions (collectively) with respect to the native sequence (e.g., SEQ ID NOs: 23, 37, 38, or 39), and in each case retaining the activity of the peptide. For example, the functional analog of GLP-1 or exendin-4 may have from 1 to about 3, 4, or 5 insertions, deletions and/or substitutions (collectively) with respect to SEQ ID NOS: 23, 37, 38, or 39. In some embodiments, the exendin-4 variant is exendin-4 (9-39) (SEQ ID NO: 33), exendin-4 (9-31) (SEQ ID NO: 34), or exendin-4 (9-30) (SEQ ID NO: 56). Such activity may be confirmed or assayed using any available assay. In these or other embodiments, the GLP-1 receptor agonist component has at least about 50%, 75%, 80%, 85%, 90%, 95%, or 99% identity with the native sequence (SEQ ID NOS: 23, 37, 38, or 39). Such functional analogs may further comprise additional chemical modifications, such as those described in this section and/or others known in the art.

In some embodiments, the GLP-1 receptor agonist is a dual agonist having an amino acid sequence described in US 2011/0257092, which is hereby incorporated by reference in its entirety. Other dual or multi receptor agonists are described in US 2011/016602 and US 2010/00190701, each of which is hereby incorporated by reference, in particular with regard to the structures and sequences of GLP-1 receptor co-agonists described therein.

Additional descriptions of GLP-1 receptor co-agonists can be found in Pocai A et al., Glucagon-Like Peptide 1/Glucagon Receptor Dual Agonism Reverses Obesity in Mice, *Diabetes* 58:2258-2266 (2009) and Patterson J T, et al., Functional association of the N-terminal residues with the central region in glucagon-related peptides, *J. Pept. Sci.* 17:659-666 (2011), Finan et al., A rationally designed monomeric peptide triagonist corrects obesity and diabetes in rodents, *Nature Medicine* 21:27-36, each of which are hereby incorporated by reference in their entirety.

In another aspect, the present disclosure provides methods for treating or preventing type 2 diabetes, impaired glucose tolerance, type 1 diabetes, hyperglycemia, obesity, binge eating, bulimia, hypertension, syndrome X, dyslipidemia, cognitive disorders, atherosclerosis, non-fatty liver disease, myocardial infarction, coronary heart disease and other cardiovascular disorders, or hyperinsulinism, such as congenital hyperinsulinism or acquired hyperinsulinism following gastric surgery, for instance gastric surgery to treat obesity.

The methods include administering a therapeutic agent including the elastin-like peptide (ELP) and an GLP-1 receptor agonist (as described above) to a patient in need of such treatment. In these or other embodiments, the present disclosure provides methods for decreasing food intake, decreasing β-cell apoptosis, increasing β-cell function and β-cell mass, and/or for restoring glucose sensitivity to β-cells. Generally, the patient may be a human or non-human animal patient (e.g., dog, cat, cow, or horse). Preferably, the patient is human.

In some embodiments, the treatment with a ELP/GLP-1 receptor agonist compound according to the present disclosure may also be combined with one or more pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. In the present context, the expression "antidiabetic agent" includes compounds for the treatment and/or prophylaxis of insulin resistance and diseases wherein insulin resistance is the pathophysiological mechanism.

The ability of a GLP-1 or exendin-4 analog, or an GLP-1 receptor agonist/ELP compound, to bind the GLP-1 receptor may be determined by standard methods, for example, by receptor-binding activity screening procedures which involve providing appropriate cells that express the GLP-1 receptor on their surface, for example, insulinoma cell lines such as RINmSF cells or INS-1 cells. In addition to measuring specific binding of tracer to membrane using radioimmunoassay methods, cAMP activity or glucose dependent insulin production can also be measured. In one method, cells recombinantly expressing the GLP-1 receptor may also be used to measure the GLP-1 receptor agonist activity. Thus, these methods may be employed for testing or confirming whether a suspected GLP-1 receptor agonist is active.

In addition, known methods can be used to measure or predict the level of biologically activity of a GLP-1 receptor agonist or GLP-1 receptor agonist/ELP in vivo (See e.g. Siegel, et al., 1999, *Regul Pept* 79(2-3): 93-102). In particular, GLP-1 receptor agonists or GLP-1 receptor agonist/ELP compounds can be assessed for their ability to induce the production of insulin in vivo using a variety of known assays for measuring GLP-1 activity. For example, an ELP/GLP-1 receptor agonist compound can be introduced into a cell, such as an immortalized β-cell, and the resulting cell can be contacted with glucose. If the cell produces insulin in response to the glucose, then the modified GLP-1 is generally considered biologically active in vivo (Fehmann et al., 1992, Endocrinology 130: 159-166). An exemplary assay is described in greater detail herein.

The ability of an GLP-1 receptor agonist/ELP compound to enhance β-cell proliferation, inhibit β-cell apoptosis, and regulate islet growth may also be measured using known assays. Pancreatic β-cell proliferation may be assessed by $^3$H-tymidine or BrdU incorporation assays (See e.g. Buteau et al., 2003, *Diabetes* 52: 124-32), wherein pancreatic β-cells such as INS(832/13) cells are contacted with an ELP/GLP-1 receptor agonist compound and analyzed for increases in $^3$H-thymidine or BrdU incorporation. The anti-apoptotic activity of an ELP/GLP-1 receptor agonist compound can be measured in cultured insulin-secreting cells and/or in animal models where diabetes occurs as a consequence of an excessive rate of beta-cell apoptosis (See e.g. Bulotta et al., 2004, *Cell Biochem Biophys* 40(3 suppl): 65-78).

In addition to GLP-1, other peptides of this family, such as those derived from processing of the pro-glucagon gene, such as GLP-2, GIP, and oxyntomodulin, can be conjugated or fused to the ELP component (as described herein) to enhance the therapeutic potential.

In various embodiments, the disclosure encompasses doses and/or regimens such as those that do not induce substantial appetite suppression in a patient and/or those that do not induce substantial nausea in the patient, such as those described in PCT/US12/44383, which is hereby incorporated by reference.

Human Growth Hormone

In some aspects, the protein active agent is a growth hormone. An exemplary growth hormone sequences includes the sequence underlined in FIGS. 24, 26, 28, and 30 (e.g. SEQ ID NO: 22). Additional suitable sequences include those described in Seeburg et al., "The human growth hormone gene family: nucleotide sequences show recent divergence and predict a new polypeptide hormone, DNA 1 (3), 239-249 (1982), which includes the sequence associated with Accession No. AAA98618. In addition to the exact sequence of AAA98616, other derivatives may be used. For examples, the growth hormone may be truncated at the N-terminus by up to 3 amino acids, up to 5 amino acids, up to 10 amino acids, up to 15 amino acids, up to 20 amino acids, up to 25 amino acids, up to 30 amino acids, up to 35 amino acids, up to 40 amino acids. In particular aspects about 15 to about 30 amino acids may be deleted from the N-terminus. In other aspects, the growth hormone may be truncated at the C-terminus by up to 3 amino acids, up to 5 amino acids, up to 10 amino acids, up to 15 amino acids, up to 20 amino acids, up to 25 amino acids, up to 30 amino acids, up to 35 amino acids, or up to 40 amino acids. In particular aspects about 20 to about 30 amino acids may be deleted from the C-terminus.

Other growth hormone derivatives include those having certain sequence identity to SEQ ID NO: 22. For example, growth hormones include amino acids sequences that share at least about 75% identity, about 80% identity, about 90% identity, about 95% identity, about 96% identity, about 97% identity, about 98% identity, or about 99% identity, with SEQ ID NO: 22.

In certain aspects, the deleted portions may be replaced with one or more amino acids, such as methionine or glycine, which may serve functions such as initiating expression or providing spatial separation. In certain aspects, the N- and C-terminal truncations may be combined to arrive at a particular growth hormone.

In some embodiments, the growth hormone peptide is in a fusion protein with more than one ELP sequence. In some embodiments, the growth hormone peptide has one or more ELPs at both the N- and C-termini. In some embodiments, the two or more ELPs at the N- and C-termini are approximately the same size. In some embodiments, the two or more ELPs at the N- and C-termini differ in size. In some embodiments, the ELP at the N-terminus of the growth hormone peptide is larger than the ELP at the C-terminus of the growth hormone peptide. In some embodiments, the ELP at the N-terminus of the growth hormone peptide includes about 90 to about 120 repeating structural units. In some embodiments, the ELP at the C-terminus of the growth hormone peptide includes about 5 to about 20 repeating structural units. In some embodiments, the ELP at the C-terminus of the growth hormone peptide is larger than the ELP at the N-terminus of the growth hormone peptide. In some embodiments, the ELP at the C-terminus of the growth hormone peptide includes about 90 to about 120 repeating structural units. In some embodiments, the ELP at the N-terminus of the growth hormone peptide includes about 5 to about 20 repeating structural units.

Insulin

Human proinsulin consists of A and B chains linked together with the 31 amino acid C peptide (SEQ ID NOs: 44 or 46). Once the preproinsulin reaches the endoplasmic reticulum, a protease cleaves off the signal peptide to create proinsulin. Specifically, once disulfide bonds are formed between the A and B chains the proinsulin is converted into mature insulin in vivo by removal of the C peptide by a trypsin/carboxypeptidase B-like system. Human insulin is composed of two chains of amino acids named chain A (21 amino acids—GIVEQCCTSICSLYQLENYCN) (SEQ ID NO: 47) and chain B (30 amino acids FVNQHLCG-SHLVEALYLVCGERGFFYTPKT) (SEQ ID NO: 48) that are linked together by two disulfide bridges. There is a 3rd disulfide bridge within the A chain that links the 6th and 11th residues of the A chain together. In most species, the length and amino acid compositions of chains A and B are similar, and the positions of the three disulfide bonds are highly conserved. For this reason, pig insulin can replace deficient human insulin levels in diabetes patients. Today, porcine insulin has largely been replaced by the mass production of human proinsulin by bacteria (recombinant insulin).

Insulin molecules have a tendency to form dimers in solution, and in the presence of zinc ions, insulin dimers associate into hexamers. Whereas monomers of insulin readily diffuse through the blood and have a rapid effect, hexamers diffuse slowly and have a delayed onset of action. In the design of recombinant insulin, the structure of insulin can be modified in a way that reduces the tendency of the insulin molecule to form dimers and hexamers but that does not interrupt binding to the insulin receptor. In this way, a range of preparations are made, varying from short acting to long acting.

Within the endoplasmic reticulum, proinsulin is exposed to several specific peptidases that remove the C-peptide and generate the mature and active form of insulin. In the Golgi apparatus, insulin and free C-peptide are packaged into secretory granules, which accumulate in the cytoplasm of the β-cells. Exocytosis of the granules is triggered by the entry of glucose into the beta cells. The secretion of insulin has a broad impact on metabolism.

There are two phases of insulin release in response to a rise in glucose. The first is an immediate release of insulin. This is attributable to the release of preformed insulin, which is stored in secretory granules. After a short delay, there is a second, more prolonged release of newly synthesized insulin.

Once released, insulin is active for only a brief time before it is degraded by enzymes. Insulinase found in the liver and kidneys breaks down insulin circulating in the plasma, and as a result, insulin has a half-life of only about 6 minutes. This short duration of action results in rapid changes in the circulating levels of insulin.

Insulin analogs have been developed with improved therapeutic properties (Owens et al., 2001, Lancet 358: 739-46; Vajo et al., 2001, Endocr Rev 22: 706-17), and such analogs may be employed in connection with the present disclosure. Various strategies, including elongation of the COOH-terminal end of the insulin B-chain and engineering of fatty acid-acylated insulins with substantial affinity for albumin are used to generate longer-acting insulin analogs. However, in vivo treatments with available longer-acting insulin compounds still result in a high frequency of hypo- and hyperglycemic excursions and modest reduction in HbA1c. Accordingly, development of a truly long-acting and stable human insulin analog still remains an important task.

Functional analogs of insulin that may be employed in accordance with the disclosure include rapid acting analogs such as insulin lispro, insulin aspart and insulin glulisine, which are absorbed rapidly (<30 minutes) after subcutaneous injection, peak at one hour, and have a relatively short duration of action (3 to 4 hours). In addition, three long acting insulin analogs have been developed: insulin glargine, insulin detemir, and insulin degludec, and which may be employed in connection with the disclosure. The long acting insulin analogs have an onset of action of approximately two hours and reach a plateau of biological action at 4 to 6 hours, and may last up to 24 hours.

Thus, in some embodiments, the insulin amino acid sequence may contain the A and/or B chain of insulin lispro (also known as HUMALOG, Eli Lilly). Insulin lispro differs from human insulin by the substitution of proline with lysine at position 28 and the substitution of lysine with proline at position 29 of the insulin B chain. Although these modifications do not alter receptor binding, they help to block the formation of insulin dimers and hexamers, allowing for larger amounts of active monomeric insulin to be available for postprandial injections.

In other embodiments, the insulin amino acid sequence may contain an A and/or B chain of aspart (also known as NOVOLOG®, Novo Nordisk). Insulin aspart is designed with the single replacement of the amino acid proline by aspartic acid at position 28 of the human insulin B chain. This modification helps block the formation for insulin hexamers, creating a faster acting insulin.

In yet other embodiments, the insulin amino acid sequence may contain an A and/or B chain of glulisine (also known as APIDRA®, Sanofi-Aventis). Insulin glulisine is a short acting analog created by substitution of asparagine at position 3 by lysine and lysine at position 29 by glutamine of human insulin B chain. Insulin glulisine has more rapid onset of action and shorter duration of action compared to regular human insulin.

In other embodiments, the insulin amino acid sequence may contain an A and/or B chain of insulin glargine (also known as LANTUS®, Sanofi-Aventis). Insulin glargine has delayed absorption due to its acidic pH that causes microprecipitate formation of insulin crystals in the presence of neutral physiologic pH. Insulin glargine differs from human insulin in that the amino acid asparagine at position 21 of the A chain is replaced by glycine and two arginines are added to the C-terminus of the B-chain. Compared with bedtime neutral protamine Hagedorn (NPH) insulin (an intermediate acting insulin), insulin glargine is associated with less nocturnal hypoglycemia in patients with type 2 diabetes.

In yet other embodiments, the insulin amino acid sequence may contain an A and/or B chain from insulin detemir (also known as LEVEMIR®, Novo Nordisk). Insulin detemir is a soluble (at neutral pH) long-acting insulin analog, in which the amino acid threonine at B30 is removed and a 14-carbon, myristoyl fatty acid is acetylated to the epsilon-amino group of LysB29. After subcutaneous injection, detemir dissociates, thereby exposing the free fatty acid which enables reversible binding to albumin molecules. So at steady state, the concentration of free unbound insulin is greatly reduced resulting in stable plasma glucose levels.

In yet other embodiments, the insulin amino acid sequence may contain an A and/or B chain from insulin degludec (also known as TRESIBA®, Novo Nordisk). Insulin degludec is a soluble (at neutral pH) long-acting insulin analog, in which the amino acid threonine at B30 is removed and a side-chain consisting of glutamic acid and a C16 fatty acid has been attached. After subcutaneous injection, insulin degludec dissociates, thereby exposing the fatty acid which enables reversible binding to albumin molecules. So at steady state, the concentration of free unbound insulin is greatly reduced resulting in stable plasma glucose levels.

In some embodiments, the insulin amino acid sequence may be a single-chain insulin analog (SIA) (e.g. as described in U.S. Pat. No. 6,630,438 and WO 2008/019368, which are hereby incorporated by reference in their entirety). Single-chain insulin analogs encompass a group of structurally-related proteins wherein the A and B chains are covalently linked by a polypeptide linker. The polypeptide linker connects the C-terminus of the B chain to the N-terminus of the A chain. The linker may be of any length so long as the linker provides the structural conformation necessary for the SIA to have a glucose uptake and insulin receptor binding effect. In some embodiments, the linker is about 5-18 amino acids in length. In other embodiments, the linker is about 9-15 amino acids in length. In certain embodiments, the linker is about 12 amino acids long. In certain exemplary embodiments, the linker has the sequence KDDNPNL-PRLVR (SEQ ID NO.: 51) or GAGSSSRRAPQT (SEQ ID NO.: 52). However, it should be understood that many variations of this sequence are possible such as in the length (both addition and deletion) and substitutions of amino acids without substantially compromising the effectiveness of the produced SIA in glucose uptake and insulin receptor binding activities. For example, several different amino acid residues may be added or removed from either end without substantially decreasing the activity of the produced SIA.

An exemplary single-chain insulin analog currently in clinical development is albulin (Duttaroy et al., 2005, Diabetes 54: 251-8). Albulin can be produced in yeast or in mammalian cells. It consists of the B and A chain of human insulin (100% identity to native human insulin) linked together by a dodecapeptide linker and fused to the NH2 terminals of the native human serum albumin. For expression and purification of albulin, Duttaroy et al. constructed a synthetic gene construct encoding a single-chain insulin containing the B- and A-chain of mature human insulin linked together by a dodecapeptide linker using four overlapping primers and PCR amplification. The resulting PCR product was ligated in-frame between the signal peptide of human serum albumin (HSA) and the NH2 terminus of mature HSA, contained within a pSAC35 vector for expression in yeast. In accordance with the present disclosure, the HSA component of abulin may be replaced with an amino acid sequence providing a sustained release as described herein.

Thus, in some aspects, the present disclosure provides therapeutic agents including an amino acid sequence providing a sustained release, including, for example, an elastin-like peptide (ELP), and an insulin amino acid sequence. For example, in certain embodiments, the insulin is a mammalian insulin, such as human insulin or porcine insulin. In accordance with the disclosure, the amino acid sequence providing a sustained release component may be coupled (e.g., via recombinant fusion or chemical conjugation) to the insulin A chain, or B chain, or both. In some embodiments, the amino acid sequence that provides a slow absorption from the injection site is covalently bound to the insulin A chain. The insulin may comprise each of chains A, B, and C (e.g. SEQ ID NOs: 44 or 46), or may contain a processed form, containing only chains A and B. In some embodiments, chains A and B are connected by a short linking peptide, to create a single chain insulin. The insulin may be a functional analog of human insulin, including functional fragments truncated at the N-terminus and/or C-terminus (of either or both of chains A and B) by from 1 to 10 amino acids, including by 1, 2, 3, or about 5 amino acids. Functional analogs may contain from 1 to 10 amino acid insertions, deletions, and/or substitutions (collectively) with respect to the native sequence (e.g., SEQ ID NOs: 44, 46, 47 or 48), and in each case retaining the activity of the peptide. For example, functional analogs may have 1, 2, 3, 4, or 5 amino acid insertions, deletions, and/or substitutions (collectively) with respect to the native sequence (which may contain chains A and B, or chains A, B, and C). Such activity may be confirmed or assayed using any available assay, including those described herein. In these or other embodiments, the insulin component has at least about 75%, about 80%, about 85%, about 90%, about 95%, or about 98% identity with each of the native sequences for chains A and B (SEQ ID NOs: 47 or 48). The determination of sequence identity between two sequences (e.g., between a native sequence and a functional analog) can be accomplished using any alignment tool, including Tatusova et al., Blast 2 sequences—a new tool for comparing protein and nucleotide sequences, FEMS Microbiol Lett. 174:247-250 (1999). The insulin component may contain additional chemical modifications known in the art.

To characterize the in vitro binding properties of an insulin analog or an amino acid sequence providing a sustained release-containing insulin analog, competition binding assays may be performed in various cell lines that express the insulin receptor (Jehle et al., 1996, Diabetologia 39: 421-432). For example, competition binding assays using CHO cells overexpressing the human insulin receptor may be employed. Insulin can also bind to the IGF-1 receptor with a lower affinity than the insulin receptor. To determine the binding affinity of an amino acid sequence providing a sustained release-containing insulin analog, a competition binding assay can be performed using $^{125}$I-labeled IGF-1 in L6 cells.

The activities of insulin include stimulation of peripheral glucose disposal and inhibition of hepatic glucose production. The ability of an amino acid sequence providing a sustained release-containing insulin analog to mediate these biological activities can be assayed in vitro using known methodologies. For example, the effect of an amino acid sequence providing a sustained release-containing analog on glucose uptake in 3T3-L1 adipocytes can be measured and compared with that of insulin. Pretreatment of the cells with a biologically active analog will generally produce a dose-dependent increase in 2-deoxyglucose uptake. The ability of an amino acid sequence providing a sustained release-containing insulin analog to regulate glucose production may be measured in any number of cells types, for example, H4IIe hepatoma cells. In this assay, pretreatment with a biologically active analog will generally result in a dose-dependent inhibition of the amount of glucose released.

Vasoactive Intestinal Peptides

Vasoactive intestinal peptide (VIP) is a 28 amino acid neuropeptide which binds to two receptors, VPAC1 and VPAC2, found in a variety of tissues including the airway, small intestine, testes, and pancreas. VIP and its functionally and structurally related analogs are known to have many physiological functions, including, relaxing airway smooth muscle thereby acting as a bronchodilator, stimulating fluid secretion in airway submucosal glands, and regulating water and electrolyte secretion in the intestines and pancreas (Wine (2007); Wu (2011); Derand (2004)).

VIP-producing nerve fibers are co-localized with acetylcholine secreting neurons surrounding exocrine glands (Lundberg (1980); Heinz-Erian (1986)). In glands from subjects with functional CFTR protein, VIP induces fluid secretion, but this induction is impaired or absent in Cystic Fibrosis patients (Joo (2002); Joo (2012)). Further, in human and pig airway glands, administration of low concentrations of both VIP and acetylcholine stimulates the secretion mucus, but this synergism is lost in cystic fibrosis patients (Choi (2007)).

VIP increases CFTR membrane insertion, stability, and function in human airway epithelial cells (Alshafie (2014)). In a murine VIP knockout model CFTR does not localize to the apical cell membrane, but instead remains mainly intracellular (Chappe and Said (2012)). The absence of CFTR from the apical membrane is associated with a lung pathology similar to that seen in Cystic Fibrosis patients, with inflammatory cell infiltration, thickening of the alveolar wall and the bronchiolar mucosa, and goblet cell hyperplasia. Administration of VIP intraperitoneally for three weeks restores CFTR apical membrane localization, and prolonged VIP stimulation increases the number of CFTR channels at the cell membrane (Chappe (2008)). This increase in apical CFTR density, which occurs via stabilization of CFTR at the membrane, is associated with an increase in CFTR-dependent function as measured by iodide efflux assays (Chappe (2008)).

In some aspects the disclosure provides therapeutic compositions that may include one or more various VIP peptides. For example, the VIP peptide may comprise or consist of a polypeptide having SEQ ID NO: 53, SEQ ID NO: 54, or SEQ ID NO: 55. In some embodiments, the present disclosure provides a VIP without the N-terminal Methionine (e.g. SEQ ID NO: 55). In some embodiments, the present disclosure provides a VIP with the N-terminal Methionine (e.g. SEQ ID NO: 53).

Mature human VIP has 28 amino acid residues with the following sequence: HSDAVFTDNYTRLRKQMAVKKYLNSILN (SEQ ID NO: 55). VIP results from processing of the 170-amino acid precursor molecule prepro-VIP. Structures of VIP and exemplary analogs have been described in U.S. Pat. Nos. 4,835,252, 4,939,224, 5,141,924, 4,734,400, 4,605,641, 6,080,837, 6,316,593, 5,677,419, 5,972,883, 6,489,297, 7,094,755, and 6,608,174.

A number of mutations to improve peptide stability against proteases etc. are detailed in the literature (see Onune et al *Physicochemical and pharmacological characterization of novel vasoactive intestinal peptide derivatives with improved stability, Eur. J. Pharm. Biopharm.* 2009). For example, modified VIP peptides include the sequences of SEQ ID NOs: 53, 54, or 55 In some aspects, the present disclosure provides modified VIP peptides that include one or more of these modifications. In some embodiments, the present disclosure provides modified VIP peptides that include one or more of these modifications and further include additional VIP modifications described herein.

In various embodiments, the present disclosure provides a modified VIP (e.g., including SEQ ID NO: 55) or a functional analog as described herein. Generally, functional analogs of VIP, include functional fragments truncated at the N- or C-terminus by from 1 to 10 amino acids, including by 1, 2, 3, or up to about 5 amino acids (with respect to SEQ ID NO: 55). Such functional analogs may contain from 1 to 5 amino acid insertions, deletions, and/or substitutions (collectively) with respect to the native sequence (e.g., SEQ ID NO: 55), and in each case retain the activity of the native peptide (e.g., through VPAC2 and/or VPAC1 binding). Such activity may be confirmed or assayed using any available assay, including an assay described herein, and including any suitable assay to determine or quantify an activity described in Delgado et al., *The Significance of Vasoactive Intestinal Peptide in Immunomodulation, Pharmacol. Reviews* 56(2):249-290 (2004). In these or other embodiments, the VIP component of the modified VIP has at least about 50%, about 75%, about 80%, about 85%, about 90%, about 95%, about 97% identity, about 98% identity, or about 99% identity with the native mature sequence (SEQ ID NO: 55). The determination of sequence identity between two sequences (e.g., between a native sequence and a functional analog) can be accomplished using any alignment tool, including for example, that disclosed in Tatusova et al., *Blast 2 sequences—a new tool for comparing protein and nucleotide sequences, FEMS Microbiol Lett.* 174:247-250 (1999). In various aspects, the present disclosure provides a modified VIP molecule having receptor preference for VPAC2 or VPAC1, as compared to unmodified VIP (e.g., a peptide consisting of the amino acid sequence of SEQ ID NO: 55). For example, the modified VIP may have a relative binding preference for VPAC2 over VPAC1 of at least about 2:1, about 5:1, about 10:1, about 25:1, about 50:1, about 100:1, about 500:1 or more. In other embodiments, the modified VIP may have a relative binding preference for VPAC1 over VPAC2 of at least about 2:1, about 5:1, about 10:1, about 25:1, about 50:1, about 100:1, about 500:1, or more. For example, in certain embodiments, the modified VIP activates the VPAC2 receptor with an EC50 within a factor of about 2 of mature, unmodified, human VIP (SEQ ID NO: 55). However, this same modified VIP is 50- or 100-fold or more less potent than mature, unmodified, human VIP in activating the VPAC1 receptor. In some embodiments, the modified VIP may have relatively equipotent binding preferences for VPAC1 and VPAC2.

Such modified VIP molecules may contain modified N-terminal regions, such as an addition of from 1 to about 500 amino acids to the N-terminal histidine of VIP, which may include heterologous mammalian amino acid sequences. For example, the modified VIP may contain a single methionine at the N-terminal side of the natural N-terminal histidine of mature VIP. This can be prepared in *E. coli* or other bacterial expression system, since the methionine will not be removed by *E. coli* when the adjacent amino acid is histidine. Alternatively, the N-terminal amino acid may be any of the naturally-occurring amino acids, namely alanine, arginine, asparagine, aspartic acid, cysteine, glutamic acid, glutamine, glycine, histidine, isoleucine, leucine, lysine, methionine, phenylalanine, serine, threonine, tryptophan, tyrosine, valine, and proline.

The additional sequence added to the N-terminus of VIP may be of any sequence, including biologically active and biologically inert sequences of from 1 to about 100, 1 to about 50, 1 to about 20, 1 to about 10, and 1 to about 5 amino acids.

The N-terminus of the modified VIP may have the structure M-N, where M is methionine, and N is the N-terminus of the VIP molecule (e.g., SEQ ID NO: 53). This methionine supports translation of the protein in a bacterial or eukaryotic host cell. Thus, the modified VIP can be made in a biological system, including bacterial and yeast expression systems (e.g., *E. coli*). While methionine can sometimes be removed by methionine aminopeptidase (MA) in bacterial expression systems, histidine (H) is one of the least favored residues at position 2 for MA.

In some embodiments, the VIP is modified at the N-terminus. In some embodiments, the VIP is modified at the C-terminus.

In other embodiments, VIP is activatable by a peptidase or protease, such as an endogenous peptidase or protease. Such activatable sequences are described in International Application No. PCT/US2009/068656. As used herein, the terms "peptidase" and "protease" are interchangeable. For example, the VIP may be designed to be activatable by a dipeptidyl peptidase. Exemplary dipeptidyl peptidases include dipeptidyl peptidase-1 (DPP-I), dipeptidyl peptidase-3 (DPP-III), dipeptidyl peptidase-4 (DPP-IV), dipeptidyl peptidase-6 (DPP-VI), dipeptidyl peptidase-7 (DPP-VII), dipeptidyl peptidase-8 (DPP-VIII), dipeptidyl peptidase-9 (DPP-IX), dipeptidyl peptidase-10 (DPP-X). Substrate sequences for such dipeptidases are known.

In some embodiments, the N-terminus of an activatable VIP may have the structure Z—N, where Z is a substrate for a dipeptidase (e.g., Z is removed by dipeptidase exposure), and N is the N-terminus of VIP. The activatable VIP may have an N-terminal sequence with the formula M-X—N where M is methionine, X is Pro, Ala, or Ser, and N is the N-terminal of VIP or VIP analog. In this manner, M and X will be sensitive to, and removed by a host cell (e.g., *E. coli*), and/or a dipeptidase (e.g., DPP-IV), subsequently. Alternatively, the N-terminal sequence of the activatable VIP may be X1-X2-N, where X1 is Gly, Ala, Ser, Cys, Thr, Val, or Pro; X2 is Pro, Ala, or Ser; and N is the N-terminal of VIP. X1-X2 is a substrate for dipeptidase (e.g., DPP-IV), and dipeptidase digestion will expose N, the desired N-terminus of the VIP or the VIP analog. In such embodiments, the protein may be produced by expression of a construct encoding M-X1-X2-N (where M is methionine) in a host cell (e.g., *E. coli.*), since Gly, Ala, Ser, Cys, Thr, Val, or Pro at the second position will signal the removal of the Met, thereby leaving X1-X2 on the N-terminus, which can be activated by a dipeptidase (e.g., DPP-IV) in vivo. In some embodiments, the peptidase may be present in the body and act on the activatable VIP after injection.

In other embodiments, the N-terminus of the modified activatable VIP has the structure M-Z—N, where M is methionine, Z is a substrate for a dipeptidase (e.g., Z is removed by dipeptidase exposure), and N is a non-His N-terminal of an active VIP (modified VIP).

For example, the modified activatable VIP may have an N-terminal sequence with the formula M-X—N where M is methionine; X is Pro, Ala, or Ser; and N is a non-His N-terminal of the active VIP. In this manner, M and X will be sensitive to, and removed by a host cell (e.g., *E. coli.*), and/or a dipeptidase (e.g., DPP-IV), subsequently. Alternatively, the N-terminal sequence of the activatable VIP may be X1-X2-N, where X1 is Gly, Ala, Ser, Cys, Thr, Val, or Pro; X2 is Pro, Ala, or Ser; and N is a non-His N-terminal of the active VIP. X1-X2 is a substrate for dipeptidase (e.g., DPP-IV), and dipeptidase digestion will expose N, the desired non-His N-terminus of the VIP.

In still other embodiments, the N-terminus of a modified activatable VIP has the structure M-Z—S—N, where M is methionine; Z is a substrate for a dipeptidase (e.g., Z is removed by dipeptidase exposure); N is the N-terminus of mature VIP (His); and S is one or more amino acids which will be exposed after dipeptidase digestion, and which provide a modified VIP as previously described. For example, the modified activatable VIP may have an N-terminal sequence with the formula M-X—S—N where M is methionine, X is Pro, Ala, or Ser; N is the N-terminal of mature VIP; and S is one or more amino acids which will be exposed after dipeptidase digestion, and will provide receptor preference. Alternatively, the N-terminal sequence of the activatable VIP may be X1-X2-S—N, where X1 is Gly, Ala, Ser, Cys, Thr, Val, or Pro; X2 is Pro, Ala, or Ser; N is a non-His N-terminal of VIP; and S is one or more amino acids which will be exposed after dipeptidase digestion. X1-X2 is a substrate for dipeptidase (e.g., DPP-IV), and dipeptidase digestion will expose S.

In some embodiments, N-terminal chemical modifications to the VIP N-terminus provides receptor preference. Chemical modification of proteins and methods thereof are well known in the art. Non-limiting exemplary chemical modifications are PEGylation, methylglyoxalation, reductive alkylation, performic acid oxidation, succinylation, aminoethylation, and lipidation (Clifton, New Protein Techniques, New Jersey: Humana Press, 1985. ISBX. 0-89603-126-8. Volume. 3 of. Methods in Molecular Biology). Chemical groups, such as PEGylation, may be attached by modifications of cysteine, methionine, histidine, lysine, arginine, tryptophan, tyrosine, carboxyl groups have been described previously (see Lundblad, Techniques in Protein Modification, CRC Press, 1995).

The VIP active agent finds use in a method of treating a condition selected from uncontrolled or resistant hypertension, or pulmonary arterial hypertension (PAH), or chronic obstructive pulmonary disease (COPD), or cardiomyopathy secondary to muscular dystrophy, among others.

Small Molecules

In other embodiments, the therapeutic agent is a chemical conjugate between the active agent and the amino acid sequence capable of forming the matrix at the body temperature of the subject (e.g. an ELP). For example, the active agent may be a chemotherapeutic agent, such as a chemotherapeutic agent selected from methotrexate, daunomycin, mitomycin, cisplatin, vincristine, epirubicin, fluorouracil, verapamil, cyclophosphamide, cytosine arabinoside, aminopterin, bleomycin, mitomycin C, democolcine, etoposide, mithramycin, chlorambucil, melphalan, daunorubicin, doxorubicin, tamoxifen, paclitaxel, vinblastine, camptothecin, actinomycin D, cytarabine, and combrestatin. Alternatively, the agent may be an immunogenic molecule, or an immunomodulator, or an anti-inflammatory agent, such as an agent described in U.S. Patent Publication No. 2009/0004104, which is hereby incorporated by reference in its entirety. Also, the agent may be an opioid molecule, such as, for example oxycodone, morphine, or codeine, such as described in U.S. Provisional Application No. 61/597,898, which is hereby incorporated by reference. The chemical conjugate may be through a cleavable linker, for which numerous types are known in the art. See U.S. Pat. No. 6,328,996, which is hereby incorporated by reference in its entirety.

Formulations

The present disclosure provides sustained release formulations including a therapeutic agent disclosed herein and one or more pharmaceutically acceptable excipients and/or diluents. For example, such excipients include salts, and other excipients that may act to stabilize hydrogen bonding. Any appropriate excipient known in the art may be used. Exemplary excipients include, but are not limited to, amino acids such as histidine, glycine, or arginine; glycerol; sugars, such as sucrose; surface active agents such as polysorbate 20 and polysorbate 80; citric acid; sodium citrate; antioxidants; salts including alkaline earth metal salts such as sodium, potassium, and calcium; counter ions such as chloride and phosphate; sugar alcohols (e.g. mannitol); preservatives; sugar alcohols (e.g. mannitol, sorbitol); and buffering agents. Exemplary salts include sodium chloride, potassium chloride, magnesium chloride, calcium chloride, sodium phosphate dibasic, sodium phosphate monobasic, sodium phosphate, and potassium phosphate.

The therapeutic agent is formulated at a pH, ionic strength, and generally with excipients sufficient to enable the formation of the matrix at body temperature (e.g., 37° C., or at from 34 to 36° C. in some embodiments). The therapeutic agent is generally prepared such that it does not form the matrix at storage conditions. The formulation can be stored frozen, refrigerated or at room temperature. Storage conditions are generally less than the transition temperature of the formulation, such as less than about 32° C., or less than about 30° C., or less than about 27° C., or less than about 25° C., or less than about 20° C., or less than about 15° C. For example, the formulation may be isotonic with blood or have an ionic strength that mimics physiological conditions. For example, the formulation may have an ionic strength of at least that of 25 mM Sodium Chloride, or at least that of 30 mM Sodium chloride, or at least that of 40 mM Sodium Chloride, or at least that of 50 mM Sodium Chloride, or at least that of 75 mM Sodium Chloride, or at least that of 100 mM Sodium Chloride, or at least that of 150 mM Sodium Chloride. In certain embodiments, the formulation has an ionic strength equivalent to that of 0.9% saline (154 mM sodium chloride).

In some embodiments, the formulation is stable at storage conditions. Stability can be measured using any appropriate means in the art. Generally, a stable formulation is one that shows less than a 5% increase in degradation products or impurities. In some embodiments, the formulation is stable for at least about 1 month, at least about 2 months, at least about 3 months, at least about 4 months, at least about 5 months, at least about 6 months, or at least about one year or more at the storage conditions. In some embodiments, the formulation is stable for at least about 1 month, at least about 2 months, at least about 3 months, at least about 4 months, at least about 5 months, at least about 6 months, or at least about one year or more at 25° C.

In some embodiments, the formulation includes two or more of calcium chloride, magnesium chloride, potassium chloride, potassium phosphate monobasic, sodium chloride, sodium phosphate dibasic, sodium phosphate monobasic, histidine, arginine, glycine, glycerol, antimicrobial preservative (e.g. metacresol), tonicity-adjusting agent (e.g. mannitol), glacial acetic acid, sodium acetate trihydrate; sucrose, carboxymethylcellulose sodium, sodium phosphate monobasic monohydrate, sodium phosphate dibasic heptahydrate, zinc, m-cresol, phenol, sorbitol, polysorbate 80, and polysorbate 20. In some embodiments, the formulation does not include carboxymethylcellulose.

In some embodiments, the formulation includes histidine or another amino acid at a range of about 10 mM to about 100 mM histidine. In some embodiments, the formulation includes histidine or another amino acid at a range of about 10 mM to about 30 mM histidine. In some embodiments, the formulation includes histidine or another amino acid at a range of about 15 mM to about 25 mM histidine. In some embodiments, the formulation includes NaCl at a range of about 10 mM to about 165 mM NaCl. In some embodiments, the formulation includes between about 50 mM and about 165 mM NaCl. In some embodiments, the formulation includes between about 54 mM and about 162 mM NaCl. In some embodiments, the formulation includes between about 110 mM and about 162 mM NaCl. In some embodiments, the formulation includes sodium phosphate at a range of about 1 mM to about 20 mM. In some embodiments, the formulation includes sodium phosphate at a range of about 5 mM to about 15 mM. In some embodiments, the formulation includes sodium phosphate monobasic at a range of about 2 mM to about 10 mM. In some embodiments, the formulation includes sodium phosphate monobasic at a range of about 4 mM to about 8 mM. In some embodiments, the formulation includes sodium phosphate dibasic at a range of about 1 mM to about 10 mM. In some embodiments, the formulation includes sodium phosphate dibasic at a range of about 2 mM to about 7 mM. In some embodiments, the formulation includes sodium phosphate dibasic at a range of about 2 mM to about 5 mM. In some embodiments, the formulation includes polysorbate 20 at a range of about 0.01% to about 0.2%. In some embodiments, the formulation includes polysorbate 80 at a range of about 0.01% to about 0.2%. In some embodiments, the formulation includes sodium phosphate, sodium chloride, sodium phosphate monobasic, sodium phosphate dibasic, and Polysorbate 20. In some embodiments, the formulation includes about 10 mM sodium phosphate (about 7 mM sodium phosphate monobasic and about 3 mM sodium phosphate dibasic), about 110 mM sodium chloride, and about 0.1% polysorbate 20.

In some embodiments, the formulation is formulated at physiological pH. In In some embodiments, the formulation is formulated at a pH in the range of about 5.5 to about 7.5. In some embodiments, the formulation is formulated at a pH in the range of about 6.0 to about 7.0. In some embodiments, the formulation is formulated at a pH in the range of about 6.5 to about 7.0. In some embodiments, formulations with a lower pH demonstrate improved formulation stability compared to formulations at a higher pH. In some embodiments, formulations with a pH of about 6.5 demonstrate improved stability compared to formulations with a pH of about 7.0. In some embodiments, formulations with a pH of about 6.0 demonstrate improved stability compared to formulations with a pH of about 6.5. In some embodiments, formulations with a lower pH maintain a higher percentage of monomers compared to formulations at a higher pH. In some embodiments, formulations with a pH of about 6.5 maintain a higher percentage of monomers compared to formulations with a pH of about 7.0. In some embodiments, formulations with a pH of about 6.0 maintain a higher percentage of monomers compared to formulations with a pH of about 6.5.

The protein concentration of the therapeutic agent in the formulation is tailored to drive the formation of the matrix at the temperature of administration. For example, higher protein concentrations help drive the formation of the matrix, and the protein concentration needed for this purpose varies depending on the ELP series used. For example, in embodiments using an ELP1-120, or amino acid sequences with comparable transition temperatures, the protein is present in the range of about 1 mg/mL to about 200 mg/mL, or is present in the range of about 30 mg/mL to about 150 mg/mL. In embodiments using an ELP4-120, or amino acid sequences with comparable transition temperatures, the protein is present in the range of about 0.005 mg/mL to about 10 mg/mL, or is present in the range of about 0.01 mg/mL to about 5 mg/mL.

In some embodiments, the therapeutic agent may be present in the range of about 0.5 mg/mL to about 200 mg/mL, or is present in the range of about 30 mg/mL to about 150 mg/mL. In some embodiments, the therapeutic agent is present in the range of about 50 mg/mL to about 125 mg/mL, or the range of about 75 mg/mL to about 110 mg/mL. In some embodiments, the therapeutic agent is present at a concentration of about 100 mg/mL.

In some aspects, the disclosure provides a method for delivering a sustained release regimen of an active agent disclosed herein. The method includes administering the pharmaceutical composition described herein to a subject in need, wherein the pharmaceutical composition is administered from about 1 to about 8 times per month. In some embodiments, the pharmaceutical composition is administered about 1 time, about 2 times, about 3 times, and/or about 4 times per month. In some embodiments, the pharmaceutical composition is administered weekly. In some embodiments, the pharmaceutical composition is administered daily. In some embodiments, the pharmaceutical composition is administered from one to three times weekly. In some embodiments, the pharmaceutical composition is administered once every two weeks. In some embodiments, the pharmaceutical composition is administered from one to two times a month. In particular embodiments, the pharmaceutical composition is administered about 1 time per month. In some embodiments, the pharmaceutical composition is administered about once every 2 months, about once every 3 months, about once every 4 months, about once every 5 months, and/or about once every 6 months. The pharmaceutical composition can be packaged in the form of pre-filled pens or syringes for administration once per week, twice per week, or from one to eight times per month, or alternatively filled in conventional vials and the like.

In some embodiments, the formulation is administered about monthly, and may be administered subcutaneously or intramuscularly. In some embodiments, the formulation is administered about weekly, and may be administered subcutaneously or intramuscularly.

In some embodiments, the site of administration is not a pathological site, for example, is not the intended site of action.

In some embodiments, the pharmaceutical compositions disclosed herein are administered chronically. In some embodiments, the pharmaceutical compositions disclosed herein are administered for about 6 months, for about 7 months, for about 8 months, for about 9 months, for about 10 months, for about 11 months, for about 1 year, for about 2 years, for about 3 years, for about 4 years, for about 5 years, for about 10 years or more. The pharmaceutical compositions may be administered at any required dose and/or frequency disclosed herein.

In some embodiments, the pharmaceutical compositions disclosed herein are administered until disease or disorder symptoms improve. In some embodiments, the pharmaceutical compositions disclosed herein are administered until disease or disorder symptoms are ameliorated, delayed, and/or cured.

In some embodiments, the pharmaceutical compositions disclosed herein are administered before the patient begins to exhibit one or more disease or disorder symptoms. In some embodiments, the pharmaceutical compositions disclosed herein are administered at the onset of disease or disorder symptoms.

The therapeutic agent is formulated generally for "systemic delivery," meaning that the agent is not delivered locally to a pathological site or a site of action. Instead, the agent is absorbed into the bloodstream from the injection site, where the agent acts systemically or is transported to a site of action via the circulation. The therapeutic agent may be administered by any known route, such as for example, orally, intravenously, intramuscularly, nasally, subcutaneously, intra-vaginally, and intra-rectally. In some embodiments, the formulation is generally for subcutaneous administration. In some embodiments, the pharmacokinetic (PK) parameters are prolonged when the agent is administered subcutaneously. In some embodiments, the half-life of the fusion protein is prolonged. In some embodiments, the PK parameters when the agent is administered subcutaneously are prolonged compared with the agent administered by other means (e.g. intravenously). In some embodiments, the depot of the agent is prolonged when the agent is administered subcutaneously compared with the agent administered by other means (e.g. intravenously). By providing a slow absorption from the injection site, renal clearance and degradation can be controlled, thereby achieving the desired PK profile.

Figure 20A:
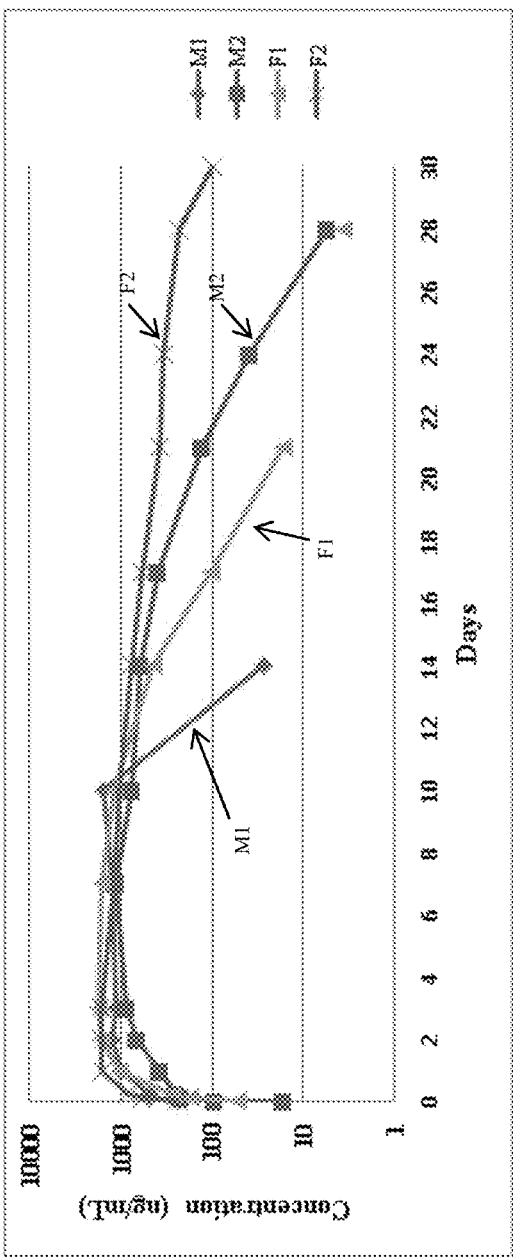
FIGS. 20A and B show the PK results of a single subcutaneous dose of PE0256 (delta) at 10 mg/kg into four protein naïve monkeys, 2 male and 2 female. Figure A shows the data from the individual animals while Figure B shows the mean.
Figure 20B:
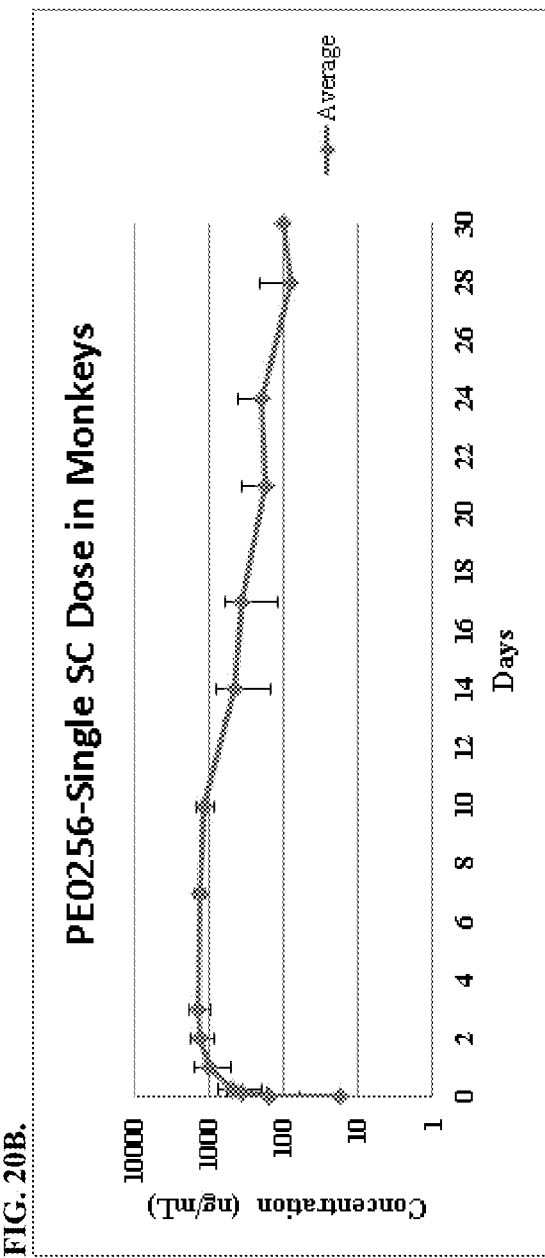

Advantageously, the compositions provide for prolonged pharmacokinetic exposure due to sustained release of the active agent. In particular aspects, the maximal exposure level may be achieved at about 10 hours, about 24 hours, about 48 hours or about 72 hours after administration; typically the maximum exposure level is achieved between about 10 hours and about 48 hours after administration. After the maximal exposure level is achieved the compositions may achieve a sustained rate of release whereby a substantial percentage of the maximal level is obtained for a period of time. For example, the sustained rate may about 50%, about 60%, about 70%, about 80%, about 90% or about 100% of the maximal exposure level. Exemplary periods of time for maintaining the sustained rate are about 3 days, about 4 days, about 5 days, about 6 days, about 1 week, about 2 weeks, about 4 weeks, about 6 weeks, or about 8 weeks, after the maximal exposure level is achieved. Subsequently, the sustained rate may lower to a reduced exposure rate. Such reduced exposure rates may be about 5%, about 10%, about 20%, about 30%, about 40%, about 50% or about 60% of the maximal exposure level. FIG. 20B illustrates an embodiment (PE0256) whereby a maximal exposure level of 1000 ng/mL is obtained within about 1-2 days. After this period, a sustained rate of about 70-100% of the maximal exposure level is maintained until about days 10-12 whereupon a reduced exposure rate from about 60% decreasing down to about 10% is obtained for the remainder of the study.

In various embodiments, the plasma concentration of the active agent does not change by more than a factor of about 20, or a factor of about 10, or a factor of about 5, or a factor of about 3 over the course of a plurality of administrations, such as at least 2, at least about 5, or at least about 10 administrations of the formulation. In some embodiments, the plasma concentration of the active agent does not change by more than a factor of about 20, or a factor of about 10, or a factor of about 5, or a factor of about 3 between each administration. In some embodiments, there is some accumulation until steady state is reached (e.g. after about 3 to about 4 administrations). The administrations are substantially evenly spaced, such as, for example, about daily, or about once per week, or from one to about five times per month, or about once every two months, or about once every three months. In other embodiments, the dose may be steadily increased over several administrations, so steady state is reached after 5 or more administrations.

The pharmaceutical compositions disclosed herein may be administered in smaller doses and/or less frequently than unfused or unconjugated counterparts. While one of skill in the art can determine the desirable dose in each case, a suitable dose of the therapeutic agent for achievement of therapeutic benefit, may, for example, be in a range of about 1 microgram (µg) to about 100 milligrams (mg) per kilogram body weight of the recipient per dose, preferably in a range of about 10 µg to about 50 mg per kilogram body weight per dose and most preferably in a range of about 10 µg to about 50 mg per kilogram body weight per dose. In some embodiments, the pharmaceutical composition is administered at a low dose. In some embodiments, the pharmaceutical composition is administered at a dose between 1 mg per kilogram per body weight per dose to about 9 mg per kilogram per body weight per dose. In some embodiments, the pharmaceutical composition is administered at about 1 mg per kilogram body weight per dose, about 3 mg per kilogram body weight per dose, and/or about 9 mg per kilogram body weight per dose. The desired dose may be presented as one dose or two or more sub-doses administered at appropriate intervals throughout the day. These sub-doses can be administered in unit dosage forms, for example, containing from about 10 µg to about 1000 mg, preferably from about 50 µg to about 500 mg, and most preferably from about 50 µg to about 250 mg of active ingredient per unit dosage form. Alternatively, if the condition of the recipient so requires, the doses may be administered as a continuous infusion.

In certain embodiments, the subject is a human, but in other embodiments may be a non-human mammal, such as a domesticated pet (e.g., dog or cat), or livestock or farm animal (e.g., horse, cow, sheep, or pig).

It should be understood that singular forms such as "a," "an," and "the" are used throughout this application for convenience, however, except where context or an explicit statement indicates otherwise, the singular forms are intended to include the plural. All numerical ranges should be understood to include each and every numerical point within the numerical range, and should be interpreted as reciting each and every numerical point individually. The endpoints of all ranges directed to the same component or property are inclusive, and intended to be independently combinable.

The term "about" when used in connection with a referenced numeric indication means the referenced numeric indication plus or minus up to 10% of that referenced numeric indication. For example, the language "about 50" covers the range of 45 to 55.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features. Although the open-ended term "comprising," as a synonym of terms such as including, containing, or having, is used herein to describe and claim the disclosure, the present technology, or embodiments thereof, may alternatively be described using more limiting terms such as "consisting of" or "consisting essentially of" the recited ingredients.

As used herein, "half-life" (which generally refers to in vivo half-life or circulatory half-life) is the period of time that is required for a 50% diminution of bioactivity of the active agent to occur. In some embodiments, this term includes both prolonged exposure and a long half-life (e.g. both a slow uptake from the injection site and retardation of clearance compared to the unconjugated peptide).

Unless defined otherwise, all technical and scientific terms herein have the same meaning as commonly understood by one of ordinary skill in the art to which this disclosure belongs. Although any methods and materials, similar or equivalent to those described herein, can be used in the practice or testing of the present disclosure, the preferred methods and materials are described herein.

This disclosure is further illustrated by the following non-limiting examples.

EXAMPLES

Example 1: Phase Transition Properties of ELP Fusions

Figure 2:
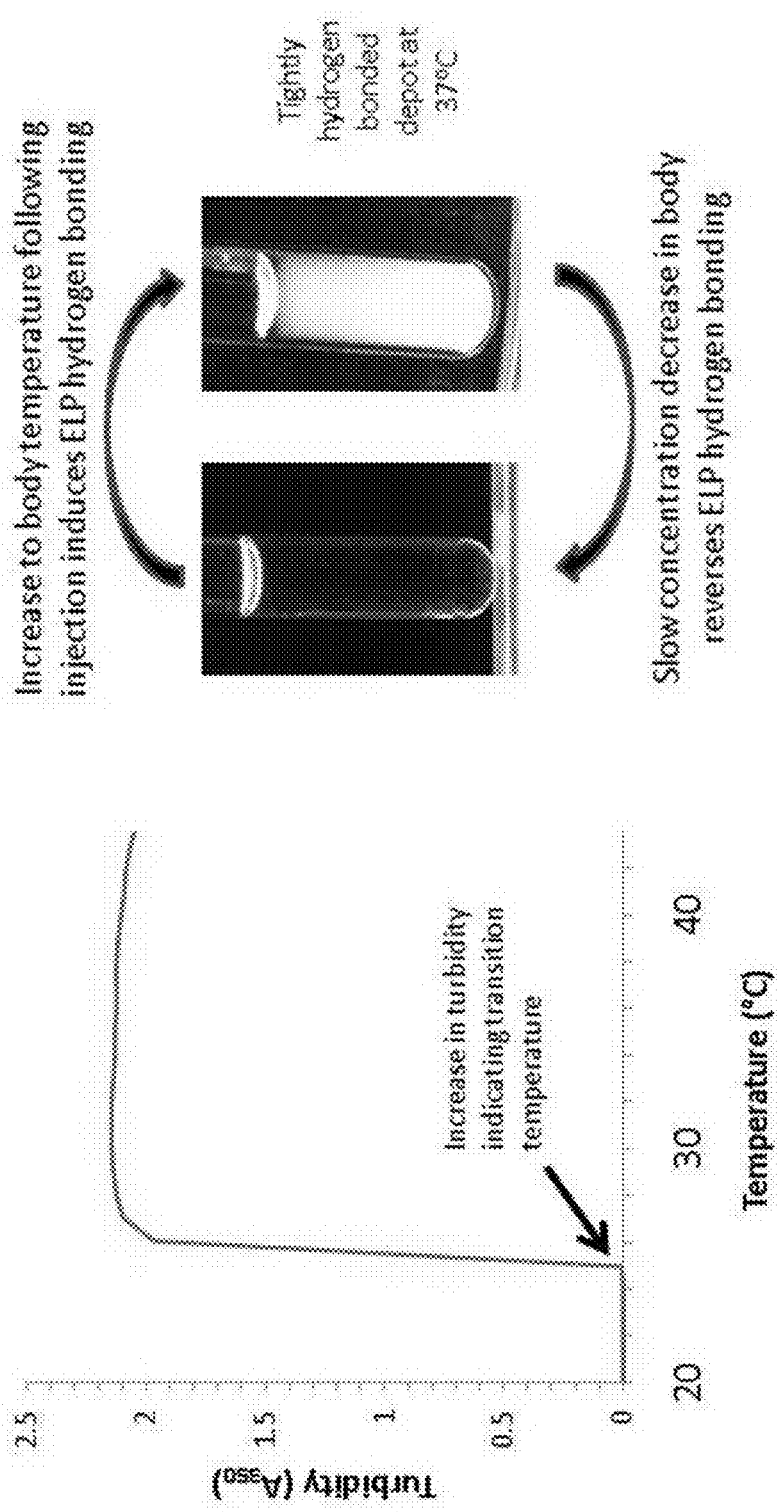
FIG. 2 shows the phase transition (as shown by an increase in turbidity) of an ELP4 protein, induced by a change in temperature to 25° C. or above. This property provides for a depot-like delivery.
Figure 3:
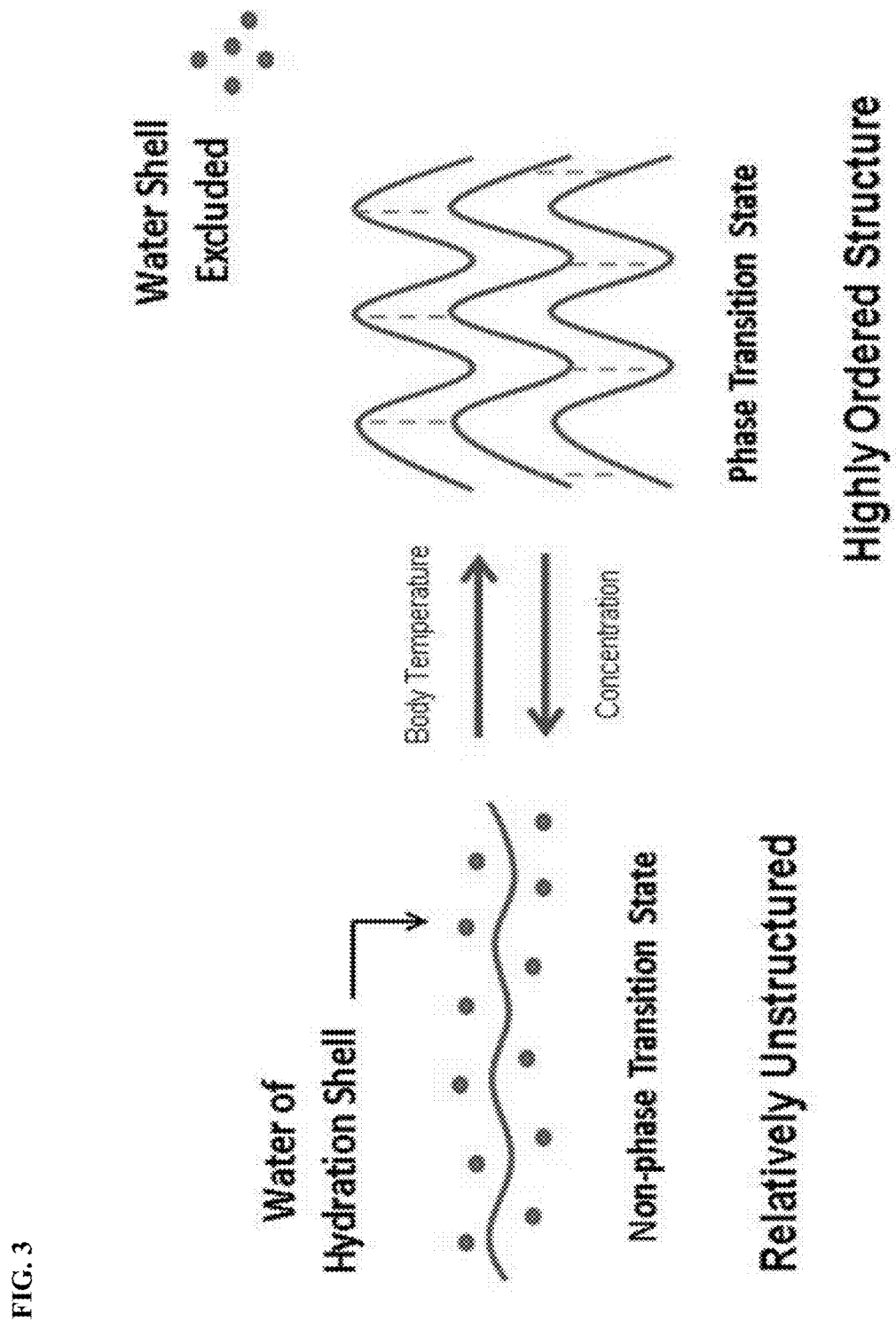
FIG. 3 illustrates, without wishing to be bound by theory, a potential mechanism for the observed transition, in which a water shell is excluded under certain conditions, allowing for hydrogen bonds to form.

The phase transition property exhibited by certain amino acid sequences is illustrated in FIG. 1 (for ELP1) and FIG. 2 (for ELP4). Phase transition can be observed as an increase in turbidity. FIG. 3 illustrates, without wishing to be bound by theory, a potential mechanism for phase transition, driven by exclusion of a water shell and formation of hydrogen bonds at a temperature above the phase transition temperature for a given concentration.

Example 2: Monthly ELP Fusion Polypeptides

Changing the amino acid in the guest residue position X in the VPGXG (SEQ ID NO:3) sequence of the ELP motif can change stability or strength of a coacervate of an ELP biopolymer in the transitioned state, resulting in slower release of drug and a prolonged depot when dosed subcutaneously. A collection of ELP biopolymers with different coacervation strengths was built by changing the ratio of guest amino acids used in nine VPGXG (SEQ ID NO:3) pentamer (9mer) blocks (alpha, beta, and beta v2). In addition to substituting the guest residue of VPGXG (SEQ ID NO:3), a pentamer with the motif XPGVG (SEQ ID NO:3) was also constructed (delta). The ELP pentamers can be combined to any length but for exemplification and ease of DNA synthesis and manipulation subunits of 9 ELP pentamers (9mers) were constructed. These 9mers can be combined to make polymers of any length but the overall ratio of valine to other amino acids at the guest residue position will remain the same. FIG. 4 shows an alignment of these 9mers (alpha, beta, beta v2, and delta). The 9mers were designed to create ELP biopolymers with hydrophobicity and thus transition temperatures between the ELP 1 series (VPGXG (SEQ ID NO:3): V5A2G3) and ELP 4 series (VPGXG (SEQ ID NO:3): V-5) biopolymers previously examined. Another ELP polymer was developed which is not depicted in FIG. 10. This polymer (ELPgamma) includes the VPGXG pentamer motif with a ratio of V5:A2:G2. Table 1 compares the ratios of guest residue occupancy between 9mers of the new ELP series and the 1 and 4 series.

Figure 5:
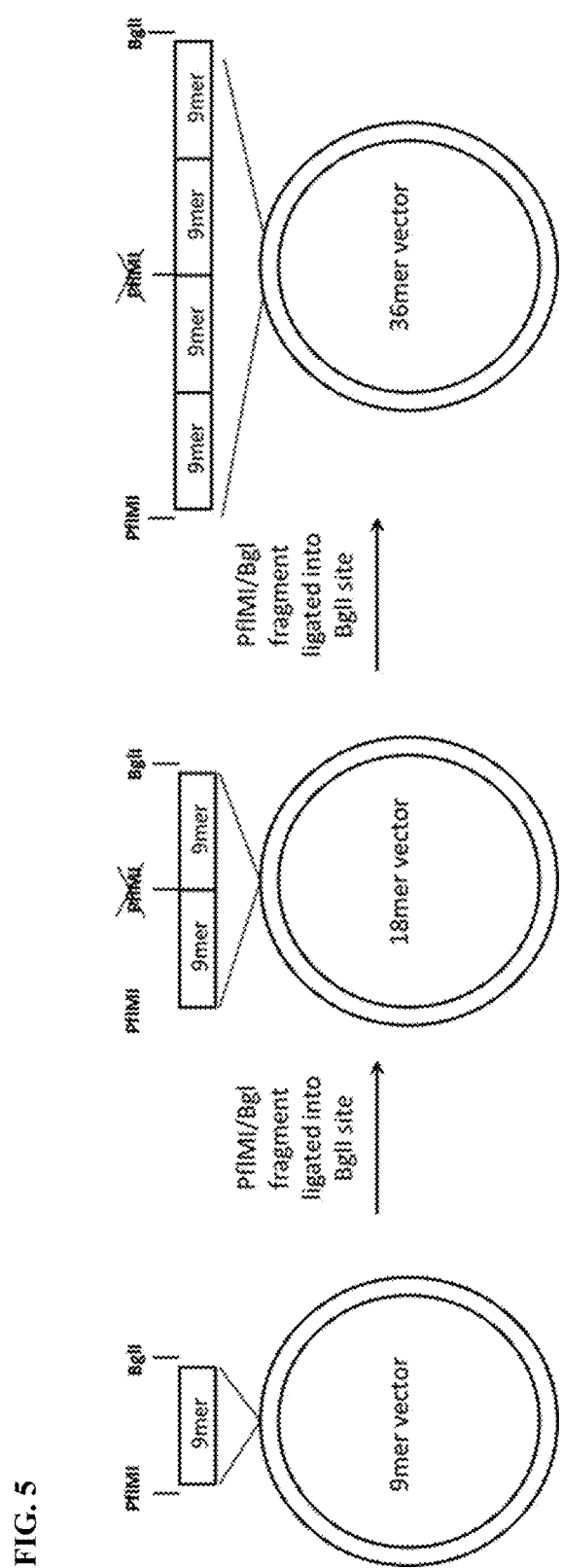
FIG. 5 shows a recursive ligation strategy used to make ELP polymers. The ELP pentamer polymer insert can continually be doubled in size using recursive ligation. The PflMI and BglI sites have homologous overhangs but when ligated the PflMI site is destroyed. This allows the newly constructed ELP to be doubled again using the same digestion strategy.

The 9mers were repeated using recursive ligation to build biopolymers of different lengths. FIG. 5 illustrates this ligation technique. The 9mers were synthesized (Integrated DNA Technologies, Coralville, Iowa) in a background vector (pIDT) to create synthesis vectors. These synthesis vectors were cut with BglI/PflMI restriction enzymes and sub-cloned back into the same synthesis vector cut with BglI and dephosphorylated. This gives a vector containing two copies of the 9mer. This doubling technique was continued until vectors containing 16 copies of the 9mer (144mer) were built. ELPs of varying numbers of 9mers can be combined to produce ELPs with, for instance, 18, 27, 36, 45, 54, 63, 72, 81, 90, 99, 108, 117, 126, 135, 144, 153, 162, 171, 180 copies of the 9mer. The units described in Table 1 can also be combined in various ratios to produce additional ELP biopolymers with intermediate characteristics. For instance, the gamma ELP polymer was constructed by alternating between an alpha 9mer and a beta 9mer until a 144mer was constructed. These ELP 144mers were then sub-cloned into a pET-based intermediate vector, pPE0248 (FIG. 6) which contains a linker region (FIG. 7) that allows the ELP144mers to be cloned into the correct reading frame for expression. pPE0248 adds an additional pentamer repeat to the N terminus of the 144mer with valine in the guest position and an additional pentamer to the C terminus with a tryptophan in the guest residue. The tryptophan may be used as a means to increase the extinction coefficient of the molecule, allowing for better measurement of absorbance, for instance at 280 nm, which can be useful for determination of protein concentration, or for monitoring protein content during purification. The pentamers added to either end can also be designed so as the encoding DNA contains restriction enzyme recognition sites for cloning of fusion partners on to either end of the ELP coding sequence. The 144mer expression plasmids were designated pPE0249 (ELPalpha-144), pPE0250 (ELPbetaV1-144), pPE0362 (ELPbetaV2-144), pPE0251 (ELPgamma-144), and pPE0252 (ELPdelta-144). FIGS. 8 through 17 contain the ELP amino acid sequences of the biopolymers and maps of the vectors.

Figure 18:
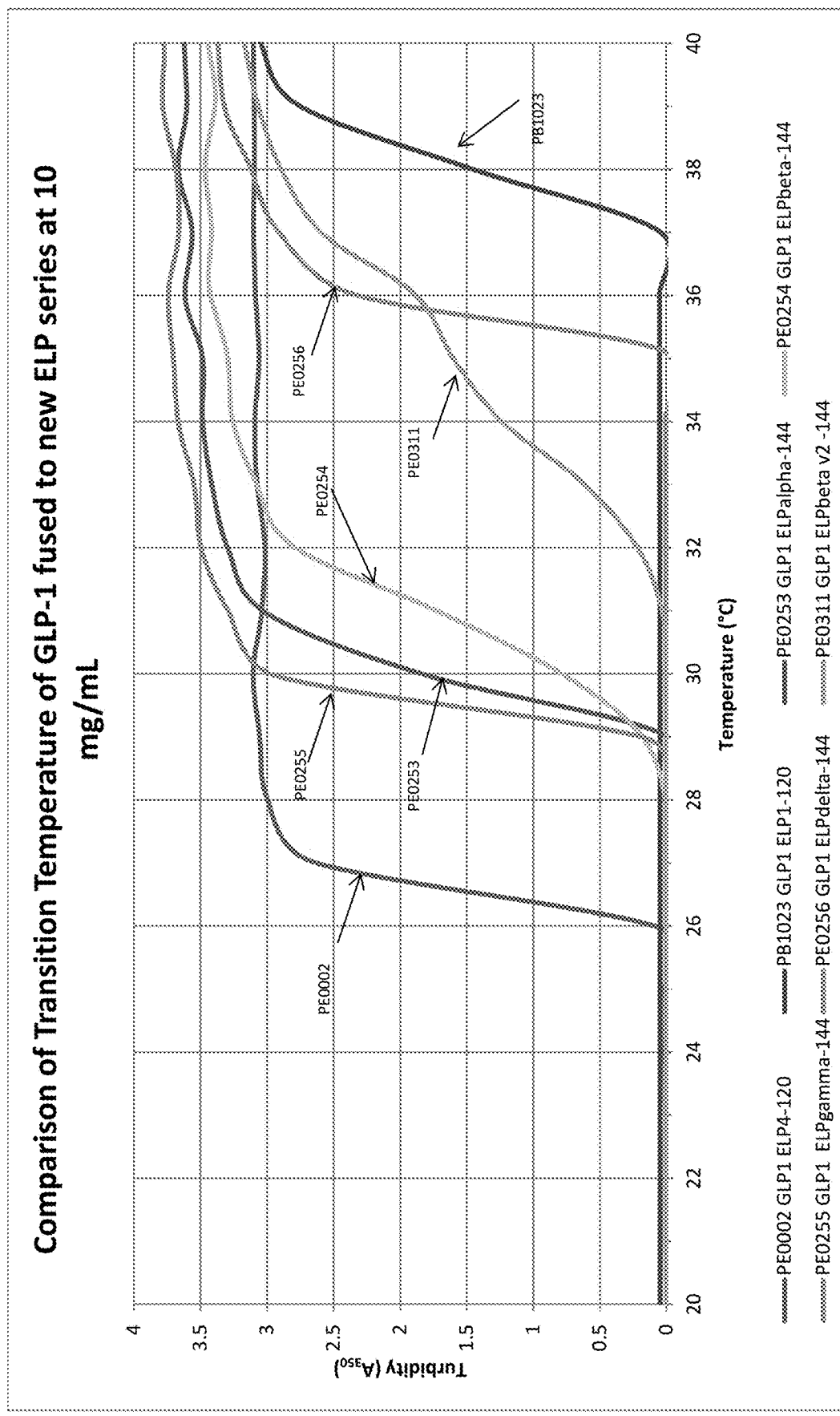
FIG. 18 shows the raw Cary turbidity data of the different ELP biopolymers after administration at 10 mg/mL.

The GLP-1 peptide was cloned onto the N-terminus of different ELP sequences. A synthesized GLP-1 gene was digested XbaI/BsrGI and cloned XbaI/Acc65i into pPE0249, pPE0250, pPE0362, pPE0251, and pPE0252 making vectors pPE0253 (GLP-1:ELPalpha-144), pPE0254 (GLP-1:ELPbetaV1-144), pPE0311 (GLP-1:ELPbetaV2-144), pPE0255 (GLP-1:ELPgamma-144), and pPE0256 (GLP-1:ELPdelta-144) respectively. These vectors were expressed in *E. coli* strain BLR(DE3). Following fermentation and purification, the peptide fusions including the different ELP polymers were formulated at 10 mg/mL in 20 mM histidine, 110 mM NaCl, and the transition temperatures measured using a Cary 300 UV Spectrophotometer. As shown in FIG. 18 and Table 2, the transition temperatures of ELPalpha-144, ELPbetaV1-144, ELPbetaV2-144, ELPgamma-144, and ELPdelta-144 fall between, but do not include, the temperatures for the series 4 ELPs (PE0002) and the series 1 ELPs (PB1023).

Figure 19:
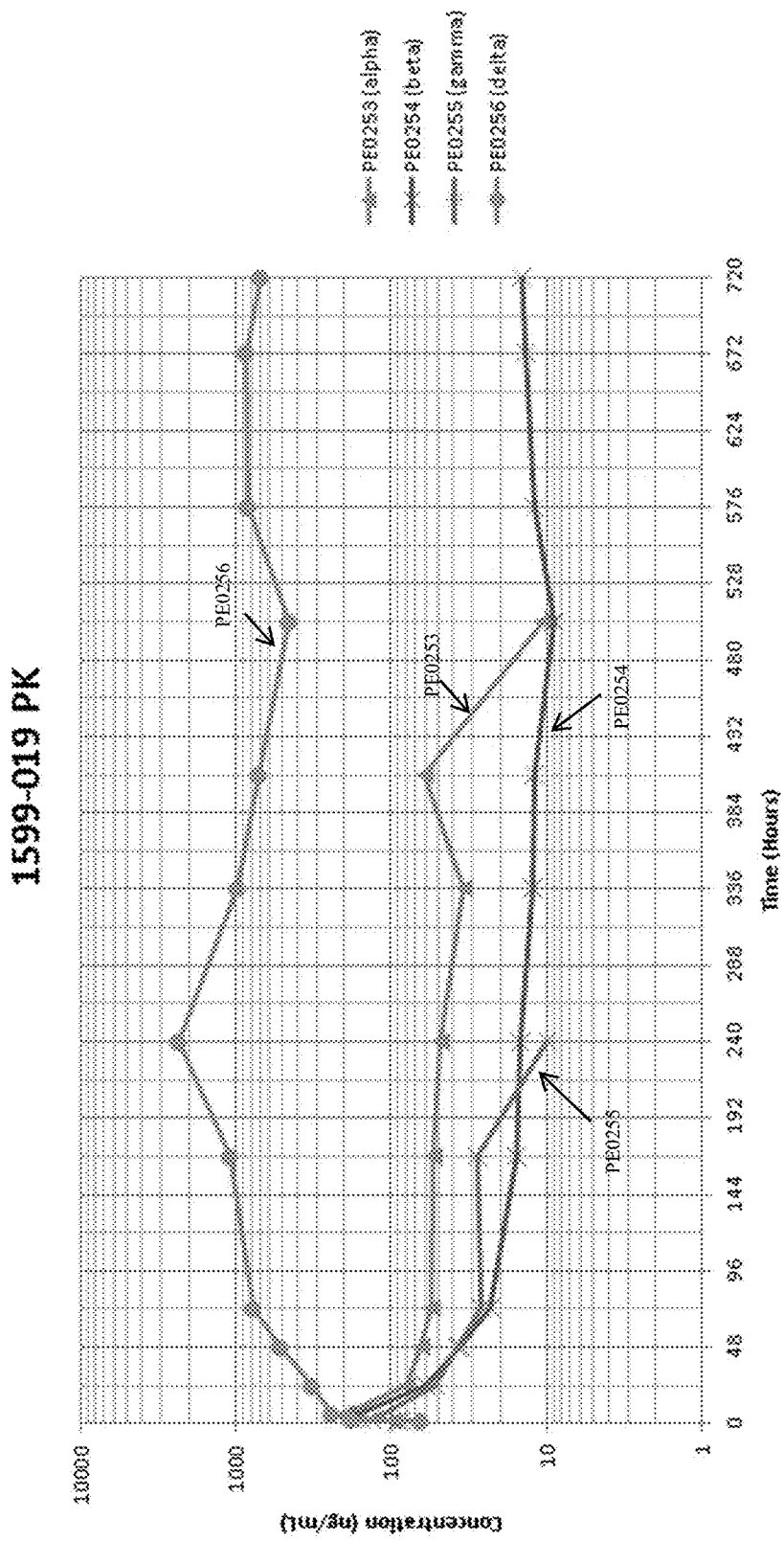
FIG. 19 shows the PK results from non-naïve monkeys, 1 male and 1 female per group, each dosed with a single subcutaneous injection of 20 mg/kg of either PE0253 (alpha), PE0254 (beta v1), PE0255 (gamma), or PE0256 (delta).
Figure 21A:
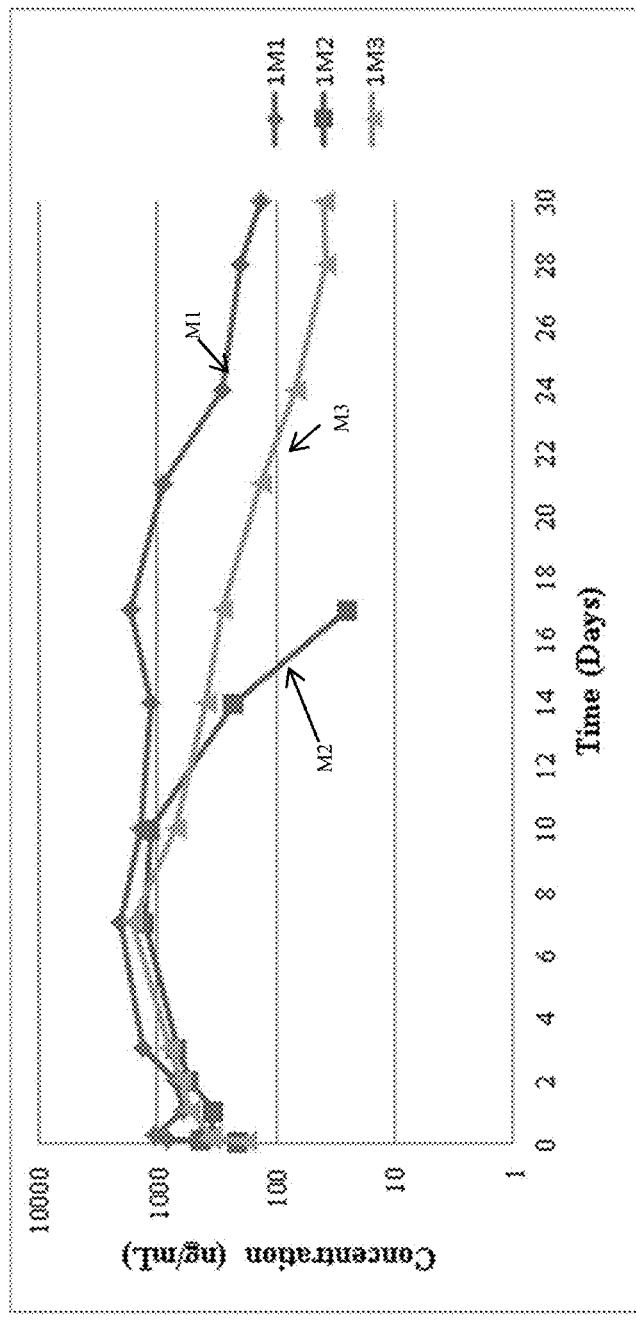
FIGS. 21A and B show the PK results of a single subcutaneous dose of PE0311 (beta v2) at 10 mg/kg into three protein naïve monkeys, all male. Figure A shows the data from the individual animals while Figure B shows the mean.
Figure 21B:
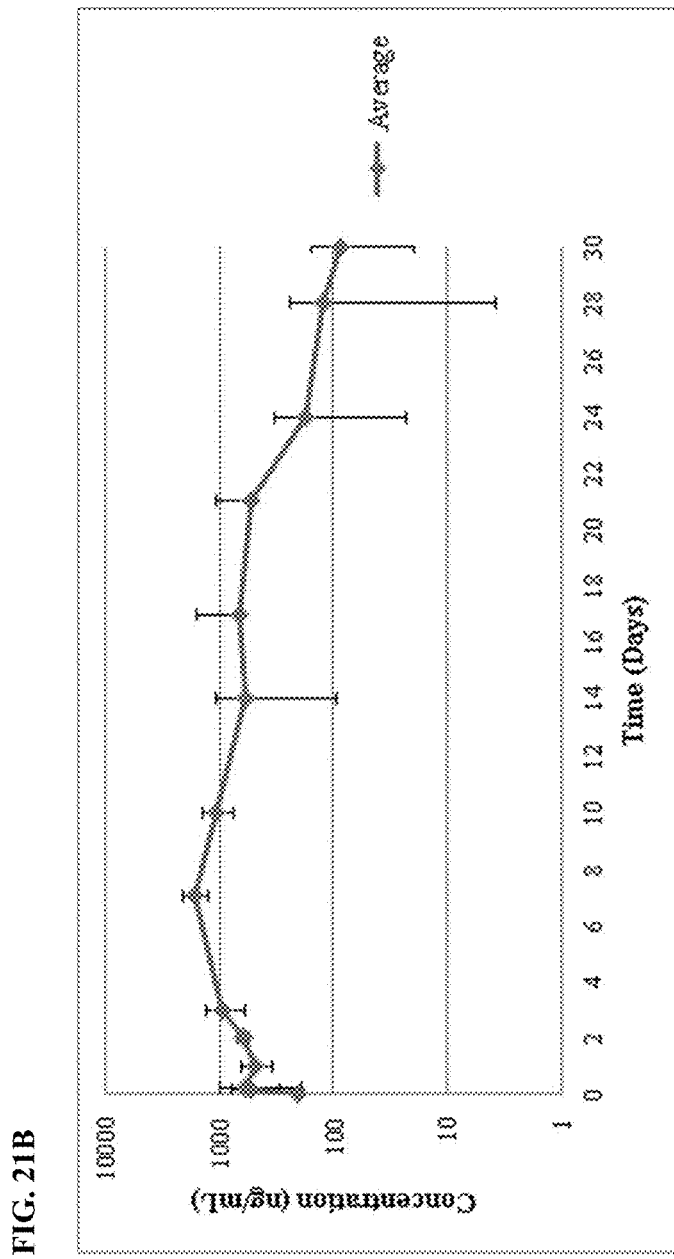
Figure 22:
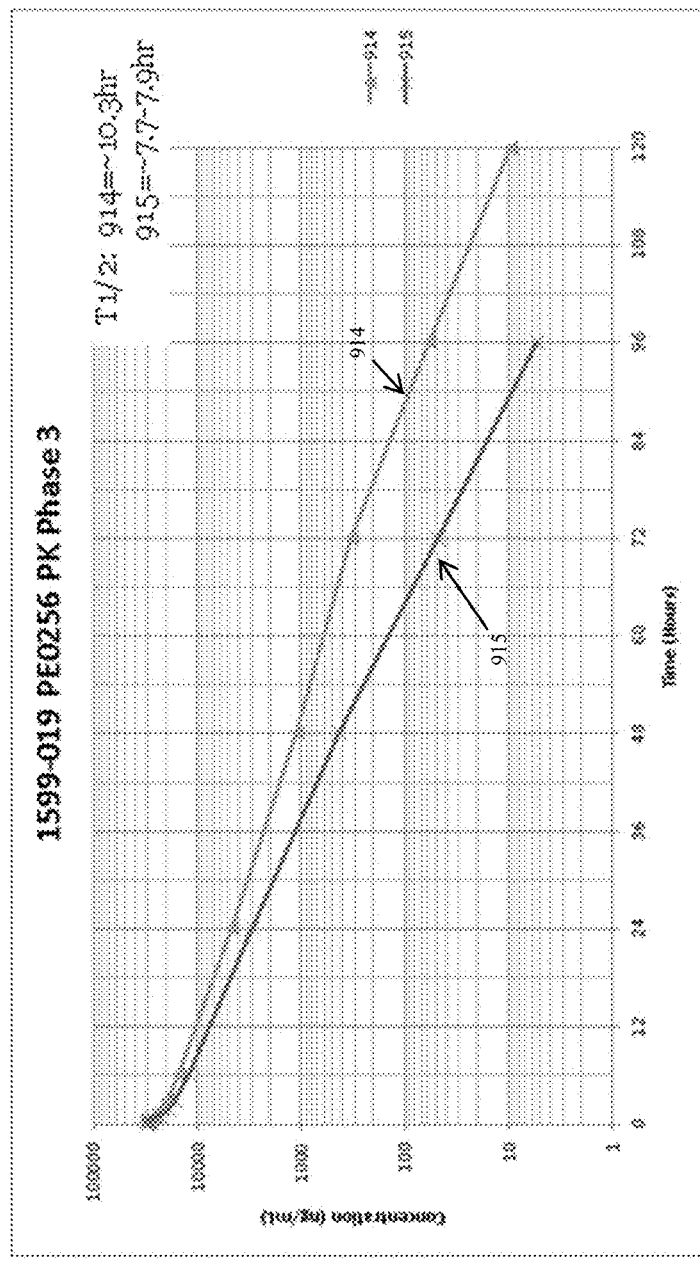
FIG. 22 shows the PK results of non-naïve monkeys dosed with a single IV injection of PE0256 (delta) at 2 mg/kg.

The PK of the PE0253 (alpha), PE0254 (beta v1), PE0255 (gamma), PE0256 (delta), and PE0311 (beta v2) were evaluated in Cynomolgus monkeys. FIG. 19 and Table 4 display the PK results of non-naïve monkeys, 1 male and 1 female per group, each dosed with a single subcutaneous injection of 20 mg/kg of either PE0253, PE0254, PE0255, or PE0256. FIG. 20 and Table 5 show the PK results of a single subcutaneous dose of PE0256 at 10 mg/kg into four protein naïve monkeys, 2 male and 2 female. FIG. 21 and Table 6 demonstrate the PK results of a single subcutaneous dose of PE0311 at 10 mg/kg into three protein naïve monkeys, all male. In contrast, FIG. 22 and Table 7 show the PK results of non-naïve monkeys dosed with a single IV injection of PE0256 at 2 mg/kg.

Example 3: Preparation of Growth Hormone ELP Constructs

An human growth hormone (hGH) sequence was synthesized, digested with restriction enzymes PflM1/Bgl I, and then sub-cloned into plasmid pE0362 to provide plasmid pPE0429, placing a ELPbetaV2-144 on the N-terminus of the hGH sequence. FIG. 23 shows the plasmid map of pPE0429. FIG. 24 shows the sequence of the fusion protein. This construct provides an ELP with 16 repeats of the ELPbetaV2 9mer.

In a further fusion protein, an ELP1 30mer was appended to the C-terminus of the fusion protein in pPE0429 to provide plasmid pPE0430. Adding the ELP1 30mer disrupts receptor mediated clearance and thus further increases circulatory half-life of the hGH fusion protein. FIG. 27 shows the plasmid map for plasmid pPE0430. FIG. 28 shows the sequence of the fusion protein.

In other experiments, the hGH protein was fused to a series 1 ELP 120mer, both alone and with a C-terminal ELP1 series 30 mer. FIG. 25 shows the plasmid map for plasmid pPE0431, prepared by inserting hGH into the pPB1031, providing a ELP1 series 120mer with a C-terminal hGH sequence. FIG. 26 shows the sequence of the fusion protein. The ELP1 120mer protein was inserted into the plasmid pPE0431 to append an ELP1 30mer protein to the C-terminus of the ELP1-120 hGH fusion protein. The resulting plasmid was termed pPE0432. FIG. 29. The resulting amino acid sequence of the ELP1-120mer-hGH-ELP1 30mer is shown in FIG. 30.

Example 4: Preparation of Exendin-4 ELP Constructs

An exendin-4 encoding sequence was synthesized, digested with restriction enzymes XbaI/BsrGI, and then sub-cloned into plasmid pE0362 to provide plasmid pPE0364, placing the exendin-4 sequence on the N-terminus of the ELPbetaV2-144 sequence. FIG. 31 shows the plasmid map of pPE0364. FIG. 32 shows the sequence of the fusion protein. This construct provides an ELP with 16 repeats of the ELPbetaV2 9mer.

INCORPORATION BY REFERENCE

All patents and publications referenced herein are hereby incorporated by reference in their entireties, including the publications disclosed below.

The publications discussed herein are provided solely for their disclosure prior to the filing date of the present application. Nothing herein is to be construed as an admission that the present disclosure is not entitled to antedate such publication by virtue of prior disclosure.

This application incorporates by reference the following publications in their entireties for all purposes: US 2001/0034050 A1; US 2009/0220455; U.S. Pat. No. 8,334,257; US 2013/0310538; US 2013/0172274; US 2011/0236384; U.S. Pat. Nos. 6,582,926; 7,429,458; 7,364,859; 8,178,495; US 2013/0079277; US 2013/0085099; US 2013/0143802; US 2014/0024600; US 2011/0178017; U.S. Pat. No. 7,709,227; US 2011/0123487; U.S. Pat. No. 8,729,018; US 2014/0171370; US 2013/0150291; WO/2014/113434; and US 2014/0213516.

TABLE 4

PK results from non-naïve monkeys, 1 male and 1 female per group, each dosed with a single subcutaneous injection of 20 mg/kg of either PE0253 (alpha), PE0254 (beta v1), PE0255 (gamma), or PE0256 (delta).
PK Results (ng/mL)

|  | PE0253 (alpha) | | | PE0254 (betav1) | | |
|---|---|---|---|---|---|---|
| Time (Hours) | 905 | 906 | Average | 907 | 908 | Average |
| 0 | BLQ | BLQ | BLQ | BLQ | BLQ | BLQ |
| 1 | 84.3 | 111 | 97.65 | 69.6 | 112 | 90.8 |
| 3 | 170 | 201 | 185.5 | 139 | 180 | 159.5 |
| 6 | 136 | 256 | 196 | 167 | 160 | 163.5 |
| 24 | 98.7 | 63.1 | 80.9 | 50.9 | 67.2 | 59.05 |
| 48 | 80.8 | 48.7 | 64.75 | 33.6 | 39.3 | 36.45 |
| 72 | 64.8 | 44.6 | 54.7 | 21.8 | 24.8 | 23.3 |
| 168 | 51.8 | 54.8 | 53.3 | 16.5 | 14.8 | 15.65 |
| 240 | 46.7 | 50.3 | 48.5 | 16.1 | 13.6 | 14.85 |
| 336 | 5.87 | 62.1 | 33.985 | 9.23 | 15.5 | 12.365 |
| 408 | BLQ | 61.7 | 61.7 | 10.4 | 13.5 | 11.95 |
| 504 | BLQ | 10.6 | 10.6 | 2.85 | 15 | 8.925 |
| 576 | BLQ | BLQ | BLQ | BLQ | 11.9 | 11.9 |

TABLE 4-continued

PK results from non-naïve monkeys, 1 male and 1 female per group, each dosed with a single subcutaneous injection of 20 mg/kg of either PE0253 (alpha), PE0254 (beta v1), PE0255 (gamma), or PE0256 (delta).
PK Results (ng/mL)

| | | | | | | |
|---|---|---|---|---|---|---|
| 672 | BLQ | BLQ | BLQ | BLQ | 13.5 | 13.5 |
| 720 | BLQ | BLQ | BLQ | BLQ | 14.5 | 14.5 |

BLQ < 2.44 ng/mL
BLQ < 4.88 ng/mL

| | PE0255 (gamma) | | | PE0256 (delta) | | |
|---|---|---|---|---|---|---|
| Time (Hours) | 909 | 910 | Average | 911 | 912 | Average |
| 0 | BLQ | BLQ | BLQ | BLQ | BLQ | BLQ |
| 1 | 93.5 | 78 | 85.75 | 33 | 97.9 | 65.45 |
| 3 | 124 | 148 | 136 | 164 | 196 | 180 |
| 6 | 84.4 | 142 | 113.2 | 214 | 266 | 240 |
| 24 | 49.4 | 54.1 | 51.75 | 190 | 454 | 322 |
| 48 | 32.4 | 42.2 | 37.3 | 490 | 543 | 516.5 |
| 72 | 21.9 | 31.2 | 26.55 | 951 | 594 | 772.5 |
| 168 | 26.5 | 29.3 | 27.9 | 1430 | 754 | 1092 |
| 240 | 4.51 | 15.4 | 9.955 | 3490 | 1170 | 2330 |
| 336 | BLQ | BLQ | BLQ | 483 | 1450 | 966.5 |
| 408 | BLQ | BLQ | BLQ | 73.8 | 1350 | 711.9 |
| 504 | BLQ | BLQ | BLQ | 4.3 | 914 | 459.15 |
| 576 | BLQ | BLQ | BLQ | BLQ | 839 | 839 |
| 672 | BLQ | BLQ | BLQ | BLQ | 852 | 852 |
| 720 | BLQ | BLQ | BLQ | BLQ | 691 | 691 |

BLQ < 2.44 ng/mL
BLQ < 4.88 ng/mL

TABLE 5

PK results (ng/mL) from of a single subcutaneous dose of PE0256 (delta) at 10 mg/kg into four protein naïve monkeys, 2 male and 2 female.
PK results (ng/mL)

| Hours | Days | M1 | M2 | F1 | F2 |
|---|---|---|---|---|---|
| 0 | 0 | blq | 17 | blq | blq |
| 1 | 0.042 | 232 | 94 | 52.9 | 241 |
| 3 | 0.125 | 482 | 217 | 176 | 596 |
| 6 | 0.25 | 492 | 257 | 277 | 831 |
| 24 | 1 | 997 | 374 | 1030 | 1610 |
| 48 | 2 | 1260 | 677 | 1630 | 1640 |
| 72 | 3 | 1130 | 875 | 1780 | 1660 |
| 168 | 7 | 1230 | 1140 | 1620 | 1210 |
| 240 | 10 | 1540 | 783 | 1220 | 1030 |
| 336 | 14 | 27 | 617 | 440 | 758 |
| 408 | 17 | blq | 395 | 102 | 587 |
| 504 | 21 | blq | 128 | 16.6 | 383 |
| 576 | 24 | blq | 38.3 | blq | 348 |
| 672 | 28 | blq | 5.6 | 3.6 | 230 |
| 720 | 30 | blq | blq | blq | 97.5 |

TABLE 6

PK results of a single subcutaneous dose of PE0311 (beta v2) at 10 mg/kg into three protein naïve monkeys, all male.
PK Results (ng/mL)

| Time (hrs) | Days | 1M1 | 1M2 | 1M3 | Average | SD |
|---|---|---|---|---|---|---|
| 0 | 0 | BLQ | BLQ | BLQ | 0 | 0 |
| 1 | 0.042 | 230 | 206 | 181 | 205.7 | 24.5 |
| 3 | 0.125 | 826 | 426 | 368 | 540.0 | 249.4 |
| 6 | 0.25 | 1050 | 360 | 355 | 588.3 | 399.8 |
| 24 | 1 | 619 | 333 | 533 | 495.0 | 146.7 |
| 48 | 2 | 702 | 548 | 621 | 623.7 | 77.0 |
| 72 | 3 | 1340 | 695 | 799 | 944.7 | 346.3 |
| 168 | 7 | 2110 | 1270 | 1640 | 1673.3 | 421.0 |
| 240 | 10 | 1370 | 1130 | 726 | 1075.3 | 325.5 |
| 336 | 14 | 1150 | 224 | 393 | 589.0 | 493.1 |
| 408 | 17 | 1690 | 24.8 | 290 | 668.3 | 894.7 |
| 504 | 21 | 908 | BLQ | 133 | 520.5 | 548.0 |
| 576 | 24 | 289 | BLQ | 68.9 | 179.0 | 155.6 |
| 672 | 28 | 205 | BLQ | 38.3 | 121.7 | 117.9 |
| 720 | 30 | 137 | BLQ | 39.8 | 88.4 | 68.7 |

TABLE 7

PK results (in ng/mL) of non-naïve monkeys dosed with a single IV injection of PE0256 (delta) at 2 mg/kg.
PE0256 (delta)

| Time (Hours) | 914 | 915 | Average |
|---|---|---|---|
| 0 | BLQ | BLQ | BLQ |
| 0.083 | 31300 | 30400 | 30850 |
| 0.25 | 28600 | 29400 | 29000 |
| 0.5 | 30400 | 29000 | 29700 |
| 0.75 | 25500 | 26500 | 26000 |
| 1 | 25900 | 23600 | 24750 |
| 2 | 22200 | 18800 | 20500 |
| 3 | 19300 | 16400 | 17850 |
| 6 | 15500 | 12000 | 13750 |
| 24 | 4700 | 2960 | 3830 |
| 48 | 1120 | 434 | 777 |
| 72 | 334 | 48.6 | 191.3 |
| 96 | 57.6 | 5.38 | 31.49 |
| 120 | 9.81 | BLQ | 9.81 |
| 144 | BLQ | BLQ | BLQ |
| 168 | BLQ | BLQ | BLQ |

What is claimed is:

1. A sustained release pharmaceutical formulation comprising:
   a therapeutic agent for systemic administration, the therapeutic agent comprising an active agent and at least 90 elastin-like peptide (ELP) structural units of SEQ ID NO: 3, wherein the ELP exhibits a transition temperature between 26° C. and 37° C.,
   wherein each Xaa is selected from V, G, and A, and wherein the ratio of V:G:A is selected from the group consisting of about:
   a) 7:2:0;
   b) 7:0:2; and
   c) 6:0:3;
   and
   one or more pharmaceutically acceptable excipients.

2. The pharmaceutical formulation of claim 1, wherein formation of a reversible matrix at body temperature reverses as therapeutic agent concentration decreases at an injection site.

3. The pharmaceutical formulation of claim 1, wherein the ELP comprises 144 repeating units of VPGXG (SEQ ID NO: 3).

4. The pharmaceutical formulation of claim 1, formulated for administration to a human subject.

5. The pharmaceutical formulation of claim 1, formulated for administration to a non-human mammal.

6. The pharmaceutical formulation of claim 1, wherein the active agent is a protein.

7. The pharmaceutical formulation of claim 6, wherein the therapeutic agent is a recombinant fusion protein between the protein active agent and ELP.

8. The pharmaceutical formulation of claim 6, wherein the protein active agent has a circulatory half-life in the range of from about 30 seconds to about 10 hours.

9. The pharmaceutical formulation of claim 6, wherein the protein active agent is a GLP-1 receptor agonist, a VPAC2 selective agonist, a GIP receptor agonist, a glucagon receptor agonist, exendin-4, or insulin.

10. The pharmaceutical formulation of claim 9, wherein the formulation is a co-formulation comprising at least two of a GLP1 receptor agonist, a glucagon receptor agonist, a GIP receptor agonist, exendin-4, and insulin.

11. The pharmaceutical formulation of claim 1, wherein the therapeutic agent is a chemical conjugate between the active agent and ELP.

12. The pharmaceutical formulation of claim 11, wherein the active agent is a chemotherapeutic agent selected from methotrexate, daunomycin, mitomycin, cisplatin, vincristine, epirubicin, fluorouracil, verapamil, cyclophosphamide, cytosine arabinoside, aminopterin, bleomycin, mitomycin C, democolcine, etoposide, mithramycin, chlorambucil, melphalan, daunorubicin, doxorubicin, tamoxifen, paclitaxel, vinblastine, camptothecin, actinomycin D, cytarabine, and combrestatin.

13. The pharmaceutical formulation of claim 1, wherein the therapeutic agent is present in the range of about 0.5 mg/mL to about 200 mg/mL.

14. The pharmaceutical formulation of claim 13, wherein the therapeutic agent is present in the range of about 30 mg/mL to about 150 mg/mL.

15. The pharmaceutical formulation of claim 14, wherein the therapeutic agent is present in the range of about 50 mg/mL to about 125 mg/mL.

16. The pharmaceutical formulation of claim 15, wherein the therapeutic agent is present in the amount of about 100 mg/mL.

17. The pharmaceutical formulation of claim 1, wherein the therapeutic agent does not form a phase-transitioned matrix at storage conditions.

18. The pharmaceutical formulation of claim 17, wherein the storage conditions are less than about 40° C.

19. The pharmaceutical formulation of claim 18, wherein the formulation is stable for more than 1 month at the storage conditions.

20. The pharmaceutical formulation of claim 19, wherein the formulation is stable for more than about 1 month at about 25° C.

21. The pharmaceutical formulation of claim 1, wherein the formulation comprises two or more of calcium chloride, magnesium chloride, potassium chloride, potassium phosphate monobasic, sodium chloride, polysorbate 20, sodium phosphate, sodium phosphate monobasic, and sodium phosphate dibasic.

22. The pharmaceutical formulation of claim 21, wherein the formulation comprises sodium phosphate, sodium chloride and polysorbate 20.

23. The pharmaceutical formulation of claim 22, wherein the formulation comprises 10 mM sodium phosphate, 110 mM sodium chloride, and 0.1% w/w polysorbate 20.

24. The pharmaceutical formulation of claim 1, wherein the formulation is packaged in the form of pre-dosed pens or syringes for administration about once per week, about twice per week, or from one to eight times per month.

25. A method for delivering a sustained release regimen of a therapeutic agent, comprising administering the formulation of claim 1 to a subject in need thereof, wherein the formulation is administered from about 1 to about 8 times per month.

26. The method of claim 25, wherein the formulation is administered about weekly.

27. The method of claim 25, wherein the formulation is administered subcutaneously or intramuscularly.

28. The method of claim 25, wherein the site of administration is not a pathological site.

\* \* \* \* \*